US012617849B2

(12) United States Patent
Aftab

(10) Patent No.: US 12,617,849 B2
(45) Date of Patent: May 5, 2026

(54) ANTIGEN SPECIFIC CD19-TARGETED CAR-T CELLS

(71) Applicant: Atara Biotherapeutics, Inc., South San Francisco, CA (US)

(72) Inventor: Blake T. Aftab, South San Francisco, CA (US)

(73) Assignee: Atara Biotherapeutics, Inc., Thousand Oaks, CA (US)

( * ) Notice: Subject to any disclaimer, the term of this patent is extended or adjusted under 35 U.S.C. 154(b) by 1045 days.

(21) Appl. No.: 17/607,592

(22) PCT Filed: Apr. 29, 2020

(86) PCT No.: PCT/US2020/030435
§ 371 (c)(1),
(2) Date: Oct. 29, 2021

(87) PCT Pub. No.: WO2020/223327
PCT Pub. Date: Nov. 5, 2020

(65) Prior Publication Data
US 2022/0348649 A1    Nov. 3, 2022

Related U.S. Application Data

(60) Provisional application No. 62/840,774, filed on Apr. 30, 2019.

(51) Int. Cl.
| | |
|---|---|
| *C07K 16/28* | (2006.01) |
| *A61K 38/00* | (2006.01) |
| *A61K 39/00* | (2006.01) |
| *A61K 40/11* | (2025.01) |
| *A61K 40/31* | (2025.01) |
| *A61K 40/42* | (2025.01) |
| *A61K 40/46* | (2025.01) |
| *A61P 35/00* | (2006.01) |
| *A61P 35/02* | (2006.01) |
| *C07K 14/705* | (2006.01) |
| *C07K 14/725* | (2006.01) |
| *C12N 5/0783* | (2010.01) |

(52) U.S. Cl.
CPC .......... *C07K 16/2803* (2013.01); *A61K 40/11* (2025.01); *A61K 40/31* (2025.01); *A61K 40/4211* (2025.01); *A61K 40/46* (2025.01); *A61P 35/00* (2018.01); *A61P 35/02* (2018.01); *C07K 14/7051* (2013.01); *C07K 14/70517* (2013.01); *C07K 14/70521* (2013.01); *C07K 14/70578* (2013.01); *C12N 5/0636* (2013.01); *A61K 38/00* (2013.01); *A61K 2039/505* (2013.01); *A61K 2239/38* (2023.05); *A61K 2239/48* (2023.05); *C07K 2317/31* (2013.01); *C07K 2317/622* (2013.01); *C07K 2317/76* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | | | |
|---|---|---|---|---|
| 10,253,086 B2 * | 4/2019 | Bitter | ............... | A61K 45/06 |
| 2016/0362472 A1 | 12/2016 | Bitter et al. | | |
| 2020/0215108 A1 * | 7/2020 | Jensen | ............. | A61K 31/713 |

FOREIGN PATENT DOCUMENTS

| | | |
|---|---|---|
| WO | WO-2015/075468 A1 | 5/2015 |
| WO | WO-2016/164731 A2 | 10/2016 |
| WO | WO-2017/027291 A1 | 2/2017 |
| WO | WO-2017/028374 A1 | 2/2017 |
| WO | WO-2018/067992 A1 | 4/2018 |
| WO | WO-2018/132494 A1 | 7/2018 |
| WO | WO-2019/010383 A1 | 1/2019 |
| WO | WO-2019/060174 A1 | 3/2019 |
| WO | WO-2019/161796 A1 | 8/2019 |
| WO | WO-2020/223327 A1 | 11/2020 |

OTHER PUBLICATIONS

Extended European Search Report for EP Application No. 20798656.3 dated Apr. 20, 2023.
Bridgeman et al., "CD3zeta-based chimeric antigen receptors mediate T cell activation via cis- and trans-signalling mechanisms: implications for optimization of receptor structure for adoptive cell therapy," Clinical and Experimental Immunology 175 (2013): 258-267.
Curran et al., "Validation of donor derived virus specific T-lymphocytes genetically modified to target the CD19 antigen for the treatment of relapsed leukemia." Mol Ther 19 (2011): S90.
Boucher et al., "Mutation of the CD28 costimulatory domain confers decreased CAR T cell exhaustion," Blood, Supplement 1: 966 (2018).
Boucher et al., "Mutation of the CD28 costimulatory domain confers increased CAR T cell persistence and decreased exhaustion," The Journal of Immunology, <https://www.jimmunol.org. content200/1_Supplement/57.28.abstract>: Abstract 5 pages (2018).
GenBank: ADM64594.1, FMC63-28Z receptor protein [synthetic construct]: 3 pages (2012).
International Search Report and Written Opinion for International Application No. PCT/US2020/030435 dated Jul. 27, 2020.
Kochenderfer et al., "B-cell depletion and remissions of malignancy along with cytokine-associated toxicity in a clinical trial of anti-CD19 chimeric-antigen-receptor-transduced T cells," Blood, 119(12):2709-2720 (2012).

(Continued)

*Primary Examiner* — Blaine Lankford
(74) *Attorney, Agent, or Firm* — Foley Hoag LLP

(57) ABSTRACT

Disclosed are compositions and methods for targeted treatment of cancer, such as hematologic cancer. In particular, chimeric antigen receptor (CAR) T cells are disclosed that can be used with adoptive cell transfer to target and kill cancer cells with reduced antigen escape. Therefore, also disclosed are methods of providing an anti-tumor immunity in a subject with hematologic cancer that involves adoptive transfer of the disclosed CAR T cells.

9 Claims, 16 Drawing Sheets

Specification includes a Sequence Listing.

(56) References Cited

OTHER PUBLICATIONS

Kochenderfer et al., "Construction and pre-clinical evaluation of an anti-CD19 chimeric antigen receptor," Journal of Immunotherapy, 32(7):689-702 (2009).

Love et al., "ITAM-mediated signaling by the T-cell antigen receptor," Cold Spring Harbor Perspectives in Biology, 1(6):13 pages (2010).

Pule et al., "Virus-specific T cells engineered to coexpress tumor-specific receptors: presistence and antitumor activity in individuals with neuroblastoma," Nature Medicine, 14(11):1264-1270 (17 pages)(2008).

Qin et al., "Incorporation of a hinge domain improves the expansion of chimeric antigen receptor T cells," Journal of Hematology & Oncology, 10(1):1-11 (2017).

Rafiq et al., "Targeted delivery of a PD-1-blocking scFv by CAR-T cells enhances anti-tumor efficacy in vivo," Nature Biotechnology, 36(9): 847-856 (2018).

Yoon et al., "Incorporation of immune checkpoint blockade into chimeric antigen receptor T cells (CAR-Ts): combination or built-in CAR-T," International Journal of Molecular Sciences, 19(2):340 (16 pages)(2018).

Zhang et al., "CRISPR-Cas9 mediated LAG-3 disruption in CAR-T cells," Frontiers of Medicine, 11(4):554-562 (2017).

Feucht et al., "Calibration of CAR activation potential directs alternative T cell fates and therapeutic potency." Nature Medicine, vol. 25, pp. 82-88.

* cited by examiner

TH2 Pro-inflammatory
Cytokine Release
48hr; 1:1

SEQUENCE LISTING

```
<160> NUMBER OF SEQ ID NOS: 17

<210> SEQ ID NO 1
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggctctcc cagtgactgc cctactgctt cccctagcgc ttctcctgca tgcagacatc      60
cagatgaccc agaccacaag cagcctgtct gccagcctgg gcgatagagt gaccatcagc     120
tgtagagcca gccaggacat cagcaagtac ctgaactggt atcagcagaa acccgacggc     180
accgtgaagc tgctgatcta ccacaccagc agactgcaca gcggcgtgcc aagcagattt     240
tctggcagcg gctctggcac cgactacagc ctgacaatca gcaacctgga acaagaggat     300
atcgctacct acttctgcca gcaaggcaac accctgcctt acacctttgg cggaggcacc     360
aagctggaaa tcaccggctc tacaagcggc agcggcaaac ctggatctgg cgagggatct     420
accaagggcg aagtgaaact gcaagagtct ggccctggac tggtggcccc atctcagtct     480
ctgagcgtga cctgtacagt cagcggagtg tccctgcctg attacggcgt gtcctggatc     540
agacagcctc ctcggaaagg cctggaatgg ctgggagtga tctggggcag cgagacaacc     600
tactacaaca gcgccctgaa gtcccggctg accatcatca aggacaactc caagagccag     660
gtgttcctga agatgaacag cctgcagacc gacgacaccg ccatctacta ttgcgccaag     720
cactactact acggcggcag ctacgccatg gattattggg gccagggcac cagcgtgacc     780
gtttcttctg cggccgcaat tgaagttatg tatcctcctc cttacctaga caatgagaag     840
agcaatggaa ccattatcca tgtgaaaggg aaacaccttt gtccaagtcc cctatttccc     900
ggaccttcta agcccttttg ggtgctggtg gtggttggtg gagtcctggc ttgctatagc     960
ttgctagtaa cagtggcctt tattattttc tgggtgagga gtaagaggag caggctcctg    1020
cacagtgact acatgaacat gactccccgc cgccccgggc ccacccgcaa gcattaccag    1080
ccctatgccc caccacgcga cttcgcagcc tatcgctcca gagtgaagtt cagcaggagc    1140
```

```
gcagacgccc ccgcgtacca gcagggccag aaccagctct ataacgagct caatctagga      1200
cgaagagagg agtacgatgt tttggacaag agacgtggcc gggaccctga gatgggggga      1260
aagccgagaa ggaagaaccc tcaggaaggc ctgttcaatg aactgcagaa agataagatg      1320
gcggaggcct tcagtgagat tgggatgaaa ggcgagcgcc ggagggggcaa ggggcacgat      1380 ggccttttcc aggggctcag tacagccacc aaggacacct tcgacgccct tcacatgcag      1440
gccctgcccc ctcgc                                                       1455
```

```
<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atggctctcc cagtgactgc cctactgctt cccctagcgc ttctcctgca tgca            54
```

```
<210> SEQ ID NO 3
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gacatccaga tgacccagac cacaagcagc ctgtctgcca gcctgggcga tagagtgacc      60
atcagctgta gagccagcca ggacatcagc aagtacctga actggtatca gcagaaaccc     120
gacggcaccg tgaagctgct gatctaccac accagcagac tgcacagcgg cgtgccaagc     180
agattttctg gcagcggctc tggcaccgac tacagcctga caatcagcaa cctggaacaa     240
gaggatatcg ctacctactt ctgccagcaa ggcaacaccc tgccttacac ctttggcgga     300
ggcaccaagc tggaaatcac cggctctaca agcggcagcg gcaaacctgg atctggcgag     360
ggatctacca agggcgaagt gaaactgcaa gagtctggcc ctggactggt ggccccatct     420
cagtctctga gcgtgacctg tacagtcagc ggagtgtccc tgcctgatta cggcgtgtcc     480
tggatcagac agcctcctcg gaaaggcctg aatggctgg gagtgatctg gggcagcgag      540
acaacctact acaacagcgc cctgaagtcc cggctgacca tcatcaagga caactccaag     600
agccaggtgt tcctgaagat gaacagcctg cagaccgacg acaccgccat ctactattgc     660
gccaagcact actactacgg cggcagctac gccatggatt attggggcca gggcaccagc     720
gtgaccgttt cttct                                                      735
```

```
<210> SEQ ID NO 4
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
attgaagtta tgtatcctcc tccttaccta gacaatgaga gagcaatgg aaccattatc      60 catgtgaaag ggaaacacct ttgtccaagt cccctatttc ccggaccttc taagcccttt     120
tgggtgctgg tggtggttgg tggagtcctg gcttgctata gcttgctagt aacagtggcc     180
```

```
tttattattt tctgggtgag gagtaagagg agcaggctcc tgcacagtga ctacatgaac      240
atgactcccc gccgccccgg gcccacccgc aagcattacc agccctatgc cccaccacgc      300
gacttcgcag cctatcgctc c                                                321
```

<210> SEQ ID NO 5
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
agagtgaagt tcagcaggag cgcagacgcc cccgcgtacc agcagggcca gaaccagctc       60
tataacgagc tcaatctagg acgaagagag gagtacgatg ttttggacaa gagacgtggc      120
cgggaccctg agatgggggg aaagccgaga aggaagaacc ctcaggaagg cctgttcaat      180
gaactgcaga aagataagat ggcggaggcc ttcagtgaga ttgggatgaa aggcgagcgc      240 cggagggggca aggggcacga tggccttttc caggggctca gtacagccac caaggacacc      300
ttcgacgccc ttcacatgca ggccctgccc cctcgc                                336
```

<210> SEQ ID NO 6
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ala Leu Pro Val Thr Ala Leu Leu Leu Pro Leu Ala Leu Leu Leu
1               5                   10                  15

His Ala Asp Ile Gln Met Thr Gln Thr Thr Ser Ser Leu Ser Ala Ser
            20                  25                  30

Leu Gly Asp Arg Val Thr Ile Ser Cys Arg Ala Ser Gln Asp Ile Ser
        35                  40                  45

Lys Tyr Leu Asn Trp Tyr Gln Gln Lys Pro Asp Gly Thr Val Lys Leu
    50                  55                  60

Leu Ile Tyr His Thr Ser Arg Leu His Ser Gly Val Pro Ser Arg Phe
65                  70                  75                  80

Ser Gly Ser Gly Ser Gly Thr Asp Tyr Ser Leu Thr Ile Ser Asn Leu
                85                  90                  95

Glu Gln Glu Asp Ile Ala Thr Tyr Phe Cys Gln Gln Gly Asn Thr Leu
            100                 105                 110

Pro Tyr Thr Phe Gly Gly Gly Thr Lys Leu Glu Ile Thr Gly Ser Thr
        115                 120                 125

Ser Gly Ser Gly Lys Pro Gly Ser Gly Glu Gly Ser Thr Lys Gly Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
            195                 200                 205
```

-continued

```
Arg Leu Thr Ile Ile Lys Asp Asn Ser Lys Ser Gln Val Phe Leu Lys
    210             215             220

Met Asn Ser Leu Gln Thr Asp Asp Thr Ala Ile Tyr Tyr Cys Ala Lys
225             230             235             240

His Tyr Tyr Tyr Gly Gly Ser Tyr Ala Met Asp Tyr Trp Gly Gln Gly
            245             250             255

Thr Ser Val Thr Val Ser Ser Ala Ala Ala Ile Glu Val Met Tyr Pro
            260             265             270

Pro Pro Tyr Leu Asp Asn Glu Lys Ser Asn Gly Thr Ile Ile His Val
            275             280             285

Lys Gly Lys His Leu Cys Pro Ser Pro Leu Phe Pro Gly Pro Ser Lys
    290             295             300

Pro Phe Trp Val Leu Val Val Val Gly Gly Val Leu Ala Cys Tyr Ser
305             310             315             320

Leu Leu Val Thr Val Ala Phe Ile Ile Phe Trp Val Arg Ser Lys Arg
            325             330             335

Ser Arg Leu Leu His Ser Asp Tyr Met Asn Met Thr Pro Arg Arg Pro
            340             345             350

Gly Pro Thr Arg Lys His Tyr Gln Pro Tyr Ala Pro Pro Arg Asp Phe
            355             360             365

Ala Ala Tyr Arg Ser Arg Val Lys Phe Ser Arg Ser Ala Asp Ala Pro
    370             375             380

Ala Tyr Gln Gln Gly Gln Asn Gln Leu Tyr Asn Glu Leu Asn Leu Gly
385             390             395             400

Arg Arg Glu Glu Tyr Asp Val Leu Asp Lys Arg Arg Gly Arg Asp Pro
            405             410             415

Glu Met Gly Gly Lys Pro Arg Arg Lys Asn Pro Gln Glu Gly Leu Phe
            420             425             430

Asn Glu Leu Gln Lys Asp Lys Met Ala Glu Ala Phe Ser Glu Ile Gly
    435             440             445

Met Lys Gly Glu Arg Arg Arg Gly Lys Gly His Asp Gly Leu Phe Gln
    450             455             460

Gly Leu Ser Thr Ala Thr Lys Asp Thr Phe Asp Ala Leu His Met Gln
465             470             475             480

Ala Leu Pro Pro Arg
            485
```

```
<210> SEQ ID NO 7
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Asp Ile Gln Met Thr Gln Thr Thr Ser Ser Leu Ser Ala Ser Leu Gly
1               5               10              15

Asp Arg Val Thr Ile Ser Cys Arg Ala Ser Gln Asp Ile Ser Lys Tyr
            20              25              30

Leu Asn Trp Tyr Gln Gln Lys Pro Asp Gly Thr Val Lys Leu Leu Ile
            35              40              45

Tyr His Thr Ser Arg Leu His Ser Gly Val Pro Ser Arg Phe Ser Gly
    50              55              60

Ser Gly Ser Gly Thr Asp Tyr Ser Leu Thr Ile Ser Asn Leu Glu Gln
```

```
65                   70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
            115                 120                 125

Leu Gln Glu Ser Gly Pro Gly Leu Val Ala Pro Ser Gln Ser Leu Ser
        130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
            195                 200                 205

Ser Leu Gln Thr Asp Asp Thr Ala Ile Tyr Tyr Cys Ala Lys His Tyr
        210                 215                 220

Tyr Tyr Gly Gly Ser Tyr Ala Met Asp Tyr Trp Gly Gln Gly Thr Ser
225                 230                 235                 240

Val Thr Val Ser Ser Ala Ala Ala Ile Glu Val Met Tyr Pro Pro Pro
                245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Val Gly Gly Val Leu Ala Cys Tyr Ser Leu Leu
        290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
        370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Phe Asn Glu
                405                 410                 415

Leu Gln Lys Asp Lys Met Ala Glu Ala Phe Ser Glu Ile Gly Met Lys
            420                 425                 430

Gly Glu Arg Arg Arg Gly Lys Gly His Asp Gly Leu Phe Gln Gly Leu
            435                 440                 445

Ser Thr Ala Thr Lys Asp Thr Phe Asp Ala Leu His Met Gln Ala Leu
        450                 455                 460

Pro Pro Arg
465
```

<210> SEQ ID NO 8

<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Met Ala Leu Pro Val Thr Ala Leu Leu Leu Pro Leu Ala Leu Leu Leu
1               5                   10                  15

His Ala

<210> SEQ ID NO 9
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
            35                  40                  45

Tyr His Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245

<210> SEQ ID NO 10
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 10

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 11
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Phe Asn Glu Leu Gln Lys
    50                  55                  60

Asp Lys Met Ala Glu Ala Phe Ser Glu Ile Gly Met Lys Gly Glu Arg
65                  70                  75                  80

Arg Arg Gly Lys Gly His Asp Gly Leu Phe Gln Gly Leu Ser Thr Ala
                85                  90                  95

Thr Lys Asp Thr Phe Asp Ala Leu His Met Gln Ala Leu Pro Pro Arg
            100                 105                 110

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 14
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Met Asn Met
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Arg Arg Pro
1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Tyr Ala Pro
1

ANTIGEN SPECIFIC CD19-TARGETED CAR-T CELLS

RELATED APPLICATIONS

This application is a national stage filing under 35 U.S.C. § 371 of PCT/US20/30435, filed Apr. 29, 2020, which claims the benefit of priority to U.S. Provisional Application Ser. No. 62/840,774, filed Apr. 30, 2019, which is incorporated by reference in its entirety.

SEQUENCE LISTING

The instant application contains a Sequence Listing, which has been filed electronically in ASCII format and is hereby incorporated by reference in its entirety. Said ASCII copy, created on Oct. 29, 2021, is named ABH-00701_SL.txt and is 20,054 bytes in size.

BACKGROUND

Hematologic malignancies represent some of the most common cancers occurring in both children and adults. For example, approximately 4,000 de novo cases of the aggressive B-cell lineage malignancy B-cell acute lymphoblastic leukemia (B-ALL) are diagnosed each year in the United States and represents the most common malignancy of childhood. Genetic mutations that induce aberrant arrest of normal lymphoid maturation, evasion of apoptosis and uncontrolled cellular proliferation result in over-production of B-cell lymphoblasts. In adults, over 6000 incident cases of acute lymphoblastic leukemia (ALL) occur each year. (Hanahan, D. and Weinberg, R. (2000) The hallmarks of cancer. Cell 100: 57-70; Teitell, M. and Pandolfi, P. (2009) Molecular genetics of acute lymphoblastic leukemia. Annu Rev Pathol 4: 175-198) Moreover, lymphomas (e.g., neoplasms of the lymphatic tissues) account for approximately 5% of all cases of cancer in the United States. The main classes are malignant neoplasms (that is, cancers) of the lymphocytes, a cell type present in both the lymph and the blood. In this way, lymphomas and leukemias are both malignancies (e.g., tumors) of the hematopoietic and lymphoid tissues. As lymphoproliferative disorders, lymphomas and lymphoid leukemias are closely related, to the point that some of them are called by either name (for example adult T-cell leukemia/lymphoma).

Preclinical and clinical research efforts have been focused on investigating immunotherapeutic modalities that include antibody-based and/or adoptive cellular therapeutics for high-risk cancers. Such strategies rely on tumor-associated antigens so as to enable specific targeting of cancerous cells and sparing non-cancerous cells (i.e., on target/off tumor or bystander effects). Particular interest has been paid to adoptive immunotherapy approaches that involve the genetic engineering of human immune effector cells with synthetic chimeric antigen receptors (CARs) that target tumor-associated antigens expressed on the cell surface in a major histocompatibility complex (MHC) antigen-independent manner. Without being bound to any particular theory, engagement of the CAR expressed on a T cell with a cancer-associated antigen results in intracellular signaling via T cell costimulatory domains, and subsequent expansion of the CAR T cells, to induce further cancer cell killing. However, despite positive results from early-phase trials, infusion of CD19 CAR T cells into patients still results in a number of 'on target/on tumor' and 'on target/off tumor' side effects of varying severity, such as Tumor lysis syndrome (TLS), cytokine release syndrome (CRS) and macrophage activation syndrome, CNS trafficking, prolonged B-cell aplasia, and immune escape. Therefore, in view of the long-felt and unmet need described herein, improved therapies for hematologic malignancies are needed.

SUMMARY

The present invention is based, at least in part, on the discovery that B-lymphocyte antigens such as CD19 (B-lymphocyte antigen CD19) can be used for the targeted treatment of blood cancers (i.e. cancers of the hematopoietic and lymphoid tissues). In some aspects, provided herein are immune cells that express a chimeric antigen receptor (CAR) polypeptide that targets B lineage cells and cancer cells that arise therefrom. In some embodiments, the CARs disclosed herein comprise a B-lymphocyte antigen-targeting domain such as a CD19, CD20, and/or CD22-binding domain, a transmembrane domain, and an intracellular signaling domain. In certain preferred embodiments, the B-lymphocyte antigen-binding domain targets a wildtype and/or mutant CD19 antigen.

In certain aspects, provided herein are bi-specific chimeric antigen receptor (CAR) T cells, said cells expressing a CAR polypeptide comprising a targeting domain that selectively binds a B-lymphocyte antigen (e.g., a CD19, CD20, and/or CD22 antigen associated with a hematologic malignancy such as leukemia and/or lymphoma) and a CAR polypeptide comprising a targeting domain that selectively binds to another different tumor-associated antigen. In some such embodiments, the targeting domain of the chimeric antigen receptor (e.g., a CD19 antigen-binding domain and/or the other different tumor-associated antigen-binding domain) comprise a functional antibody fragment. Preferably, the antigen-binding domain of the chimeric antigen receptors comprise a single-chain variable fragment (scFv). In the most preferred embodiments, the functional antibody fragment (e.g., an scFv) is derived from the monoclonal antibody FMC63.

In some embodiments, the transmembrane domain of the CARs disclosed herein comprise at least one transmembrane domain of any of CD28, 41BB, mutants thereof, or any combination thereof. In some preferred embodiments, the intracellular signaling domain of the CARs disclosed herein comprise at least one signaling domain of CD3$\zeta$, mutants thereof, or any combination thereof. In some embodiments, the CARs disclosed herein further comprise at least one co-stimulatory signaling region, such as a co-stimulatory signaling region comprising a signaling domain of any one of CD28 or a mutant thereof, CD137 (41BB) or a mutant thereof, or any combination thereof. In some embodiments, the costimulatory signaling region contains 1, 2, 3, or 4 cytoplasmic domains of one or more intracellular signaling and/or costimulatory molecules. In some embodiments, the costimulatory signaling region contains one or more mutations in the cytoplasmic domains of CD28 and/or 4-1BB that attenuate or preferably enhance signaling. In certain embodiments, the CAR-expressing immune cell no longer expresses one or more immune checkpoint molecules. In some such embodiments, the immune checkpoint molecules are blocked and/or suppressed by methods known in the art.

In some embodiments, the CAR polypeptide contains an incomplete endodomain. For example, the CAR polypeptide may contain either an intracellular signaling domain or a co-stimulatory domain, but not both. In these embodiments, the immune effector cell is not activated unless it and a second CAR polypeptide (or endogenous T-cell receptor) that contains the missing domain both bind their respective antigens. Therefore, in some embodiments, the CAR polypeptide contains a CD3 zeta (CD3ζ) signaling domain but does not contain a costimulatory signaling region (CSR). In other embodiments, the CAR polypeptide contains the cytoplasmic domain of CD28, 4-1BB, or a combination thereof, but does not contain a CD3ζ signaling domain (SD).

In some aspects, provided herein are methods of treating B-lymphocyte antigen (e.g., CD19)-associated cancer (e.g., blood cancers including leukemias and lymphomas) in a subject, the method comprising administering an effective amount of an adoptive immunotherapy composition comprising CAR-expressing cells as disclosed herein. In some embodiments, the CAR-expressing cells of the adoptive immunotherapy composition are derived from the subject (e.g., autologous). Preferably, the CAR-expressing cells of the adoptive immunotherapy composition are derived from a donor sample, or from a bank or library comprising immune cells not derived from the subject (e.g., allogeneic). For example, the methods disclosed herein include selecting allogeneic T cells (e.g., a PBMC sample, CD4$^+$ T cells, and/or CD8$^+$ T cells, such as CTLs) from a cell bank (e.g., a pre-generated third-party-donor-derived bank of epitope-specific CTLs). In some embodiments, the method further comprises administering at least one immune checkpoint inhibitor.

In some aspects, disclosed herein are isolated nucleic acids encoding the disclosed CAR polypeptides, as well as nucleic acid vectors containing said isolated nucleic acids operably linked to an expression control sequence. Additionally, disclosed herein are cells transfected with these vectors, or that otherwise comprise the disclosed nucleic acids, and the use of these cells to express and/or produce the disclosed CAR polypeptides. Without intending to be an exhaustive list, the cell may be an immune effector cell such as an αβT cell, a γδT cell, a Natural Killer (NK) cell, a Natural Killer T (NKT) cell, a B cell, an innate lymphoid cell (ILC), a cytokine induced killer (CIK) cell, a cytotoxic T lymphocyte (CTL), a lymphokine activated killer (LAK) cell, or a regulatory T cell. In some embodiments, the cell exhibits an anti-tumor immunity (e.g., mounts an immune response against a tumor) when the antigen-binding domain of the CAR binds to a B-lymphocyte antigen such as CD19, CD20, and/or CD22.

In further aspects of the invention, disclosed herein are pharmaceutical compositions comprising the molecules disclosed herein in a pharmaceutically acceptable carrier. Also disclosed herein are methods for treating cancer in a subject that involve administering to the subject a therapeutically effective amount of a pharmaceutical compositions as disclosed herein. In some embodiments, the cancer can be, for example, any B-lymphocyte antigen-expressing malignancy (e.g., expressing CD19, CD20, and/or CD22.

In some embodiments, the B-lymphocyte antigen-binding agents disclosed herein comprise an antibody fragment that specifically binds a B-lymphocyte surface peptide such as CD19, CD20, and/or CD22. For example, and without limitation, the antigen-binding domain can be a Fab or a single-chain variable fragment (scFv) of an antibody that specifically binds CD19, CD20, and/or CD22. In some such embodiments, the antigen-binding agent is an aptamer that specifically binds B-lymphocyte antigens such as CD19, CD20, and/or CD22. For example, in certain embodiments the antigen-binding agent is, or otherwise comprises, a peptide aptamer selected from a random sequence pool based on its ability to bind B-lymphocyte antigens such as CD19, CD20, and/or CD22. In some embodiments, the B-lymphocyte antigen-binding agents may also comprise a natural ligand, or a variant and/or fragment thereof, capable of binding the B-lymphocyte antigen.

The CAR (or CAR-associated) polypeptides disclosed herein can also contain a transmembrane domain and an endodomain capable of activating an immune effector cell. For example, the endodomain can contain a signaling domain and one or more costimulatory signaling regions.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Figure 9:
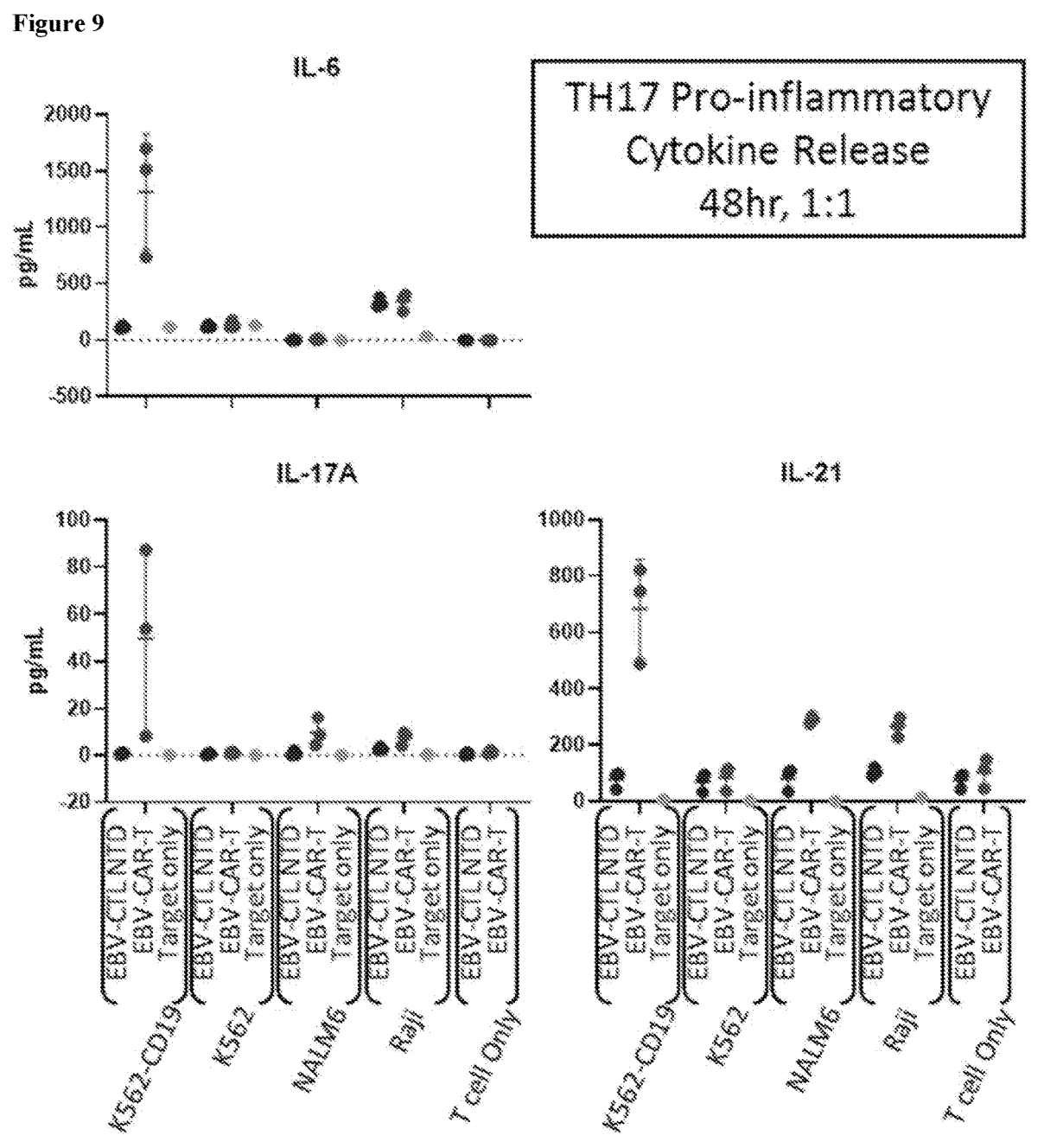

FIG. 9 shows TH17 pro-inflammatory cytokine release data across multiple target cells lines.

Figure 11:
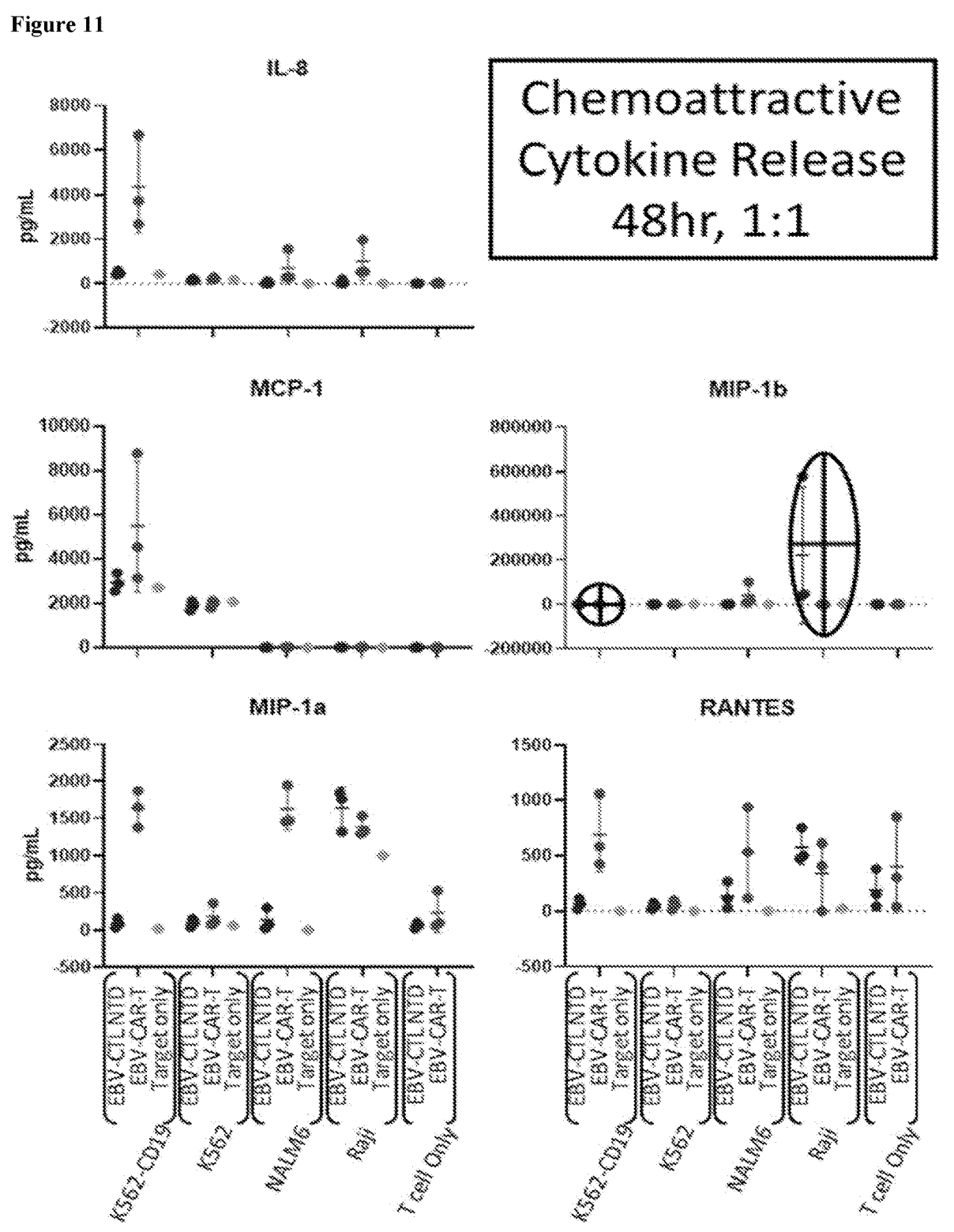

FIG. 11 shows chemoattractive cytokine release data across multiple target cells lines.

Figure 12:
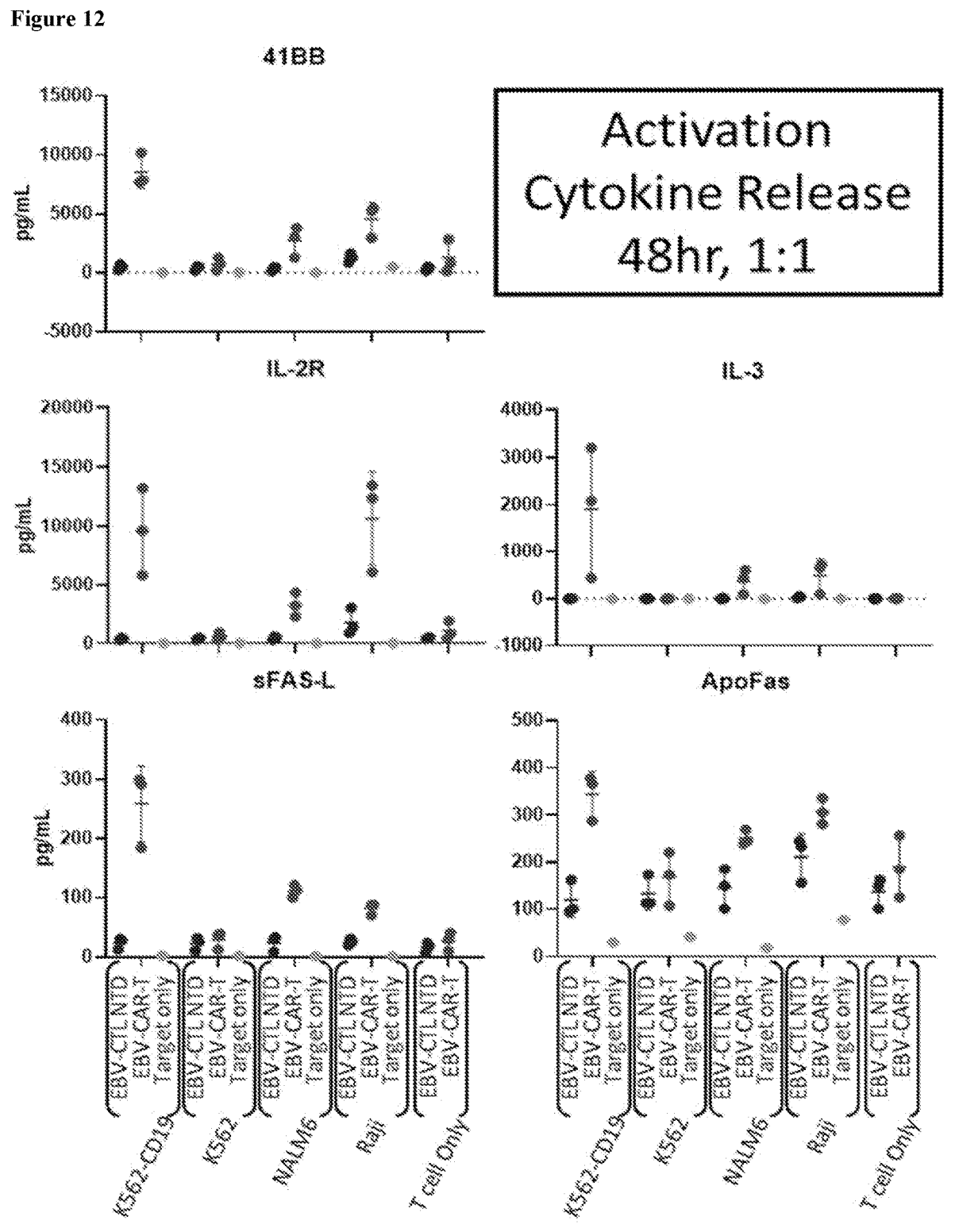

FIG. 12 shows activation cytokine release data across multiple target cells lines.

DETAILED DESCRIPTION

Details

Figure 1:
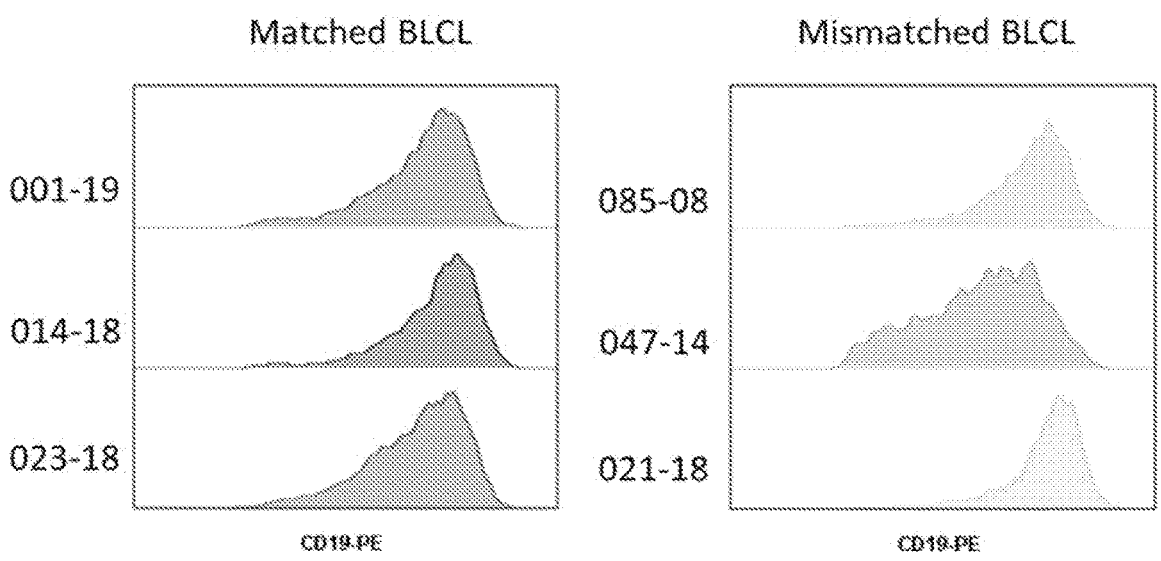
FIG. 1 shows characterization of CD19 protein expression in donor-derived target BLCLs.
Figure 1:
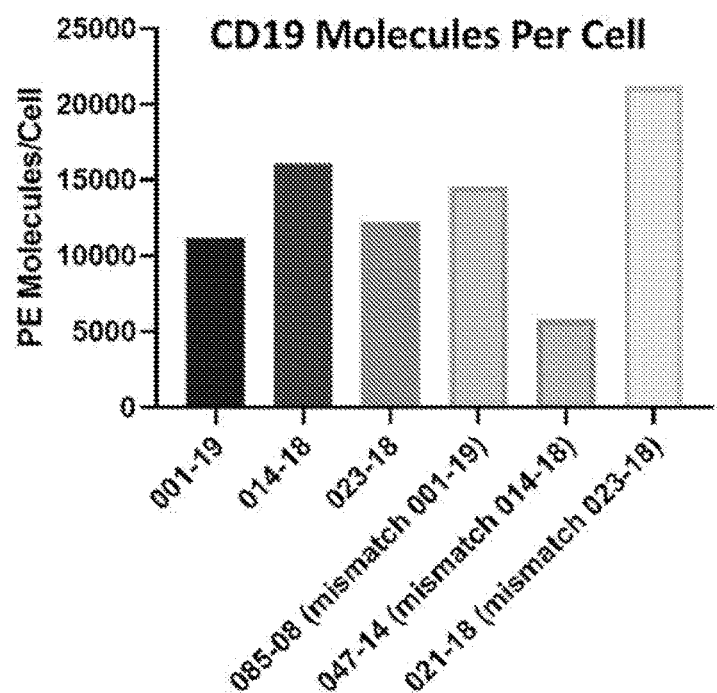

As disclosed herein, the present invention relates, at least in part, to immune cells which recombinantly express a chimeric antigen receptor (CAR) that target cancer-associated B-lymphocyte antigens. Such B-lymphocyte antigens include, but are not limited to, CD19, CD20, and CD22. In some such embodiments, the antigen is CD19 and is associated with a hematologic malignancy such as leukemias and lymphomas. In preferred embodiments, CD19 is targeted by an immune effector cell (i.e., T cells or Natural Killer (NK) cells) that is engineered to express a chimeric antigen receptor (CAR) polypeptide that selectively binds a CD19.

A major advance for T cell therapy was the development of chimeric antigen receptors (CARs). First generation CARs were developed as an artificial receptor that, when expressed by T cells, could retarget them to a predetermined disease-associated antigen (e.g., tumor-associated antigens). Such CARs typically comprise a single chain variable fragment (scFv) derived from a target-specific antibody, fused to signaling domains from a T cell receptor (TCR), such as CD3ζ. Upon binding antigen, CARs trigger phosphorylation of immunoreceptor tyrosine-based activation motifs (ITAMS) and initiate the signal cascade required for cytolysis, cytokine secretion and proliferation, bypassing the endogenous antigen-processing pathway and MHC restriction. Second generation CAR designs include further signaling domains to enhance activation and co-stimulation, such as CD28 and/or 4-1BB. Compared to their earlier counterparts, second generation CARs were observed to induce more IL-2 secretion, increase T cell proliferation and persistence, mediate greater tumor rejection, and extend T cell survival. The third generation CARs are made by combining multiple signaling domains, such as CD3ζ-CD28-OC40 or CD3ζ-CD28-41BB, to augment potency with stronger cytokine production and killing ability.

In some embodiments, the CAR T cells described herein are engineered so as to counteract any tolerogenic effects of the malignant cellular microenvironment (e.g., a tumor microenvironment) by, for example and without limitation, suppressing or inhibiting PD-1 signaling. In certain embodiments, the CARs described herein may be sensitized to or selectively target a viral or non-viral antigen. An ideal target should not be expressed on any normal tissue/organ, or at least not in vital normal tissues (heart, liver, CNS, lung, and other tissues that may be particularly sensitive to transient damage) nor in closely related normal cellular counterparts, e.g., stem and/or progenitor cells, in order to minimize side effects (e.g., on target/off tumor or bystander effects). Also disclosed herein are immune effector cells, such as T cells or Natural Killer (NK) cells, that are engineered to express chimeric antigen receptor (CAR) polypeptides that selectively bind B-lymphocyte antigens (e.g., wildtype and/or mutant CD19). Therefore, also disclosed are methods for providing targeted immunity (e.g., anti-tumor immunity) in a subject with a hematologic malignancy that involves adoptive transfer of the disclosed immune effector cells engineered to express the disclosed CAR polypeptides.

In the tumor microenvironment cancer cells and host immune cells interact, potentially leading to promotion or inhibition of cancer progression. Ideally, the immune system would identify cancer cells and mobilize an immune response to eliminate the cancer. Unfortunately, at the T cell level, upregulation of inhibitory receptors, such as PD-1 and Tim-3, correlate with T cell dysfunction. This has been observed on both hepatitis C virus (HCV)-specific and HCV-nonspecific CD8$^+$ T cells in the circulation and livers of patients with chronic HCV infection. Partial restoration of T cell proliferation and IFN-γ secretion can be achieved ex vivo by inhibiting the binding of PD-1 and Tim-3 to their respective ligands (i.e., B7-H1, also known as PD-L1, and Galectin-9). What is more, recent reports have demonstrated that prolonged administration of IFN-α, a standard therapy for persistent HCV infection, promoted telomere loss in naïve T cells. Given the correlation between shortened T cell telomeres and terminal differentiation (characterized by diminished proliferative potential), IFN-α-induced T cell "exhaustion" likely represents a significant barrier for immunotherapy in HCV-infected patients. In certain aspects disclosed herein, the invention employs checkpoint inhibition strategies. Checkpoint inhibitor therapies target key regulators of the immune system that either stimulate or inhibit the immune response. Such immune checkpoints can be exploited in the cancer disease state (e.g., by tumors) to evade attacks by the immune system. Checkpoint inhibitor studies have noted the activity of PD-1 inhibitor therapy (El-Khoueiry et al., (2017). "Nivolumab in patients with advanced hepatocellular carcinoma (CheckMate 040): an open-label, non-comparative, phase 1/2 dose escalation and expansion trial." Lancet 389 (10088): 2492-2502) and the FDA has approved Nivolumab for second line treatment of HCC with an objective response rate of 20%.

Definitions

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class, such as anti-CD19 antibody, clone FMC63. In addition to intact immunoglobulin molecules, also included in the term "antibodies" are chimeras, fragments, or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

The term "carrier" means a compound, composition, substance, or structure that, when in combination with a compound or composition, aids or facilitates preparation, storage, administration, delivery, effectiveness, selectivity, or any other feature of the compound or any degradation of the active ingredient and to minimize any adverse side effects in the subject.

The term "chimeric molecule" refers to a single molecule created by joining two or more molecules that exist separately in their native state. The single, chimeric molecule has the desired functionality of all of its constituent molecules. One type of chimeric molecules is a fusion protein.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

The term "fusion protein" refers to a polypeptide formed by the joining of two or more polypeptides through a peptide bond formed between the amino terminus of one polypeptide and the carboxyl terminus of another polypeptide. The fusion protein can be formed by the chemical coupling of the constituent polypeptides or it can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc.), may be transfected into cells, e.g., mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "operably linked to" refers to the functional relationship of a nucleic acid with another nucleic acid sequence. Promoters, enhancers, transcriptional and translational stop sites, and other signal sequences are examples of nucleic acid sequences operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In other embodiments, a fragment may have immunogenic properties.

The term "single chain variable fragment" or "scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

A "spacer" as used herein refers to a peptide that joins the proteins comprising a fusion protein. Generally, a spacer has no specific biological activity other than to join the proteins or to preserve some minimum distance or other spatial relationship between them. However, the constituent amino acids of a spacer may be selected to influence some property of the molecule such as the folding, net charge, or hydrophobicity of the molecule.

The term "specifically binds" or "specific binding", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule. For example, in the case of the ability of a TCR to bind to a peptide presented on an MHC (e.g., class I MHC or class II MHC); typically, a TCR specifically binds to its peptide/MHC with an affinity of at least a KD of about 10-4 M or less, and binds to the predetermined antigen/binding partner with an affinity (as expressed by KD) that is at least 10 fold less, at least 100 fold less or at least 1000 fold less than its affinity for binding to a non-specific and unrelated peptide/MHC complex (e.g., one comprising a BSA peptide or a casein peptide).

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

In certain embodiments, agents of the invention may be used alone or conjointly administered with another type of therapeutic agent. As used herein, the phrase "conjoint administration" or "administered conjointly" refers to any form of administration of two or more different therapeutic agents (e.g., a composition comprising a CAR T disclosed herein and an inhibitor of an immune checkpoint) such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In some preferred embodiments, the CAR T cells express (e.g., present on the cell surface or secrete) further therapeutic agents. In certain embodiments, the different therapeutic agents (e.g., CAR T cells and immune checkpoint-blocking molecules) can be administered within about one hour, about 12 hours, about 24 hours, about 36 hours, about 48 hours, about 72 hours, or about a week of one another. Thus, a subject who receives such treatment can benefit from a combined effect of different therapeutic agents.

The terms "transformation" and "transfection" mean the introduction of a nucleic acid, e.g., an expression vector, into a recipient cell including introduction of a nucleic acid to the chromosomal DNA of said cell.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated," for example, if one or more symptoms associated with a particular disease, disorder, or condition are mitigated or eliminated.

The term "variant" refers to an amino acid or peptide sequence having conservative amino acid substitutions, non-conservative amino acid substitutions (e.g., a degenerate variant), substitutions within the wobble position of each codon (e.g., DNA and RNA) encoding an amino acid, amino acids added to the C-terminus of a peptide, or a peptide having 60%, 70%, 80%, 90%, 95%, 96%, 97%, 98%, 99% sequence identity to a reference sequence.

The term "vector" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element).

The term "B-lymphocyte antigen" and, in particular, "CD19" is intended to include fragments, variants (e.g., allelic variants), and derivatives of the antigen molecule, e.g., the CD19 molecule. For example and without limitation, in some embodiments, CD19 is a wildtype CD19 or a mutant CD19. In some such embodiments, B-lymphocyte antigen is expressed on the cell surface (e.g., on the surface of a pre-cancerous or malignant cell).

Anti-CD19 antibodies (and scFv formats thereof) suitable for binding CD19 are well-known in the art and include, for example and without limitation, antibodies FMC63, SJ25C1 (JCAR015), and HD37 (blinatumomab).

Chimeric Antigen Receptors (CAR)

Disclosed herein are chimeric antigen receptor (CAR) polypeptides that can be expressed in immune effector cells to enhance activity against specific targets (e.g., antitumor activity against hematologic cancers).

In some aspects, the CARs disclosed herein are made up of three domains: an ectodomain, a transmembrane domain, and an endodomain.

In certain embodiments, the ectodomain comprises a B-lymphocyte antigen-binding region such as a CD19-binding region and is responsible for antigen recognition. CD19 may be wildtype CD19 or mutant CD19. It also optionally contains a signal peptide (SP) so that the CAR can be glycosylated and anchored in the cell membrane of the immune effector cell.

In some embodiments, the transmembrane domain (TD) connects the ectodomain (i.e., the extracellular domain) to the endodomain (i.e., the intracellular domain) and resides within the cell membrane when expressed by a cell.

In some embodiments, the endodomain transmits an activation signal to the immune effector cell after antigen recognition. In some such embodiments, the endodomain can contain an intracellular signaling domain (ISD) and, optionally, a co-stimulatory signaling region (CSR). A "signaling domain (SD)", such as an ISD, generally contains immunoreceptor tyrosine-based activation motifs (ITAMs) that activate a signaling cascade when the ITAM is phosphorylated. The term "co-stimulatory signaling region (CSR)" refers to intracellular signaling domains from costimulatory protein receptors, such as CD28, 41BB, and ICOS, that are able to enhance T-cell activation by T-cell receptors.

In some embodiments, the endodomain contains an SD or a CSR, but not both. In these embodiments, an immune effector cell containing the disclosed CAR is only activated if another CAR (or a T-cell receptor) containing the missing domain also binds its respective antigen.

In some embodiments, the disclosed CAR is defined by the formula:

SP-BCA-HG-TM-CSR-SD; or

SP-BCA-HG-TM-SD-CSR;

wherein "SP" represents an optional signal peptide (e.g., derived from CD8α leader sequence), wherein "BCA" represents a B-lymphocyte antigen binding region (e.g., FMC63 and derivatives thereof), wherein "HG" represents an optional hinge domain (spacer domain; e.g., derived from CD28), wherein "TM" represents a transmembrane domain (e.g., derived from CD28), wherein "CSR" represents one or more co-stimulatory signaling regions (e.g., derived from CD28), wherein "SD" represents a signaling domain (e.g., derived from CD3ζ and mutants thereof), and wherein "-" represents a peptide bond or linker.

Additional CAR constructs are described, for example, in Fresnak, et al. Engineered T cells: the promise and challenges of cancer immunotherapy. Nat Rev Cancer. 2016 Aug. 23; 16(9):566-81, which is incorporated by reference in its entirety for the teaching of these CAR models.

In certain embodiments, the CAR can be, for example (and without limitation), a TRUCK, a Universal CAR, a Self-driving CAR, an Armored CAR, a Self-destruct CAR, a Conditional CAR, a Marked CAR, a TenCAR, a Dual CAR, or a sCAR.

TRUCKs (T cells redirected for universal cytokine killing) co-express a chimeric antigen receptor (CAR) and an antitumor cytokine. Cytokine expression may be constitutive or induced by T cell activation. Targeted by CAR specificity, localized production of pro-inflammatory cytokines recruits endogenous immune cells to tumor sites and may potentiate an antitumor response.

Universal, allogeneic CAR T cells are engineered to no longer express endogenous T cell receptor (TCR) and/or major histocompatibility complex (MHC) molecules, thereby preventing graft-versus-host disease (GVHD) or rejection, respectively.

Self-driving CARs co-express a CAR and a chemokine receptor, which binds to a tumor ligand, thereby enhancing tumor homing.

CAR T cells engineered to be resistant to immunosuppression (Armored CARs) may be genetically modified to no longer express various immune checkpoint molecules (e.g., cytotoxic T lymphocyte-associated antigen 4 (CTLA4) or programmed cell death protein 1 (PD-1)). Exemplary "Knockdown" and "Knockout" techniques include, but are not limited to, RNA interference (RNAi) (e.g., asRNA, miRNA, shRNA, siRNA, etc.) and CRISPR interference (CRISPRi) (e.g., CRISPR-Cas9). In certain embodiments, CAR T cells are engineered to express a dominant-negative form of a checkpoint molecule. In some such embodiments, the extracellular ligand-binding domain (i.e., ectodomain) of the immune checkpoint molecule is fused to a transmembrane membrane in order to compete for ligand binding. For example, the extracellular ligand-binding domain of PD-1 may be fused to a CD8 transmembrane domain, thus competing for PD-1 ligand from the target cell. In some embodiments, CAR T cells are engineered to express an immune checkpoint switch receptor to exploit the inhibitory immune checkpoint ligand present on a target cell. In such embodiments, the extracellular ligand-binding domain of the immune checkpoint molecule is fused to a signaling, stimulatory, and/or co-stimulatory domain. For example, the extracellular ligand-binding domain of PD-1 may be fused to a CD28 domain, thus providing CD28 costimulation while blocking PD-1 signaling. In further embodiments, the CAR T cells may be administered with an aptamer or a monoclonal antibody that blocks immune checkpoint signaling. In some such embodiments, the CAR T cells (e.g., CAR T cell therapy) are combined with a PD-1 blockade method, such as administration with PD-1/PD-L1 antagonistic aptamers or anti-PD-1/PD-L1 antibodies. In preferred embodiments, the CAR T cells and PD-1 pathway-blocking antibodies are administered conjointly. In further embodiments, the CAR T cells are engineered to express or express and secrete an immune checkpoint-blocking antibody, such as anti-PD-1 or anti-PD-L1, or fragments thereof. In yet further embodiments, the CAR T cells are administered with a vector (e.g., an engineered virus) that expresses an immune checkpoint-blocking molecule described herein.

A self-destruct CAR may be designed using RNA delivered by electroporation to encode the CAR. Alternatively, inducible apoptosis of the T cell may be achieved based on ganciclovir binding to thymidine kinase in gene-modified lymphocytes or the more recently described system of activation of human caspase 9 by a small-molecule dimerizer.

A conditional CAR T cell is by default unresponsive, or switched 'off', until the addition of a small molecule to complete the "circuit" (e.g., molecular pathway), enabling full transduction of both signal 1 and signal 2, thereby activating the CAR T cell. Alternatively, T cells may be engineered to express an adaptor-specific receptor with affinity for subsequently administered secondary antibodies directed at target antigen.

Marked CAR T cells express a CAR plus a tumor epitope to which an existing monoclonal antibody agent binds. In the setting of intolerable adverse effects, administration of the monoclonal antibody clears the CAR T cells and alleviates symptoms with no additional off-tumor effects.

A tandem CAR (TanCAR) T cell expresses a single CAR consisting of two linked single-chain variable fragments (scFvs) that have different affinities fused to intracellular co-stimulatory domain(s) and a CD3ζ domain. TanCAR T cell activation is achieved only when target cells co-express both targets.

A dual CAR T cell expresses two separate CARs with different ligand binding targets. By way of non-limiting example, one CAR may include only the CD3ζ domain while the other CAR includes only the co-stimulatory domain(s). In some such embodiments, the dual CAR T cell is activated when both targets are expressed on the tumor.

A safety CAR (sCAR) consists of an extracellular scFv fused to an intracellular inhibitory domain. sCAR T cells co-expressing a standard CAR become activated only when encountering target cells that possess the standard CAR target but lack the sCAR target.

In some embodiments, the antigen recognition domain of the disclosed CAR is an scFv. In further embodiments, the antigen recognition domain is from native T-cell receptor (TCR) a and R single chains as have been described herein. Preferably, such antigen recognition domains have simple ectodomains (e.g., a CD4 ectodomain to recognize HIV infected cells). Alternatively, such antigen recognition domains comprise exotic recognition components such as a linked cytokine (which can lead to recognition of cells bearing the cytokine receptor). Generally, with respect to the methods disclosed herein, almost anything that binds a given target with high affinity can be used as an antigen recognition region.

The intracellular endodomain transmits a signal to the immune effector cell expressing the CAR after antigen recognition, activating at least one of the normal effector functions of said immune effector cell. In certain embodiments, the effector function of a T cell, for example, may be cytolytic activity or helper activity, including the secretion of cytokines. Therefore, the endodomain may comprise the "intracellular signaling domain" of a T cell receptor (TCR) and optional co-receptors. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal.

Cytoplasmic signaling sequences that regulate primary activation of the TCR complex that act in a stimulatory manner may contain signaling motifs which are known as immunoreceptor tyrosine-based activation motifs (ITAMs). Examples of ITAM-containing cytoplasmic signaling sequences include those derived from CD8, CD3ζ, CD3δ, CD3γ, CD3ε, CD32 (FcγRIIA), DAP10, DAP12, CD79a, CD79b, FcγRIγ, FcγRIIIγ, FcεRIβ (FCERIB), and FεPRIγ (FCERIG).

In particular embodiments, the intracellular signaling domain is derived from CD3 zeta (CD3ζ; e.g., TCR zeta, GenBank acc. no. BAG36664.1). T-cell surface glycoprotein CD3ζ chain, also known as T-cell receptor T3 zeta chain or CD247 (Cluster of Differentiation 247), is a protein that in humans is encoded by the CD247 gene. The intracellular tails of the CD3 molecules contain a single ITAM, which is essential for the signaling capacity of the TCR. The intracellular tail of the ζ chain (CD3ζ) contains 3 ITAMs. In some embodiments, the ζ chain is a mutant ζ chain. For example, the mutant ζ chain comprises a mutation, such as a point mutation, in at least one ITAM so as to render said ITAM non-functional. In some such embodiments, either the membrane-proximal ITAM (ITAM1), the membrane-distal ITAM (C-terminal third ITAM, ITAM3), or both are non-functional. In further embodiments, either two membrane-proximal ITAMS (ITAM1 and ITAM2) or two membrane-distal ITAMS (ITAM2 and ITAM3) are non-functional. In yet further embodiments, only ITAM2 is non-functional. In some embodiments, the mutant ζ chain comprises a deletion (e.g., truncation) mutation such that at least one ITAM is missing. In some such embodiments, the ζ chain is missing the membrane-proximal ITAM (ITAM1), the membrane-distal ITAM (ITAM3), or both. In other embodiments, the ζ chain is missing either two membrane-proximal ITAMS (ITAM1 and ITAM2) or two membrane-distal ITAMS (ITAM2 and ITAM3). In further embodiments, the ζ chain is missing ITAM2. Methods to produce mutant CD3ζ is known to those skilled in the art (Bridgeman J S, et al., Clin Exp Immunol. 2014 February; 175(2):258-67). Removing at least one ITAM from the introduced CAR may reduce CD3ζ-mediated apoptosis. Alternatively, removing at least one ITAM from the introduced CAR can reduce its size without loss of function. CARs comprising such altered CD3ζ domains are contemplated by the present invention.

Also contemplated are CARs comprising an altered CD28 domain that imparts unique functional properties to the CAR. In this regard, the native CD28 domain comprises three intracellular subdomains consisting of the amino acid sequences YMNM, PRRP, and PYAP that regulate signaling pathways post stimulation (see, e.g., WO 2019/010383 incorporated herein by reference for this teaching). The CAR constructs described herein may comprise a modified CD28 domain wherein one or more of the YMNM, PRRP, and/or PYAP subdomains are mutated or deleted, so as to amplify, attenuate, or inactivate said subdomain(s), thereby modulating CAR-T function.

First-generation CARs typically had the intracellular domain from the CD3ζ chain, which is the primary transmitter of signals from endogenous TCRs. Second-generation CARs add intracellular signaling domains from various costimulatory protein receptors (e.g., CD28, 41BB, ICOS) to the endodomain of the CAR to provide additional signals to the T cell. For example, a target-specific ScFv fused to the extracellular, transmembrane and intracellular signaling domains of the co-stimulatory receptor CD28 and the cytoplasmic signaling domain of the T cell receptor-associated CD3 ζ chain. Preclinical studies have indicated that the second generation of CAR designs improves the antitumor activity of T cells. More recent, third-generation CARs combine multiple signaling domains to further augment potency. T cells grafted with these CARs have demonstrated improved expansion, activation, persistence, and tumor-eradicating efficiency independent of costimulatory receptor/ligand interaction (Imai C, et al. Leukemia 2004 18:676-84; Maher J, et al. Nat Biotechnol 2002 20:70-5).

For example, the endodomain of the CAR can be designed to comprise the CD3ζ signaling domain by itself or combined with any other desired cytoplasmic domain(s) useful in the context of the CAR of the invention. For example, the cytoplasmic domain of the CAR can comprise a CD3ζ chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, NKG2D, and mutants thereof. Thus, while the CAR is exemplified primarily with CD28 as the co-stimulatory signaling element, other costimulatory elements can be used alone or in combination with other co-stimulatory signaling elements.

In some embodiments, the CAR comprises a hinge sequence. A hinge sequence is a short sequence of amino acids that facilitates antibody flexibility (see, e.g., Woof et al., Nat. Rev. Immunol., 4(2): 89-99 (2004)). The hinge sequence may be positioned between the antigen recognition moiety (e.g., anti-CD19, -CD20, -CD22, or scFv) and the transmembrane domain. The hinge sequence can be any suitable sequence derived or obtained from any suitable molecule. In some embodiments, for example, the hinge sequence is derived from a CD8α molecule or a CD28 molecule.

The transmembrane domain may be derived either from a natural or from a synthetic source. Where the source is natural, the domain may be derived from any membrane-bound or transmembrane protein. For example, the trans-membrane region may be derived from (i.e., comprise at least the transmembrane region(s) of the alpha (α), beta (β) or zeta (ζ) chain of the T-cell receptor, CD28, CD3ε, CD45, CD4, CD5, CD8 (e.g., CD8α, CD8β), CD9, CD16, CD22, CD33, CD37, CD64, CD80, CD86, CD134, CD137, or CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2Rβ, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, and PAG/Cbp). Alternatively, the transmembrane domain may be synthetic, in which case it will comprise predominantly hydrophobic residues such as leucine and valine. In some embodiments, a triplet of phenylalanine, tryptophan and valine will be found at each end of a synthetic transmembrane domain. A short oligo- or polypeptide linker, such as between 2 and 10 amino acids in length, may form the linkage between the transmembrane domain and the endoplasmic domain of the CAR.

Accordingly, in preferred embodiments of the invention disclosed herein, the CAR is defined by the formula:

SP-BCA-HG-TM-CSR-SD wherein the optional signal peptide/leader sequence is derived from CD8α leader sequence,
wherein B-lymphocyte antigen binding region is an scFv derived from anti-CD19 antibody clone FMC63, wherein the hinge domain is derived from human CD28 (e.g., SEQ ID NO. 12),
wherein the transmembrane domain is derived from human CD28 (e.g., SEQ ID NO. 13),
wherein the co-stimulatory signaling region is derived from human CD28 (e.g., SEQ ID NO. 14), and
wherein the signaling domain comprises a CD3ζ chain wherein only the membrane-proximal ITAM (ITAM1) is functional (e.g., SEQ ID NO. 11). Optionally, the CAR may further comprise at least one molecular tag known in the art. For example, and without limitation, the CAR may comprise Low-Affinity Nerve Growth Factor Receptor (LNGFR) as a tag which binds labeled ligand, e.g., $^{124}$I-NGF, and such an interaction, e.g., $^{124}$I-NGF/LNGFR can be monitored, preferably non-invasively (e.g., by positron emission tomography).

In some embodiments, the CAR has more than one transmembrane domain, which can be a repeat of the same transmembrane domain, or can be different transmembrane domains.

In some embodiments, the CAR is a multi-chain CAR, as described in WO2015/039523, which is incorporated by reference for this teaching. A multi-chain CAR can comprise separate extracellular ligand binding and signaling domains in different transmembrane polypeptides. The signaling domains can be designed to assemble in juxtamembrane position, which forms flexible architecture closer to natural receptors, that confers optimal signal transduction. For example, the multi-chain CAR can comprise a part of an FcεRI α chain and a part of an FcεRI β chain such that the FcεRI chains spontaneously dimerize together to form a CAR.

In some embodiments, the CAR contains one signaling domain. In other embodiments, the CAR contains one or more signaling domain (co-stimulatory signaling domain). The one or more signaling domain may be a polypeptide selected from: CD8, CD3ζ, CD3δ, CD3γ, CD3ε, FcγRI-γ, FcγRIII-γ, FcγRIβ, FcεRIγ, DAP10, DAP12, CD32, CD79a, CD79b, CD28, CD3C, CD4, b2c, CD137 (41BB), ICOS, CD27, CD28δ, CD80, NKp30, OX40, and mutants thereof.

Tables 1, 2, and 3 below provide some example combinations of target-binding domains, co-stimulatory signaling domains, and intracellular signaling domains. Such examples are for the purpose of illustration and are not meant to be an exhaustive list of combinations that can occur in the CARs disclosed herein.

TABLE 1

| First Generation CARs | |
|---|---|
| ScFv | Signal Domain |
| CD19 | CD8 |
| CD19 | CD3ζ |
| CD19 | CD3δ |
| CD19 | CD3γ |
| CD19 | CD3ε |
| CD19 | FcγRI-γ |
| CD19 | FcγRIII-γ |
| CD19 | FcεRIβ |
| CD19 | FcεRIγ |
| CD19 | DAP10 |
| CD19 | DAP12 |
| CD19 | CD32 |
| CD19 | CD79a |

TABLE 2

Second Generation CARs

| ScFv | Co-stimulatory Signal | Signal Domain |
|---|---|---|
| CD19 | CD28 | CD8 |
| CD19 | CD28 | CD3ζ |
| CD19 | CD28 | CD3δ |
| CD19 | CD28 | CD3γ |
| CD19 | CD28 | CD3ε |
| CD19 | CD28 | FcγRI-γ |
| CD19 | CD28 | FcγRIII-γ |
| CD19 | CD28 | FcεRIβ |
| CD19 | CD28 | FcεRIγ |
| CD19 | CD28 | DAP10 |
| CD19 | CD28 | DAP12 |
| CD19 | CD28 | CD32 |
| CD19 | CD28 | CD79a |
| CD19 | CD28 | CD79b |
| CD19 | CD8 | CD8 |
| CD19 | CD8 | CD3ζ |
| CD19 | CD8 | CD3δ |
| CD19 | CD8 | CD3γ |
| CD19 | CD8 | CD3ε |
| CD19 | CD8 | FcγRI-γ |
| CD19 | CD8 | FcγRIII-γ |
| CD19 | CD8 | FcεRIβ |
| CD19 | CD8 | FcεRIγ |
| CD19 | CD8 | DAP10 |
| CD19 | CD8 | DAP12 |
| CD19 | CD8 | CD32 |
| CD19 | CD8 | CD79a |
| CD19 | CD8 | CD79b |
| CD19 | CD4 | CD8 |
| CD19 | CD4 | CD3ζ |
| CD19 | CD4 | CD3δ |
| CD19 | CD4 | CD3γ |
| CD19 | CD4 | CD3ε |
| CD19 | CD4 | FcγRI-γ |
| CD19 | CD4 | FcγRIII-γ |
| CD19 | CD4 | FcεRIβ |
| CD19 | CD4 | FcεRIγ |
| CD19 | CD4 | DAP10 |
| CD19 | CD4 | DAP12 |
| CD19 | CD4 | CD32 |
| CD19 | CD4 | CD79a |
| CD19 | CD4 | CD79b |
| CD19 | b2c | CD8 |
| CD19 | b2c | CD3ζ |
| CD19 | b2c | CD3δ |
| CD19 | b2c | CD3γ |
| CD19 | b2c | CD3ε |
| CD19 | b2c | FcγRI-γ |
| CD19 | b2c | FcγRIII-γ |
| CD19 | b2c | FcεRIβ |
| CD19 | b2c | FcεRIγ |
| CD19 | b2c | DAP10 |
| CD19 | b2c | DAP12 |
| CD19 | b2c | CD32 |
| CD19 | b2c | CD79a |
| CD19 | b2c | CD79b |
| CD19 | CD137/41BB | CD8 |
| CD19 | CD137/41BB | CD3ζ |
| CD19 | CD137/41BB | CD3δ |
| CD19 | CD137/41BB | CD3γ |
| CD19 | CD137/41BB | CD3ε |
| CD19 | CD137/41BB | FcγRI-γ |
| CD19 | CD137/41BB | FcγRIII-γ |
| CD19 | CD137/41BB | FcεRIβ |
| CD19 | CD137/41BB | FcεRIγ |
| CD19 | CD137/41BB | DAP10 |
| CD19 | CD137/41BB | DAP12 |
| CD19 | CD137/41BB | CD32 |
| CD19 | CD137/41BB | CD79a |
| CD19 | CD137/41BB | CD79b |
| CD19 | ICOS | CD8 |
| CD19 | ICOS | CD3ζ |
| CD19 | ICOS | CD3δ |
| CD19 | ICOS | CD3γ |
| CD19 | ICOS | CD3ε |

TABLE 2-continued

Second Generation CARs

| ScFv | Co-stimulatory Signal | Signal Domain |
|---|---|---|
| CD19 | ICOS | FcγRI-γ |
| CD19 | ICOS | FcγRIII-γ |
| CD19 | ICOS | FcεRIβ |
| CD19 | ICOS | FcεRIγ |
| CD19 | ICOS | DAP10 |
| CD19 | ICOS | DAP12 |
| CD19 | ICOS | CD32 |
| CD19 | ICOS | CD79a |
| CD19 | ICOS | CD79b |
| CD19 | CD27 | CD8 |
| CD19 | CD27 | CD3ζ |
| CD19 | CD27 | CD3δ |
| CD19 | CD27 | CD3γ |
| CD19 | CD27 | CD3ε |
| CD19 | CD27 | FcγRI-γ |
| CD19 | CD27 | FcγRIII-γ |
| CD19 | CD27 | FcεRIβ |
| CD19 | CD27 | FcεRIγ |
| CD19 | CD27 | DAP10 |
| CD19 | CD27 | DAP12 |
| CD19 | CD27 | CD32 |
| CD19 | CD27 | CD79a |
| CD19 | CD27 | CD79b |
| CD19 | CD28δ | CD8 |
| CD19 | CD28δ | CD3ζ |
| CD19 | CD28δ | CD3δ |
| CD19 | CD28δ | CD3γ |
| CD19 | CD28δ | CD3ε |
| CD19 | CD28δ | FcγRI-γ |
| CD19 | CD28δ | FcγRIII-γ |
| CD19 | CD28δ | FcεRIβ |
| CD19 | CD28δ | FcεRIγ |
| CD19 | CD28δ | DAP10 |
| CD19 | CD28δ | DAP12 |
| CD19 | CD28δ | CD32 |
| CD19 | CD28δ | CD79a |
| CD19 | CD28δ | CD79b |
| CD19 | CD80 | CD8 |
| CD19 | CD80 | CD3ζ |
| CD19 | CD80 | CD3δ |
| CD19 | CD80 | CD3γ |
| CD19 | CD80 | CD3ε |
| CD19 | CD80 | FcγRI-γ |
| CD19 | CD80 | FcγRIII-γ |
| CD19 | CD80 | FcεRIβ |
| CD19 | CD80 | FcεRIγ |
| CD19 | CD80 | DAP10 |
| CD19 | CD80 | DAP12 |
| CD19 | CD80 | CD32 |
| CD19 | CD80 | CD79a |
| CD19 | CD80 | CD79b |
| CD19 | CD86 | CD8 |
| CD19 | CD86 | CD3ζ |
| CD19 | CD86 | CD3δ |
| CD19 | CD86 | CD3γ |
| CD19 | CD86 | CD3ε |
| CD19 | CD86 | FcγRI-γ |
| CD19 | CD86 | FcγRIII-γ |
| CD19 | CD86 | FcεRIβ |
| CD19 | CD86 | FcεRIγ |
| CD19 | CD86 | DAP10 |
| CD19 | CD86 | DAP12 |
| CD19 | CD86 | CD32 |
| CD19 | CD86 | CD79a |
| CD19 | CD86 | CD79b |
| CD19 | OX40 | CD8 |
| CD19 | OX40 | CD3ζ |
| CD19 | OX40 | CD3δ |
| CD19 | OX40 | CD3γ |
| CD19 | OX40 | CD3ε |
| CD19 | OX40 | FcγRI-γ |
| CD19 | OX40 | FcγRIII-γ |
| CD19 | OX40 | FcεRIβ |
| CD19 | OX40 | FcεRIγ |
| CD19 | OX40 | DAP10 |

TABLE 2-continued

| | Second Generation CARs | |
|---|---|---|
| ScFv | Co-stimulatory Signal | Signal Domain |
| CD19 | OX40 | DAP12 |
| CD19 | OX40 | CD32 |
| CD19 | OX40 | CD79a |
| CD19 | OX40 | CD79b |
| CD19 | DAP10 | CD8 |
| CD19 | DAP10 | CD3ζ |
| CD19 | DAP10 | CD3δ |
| CD19 | DAP10 | CD3γ |
| CD19 | DAP10 | CD3ε |
| CD19 | DAP10 | FcγRI-γ |
| CD19 | DAP10 | FcγRIII-γ |
| CD19 | DAP10 | FcεRIβ |
| CD19 | DAP10 | FcεRIγ |
| CD19 | DAP10 | DAP10 |
| CD19 | DAP10 | DAP12 |
| CD19 | DAP10 | CD32 |
| CD19 | DAP10 | CD79a |
| CD19 | DAP10 | CD79b |
| CD19 | DAP12 | CD8 |
| CD19 | DAP12 | CD3ζ |
| CD19 | DAP12 | CD3δ |
| CD19 | DAP12 | CD3γ |
| CD19 | DAP12 | CD3ε |
| CD19 | DAP12 | FcγRI-γ |
| CD19 | DAP12 | FcγRIII-γ |
| CD19 | DAP12 | FcεRIβ |
| CD19 | DAP12 | FcεRIγ |
| CD19 | DAP12 | DAP10 |
| CD19 | DAP12 | DAP12 |
| CD19 | DAP12 | CD32 |
| CD19 | DAP12 | CD79a |
| CD19 | DAP12 | CD79b |
| CD19 | MyD88 | CD8 |
| CD19 | MyD88 | CD3ζ |
| CD19 | MyD88 | CD3δ |
| CD19 | MyD88 | CD3γ |
| CD19 | MyD88 | CD3ε |
| CD19 | MyD88 | FcγRI-γ |
| CD19 | MyD88 | FcγRIII-γ |
| CD19 | MyD88 | FcεRIβ |
| CD19 | MyD88 | FcεRIγ |
| CD19 | MyD88 | DAP10 |
| CD19 | MyD88 | DAP12 |
| CD19 | MyD88 | CD32 |
| CD19 | MyD88 | CD79a |
| CD19 | MyD88 | CD79b |
| CD19 | CD7 | CD8 |
| CD19 | CD7 | CD3ζ |
| CD19 | CD7 | CD3δ |
| CD19 | CD7 | CD3γ |
| CD19 | CD7 | CD3ε |
| CD19 | CD7 | FcγRI-γ |
| CD19 | CD7 | FcγRIII-γ |
| CD19 | CD7 | FcεRIβ |
| CD19 | CD7 | FcεRIγ |
| CD19 | CD7 | DAP10 |
| CD19 | CD7 | DAP12 |
| CD19 | CD7 | CD32 |
| CD19 | CD7 | CD79a |
| CD19 | CD7 | CD79b |
| CD19 | BTNL3 | CD8 |
| CD19 | BTNL3 | CD3ζ |
| CD19 | BTNL3 | CD3δ |
| CD19 | BTNL3 | CD3γ |
| CD19 | BTNL3 | CD3ε |
| CD19 | BTNL3 | FcγRI-γ |
| CD19 | BTNL3 | FcγRIII-γ |
| CD19 | BTNL3 | FcεRIβ |
| CD19 | BTNL3 | FcεRIγ |
| CD19 | BTNL3 | DAP10 |
| CD19 | BTNL3 | DAP12 |
| CD19 | BTNL3 | CD32 |
| CD19 | BTNL3 | CD79a |
| CD19 | BTNL3 | CD79b |
| CD19 | NKG2D | CD8 |

TABLE 2-continued

| | Second Generation CARs | |
|---|---|---|
| ScFv | Co-stimulatory Signal | Signal Domain |
| CD19 | NKG2D | CD3ζ |
| CD19 | NKG2D | CD3δ |
| CD19 | NKG2D | CD3γ |
| CD19 | NKG2D | CD3ε |
| CD19 | NKG2D | FcγRI-γ |
| CD19 | NKG2D | FcγRIII-γ |
| CD19 | NKG2D | FcεRIβ |
| CD19 | NKG2D | FcεRIγ |
| CD19 | NKG2D | DAP10 |
| CD19 | NKG2D | DAP12 |
| CD19 | NKG2D | CD32 |
| CD19 | NKG2D | CD79a |
| CD19 | NKG2D | CD79b |

TABLE 3

| | Third Generation CARs | | |
|---|---|---|---|
| ScFv | Co-stimulatory Signal | Co-stimulatory Signal | Signal Domain |
| CD19 | CD28 | CD28 | CD8 |
| CD19 | CD28 | CD28 | CD3ζ |
| CD19 | CD28 | CD28 | CD3δ |
| CD19 | CD28 | CD28 | CD3γ |
| CD19 | CD28 | CD28 | CD3ε |
| CD19 | CD28 | CD28 | FcγRI-γ |
| CD19 | CD28 | CD28 | FcγRIII-γ |
| CD19 | CD28 | CD28 | FcεRIβ |
| CD19 | CD28 | CD28 | FcεRIγ |
| CD19 | CD28 | CD28 | DAP10 |
| CD19 | CD28 | CD28 | DAP12 |
| CD19 | CD28 | CD28 | CD32 |
| CD19 | CD28 | CD28 | CD79a |
| CD19 | CD28 | CD28 | CD79b |
| CD19 | CD28 | CD8 | CD8 |
| CD19 | CD28 | CD8 | CD3ζ |
| CD19 | CD28 | CD8 | CD3δ |
| CD19 | CD28 | CD8 | CD3γ |
| CD19 | CD28 | CD8 | CD3ε |
| CD19 | CD28 | CD8 | FcγRI-γ |
| CD19 | CD28 | CD8 | FcγRIII-γ |
| CD19 | CD28 | CD8 | FcεRIβ |
| CD19 | CD28 | CD8 | FcεRIγ |
| CD19 | CD28 | CD8 | DAP10 |
| CD19 | CD28 | CD8 | DAP12 |
| CD19 | CD28 | CD8 | CD32 |
| CD19 | CD28 | CD8 | CD79a |
| CD19 | CD28 | CD8 | CD79b |
| CD19 | CD28 | CD4 | CD8 |
| CD19 | CD28 | CD4 | CD3ζ |
| CD19 | CD28 | CD4 | CD3δ |
| CD19 | CD28 | CD4 | CD3γ |
| CD19 | CD28 | CD4 | CD3ε |
| CD19 | CD28 | CD4 | FcγRI-γ |
| CD19 | CD28 | CD4 | FcγRIII-γ |
| CD19 | CD28 | CD4 | FcεRIβ |
| CD19 | CD28 | CD4 | FcεRIγ |
| CD19 | CD28 | CD4 | DAP10 |
| CD19 | CD28 | CD4 | DAP12 |
| CD19 | CD28 | CD4 | CD32 |
| CD19 | CD28 | CD4 | CD79a |
| CD19 | CD28 | CD4 | CD79b |
| CD19 | CD28 | b2c | CD8 |
| CD19 | CD28 | b2c | CD3ζ |
| CD19 | CD28 | b2c | CD3δ |
| CD19 | CD28 | b2c | CD3γ |
| CD19 | CD28 | b2c | CD3ε |
| CD19 | CD28 | b2c | FcγRI-γ |
| CD19 | CD28 | b2c | FcγRIII-γ |
| CD19 | CD28 | b2c | FcεRIβ |
| CD19 | CD28 | b2c | FcεRIγ |

TABLE 3-continued

Third Generation CARs

| ScFv | Co-stimulatory Signal | Co-stimulatory Signal | Signal Domain |
|---|---|---|---|
| CD19 | CD28 | b2c | DAP10 |
| CD19 | CD28 | b2c | DAP12 |
| CD19 | CD28 | b2c | CD32 |
| CD19 | CD28 | b2c | CD79a |
| CD19 | CD28 | b2c | CD79b |
| CD19 | CD28 | CD137/41BB | CD8 |
| CD19 | CD28 | CD137/41BB | CD3ζ |
| CD19 | CD28 | CD137/41BB | CD3δ |
| CD19 | CD28 | CD137/41BB | CD3γ |
| CD19 | CD28 | CD137/41BB | CD3ε |
| CD19 | CD28 | CD137/41BB | FcγRI-γ |
| CD19 | CD28 | CD137/41BB | FcγRIII-γ |
| CD19 | CD28 | CD137/41BB | FcεRIβ |
| CD19 | CD28 | CD137/41BB | FcεRIγ |
| CD19 | CD28 | CD137/41BB | DAP10 |
| CD19 | CD28 | CD137/41BB | DAP12 |
| CD19 | CD28 | CD137/41BB | CD32 |
| CD19 | CD28 | CD137/41BB | CD79a |
| CD19 | CD28 | CD137/41BB | CD79b |
| CD19 | CD28 | ICOS | CD8 |
| CD19 | CD28 | ICOS | CD3ζ |
| CD19 | CD28 | ICOS | CD3δ |
| CD19 | CD28 | ICOS | CD3γ |
| CD19 | CD28 | ICOS | CD3ε |
| CD19 | CD28 | ICOS | FcγRI-γ |
| CD19 | CD28 | ICOS | FcγRIII-γ |
| CD19 | CD28 | ICOS | FcεRIβ |
| CD19 | CD28 | ICOS | FcεRIγ |
| CD19 | CD28 | ICOS | DAP10 |
| CD19 | CD28 | ICOS | DAP12 |
| CD19 | CD28 | ICOS | CD32 |
| CD19 | CD28 | ICOS | CD79a |
| CD19 | CD28 | ICOS | CD79b |
| CD19 | CD28 | CD27 | CD8 |
| CD19 | CD28 | CD27 | CD3ζ |
| CD19 | CD28 | CD27 | CD3δ |
| CD19 | CD28 | CD27 | CD3γ |
| CD19 | CD28 | CD27 | CD3ε |
| CD19 | CD28 | CD27 | FcγRI-γ |
| CD19 | CD28 | CD27 | FcγRIII-γ |
| CD19 | CD28 | CD27 | FcεRIβ |
| CD19 | CD28 | CD27 | FcεRIγ |
| CD19 | CD28 | CD27 | DAP10 |
| CD19 | CD28 | CD27 | DAP12 |
| CD19 | CD28 | CD27 | CD32 |
| CD19 | CD28 | CD27 | CD79a |
| CD19 | CD28 | CD27 | CD79b |
| CD19 | CD28 | CD28δ | CD8 |
| CD19 | CD28 | CD28δ | CD3ζ |
| CD19 | CD28 | CD28δ | CD3δ |
| CD19 | CD28 | CD28δ | CD3γ |
| CD19 | CD28 | CD28δ | CD3ε |
| CD19 | CD28 | CD28δ | FcγRI-γ |
| CD19 | CD28 | CD28δ | FcγRIII-γ |
| CD19 | CD28 | CD28δ | FcεRIβ |
| CD19 | CD28 | CD28δ | FcεRIγ |
| CD19 | CD28 | CD28δ | DAP10 |
| CD19 | CD28 | CD28δ | DAP12 |
| CD19 | CD28 | CD28δ | CD32 |
| CD19 | CD28 | CD28δ | CD79a |
| CD19 | CD28 | CD28δ | CD79b |
| CD19 | CD28 | CD80 | CD8 |
| CD19 | CD28 | CD80 | CD3ζ |
| CD19 | CD28 | CD80 | CD3δ |
| CD19 | CD28 | CD80 | CD3γ |
| CD19 | CD28 | CD80 | CD3ε |
| CD19 | CD28 | CD80 | FcγRI-γ |
| CD19 | CD28 | CD80 | FcγRIII-γ |
| CD19 | CD28 | CD80 | FcεRIβ |
| CD19 | CD28 | CD80 | FcεRIγ |
| CD19 | CD28 | CD80 | DAP10 |
| CD19 | CD28 | CD80 | DAP12 |
| CD19 | CD28 | CD80 | CD32 |
| CD19 | CD28 | CD80 | CD79a |
| CD19 | CD28 | CD80 | CD79b |
| CD19 | CD28 | CD86 | CD8 |
| CD19 | CD28 | CD86 | CD3ζ |
| CD19 | CD28 | CD86 | CD3δ |
| CD19 | CD28 | CD86 | CD3γ |
| CD19 | CD28 | CD86 | CD3ε |
| CD19 | CD28 | CD86 | FcγRI-γ |
| CD19 | CD28 | CD86 | FcγRIII-γ |
| CD19 | CD28 | CD86 | FcεRIβ |
| CD19 | CD28 | CD86 | FcεRIγ |
| CD19 | CD28 | CD86 | DAP10 |
| CD19 | CD28 | CD86 | DAP12 |
| CD19 | CD28 | CD86 | CD32 |
| CD19 | CD28 | CD86 | CD79a |
| CD19 | CD28 | CD86 | CD79b |
| CD19 | CD28 | OX40 | CD8 |
| CD19 | CD28 | OX40 | CD3ζ |
| CD19 | CD28 | OX40 | CD3δ |
| CD19 | CD28 | OX40 | CD3γ |
| CD19 | CD28 | OX40 | CD3ε |
| CD19 | CD28 | OX40 | FcγRI-γ |
| CD19 | CD28 | OX40 | FcγRIII-γ |
| CD19 | CD28 | OX40 | FcεRIβ |
| CD19 | CD28 | OX40 | FcεRIγ |
| CD19 | CD28 | OX40 | DAP10 |
| CD19 | CD28 | OX40 | DAP12 |
| CD19 | CD28 | OX40 | CD32 |
| CD19 | CD28 | OX40 | CD79a |
| CD19 | CD28 | OX40 | CD79b |
| CD19 | CD28 | DAP10 | CD8 |
| CD19 | CD28 | DAP10 | CD3ζ |
| CD19 | CD28 | DAP10 | CD3δ |
| CD19 | CD28 | DAP10 | CD3γ |
| CD19 | CD28 | DAP10 | CD3ε |
| CD19 | CD28 | DAP10 | FcγRI-γ |
| CD19 | CD28 | DAP10 | FcγRIII-γ |
| CD19 | CD28 | DAP10 | FcεRIβ |
| CD19 | CD28 | DAP10 | FcεRIγ |
| CD19 | CD28 | DAP10 | DAP10 |
| CD19 | CD28 | DAP10 | DAP12 |
| CD19 | CD28 | DAP10 | CD32 |
| CD19 | CD28 | DAP10 | CD79a |
| CD19 | CD28 | DAP10 | CD79b |
| CD19 | CD28 | DAP12 | CD8 |
| CD19 | CD28 | DAP12 | CD3ζ |
| CD19 | CD28 | DAP12 | CD3δ |
| CD19 | CD28 | DAP12 | CD3γ |
| CD19 | CD28 | DAP12 | CD3ε |
| CD19 | CD28 | DAP12 | FcγRI-γ |
| CD19 | CD28 | DAP12 | FcγRIII-γ |
| CD19 | CD28 | DAP12 | FcεRIβ |
| CD19 | CD28 | DAP12 | FcεRIγ |
| CD19 | CD28 | DAP12 | DAP10 |
| CD19 | CD28 | DAP12 | DAP12 |
| CD19 | CD28 | DAP12 | CD32 |
| CD19 | CD28 | DAP12 | CD79a |
| CD19 | CD28 | DAP12 | CD79b |
| CD19 | CD28 | MyD88 | CD8 |
| CD19 | CD28 | MyD88 | CD3ζ |
| CD19 | CD28 | MyD88 | CD3δ |
| CD19 | CD28 | MyD88 | CD3γ |
| CD19 | CD28 | MyD88 | CD3ε |
| CD19 | CD28 | MyD88 | FcγRI-γ |
| CD19 | CD28 | MyD88 | FcγRIII-γ |
| CD19 | CD28 | MyD88 | FcεRIβ |
| CD19 | CD28 | MyD88 | FcεRIγ |
| CD19 | CD28 | MyD88 | DAP10 |
| CD19 | CD28 | MyD88 | DAP12 |
| CD19 | CD28 | MyD88 | CD32 |
| CD19 | CD28 | MyD88 | CD79a |
| CD19 | CD28 | MyD88 | CD79b |
| CD19 | CD28 | CD7 | CD8 |
| CD19 | CD28 | CD7 | CD3ζ |
| CD19 | CD28 | CD7 | CD3δ |
| CD19 | CD28 | CD7 | CD3γ |
| CD19 | CD28 | CD7 | CD3ε |

TABLE 3-continued

| | Third Generation CARs | | |
|---|---|---|---|
| ScFv | Co-stimulatory Signal | Co-stimulatory Signal | Signal Domain |
| CD19 | CD28 | CD7 | FcγRI-γ |
| CD19 | CD28 | CD7 | FcγRIII-γ |
| CD19 | CD28 | CD7 | FcεRIβ |
| CD19 | CD28 | CD7 | FcεRIγ |
| CD19 | CD28 | CD7 | DAP10 |
| CD19 | CD28 | CD7 | DAP12 |
| CD19 | CD28 | CD7 | CD32 |
| CD19 | CD28 | CD7 | CD79a |
| CD19 | CD28 | CD7 | CD79b |
| CD19 | CD28 | BTNL3 | CD8 |
| CD19 | CD28 | BTNL3 | CD3ζ |
| CD19 | CD28 | BTNL3 | CD3δ |
| CD19 | CD28 | BTNL3 | CD3γ |
| CD19 | CD28 | BTNL3 | CD3ε |
| CD19 | CD28 | BTNL3 | FcγRI-γ |
| CD19 | CD28 | BTNL3 | FcγRIII-γ |
| CD19 | CD28 | BTNL3 | FcεRIβ |
| CD19 | CD28 | BTNL3 | FcεRIγ |
| CD19 | CD28 | BTNL3 | DAP10 |
| CD19 | CD28 | BTNL3 | DAP12 |
| CD19 | CD28 | BTNL3 | CD32 |
| CD19 | CD28 | BTNL3 | CD79a |
| CD19 | CD28 | BTNL3 | CD79b |
| CD19 | CD28 | NKG2D | CD8 |
| CD19 | CD28 | NKG2D | CD3ζ |
| CD19 | CD28 | NKG2D | CD3δ |
| CD19 | CD28 | NKG2D | CD3γ |
| CD19 | CD28 | NKG2D | CD3ε |
| CD19 | CD28 | NKG2D | FcγRI-γ |
| CD19 | CD28 | NKG2D | FcγRIII-γ |
| CD19 | CD28 | NKG2D | FcεRIβ |
| CD19 | CD28 | NKG2D | FcεRIγ |
| CD19 | CD28 | NKG2D | DAP10 |
| CD19 | CD28 | NKG2D | DAP12 |
| CD19 | CD28 | NKG2D | CD32 |
| CD19 | CD28 | NKG2D | CD79a |
| CD19 | CD28 | NKG2D | CD79b |
| CD19 | CD8 | CD28 | CD8 |
| CD19 | CD8 | CD28 | CD3ζ |
| CD19 | CD8 | CD28 | CD3δ |
| CD19 | CD8 | CD28 | CD3γ |
| CD19 | CD8 | CD28 | CD3ε |
| CD19 | CD8 | CD28 | FcγRI-γ |
| CD19 | CD8 | CD28 | FcγRIII-γ |
| CD19 | CD8 | CD28 | FcεRIβ |
| CD19 | CD8 | CD28 | FcεRIγ |
| CD19 | CD8 | CD28 | DAP10 |
| CD19 | CD8 | CD28 | DAP12 |
| CD19 | CD8 | CD28 | CD32 |
| CD19 | CD8 | CD28 | CD79a |
| CD19 | CD8 | CD28 | CD79b |
| CD19 | CD8 | CD8 | CD8 |
| CD19 | CD8 | CD8 | CD3ζ |
| CD19 | CD8 | CD8 | CD3δ |
| CD19 | CD8 | CD8 | CD3γ |
| CD19 | CD8 | CD8 | CD3ε |
| CD19 | CD8 | CD8 | FcγRI-γ |
| CD19 | CD8 | CD8 | FcγRIII-γ |
| CD19 | CD8 | CD8 | FcεRIβ |
| CD19 | CD8 | CD8 | FcεRIγ |
| CD19 | CD8 | CD8 | DAP10 |
| CD19 | CD8 | CD8 | DAP12 |
| CD19 | CD8 | CD8 | CD32 |
| CD19 | CD8 | CD8 | CD79a |
| CD19 | CD8 | CD8 | CD79b |
| CD19 | CD8 | CD4 | CD8 |
| CD19 | CD8 | CD4 | CD3ζ |
| CD19 | CD8 | CD4 | CD3δ |
| CD19 | CD8 | CD4 | CD3γ |
| CD19 | CD8 | CD4 | CD3ε |
| CD19 | CD8 | CD4 | FcγRI-γ |
| CD19 | CD8 | CD4 | FcγRIII-γ |
| CD19 | CD8 | CD4 | FcεRIβ |
| CD19 | CD8 | CD4 | FcεRIγ |
| CD19 | CD8 | CD4 | DAP10 |

TABLE 3-continued

| | Third Generation CARs | | |
|---|---|---|---|
| ScFv | Co-stimulatory Signal | Co-stimulatory Signal | Signal Domain |
| CD19 | CD8 | CD4 | DAP12 |
| CD19 | CD8 | CD4 | CD32 |
| CD19 | CD8 | CD4 | CD79a |
| CD19 | CD8 | CD4 | CD79b |
| CD19 | CD8 | b2c | CD8 |
| CD19 | CD8 | b2c | CD3ζ |
| CD19 | CD8 | b2c | CD3δ |
| CD19 | CD8 | b2c | CD3γ |
| CD19 | CD8 | b2c | CD3ε |
| CD19 | CD8 | b2c | FcγRI-γ |
| CD19 | CD8 | b2c | FcγRIII-γ |
| CD19 | CD8 | b2c | FcεRIβ |
| CD19 | CD8 | b2c | FcεRIγ |
| CD19 | CD8 | b2c | DAP10 |
| CD19 | CD8 | b2c | DAP12 |
| CD19 | CD8 | b2c | CD32 |
| CD19 | CD8 | b2c | CD79a |
| CD19 | CD8 | b2c | CD79b |
| CD19 | CD8 | CD137/41BB | CD8 |
| CD19 | CD8 | CD137/41BB | CD3ζ |
| CD19 | CD8 | CD137/41BB | CD3δ |
| CD19 | CD8 | CD137/41BB | CD3γ |
| CD19 | CD8 | CD137/41BB | CD3ε |
| CD19 | CD8 | CD137/41BB | FcγRI-γ |
| CD19 | CD8 | CD137/41BB | FcγRIII-γ |
| CD19 | CD8 | CD137/41BB | FcεRIβ |
| CD19 | CD8 | CD137/41BB | FcεRIγ |
| CD19 | CD8 | CD137/41BB | DAP10 |
| CD19 | CD8 | CD137/41BB | DAP12 |
| CD19 | CD8 | CD137/41BB | CD32 |
| CD19 | CD8 | CD137/41BB | CD79a |
| CD19 | CD8 | CD137/41BB | CD79b |
| CD19 | CD8 | ICOS | CD8 |
| CD19 | CD8 | ICOS | CD3ζ |
| CD19 | CD8 | ICOS | CD3δ |
| CD19 | CD8 | ICOS | CD3γ |
| CD19 | CD8 | ICOS | CD3ε |
| CD19 | CD8 | ICOS | FcγRI-γ |
| CD19 | CD8 | ICOS | FcγRIII-γ |
| CD19 | CD8 | ICOS | FcεRIβ |
| CD19 | CD8 | ICOS | FcεRIγ |
| CD19 | CD8 | ICOS | DAP10 |
| CD19 | CD8 | ICOS | DAP12 |
| CD19 | CD8 | ICOS | CD32 |
| CD19 | CD8 | ICOS | CD79a |
| CD19 | CD8 | ICOS | CD79b |
| CD19 | CD8 | CD27 | CD8 |
| CD19 | CD8 | CD27 | CD3ζ |
| CD19 | CD8 | CD27 | CD3δ |
| CD19 | CD8 | CD27 | CD3γ |
| CD19 | CD8 | CD27 | CD3ε |
| CD19 | CD8 | CD27 | FcγRI-γ |
| CD19 | CD8 | CD27 | FcγRIII-γ |
| CD19 | CD8 | CD27 | FcεRIβ |
| CD19 | CD8 | CD27 | FcεRIγ |
| CD19 | CD8 | CD27 | DAP10 |
| CD19 | CD8 | CD27 | DAP12 |
| CD19 | CD8 | CD27 | CD32 |
| CD19 | CD8 | CD27 | CD79a |
| CD19 | CD8 | CD27 | CD79b |
| CD19 | CD8 | CD28δ | CD8 |
| CD19 | CD8 | CD28δ | CD3ζ |
| CD19 | CD8 | CD28δ | CD3δ |
| CD19 | CD8 | CD28δ | CD3γ |
| CD19 | CD8 | CD28δ | CD3ε |
| CD19 | CD8 | CD28δ | FcγRI-γ |
| CD19 | CD8 | CD28δ | FcγRIII-γ |
| CD19 | CD8 | CD28δ | FcεRIβ |
| CD19 | CD8 | CD28δ | FcεRIγ |
| CD19 | CD8 | CD28δ | DAP10 |
| CD19 | CD8 | CD28δ | DAP12 |
| CD19 | CD8 | CD28δ | CD32 |
| CD19 | CD8 | CD28δ | CD79a |
| CD19 | CD8 | CD28δ | CD79b |
| CD19 | CD8 | CD80 | CD8 |

TABLE 3-continued

| | Third Generation CARs | | |
|---|---|---|---|
| ScFv | Co-stimulatory Signal | Co-stimulatory Signal | Signal Domain |
| CD19 | CD8 | CD80 | CD3ζ |
| CD19 | CD8 | CD80 | CD3δ |
| CD19 | CD8 | CD80 | CD3γ |
| CD19 | CD8 | CD80 | CD3ε |
| CD19 | CD8 | CD80 | FcγRI-γ |
| CD19 | CD8 | CD80 | FcγRIII-γ |
| CD19 | CD8 | CD80 | FcεRIβ |
| CD19 | CD8 | CD80 | FcεRIγ |
| CD19 | CD8 | CD80 | DAP10 |
| CD19 | CD8 | CD80 | DAP12 |
| CD19 | CD8 | CD80 | CD32 |
| CD19 | CD8 | CD80 | CD79a |
| CD19 | CD8 | CD80 | CD79b |
| CD19 | CD8 | CD86 | CD8 |
| CD19 | CD8 | CD86 | CD3ζ |
| CD19 | CD8 | CD86 | CD3δ |
| CD19 | CD8 | CD86 | CD3γ |
| CD19 | CD8 | CD86 | CD3ε |
| CD19 | CD8 | CD86 | FcγRI-γ |
| CD19 | CD8 | CD86 | FcγRIII-γ |
| CD19 | CD8 | CD86 | FcεRIβ |
| CD19 | CD8 | CD86 | FcεRIγ |
| CD19 | CD8 | CD86 | DAP10 |
| CD19 | CD8 | CD86 | DAP12 |
| CD19 | CD8 | CD86 | CD32 |
| CD19 | CD8 | CD86 | CD79a |
| CD19 | CD8 | CD86 | CD79b |
| CD19 | CD8 | OX40 | CD8 |
| CD19 | CD8 | OX40 | CD3ζ |
| CD19 | CD8 | OX40 | CD3δ |
| CD19 | CD8 | OX40 | CD3γ |
| CD19 | CD8 | OX40 | CD3ε |
| CD19 | CD8 | OX40 | FcγRI-γ |
| CD19 | CD8 | OX40 | FcγRIII-γ |
| CD19 | CD8 | OX40 | FcεRIβ |
| CD19 | CD8 | OX40 | FcεRIγ |
| CD19 | CD8 | OX40 | DAP10 |
| CD19 | CD8 | OX40 | DAP12 |
| CD19 | CD8 | OX40 | CD32 |
| CD19 | CD8 | OX40 | CD79a |
| CD19 | CD8 | OX40 | CD79b |
| CD19 | CD8 | DAP10 | CD8 |
| CD19 | CD8 | DAP10 | CD3ζ |
| CD19 | CD8 | DAP10 | CD3δ |
| CD19 | CD8 | DAP10 | CD3γ |
| CD19 | CD8 | DAP10 | CD3ε |
| CD19 | CD8 | DAP10 | FcγRI-γ |
| CD19 | CD8 | DAP10 | FcγRIII-γ |
| CD19 | CD8 | DAP10 | FcεRIβ |
| CD19 | CD8 | DAP10 | FcεRIγ |
| CD19 | CD8 | DAP10 | DAP10 |
| CD19 | CD8 | DAP10 | DAP12 |
| CD19 | CD8 | DAP10 | CD32 |
| CD19 | CD8 | DAP10 | CD79a |
| CD19 | CD8 | DAP10 | CD79b |
| CD19 | CD8 | DAP12 | CD8 |
| CD19 | CD8 | DAP12 | CD3ζ |
| CD19 | CD8 | DAP12 | CD3δ |
| CD19 | CD8 | DAP12 | CD3γ |
| CD19 | CD8 | DAP12 | CD3ε |
| CD19 | CD8 | DAP12 | FcγRI-γ |
| CD19 | CD8 | DAP12 | FcγRIII-γ |
| CD19 | CD8 | DAP12 | FcεRIβ |
| CD19 | CD8 | DAP12 | FcεRIγ |
| CD19 | CD8 | DAP12 | DAP10 |
| CD19 | CD8 | DAP12 | DAP12 |
| CD19 | CD8 | DAP12 | CD32 |
| CD19 | CD8 | DAP12 | CD79a |
| CD19 | CD8 | DAP12 | CD79b |
| CD19 | CD8 | MyD88 | CD8 |
| CD19 | CD8 | MyD88 | CD3ζ |
| CD19 | CD8 | MyD88 | CD3δ |
| CD19 | CD8 | MyD88 | CD3γ |
| CD19 | CD8 | MyD88 | CD3ε |
| CD19 | CD8 | MyD88 | FcγRI-γ |

TABLE 3-continued

| | Third Generation CARs | | |
|---|---|---|---|
| ScFv | Co-stimulatory Signal | Co-stimulatory Signal | Signal Domain |
| CD19 | CD8 | MyD88 | FcγRIII-γ |
| CD19 | CD8 | MyD88 | FcεRIβ |
| CD19 | CD8 | MyD88 | FcεRIγ |
| CD19 | CD8 | MyD88 | DAP10 |
| CD19 | CD8 | MyD88 | DAP12 |
| CD19 | CD8 | MyD88 | CD32 |
| CD19 | CD8 | MyD88 | CD79a |
| CD19 | CD8 | MyD88 | CD79b |
| CD19 | CD8 | CD7 | CD8 |
| CD19 | CD8 | CD7 | CD3ζ |
| CD19 | CD8 | CD7 | CD3δ |
| CD19 | CD8 | CD7 | CD3γ |
| CD19 | CD8 | CD7 | CD3ε |
| CD19 | CD8 | CD7 | FcγRI-γ |
| CD19 | CD8 | CD7 | FcγRIII-γ |
| CD19 | CD8 | CD7 | FcεRIβ |
| CD19 | CD8 | CD7 | FcεRIγ |
| CD19 | CD8 | CD7 | DAP10 |
| CD19 | CD8 | CD7 | DAP12 |
| CD19 | CD8 | CD7 | CD32 |
| CD19 | CD8 | CD7 | CD79a |
| CD19 | CD8 | CD7 | CD79b |
| CD19 | CD8 | BTNL3 | CD8 |
| CD19 | CD8 | BTNL3 | CD3ζ |
| CD19 | CD8 | BTNL3 | CD3δ |
| CD19 | CD8 | BTNL3 | CD3γ |
| CD19 | CD8 | BTNL3 | CD3ε |
| CD19 | CD8 | BTNL3 | FcγRI-γ |
| CD19 | CD8 | BTNL3 | FcγRIII-γ |
| CD19 | CD8 | BTNL3 | FcεRIβ |
| CD19 | CD8 | BTNL3 | FcεRIγ |
| CD19 | CD8 | BTNL3 | DAP10 |
| CD19 | CD8 | BTNL3 | DAP12 |
| CD19 | CD8 | BTNL3 | CD32 |
| CD19 | CD8 | BTNL3 | CD79a |
| CD19 | CD8 | BTNL3 | CD79b |
| CD19 | CD8 | NKG2D | CD8 |
| CD19 | CD8 | NKG2D | CD3ζ |
| CD19 | CD8 | NKG2D | CD3δ |
| CD19 | CD8 | NKG2D | CD3γ |
| CD19 | CD8 | NKG2D | CD3ε |
| CD19 | CD8 | NKG2D | FcγRI-γ |
| CD19 | CD8 | NKG2D | FcγRIII-γ |
| CD19 | CD8 | NKG2D | FcεRIβ |
| CD19 | CD8 | NKG2D | FcεRIγ |
| CD19 | CD8 | NKG2D | DAP10 |
| CD19 | CD8 | NKG2D | DAP12 |
| CD19 | CD8 | NKG2D | CD32 |
| CD19 | CD8 | NKG2D | CD79a |
| CD19 | CD8 | NKG2D | CD79b |
| CD19 | CD4 | CD28 | CD8 |
| CD19 | CD4 | CD28 | CD3ζ |
| CD19 | CD4 | CD28 | CD3δ |
| CD19 | CD4 | CD28 | CD3γ |
| CD19 | CD4 | CD28 | CD3ε |
| CD19 | CD4 | CD28 | FcγRI-γ |
| CD19 | CD4 | CD28 | FcγRIII-γ |
| CD19 | CD4 | CD28 | FcεRIβ |
| CD19 | CD4 | CD28 | FcεRIγ |
| CD19 | CD4 | CD28 | DAP10 |
| CD19 | CD4 | CD28 | DAP12 |
| CD19 | CD4 | CD28 | CD32 |
| CD19 | CD4 | CD28 | CD79a |
| CD19 | CD4 | CD28 | CD79b |
| CD19 | CD4 | CD8 | CD8 |
| CD19 | CD4 | CD8 | CD3ζ |
| CD19 | CD4 | CD8 | CD3δ |
| CD19 | CD4 | CD8 | CD3γ |
| CD19 | CD4 | CD8 | CD3ε |
| CD19 | CD4 | CD8 | FcγRI-γ |
| CD19 | CD4 | CD8 | FcγRIII-γ |
| CD19 | CD4 | CD8 | FcεRIβ |
| CD19 | CD4 | CD8 | FcεRIγ |
| CD19 | CD4 | CD8 | DAP10 |
| CD19 | CD4 | CD8 | DAP12 |

TABLE 3-continued

| | Third Generation CARs | | |
| ScFv | Co-stimulatory Signal | Co-stimulatory Signal | Signal Domain |
|---|---|---|---|
| CD19 | CD4 | CD8 | CD32 |
| CD19 | CD4 | CD8 | CD79a |
| CD19 | CD4 | CD8 | CD79b |
| CD19 | CD4 | CD4 | CD8 |
| CD19 | CD4 | CD4 | CD3ζ |
| CD19 | CD4 | CD4 | CD3δ |
| CD19 | CD4 | CD4 | CD3γ |
| CD19 | CD4 | CD4 | CD3ε |
| CD19 | CD4 | CD4 | FcγRI-γ |
| CD19 | CD4 | CD4 | FcγRIII-γ |
| CD19 | CD4 | CD4 | FcεRIβ |
| CD19 | CD4 | CD4 | FcεRIγ |
| CD19 | CD4 | CD4 | DAP10 |
| CD19 | CD4 | CD4 | DAP12 |
| CD19 | CD4 | CD4 | CD32 |
| CD19 | CD4 | CD4 | CD79a |
| CD19 | CD4 | CD4 | CD79b |
| CD19 | CD4 | b2c | CD8 |
| CD19 | CD4 | b2c | CD3ζ |
| CD19 | CD4 | b2c | CD3δ |
| CD19 | CD4 | b2c | CD3γ |
| CD19 | CD4 | b2c | CD3ε |
| CD19 | CD4 | b2c | FcγRI-γ |
| CD19 | CD4 | b2c | FcγRIII-γ |
| CD19 | CD4 | b2c | FcεRIβ |
| CD19 | CD4 | b2c | FcεRIγ |
| CD19 | CD4 | b2c | DAP10 |
| CD19 | CD4 | b2c | DAP12 |
| CD19 | CD4 | b2c | CD32 |
| CD19 | CD4 | b2c | CD79a |
| CD19 | CD4 | b2c | CD79b |
| CD19 | CD4 | CD137/41BB | CD8 |
| CD19 | CD4 | CD137/41BB | CD3ζ |
| CD19 | CD4 | CD137/41BB | CD3δ |
| CD19 | CD4 | CD137/41BB | CD3γ |
| CD19 | CD4 | CD137/41BB | CD3ε |
| CD19 | CD4 | CD137/41BB | FcγRI-γ |
| CD19 | CD4 | CD137/41BB | FcγRIII-γ |
| CD19 | CD4 | CD137/41BB | FcεRIβ |
| CD19 | CD4 | CD137/41BB | FcεRIγ |
| CD19 | CD4 | CD137/41BB | DAP10 |
| CD19 | CD4 | CD137/41BB | DAP12 |
| CD19 | CD4 | CD137/41BB | CD32 |
| CD19 | CD4 | CD137/41BB | CD79a |
| CD19 | CD4 | CD137/41BB | CD79b |
| CD19 | CD4 | ICOS | CD8 |
| CD19 | CD4 | ICOS | CD3ζ |
| CD19 | CD4 | ICOS | CD3δ |
| CD19 | CD4 | ICOS | CD3γ |
| CD19 | CD4 | ICOS | CD3ε |
| CD19 | CD4 | ICOS | FcγRI-γ |
| CD19 | CD4 | ICOS | FcγRIII-γ |
| CD19 | CD4 | ICOS | FcεRIβ |
| CD19 | CD4 | ICOS | FcεRIγ |
| CD19 | CD4 | ICOS | DAP10 |
| CD19 | CD4 | ICOS | DAP12 |
| CD19 | CD4 | ICOS | CD32 |
| CD19 | CD4 | ICOS | CD79a |
| CD19 | CD4 | ICOS | CD79b |
| CD19 | CD4 | CD27 | CD8 |
| CD19 | CD4 | CD27 | CD3ζ |
| CD19 | CD4 | CD27 | CD3δ |
| CD19 | CD4 | CD27 | CD3γ |
| CD19 | CD4 | CD27 | CD3ε |
| CD19 | CD4 | CD27 | FcγRI-γ |
| CD19 | CD4 | CD27 | FcγRIII-γ |
| CD19 | CD4 | CD27 | FcεRIβ |
| CD19 | CD4 | CD27 | FcεRIγ |
| CD19 | CD4 | CD27 | DAP10 |
| CD19 | CD4 | CD27 | DAP12 |
| CD19 | CD4 | CD27 | CD32 |
| CD19 | CD4 | CD27 | CD79a |
| CD19 | CD4 | CD27 | CD79b |
| CD19 | CD4 | CD28δ | CD8 |
| CD19 | CD4 | CD28δ | CD3ζ |
| CD19 | CD4 | CD28δ | CD3δ |
| CD19 | CD4 | CD28δ | CD3γ |
| CD19 | CD4 | CD28δ | CD3ε |
| CD19 | CD4 | CD28δ | FcγRI-γ |
| CD19 | CD4 | CD28δ | FcγRIII-γ |
| CD19 | CD4 | CD28δ | FcεRIβ |
| CD19 | CD4 | CD28δ | FcεRIγ |
| CD19 | CD4 | CD28δ | DAP10 |
| CD19 | CD4 | CD28δ | DAP12 |
| CD19 | CD4 | CD28δ | CD32 |
| CD19 | CD4 | CD28δ | CD79a |
| CD19 | CD4 | CD28δ | CD79b |
| CD19 | CD4 | CD80 | CD8 |
| CD19 | CD4 | CD80 | CD3ζ |
| CD19 | CD4 | CD80 | CD3δ |
| CD19 | CD4 | CD80 | CD3γ |
| CD19 | CD4 | CD80 | CD3ε |
| CD19 | CD4 | CD80 | FcγRI-γ |
| CD19 | CD4 | CD80 | FcγRIII-γ |
| CD19 | CD4 | CD80 | FcεRIβ |
| CD19 | CD4 | CD80 | FcεRIγ |
| CD19 | CD4 | CD80 | DAP10 |
| CD19 | CD4 | CD80 | DAP12 |
| CD19 | CD4 | CD80 | CD32 |
| CD19 | CD4 | CD80 | CD79a |
| CD19 | CD4 | CD80 | CD79b |
| CD19 | CD4 | CD86 | CD8 |
| CD19 | CD4 | CD86 | CD3ζ |
| CD19 | CD4 | CD86 | CD3δ |
| CD19 | CD4 | CD86 | CD3γ |
| CD19 | CD4 | CD86 | CD3ε |
| CD19 | CD4 | CD86 | FcγRI-γ |
| CD19 | CD4 | CD86 | FcγRIII-γ |
| CD19 | CD4 | CD86 | FcεRIβ |
| CD19 | CD4 | CD86 | FcεRIγ |
| CD19 | CD4 | CD86 | DAP10 |
| CD19 | CD4 | CD86 | DAP12 |
| CD19 | CD4 | CD86 | CD32 |
| CD19 | CD4 | CD86 | CD79a |
| CD19 | CD4 | CD86 | CD79b |
| CD19 | CD4 | OX40 | CD8 |
| CD19 | CD4 | OX40 | CD3ζ |
| CD19 | CD4 | OX40 | CD3δ |
| CD19 | CD4 | OX40 | CD3γ |
| CD19 | CD4 | OX40 | CD3ε |
| CD19 | CD4 | OX40 | FcγRI-γ |
| CD19 | CD4 | OX40 | FcγRIII-γ |
| CD19 | CD4 | OX40 | FcεRIβ |
| CD19 | CD4 | OX40 | FcεRIγ |
| CD19 | CD4 | OX40 | DAP10 |
| CD19 | CD4 | OX40 | DAP12 |
| CD19 | CD4 | OX40 | CD32 |
| CD19 | CD4 | OX40 | CD79a |
| CD19 | CD4 | OX40 | CD79b |
| CD19 | CD4 | DAP10 | CD8 |
| CD19 | CD4 | DAP10 | CD3ζ |
| CD19 | CD4 | DAP10 | CD3δ |
| CD19 | CD4 | DAP10 | CD3γ |
| CD19 | CD4 | DAP10 | CD3ε |
| CD19 | CD4 | DAP10 | FcγRI-γ |
| CD19 | CD4 | DAP10 | FcγRIII-γ |
| CD19 | CD4 | DAP10 | FcεRIβ |
| CD19 | CD4 | DAP10 | FcεRIγ |
| CD19 | CD4 | DAP10 | DAP10 |
| CD19 | CD4 | DAP10 | DAP12 |
| CD19 | CD4 | DAP10 | CD32 |
| CD19 | CD4 | DAP10 | CD79a |
| CD19 | CD4 | DAP10 | CD79b |
| CD19 | CD4 | DAP12 | CD8 |
| CD19 | CD4 | DAP12 | CD3ζ |
| CD19 | CD4 | DAP12 | CD3δ |
| CD19 | CD4 | DAP12 | CD3γ |
| CD19 | CD4 | DAP12 | CD3ε |
| CD19 | CD4 | DAP12 | FcγRI-γ |
| CD19 | CD4 | DAP12 | FcγRIII-γ |

TABLE 3-continued

| Third Generation CARs | | | |
|---|---|---|---|
| ScFv | Co-stimulatory Signal | Co-stimulatory Signal | Signal Domain |
| CD19 | CD4 | DAP12 | FcεRIβ |
| CD19 | CD4 | DAP12 | FcεRIγ |
| CD19 | CD4 | DAP12 | DAP10 |
| CD19 | CD4 | DAP12 | DAP12 |
| CD19 | CD4 | DAP12 | CD32 |
| CD19 | CD4 | DAP12 | CD79a |
| CD19 | CD4 | DAP12 | CD79b |
| CD19 | CD4 | MyD88 | CD8 |
| CD19 | CD4 | MyD88 | CD3ζ |
| CD19 | CD4 | MyD88 | CD3δ |
| CD19 | CD4 | MyD88 | CD3γ |
| CD19 | CD4 | MyD88 | CD3ε |
| CD19 | CD4 | MyD88 | FcγRI-γ |
| CD19 | CD4 | MyD88 | FcγRIII-γ |
| CD19 | CD4 | MyD88 | FcεRIβ |
| CD19 | CD4 | MyD88 | FcεRIγ |
| CD19 | CD4 | MyD88 | DAP10 |
| CD19 | CD4 | MyD88 | DAP12 |
| CD19 | CD4 | MyD88 | CD32 |
| CD19 | CD4 | MyD88 | CD79a |
| CD19 | CD4 | MyD88 | CD79b |
| CD19 | CD4 | CD7 | CD8 |
| CD19 | CD4 | CD7 | CD3ζ |
| CD19 | CD4 | CD7 | CD3δ |
| CD19 | CD4 | CD7 | CD3γ |
| CD19 | CD4 | CD7 | CD3ε |
| CD19 | CD4 | CD7 | FcγRI-γ |
| CD19 | CD4 | CD7 | FcγRIII-γ |
| CD19 | CD4 | CD7 | FcεRIβ |
| CD19 | CD4 | CD7 | FcεRIγ |
| CD19 | CD4 | CD7 | DAP10 |
| CD19 | CD4 | CD7 | DAP12 |
| CD19 | CD4 | CD7 | CD32 |
| CD19 | CD4 | CD7 | CD79a |
| CD19 | CD4 | CD7 | CD79b |
| CD19 | CD4 | BTNL3 | CD8 |
| CD19 | CD4 | BTNL3 | CD3ζ |
| CD19 | CD4 | BTNL3 | CD3δ |
| CD19 | CD4 | BTNL3 | CD3γ |
| CD19 | CD4 | BTNL3 | CD3ε |
| CD19 | CD4 | BTNL3 | FcγRI-γ |
| CD19 | CD4 | BTNL3 | FcγRIII-γ |
| CD19 | CD4 | BTNL3 | FcεRIβ |
| CD19 | CD4 | BTNL3 | FcεRIγ |
| CD19 | CD4 | BTNL3 | DAP10 |
| CD19 | CD4 | BTNL3 | DAP12 |
| CD19 | CD4 | BTNL3 | CD32 |
| CD19 | CD4 | BTNL3 | CD79a |
| CD19 | CD4 | BTNL3 | CD79b |
| CD19 | CD4 | NKG2D | CD8 |
| CD19 | CD4 | NKG2D | CD3ζ |
| CD19 | CD4 | NKG2D | CD3δ |
| CD19 | CD4 | NKG2D | CD3γ |
| CD19 | CD4 | NKG2D | CD3ε |
| CD19 | CD4 | NKG2D | FcγRI-γ |
| CD19 | CD4 | NKG2D | FcγRIII-γ |
| CD19 | CD4 | NKG2D | FcεRIβ |
| CD19 | CD4 | NKG2D | FcεRIγ |
| CD19 | CD4 | NKG2D | DAP10 |
| CD19 | CD4 | NKG2D | DAP12 |
| CD19 | CD4 | NKG2D | CD32 |
| CD19 | CD4 | NKG2D | CD79a |
| CD19 | CD4 | NKG2D | CD79b |
| CD19 | b2c | CD28 | CD8 |
| CD19 | b2c | CD28 | CD3ζ |
| CD19 | b2c | CD28 | CD3δ |
| CD19 | b2c | CD28 | CD3γ |
| CD19 | b2c | CD28 | CD3ε |
| CD19 | b2c | CD28 | FcγRI-γ |
| CD19 | b2c | CD28 | FcγRIII-γ |
| CD19 | b2c | CD28 | FcεRIβ |
| CD19 | b2c | CD28 | FcεRIγ |
| CD19 | b2c | CD28 | DAP10 |
| CD19 | b2c | CD28 | DAP12 |
| CD19 | b2c | CD28 | CD32 |

TABLE 3-continued

| Third Generation CARs | | | |
|---|---|---|---|
| ScFv | Co-stimulatory Signal | Co-stimulatory Signal | Signal Domain |
| CD19 | b2c | CD28 | CD79a |
| CD19 | b2c | CD28 | CD79b |
| CD19 | b2c | CD8 | CD8 |
| CD19 | b2c | CD8 | CD3ζ |
| CD19 | b2c | CD8 | CD3δ |
| CD19 | b2c | CD8 | CD3γ |
| CD19 | b2c | CD8 | CD3ε |
| CD19 | b2c | CD8 | FcγRI-γ |
| CD19 | b2c | CD8 | FcγRIII-γ |
| CD19 | b2c | CD8 | FcεRIβ |
| CD19 | b2c | CD8 | FcεRIγ |
| CD19 | b2c | CD8 | DAP10 |
| CD19 | b2c | CD8 | DAP12 |
| CD19 | b2c | CD8 | CD32 |
| CD19 | b2c | CD8 | CD79a |
| CD19 | b2c | CD8 | CD79b |
| CD19 | b2c | CD4 | CD8 |
| CD19 | b2c | CD4 | CD3ζ |
| CD19 | b2c | CD4 | CD3δ |
| CD19 | b2c | CD4 | CD3γ |
| CD19 | b2c | CD4 | CD3ε |
| CD19 | b2c | CD4 | FcγRI-γ |
| CD19 | b2c | CD4 | FcγRIII-γ |
| CD19 | b2c | CD4 | FcεRIβ |
| CD19 | b2c | CD4 | FcεRIγ |
| CD19 | b2c | CD4 | DAP10 |
| CD19 | b2c | CD4 | DAP12 |
| CD19 | b2c | CD4 | CD32 |
| CD19 | b2c | CD4 | CD79a |
| CD19 | b2c | CD4 | CD79b |
| CD19 | b2c | b2c | CD8 |
| CD19 | b2c | b2c | CD3ζ |
| CD19 | b2c | b2c | CD3δ |
| CD19 | b2c | b2c | CD3γ |
| CD19 | b2c | b2c | CD3ε |
| CD19 | b2c | b2c | FcγRI-γ |
| CD19 | b2c | b2c | FcγRIII-γ |
| CD19 | b2c | b2c | FcεRIβ |
| CD19 | b2c | b2c | FcεRIγ |
| CD19 | b2c | b2c | DAP10 |
| CD19 | b2c | b2c | DAP12 |
| CD19 | b2c | b2c | CD32 |
| CD19 | b2c | b2c | CD79a |
| CD19 | b2c | b2c | CD79b |
| CD19 | b2c | CD137/41BB | CD8 |
| CD19 | b2c | CD137/41BB | CD3ζ |
| CD19 | b2c | CD137/41BB | CD3δ |
| CD19 | b2c | CD137/41BB | CD3γ |
| CD19 | b2c | CD137/41BB | CD3ε |
| CD19 | b2c | CD137/41BB | FcγRI-γ |
| CD19 | b2c | CD137/41BB | FcγRIII-γ |
| CD19 | b2c | CD137/41BB | FcεRIβ |
| CD19 | b2c | CD137/41BB | FcεRIγ |
| CD19 | b2c | CD137/41BB | DAP10 |
| CD19 | b2c | CD137/41BB | DAP12 |
| CD19 | b2c | CD137/41BB | CD32 |
| CD19 | b2c | CD137/41BB | CD79a |
| CD19 | b2c | CD137/41BB | CD79b |
| CD19 | b2c | ICOS | CD8 |
| CD19 | b2c | ICOS | CD3ζ |
| CD19 | b2c | ICOS | CD3δ |
| CD19 | b2c | ICOS | CD3γ |
| CD19 | b2c | ICOS | CD3ε |
| CD19 | b2c | ICOS | FcγRI-γ |
| CD19 | b2c | ICOS | FcγRIII-γ |
| CD19 | b2c | ICOS | FcεRIβ |
| CD19 | b2c | ICOS | FcεRIγ |
| CD19 | b2c | ICOS | DAP10 |
| CD19 | b2c | ICOS | DAP12 |
| CD19 | b2c | ICOS | CD32 |
| CD19 | b2c | ICOS | CD79a |
| CD19 | b2c | ICOS | CD79b |
| CD19 | b2c | CD27 | CD8 |
| CD19 | b2c | CD27 | CD3ζ |
| CD19 | b2c | CD27 | CD3δ |

TABLE 3-continued

| | Third Generation CARs | | |
|---|---|---|---|
| ScFv | Co-stimulatory Signal | Co-stimulatory Signal | Signal Domain |
| CD19 | b2c | CD27 | CD3γ |
| CD19 | b2c | CD27 | CD3ε |
| CD19 | b2c | CD27 | FcγRI-γ |
| CD19 | b2c | CD27 | FcγRIII-γ |
| CD19 | b2c | CD27 | FcεRIβ |
| CD19 | b2c | CD27 | FcεRIγ |
| CD19 | b2c | CD27 | DAP10 |
| CD19 | b2c | CD27 | DAP12 |
| CD19 | b2c | CD27 | CD32 |
| CD19 | b2c | CD27 | CD79a |
| CD19 | b2c | CD27 | CD79b |
| CD19 | b2c | CD28δ | CD8 |
| CD19 | b2c | CD28δ | CD3ζ |
| CD19 | b2c | CD28δ | CD3δ |
| CD19 | b2c | CD28δ | CD3γ |
| CD19 | b2c | CD28δ | CD3ε |
| CD19 | b2c | CD28δ | FcγRI-γ |
| CD19 | b2c | CD28δ | FcγRIII-γ |
| CD19 | b2c | CD28δ | FcεRIβ |
| CD19 | b2c | CD28δ | FcεRIγ |
| CD19 | b2c | CD28δ | DAP10 |
| CD19 | b2c | CD28δ | DAP12 |
| CD19 | b2c | CD28δ | CD32 |
| CD19 | b2c | CD28δ | CD79a |
| CD19 | b2c | CD28δ | CD79b |
| CD19 | b2c | CD80 | CD8 |
| CD19 | b2c | CD80 | CD3ζ |
| CD19 | b2c | CD80 | CD3δ |
| CD19 | b2c | CD80 | CD3γ |
| CD19 | b2c | CD80 | CD3ε |
| CD19 | b2c | CD80 | FcγRI-γ |
| CD19 | b2c | CD80 | FcγRIII-γ |
| CD19 | b2c | CD80 | FcεRIβ |
| CD19 | b2c | CD80 | FcεRIγ |
| CD19 | b2c | CD80 | DAP10 |
| CD19 | b2c | CD80 | DAP12 |
| CD19 | b2c | CD80 | CD32 |
| CD19 | b2c | CD80 | CD79a |
| CD19 | b2c | CD80 | CD79b |
| CD19 | b2c | CD86 | CD8 |
| CD19 | b2c | CD86 | CD3ζ |
| CD19 | b2c | CD86 | CD3δ |
| CD19 | b2c | CD86 | CD3γ |
| CD19 | b2c | CD86 | CD3ε |
| CD19 | b2c | CD86 | FcγRI-γ |
| CD19 | b2c | CD86 | FcγRIII-γ |
| CD19 | b2c | CD86 | FcεRIβ |
| CD19 | b2c | CD86 | FcεRIγ |
| CD19 | b2c | CD86 | DAP10 |
| CD19 | b2c | CD86 | DAP12 |
| CD19 | b2c | CD86 | CD32 |
| CD19 | b2c | CD86 | CD79a |
| CD19 | b2c | CD86 | CD79b |
| CD19 | b2c | OX40 | CD8 |
| CD19 | b2c | OX40 | CD3ζ |
| CD19 | b2c | OX40 | CD3δ |
| CD19 | b2c | OX40 | CD3γ |
| CD19 | b2c | OX40 | CD3ε |
| CD19 | b2c | OX40 | FcγRI-γ |
| CD19 | b2c | OX40 | FcγRIII-γ |
| CD19 | b2c | OX40 | FcεRIβ |
| CD19 | b2c | OX40 | FcεRIγ |
| CD19 | b2c | OX40 | DAP10 |
| CD19 | b2c | OX40 | DAP12 |
| CD19 | b2c | OX40 | CD32 |
| CD19 | b2c | OX40 | CD79a |
| CD19 | b2c | OX40 | CD79b |
| CD19 | b2c | DAP10 | CD8 |
| CD19 | b2c | DAP10 | CD3ζ |
| CD19 | b2c | DAP10 | CD3δ |
| CD19 | b2c | DAP10 | CD3γ |
| CD19 | b2c | DAP10 | CD3ε |
| CD19 | b2c | DAP10 | FcγRI-γ |
| CD19 | b2c | DAP10 | FcγRIII-γ |
| CD19 | b2c | DAP10 | FcεRIβ |
| CD19 | b2c | DAP10 | FcεRIγ |
| CD19 | b2c | DAP10 | DAP10 |
| CD19 | b2c | DAP10 | DAP12 |
| CD19 | b2c | DAP10 | CD32 |
| CD19 | b2c | DAP10 | CD79a |
| CD19 | b2c | DAP10 | CD79b |
| CD19 | b2c | DAP12 | CD8 |
| CD19 | b2c | DAP12 | CD3ζ |
| CD19 | b2c | DAP12 | CD3δ |
| CD19 | b2c | DAP12 | CD3γ |
| CD19 | b2c | DAP12 | CD3ε |
| CD19 | b2c | DAP12 | FcγRI-γ |
| CD19 | b2c | DAP12 | FcγRIII-γ |
| CD19 | b2c | DAP12 | FcεRIβ |
| CD19 | b2c | DAP12 | FcεRIγ |
| CD19 | b2c | DAP12 | DAP10 |
| CD19 | b2c | DAP12 | DAP12 |
| CD19 | b2c | DAP12 | CD32 |
| CD19 | b2c | DAP12 | CD79a |
| CD19 | b2c | DAP12 | CD79b |
| CD19 | b2c | MyD88 | CD8 |
| CD19 | b2c | MyD88 | CD3ζ |
| CD19 | b2c | MyD88 | CD3δ |
| CD19 | b2c | MyD88 | CD3γ |
| CD19 | b2c | MyD88 | CD3ε |
| CD19 | b2c | MyD88 | FcγRI-γ |
| CD19 | b2c | MyD88 | FcγRIII-γ |
| CD19 | b2c | MyD88 | FcεRIβ |
| CD19 | b2c | MyD88 | FcεRIγ |
| CD19 | b2c | MyD88 | DAP10 |
| CD19 | b2c | MyD88 | DAP12 |
| CD19 | b2c | MyD88 | CD32 |
| CD19 | b2c | MyD88 | CD79a |
| CD19 | b2c | MyD88 | CD79b |
| CD19 | b2c | CD7 | CD8 |
| CD19 | b2c | CD7 | CD3ζ |
| CD19 | b2c | CD7 | CD3δ |
| CD19 | b2c | CD7 | CD3γ |
| CD19 | b2c | CD7 | CD3ε |
| CD19 | b2c | CD7 | FcγRI-γ |
| CD19 | b2c | CD7 | FcγRIII-γ |
| CD19 | b2c | CD7 | FcεRIβ |
| CD19 | b2c | CD7 | FcεRIγ |
| CD19 | b2c | CD7 | DAP10 |
| CD19 | b2c | CD7 | DAP12 |
| CD19 | b2c | CD7 | CD32 |
| CD19 | b2c | CD7 | CD79a |
| CD19 | b2c | CD7 | CD79b |
| CD19 | b2c | BTNL3 | CD8 |
| CD19 | b2c | BTNL3 | CD3ζ |
| CD19 | b2c | BTNL3 | CD3δ |
| CD19 | b2c | BTNL3 | CD3γ |
| CD19 | b2c | BTNL3 | CD3ε |
| CD19 | b2c | BTNL3 | FcγRI-γ |
| CD19 | b2c | BTNL3 | FcγRIII-γ |
| CD19 | b2c | BTNL3 | FcεRIβ |
| CD19 | b2c | BTNL3 | FcεRIγ |
| CD19 | b2c | BTNL3 | DAP10 |
| CD19 | b2c | BTNL3 | DAP12 |
| CD19 | b2c | BTNL3 | CD32 |
| CD19 | b2c | BTNL3 | CD79a |
| CD19 | b2c | BTNL3 | CD79b |
| CD19 | b2c | NKG2D | CD8 |
| CD19 | b2c | NKG2D | CD3ζ |
| CD19 | b2c | NKG2D | CD3δ |
| CD19 | b2c | NKG2D | CD3γ |
| CD19 | b2c | NKG2D | CD3ε |
| CD19 | b2c | NKG2D | FcγRI-γ |
| CD19 | b2c | NKG2D | FcγRIII-γ |
| CD19 | b2c | NKG2D | FcεRIβ |
| CD19 | b2c | NKG2D | FcεRIγ |
| CD19 | b2c | NKG2D | DAP10 |
| CD19 | b2c | NKG2D | DAP12 |
| CD19 | b2c | NKG2D | CD32 |
| CD19 | b2c | NKG2D | CD79a |

TABLE 3-continued

TABLE 3-continued

| | Third Generation CARs | | | | | Third Generation CARs | | |
|---|---|---|---|---|---|---|---|---|
| ScFv | Co-stimulatory Signal | Co-stimulatory Signal | Signal Domain | 5 | ScFv | Co-stimulatory Signal | Co-stimulatory Signal | Signal Domain |
| CD19 | b2c | NKG2D | CD79b | | CD19 | CD137/41BB | ICOS | CD3ε |
| CD19 | CD137/41BB | CD28 | CD8 | | CD19 | CD137/41BB | ICOS | FcγRI-γ |
| CD19 | CD137/41BB | CD28 | CD3ζ | | CD19 | CD137/41BB | ICOS | FcγRIII-γ |
| CD19 | CD137/41BB | CD28 | CD3δ | | CD19 | CD137/41BB | ICOS | FcεRIβ |
| CD19 | CD137/41BB | CD28 | CD3γ | 10 | CD19 | CD137/41BB | ICOS | FcεRIγ |
| CD19 | CD137/41BB | CD28 | CD3ε | | CD19 | CD137/41BB | ICOS | DAP10 |
| CD19 | CD137/41BB | CD28 | FcγRI-γ | | CD19 | CD137/41BB | ICOS | DAP12 |
| CD19 | CD137/41BB | CD28 | FcγRIII-γ | | CD19 | CD137/41BB | ICOS | CD32 |
| CD19 | CD137/41BB | CD28 | FcεRIβ | | CD19 | CD137/41BB | ICOS | CD79a |
| CD19 | CD137/41BB | CD28 | FcεRIγ | | CD19 | CD137/41BB | ICOS | CD79b |
| CD19 | CD137/41BB | CD28 | DAP10 | 15 | CD19 | CD137/41BB | CD27 | CD8 |
| CD19 | CD137/41BB | CD28 | DAP12 | | CD19 | CD137/41BB | CD27 | CD3ζ |
| CD19 | CD137/41BB | CD28 | CD32 | | CD19 | CD137/41BB | CD27 | CD3δ |
| CD19 | CD137/41BB | CD28 | CD79a | | CD19 | CD137/41BB | CD27 | CD3γ |
| CD19 | CD137/41BB | CD28 | CD79b | | CD19 | CD137/41BB | CD27 | CD3ε |
| CD19 | CD137/41BB | CD8 | CD8 | | CD19 | CD137/41BB | CD27 | FcγRI-γ |
| CD19 | CD137/41BB | CD8 | CD3ζ | | CD19 | CD137/41BB | CD27 | FcγRIII-γ |
| CD19 | CD137/41BB | CD8 | CD3δ | 20 | CD19 | CD137/41BB | CD27 | FcεRIβ |
| CD19 | CD137/41BB | CD8 | CD3γ | | CD19 | CD137/41BB | CD27 | FcεRIγ |
| CD19 | CD137/41BB | CD8 | CD3ε | | CD19 | CD137/41BB | CD27 | DAP10 |
| CD19 | CD137/41BB | CD8 | FcγRI-γ | | CD19 | CD137/41BB | CD27 | DAP12 |
| CD19 | CD137/41BB | CD8 | FcγRIII-γ | | CD19 | CD137/41BB | CD27 | CD32 |
| CD19 | CD137/41BB | CD8 | FcεRIβ | 25 | CD19 | CD137/41BB | CD27 | CD79a |
| CD19 | CD137/41BB | CD8 | FcεRIγ | | CD19 | CD137/41BB | CD27 | CD79b |
| CD19 | CD137/41BB | CD8 | DAP10 | | CD19 | CD137/41BB | CD28δ | CD8 |
| CD19 | CD137/41BB | CD8 | DAP12 | | CD19 | CD137/41BB | CD28δ | CD3ζ |
| CD19 | CD137/41BB | CD8 | CD32 | | CD19 | CD137/41BB | CD28δ | CD3δ |
| CD19 | CD137/41BB | CD8 | CD79a | | CD19 | CD137/41BB | CD28δ | CD3γ |
| CD19 | CD137/41BB | CD8 | CD79b | | CD19 | CD137/41BB | CD28δ | CD3ε |
| CD19 | CD137/41BB | CD4 | CD8 | 30 | CD19 | CD137/41BB | CD28δ | FcγRI-γ |
| CD19 | CD137/41BB | CD4 | CD3ζ | | CD19 | CD137/41BB | CD28δ | FcγRIII-γ |
| CD19 | CD137/41BB | CD4 | CD3δ | | CD19 | CD137/41BB | CD28δ | FcεRIβ |
| CD19 | CD137/41BB | CD4 | CD3γ | | CD19 | CD137/41BB | CD28δ | FcεRIγ |
| CD19 | CD137/41BB | CD4 | CD3ε | | CD19 | CD137/41BB | CD28δ | DAP10 |
| CD19 | CD137/41BB | CD4 | FcγRI-γ | | CD19 | CD137/41BB | CD28δ | DAP12 |
| CD19 | CD137/41BB | CD4 | FcγRIII-γ | 35 | CD19 | CD137/41BB | CD28δ | CD32 |
| CD19 | CD137/41BB | CD4 | FcεRIβ | | CD19 | CD137/41BB | CD28δ | CD79a |
| CD19 | CD137/41BB | CD4 | FcεRIγ | | CD19 | CD137/41BB | CD28δ | CD79b |
| CD19 | CD137/41BB | CD4 | DAP10 | | CD19 | CD137/41BB | CD80 | CD8 |
| CD19 | CD137/41BB | CD4 | DAP12 | | CD19 | CD137/41BB | CD80 | CD3ζ |
| CD19 | CD137/41BB | CD4 | CD32 | | CD19 | CD137/41BB | CD80 | CD3δ |
| CD19 | CD137/41BB | CD4 | CD79a | 40 | CD19 | CD137/41BB | CD80 | CD3γ |
| CD19 | CD137/41BB | CD4 | CD79b | | CD19 | CD137/41BB | CD80 | CD3ε |
| CD19 | CD137/41BB | b2c | CD8 | | CD19 | CD137/41BB | CD80 | FcγRI-γ |
| CD19 | CD137/41BB | b2c | CD3ζ | | CD19 | CD137/41BB | CD80 | FcγRIII-γ |
| CD19 | CD137/41BB | b2c | CD3δ | | CD19 | CD137/41BB | CD80 | FcεRIβ |
| CD19 | CD137/41BB | b2c | CD3γ | | CD19 | CD137/41BB | CD80 | FcεRIγ |
| CD19 | CD137/41BB | b2c | CD3ε | 45 | CD19 | CD137/41BB | CD80 | DAP10 |
| CD19 | CD137/41BB | b2c | FcγRI-γ | | CD19 | CD137/41BB | CD80 | DAP12 |
| CD19 | CD137/41BB | b2c | FcγRIII-γ | | CD19 | CD137/41BB | CD80 | CD32 |
| CD19 | CD137/41BB | b2c | FcεRIβ | | CD19 | CD137/41BB | CD80 | CD79a |
| CD19 | CD137/41BB | b2c | FcεRIγ | | CD19 | CD137/41BB | CD80 | CD79b |
| CD19 | CD137/41BB | b2c | DAP10 | | CD19 | CD137/41BB | CD86 | CD8 |
| CD19 | CD137/41BB | b2c | DAP12 | 50 | CD19 | CD137/41BB | CD86 | CD3ζ |
| CD19 | CD137/41BB | b2c | CD32 | | CD19 | CD137/41BB | CD86 | CD3δ |
| CD19 | CD137/41BB | b2c | CD79a | | CD19 | CD137/41BB | CD86 | CD3γ |
| CD19 | CD137/41BB | b2c | CD79b | | CD19 | CD137/41BB | CD86 | CD3ε |
| CD19 | CD137/41BB | CD137/41BB | CD8 | | CD19 | CD137/41BB | CD86 | FcγRI-γ |
| CD19 | CD137/41BB | CD137/41BB | CD3ζ | | CD19 | CD137/41BB | CD86 | FcγRIII-γ |
| CD19 | CD137/41BB | CD137/41BB | CD3δ | 55 | CD19 | CD137/41BB | CD86 | FcεRIβ |
| CD19 | CD137/41BB | CD137/41BB | CD3γ | | CD19 | CD137/41BB | CD86 | FcεRIγ |
| CD19 | CD137/41BB | CD137/41BB | CD3ε | | CD19 | CD137/41BB | CD86 | DAP10 |
| CD19 | CD137/41BB | CD137/41BB | FcγRI-γ | | CD19 | CD137/41BB | CD86 | DAP12 |
| CD19 | CD137/41BB | CD137/41BB | FcγRIII-γ | | CD19 | CD137/41BB | CD86 | CD32 |
| CD19 | CD137/41BB | CD137/41BB | FcεRIβ | | CD19 | CD137/41BB | CD86 | CD79a |
| CD19 | CD137/41BB | CD137/41BB | FcεRIγ | 60 | CD19 | CD137/41BB | CD86 | CD79b |
| CD19 | CD137/41BB | CD137/41BB | DAP10 | | CD19 | CD137/41BB | OX40 | CD8 |
| CD19 | CD137/41BB | CD137/41BB | DAP12 | | CD19 | CD137/41BB | OX40 | CD3ζ |
| CD19 | CD137/41BB | CD137/41BB | CD32 | | CD19 | CD137/41BB | OX40 | CD3δ |
| CD19 | CD137/41BB | CD137/41BB | CD79a | | CD19 | CD137/41BB | OX40 | CD3γ |
| CD19 | CD137/41BB | CD137/41BB | CD79b | | CD19 | CD137/41BB | OX40 | CD3ε |
| CD19 | CD137/41BB | ICOS | CD8 | | CD19 | CD137/41BB | OX40 | FcγRI-γ |
| CD19 | CD137/41BB | ICOS | CD3ζ | | CD19 | CD137/41BB | OX40 | FcγRIII-γ |
| CD19 | CD137/41BB | ICOS | CD3δ | 65 | CD19 | CD137/41BB | OX40 | FcεRIβ |
| CD19 | CD137/41BB | ICOS | CD3γ | | CD19 | CD137/41BB | OX40 | FcεRIγ |

TABLE 3-continued

| | Third Generation CARs | | |
|---|---|---|---|
| ScFv | Co-stimulatory Signal | Co-stimulatory Signal | Signal Domain |
| CD19 | CD137/41BB | OX40 | DAP10 |
| CD19 | CD137/41BB | OX40 | DAP12 |
| CD19 | CD137/41BB | OX40 | CD32 |
| CD19 | CD137/41BB | OX40 | CD79a |
| CD19 | CD137/41BB | OX40 | CD79b |
| CD19 | CD137/41BB | DAP10 | CD8 |
| CD19 | CD137/41BB | DAP10 | CD3ζ |
| CD19 | CD137/41BB | DAP10 | CD3δ |
| CD19 | CD137/41BB | DAP10 | CD3γ |
| CD19 | CD137/41BB | DAP10 | CD3ε |
| CD19 | CD137/41BB | DAP10 | FcγRI-γ |
| CD19 | CD137/41BB | DAP10 | FcγRIII-γ |
| CD19 | CD137/41BB | DAP10 | FcεRIβ |
| CD19 | CD137/41BB | DAP10 | FcεRIγ |
| CD19 | CD137/41BB | DAP10 | DAP10 |
| CD19 | CD137/41BB | DAP10 | DAP12 |
| CD19 | CD137/41BB | DAP10 | CD32 |
| CD19 | CD137/41BB | DAP10 | CD79a |
| CD19 | CD137/41BB | DAP10 | CD79b |
| CD19 | CD137/41BB | DAP12 | CD8 |
| CD19 | CD137/41BB | DAP12 | CD3ζ |
| CD19 | CD137/41BB | DAP12 | CD3δ |
| CD19 | CD137/41BB | DAP12 | CD3γ |
| CD19 | CD137/41BB | DAP12 | CD3ε |
| CD19 | CD137/41BB | DAP12 | FcγRI-γ |
| CD19 | CD137/41BB | DAP12 | FcγRIII-γ |
| CD19 | CD137/41BB | DAP12 | FcεRIβ |
| CD19 | CD137/41BB | DAP12 | FcεRIγ |
| CD19 | CD137/41BB | DAP12 | DAP10 |
| CD19 | CD137/41BB | DAP12 | DAP12 |
| CD19 | CD137/41BB | DAP12 | CD32 |
| CD19 | CD137/41BB | DAP12 | CD79a |
| CD19 | CD137/41BB | DAP12 | CD79b |
| CD19 | CD137/41BB | MyD88 | CD8 |
| CD19 | CD137/41BB | MyD88 | CD3ζ |
| CD19 | CD137/41BB | MyD88 | CD3δ |
| CD19 | CD137/41BB | MyD88 | CD3γ |
| CD19 | CD137/41BB | MyD88 | CD3ε |
| CD19 | CD137/41BB | MyD88 | FcγRI-γ |
| CD19 | CD137/41BB | MyD88 | FcγRIII-γ |
| CD19 | CD137/41BB | MyD88 | FcεRIβ |
| CD19 | CD137/41BB | MyD88 | FcεRIγ |
| CD19 | CD137/41BB | MyD88 | DAP10 |
| CD19 | CD137/41BB | MyD88 | DAP12 |
| CD19 | CD137/41BB | MyD88 | CD32 |
| CD19 | CD137/41BB | MyD88 | CD79a |
| CD19 | CD137/41BB | MyD88 | CD79b |
| CD19 | CD137/41BB | CD7 | CD8 |
| CD19 | CD137/41BB | CD7 | CD3ζ |
| CD19 | CD137/41BB | CD7 | CD3δ |
| CD19 | CD137/41BB | CD7 | CD3γ |
| CD19 | CD137/41BB | CD7 | CD3ε |
| CD19 | CD137/41BB | CD7 | FcγRI-γ |
| CD19 | CD137/41BB | CD7 | FcγRIII-γ |
| CD19 | CD137/41BB | CD7 | FcεRIβ |
| CD19 | CD137/41BB | CD7 | FcεRIγ |
| CD19 | CD137/41BB | CD7 | DAP10 |
| CD19 | CD137/41BB | CD7 | DAP12 |
| CD19 | CD137/41BB | CD7 | CD32 |
| CD19 | CD137/41BB | CD7 | CD79a |
| CD19 | CD137/41BB | CD7 | CD79b |
| CD19 | CD137/41BB | BTNL3 | CD8 |
| CD19 | CD137/41BB | BTNL3 | CD3ζ |
| CD19 | CD137/41BB | BTNL3 | CD3δ |
| CD19 | CD137/41BB | BTNL3 | CD3γ |
| CD19 | CD137/41BB | BTNL3 | CD3ε |
| CD19 | CD137/41BB | BTNL3 | FcγRI-γ |
| CD19 | CD137/41BB | BTNL3 | FcγRIII-γ |
| CD19 | CD137/41BB | BTNL3 | FcεRIβ |
| CD19 | CD137/41BB | BTNL3 | FcεRIγ |
| CD19 | CD137/41BB | BTNL3 | DAP10 |
| CD19 | CD137/41BB | BTNL3 | DAP12 |
| CD19 | CD137/41BB | BTNL3 | CD32 |
| CD19 | CD137/41BB | BTNL3 | CD79a |
| CD19 | CD137/41BB | BTNL3 | CD79b |

TABLE 3-continued

| | Third Generation CARs | | |
|---|---|---|---|
| ScFv | Co-stimulatory Signal | Co-stimulatory Signal | Signal Domain |
| CD19 | CD137/41BB | NKG2D | CD8 |
| CD19 | CD137/41BB | NKG2D | CD3ζ |
| CD19 | CD137/41BB | NKG2D | CD3δ |
| CD19 | CD137/41BB | NKG2D | CD3γ |
| CD19 | CD137/41BB | NKG2D | CD3ε |
| CD19 | CD137/41BB | NKG2D | FcγRI-γ |
| CD19 | CD137/41BB | NKG2D | FcγRIII-γ |
| CD19 | CD137/41BB | NKG2D | FcεRIβ |
| CD19 | CD137/41BB | NKG2D | FcεRIγ |
| CD19 | CD137/41BB | NKG2D | DAP10 |
| CD19 | CD137/41BB | NKG2D | DAP12 |
| CD19 | CD137/41BB | NKG2D | CD32 |
| CD19 | CD137/41BB | NKG2D | CD79a |
| CD19 | CD137/41BB | NKG2D | CD79b |
| CD19 | ICOS | CD28 | CD8 |
| CD19 | ICOS | CD28 | CD3ζ |
| CD19 | ICOS | CD28 | CD3δ |
| CD19 | ICOS | CD28 | CD3γ |
| CD19 | ICOS | CD28 | CD3ε |
| CD19 | ICOS | CD28 | FcγRI-γ |
| CD19 | ICOS | CD28 | FcγRIII-γ |
| CD19 | ICOS | CD28 | FcεRIβ |
| CD19 | ICOS | CD28 | FcεRIγ |
| CD19 | ICOS | CD28 | DAP10 |
| CD19 | ICOS | CD28 | DAP12 |
| CD19 | ICOS | CD28 | CD32 |
| CD19 | ICOS | CD28 | CD79a |
| CD19 | ICOS | CD28 | CD79b |
| CD19 | ICOS | CD8 | CD8 |
| CD19 | ICOS | CD8 | CD3ζ |
| CD19 | ICOS | CD8 | CD3δ |
| CD19 | ICOS | CD8 | CD3γ |
| CD19 | ICOS | CD8 | CD3ε |
| CD19 | ICOS | CD8 | FcγRI-γ |
| CD19 | ICOS | CD8 | FcγRIII-γ |
| CD19 | ICOS | CD8 | FcεRIβ |
| CD19 | ICOS | CD8 | FcεRIγ |
| CD19 | ICOS | CD8 | DAP10 |
| CD19 | ICOS | CD8 | DAP12 |
| CD19 | ICOS | CD8 | CD32 |
| CD19 | ICOS | CD8 | CD79a |
| CD19 | ICOS | CD8 | CD79b |
| CD19 | ICOS | CD4 | CD8 |
| CD19 | ICOS | CD4 | CD3ζ |
| CD19 | ICOS | CD4 | CD3δ |
| CD19 | ICOS | CD4 | CD3γ |
| CD19 | ICOS | CD4 | CD3ε |
| CD19 | ICOS | CD4 | FcγRI-γ |
| CD19 | ICOS | CD4 | FcγRIII-γ |
| CD19 | ICOS | CD4 | FcεRIβ |
| CD19 | ICOS | CD4 | FcεRIγ |
| CD19 | ICOS | CD4 | DAP10 |
| CD19 | ICOS | CD4 | DAP12 |
| CD19 | ICOS | CD4 | CD32 |
| CD19 | ICOS | CD4 | CD79a |
| CD19 | ICOS | CD4 | CD79b |
| CD19 | ICOS | b2c | CD8 |
| CD19 | ICOS | b2c | CD3ζ |
| CD19 | ICOS | b2c | CD3δ |
| CD19 | ICOS | b2c | CD3γ |
| CD19 | ICOS | b2c | CD3ε |
| CD19 | ICOS | b2c | FcγRI-γ |
| CD19 | ICOS | b2c | FcγRIII-γ |
| CD19 | ICOS | b2c | FcεRIβ |
| CD19 | ICOS | b2c | FcεRIγ |
| CD19 | ICOS | b2c | DAP10 |
| CD19 | ICOS | b2c | DAP12 |
| CD19 | ICOS | b2c | CD32 |
| CD19 | ICOS | b2c | CD79a |
| CD19 | ICOS | b2c | CD79b |
| CD19 | ICOS | CD137/41BB | CD8 |
| CD19 | ICOS | CD137/41BB | CD3ζ |
| CD19 | ICOS | CD137/41BB | CD3δ |
| CD19 | ICOS | CD137/41BB | CD3γ |
| CD19 | ICOS | CD137/41BB | CD3ε |

TABLE 3-continued

Third Generation CARs

| ScFv | Co-stimulatory Signal | Co-stimulatory Signal | Signal Domain |
|------|------|------|------|
| CD19 | ICOS | CD137/41BB | FcγRI-γ |
| CD19 | ICOS | CD137/41BB | FcγRIII-γ |
| CD19 | ICOS | CD137/41BB | FcεRIβ |
| CD19 | ICOS | CD137/41BB | FcεRIγ |
| CD19 | ICOS | CD137/41BB | DAP10 |
| CD19 | ICOS | CD137/41BB | DAP12 |
| CD19 | ICOS | CD137/41BB | CD32 |
| CD19 | ICOS | CD137/41BB | CD79a |
| CD19 | ICOS | CD137/41BB | CD79b |
| CD19 | ICOS | ICOS | CD8 |
| CD19 | ICOS | ICOS | CD3ζ |
| CD19 | ICOS | ICOS | CD3δ |
| CD19 | ICOS | ICOS | CD3γ |
| CD19 | ICOS | ICOS | CD3ε |
| CD19 | ICOS | ICOS | FcγRI-γ |
| CD19 | ICOS | ICOS | FcγRIII-γ |
| CD19 | ICOS | ICOS | FcεRIβ |
| CD19 | ICOS | ICOS | FcεRIγ |
| CD19 | ICOS | ICOS | DAP10 |
| CD19 | ICOS | ICOS | DAP12 |
| CD19 | ICOS | ICOS | CD32 |
| CD19 | ICOS | ICOS | CD79a |
| CD19 | ICOS | ICOS | CD79b |
| CD19 | ICOS | CD27 | CD8 |
| CD19 | ICOS | CD27 | CD3ζ |
| CD19 | ICOS | CD27 | CD3δ |
| CD19 | ICOS | CD27 | CD3γ |
| CD19 | ICOS | CD27 | CD3ε |
| CD19 | ICOS | CD27 | FcγRI-γ |
| CD19 | ICOS | CD27 | FcγRIII-γ |
| CD19 | ICOS | CD27 | FcεRIβ |
| CD19 | ICOS | CD27 | FcεRIγ |
| CD19 | ICOS | CD27 | DAP10 |
| CD19 | ICOS | CD27 | DAP12 |
| CD19 | ICOS | CD27 | CD32 |
| CD19 | ICOS | CD27 | CD79a |
| CD19 | ICOS | CD27 | CD79b |
| CD19 | ICOS | CD28δ | CD8 |
| CD19 | ICOS | CD28δ | CD3ζ |
| CD19 | ICOS | CD28δ | CD3δ |
| CD19 | ICOS | CD28δ | CD3γ |
| CD19 | ICOS | CD28δ | CD3ε |
| CD19 | ICOS | CD28δ | FcγRI-γ |
| CD19 | ICOS | CD28δ | FcγRIII-γ |
| CD19 | ICOS | CD28δ | FcεRIβ |
| CD19 | ICOS | CD28δ | FcεRIγ |
| CD19 | ICOS | CD28δ | DAP10 |
| CD19 | ICOS | CD28δ | DAP12 |
| CD19 | ICOS | CD28δ | CD32 |
| CD19 | ICOS | CD28δ | CD79a |
| CD19 | ICOS | CD28δ | CD79b |
| CD19 | ICOS | CD80 | CD8 |
| CD19 | ICOS | CD80 | CD3ζ |
| CD19 | ICOS | CD80 | CD3δ |
| CD19 | ICOS | CD80 | CD3γ |
| CD19 | ICOS | CD80 | CD3ε |
| CD19 | ICOS | CD80 | FcγRI-γ |
| CD19 | ICOS | CD80 | FcγRIII-γ |
| CD19 | ICOS | CD80 | FcεRIβ |
| CD19 | ICOS | CD80 | FcεRIγ |
| CD19 | ICOS | CD80 | DAP10 |
| CD19 | ICOS | CD80 | DAP12 |
| CD19 | ICOS | CD80 | CD32 |
| CD19 | ICOS | CD80 | CD79a |
| CD19 | ICOS | CD80 | CD79b |
| CD19 | ICOS | CD86 | CD8 |
| CD19 | ICOS | CD86 | CD3ζ |
| CD19 | ICOS | CD86 | CD3δ |
| CD19 | ICOS | CD86 | CD3γ |
| CD19 | ICOS | CD86 | CD3ε |
| CD19 | ICOS | CD86 | FcγRI-γ |
| CD19 | ICOS | CD86 | FcγRIII-γ |
| CD19 | ICOS | CD86 | FcεRIβ |
| CD19 | ICOS | CD86 | FcεRIγ |
| CD19 | ICOS | CD86 | DAP10 |

TABLE 3-continued

Third Generation CARs

| ScFv | Co-stimulatory Signal | Co-stimulatory Signal | Signal Domain |
|------|------|------|------|
| CD19 | ICOS | CD86 | DAP12 |
| CD19 | ICOS | CD86 | CD32 |
| CD19 | ICOS | CD86 | CD79a |
| CD19 | ICOS | CD86 | CD79b |
| CD19 | ICOS | OX40 | CD8 |
| CD19 | ICOS | OX40 | CD3ζ |
| CD19 | ICOS | OX40 | CD3δ |
| CD19 | ICOS | OX40 | CD3γ |
| CD19 | ICOS | OX40 | CD3ε |
| CD19 | ICOS | OX40 | FcγRI-γ |
| CD19 | ICOS | OX40 | FcγRIII-γ |
| CD19 | ICOS | OX40 | FcεRIβ |
| CD19 | ICOS | OX40 | FcεRIγ |
| CD19 | ICOS | OX40 | DAP10 |
| CD19 | ICOS | OX40 | DAP12 |
| CD19 | ICOS | OX40 | CD32 |
| CD19 | ICOS | OX40 | CD79a |
| CD19 | ICOS | OX40 | CD79b |
| CD19 | ICOS | DAP10 | CD8 |
| CD19 | ICOS | DAP10 | CD3ζ |
| CD19 | ICOS | DAP10 | CD3δ |
| CD19 | ICOS | DAP10 | CD3γ |
| CD19 | ICOS | DAP10 | CD3ε |
| CD19 | ICOS | DAP10 | FcγRI-γ |
| CD19 | ICOS | DAP10 | FcγRIII-γ |
| CD19 | ICOS | DAP10 | FcεRIβ |
| CD19 | ICOS | DAP10 | FcεRIγ |
| CD19 | ICOS | DAP10 | DAP10 |
| CD19 | ICOS | DAP10 | DAP12 |
| CD19 | ICOS | DAP10 | CD32 |
| CD19 | ICOS | DAP10 | CD79a |
| CD19 | ICOS | DAP10 | CD79b |
| CD19 | ICOS | DAP12 | CD8 |
| CD19 | ICOS | DAP12 | CD3ζ |
| CD19 | ICOS | DAP12 | CD3δ |
| CD19 | ICOS | DAP12 | CD3γ |
| CD19 | ICOS | DAP12 | CD3ε |
| CD19 | ICOS | DAP12 | FcγRI-γ |
| CD19 | ICOS | DAP12 | FcγRIII-γ |
| CD19 | ICOS | DAP12 | FcεRIβ |
| CD19 | ICOS | DAP12 | FcεRIγ |
| CD19 | ICOS | DAP12 | DAP10 |
| CD19 | ICOS | DAP12 | DAP12 |
| CD19 | ICOS | DAP12 | CD32 |
| CD19 | ICOS | DAP12 | CD79a |
| CD19 | ICOS | DAP12 | CD79b |
| CD19 | ICOS | MyD88 | CD8 |
| CD19 | ICOS | MyD88 | CD3ζ |
| CD19 | ICOS | MyD88 | CD3δ |
| CD19 | ICOS | MyD88 | CD3γ |
| CD19 | ICOS | MyD88 | CD3ε |
| CD19 | ICOS | MyD88 | FcγRI-γ |
| CD19 | ICOS | MyD88 | FcγRIII-γ |
| CD19 | ICOS | MyD88 | FcεRIβ |
| CD19 | ICOS | MyD88 | FcεRIγ |
| CD19 | ICOS | MyD88 | DAP10 |
| CD19 | ICOS | MyD88 | DAP12 |
| CD19 | ICOS | MyD88 | CD32 |
| CD19 | ICOS | MyD88 | CD79a |
| CD19 | ICOS | MyD88 | CD79b |
| CD19 | ICOS | CD7 | CD8 |
| CD19 | ICOS | CD7 | CD3ζ |
| CD19 | ICOS | CD7 | CD3δ |
| CD19 | ICOS | CD7 | CD3γ |
| CD19 | ICOS | CD7 | CD3ε |
| CD19 | ICOS | CD7 | FcγRI-γ |
| CD19 | ICOS | CD7 | FcγRIII-γ |
| CD19 | ICOS | CD7 | FcεRIβ |
| CD19 | ICOS | CD7 | FcεRIγ |
| CD19 | ICOS | CD7 | DAP10 |
| CD19 | ICOS | CD7 | DAP12 |
| CD19 | ICOS | CD7 | CD32 |
| CD19 | ICOS | CD7 | CD79a |
| CD19 | ICOS | CD7 | CD79b |
| CD19 | ICOS | BTNL3 | CD8 |

TABLE 3-continued

| Third Generation CARs | | | |
|---|---|---|---|
| ScFv | Co-stimulatory Signal | Co-stimulatory Signal | Signal Domain |
| CD19 | ICOS | BTNL3 | CD3ζ |
| CD19 | ICOS | BTNL3 | CD3δ |
| CD19 | ICOS | BTNL3 | CD3γ |
| CD19 | ICOS | BTNL3 | CD3ε |
| CD19 | ICOS | BTNL3 | FcγRI-γ |
| CD19 | ICOS | BTNL3 | FcγRIII-γ |
| CD19 | ICOS | BTNL3 | FcεRIβ |
| CD19 | ICOS | BTNL3 | FcεRIγ |
| CD19 | ICOS | BTNL3 | DAP10 |
| CD19 | ICOS | BTNL3 | DAP12 |
| CD19 | ICOS | BTNL3 | CD32 |
| CD19 | ICOS | BTNL3 | CD79a |
| CD19 | ICOS | BTNL3 | CD79b |
| CD19 | ICOS | NKG2D | CD8 |
| CD19 | ICOS | NKG2D | CD3ζ |
| CD19 | ICOS | NKG2D | CD3δ |
| CD19 | ICOS | NKG2D | CD3γ |
| CD19 | ICOS | NKG2D | CD3ε |
| CD19 | ICOS | NKG2D | FcγRI-γ |
| CD19 | ICOS | NKG2D | FcγRIII-γ |
| CD19 | ICOS | NKG2D | FcεRIβ |
| CD19 | ICOS | NKG2D | FcεRIγ |
| CD19 | ICOS | NKG2D | DAP10 |
| CD19 | ICOS | NKG2D | DAP12 |
| CD19 | ICOS | NKG2D | CD32 |
| CD19 | ICOS | NKG2D | CD79a |
| CD19 | ICOS | NKG2D | CD79b |
| CD19 | CD27 | CD28 | CD8 |
| CD19 | CD27 | CD28 | CD3ζ |
| CD19 | CD27 | CD28 | CD3δ |
| CD19 | CD27 | CD28 | CD3γ |
| CD19 | CD27 | CD28 | CD3ε |
| CD19 | CD27 | CD28 | FcγRI-γ |
| CD19 | CD27 | CD28 | FcγRIII-γ |
| CD19 | CD27 | CD28 | FcεRIβ |
| CD19 | CD27 | CD28 | FcεRIγ |
| CD19 | CD27 | CD28 | DAP10 |
| CD19 | CD27 | CD28 | DAP12 |
| CD19 | CD27 | CD28 | CD32 |
| CD19 | CD27 | CD28 | CD79a |
| CD19 | CD27 | CD28 | CD79b |
| CD19 | CD27 | CD8 | CD8 |
| CD19 | CD27 | CD8 | CD3ζ |
| CD19 | CD27 | CD8 | CD3δ |
| CD19 | CD27 | CD8 | CD3γ |
| CD19 | CD27 | CD8 | CD3ε |
| CD19 | CD27 | CD8 | FcγRI-γ |
| CD19 | CD27 | CD8 | FcγRIII-γ |
| CD19 | CD27 | CD8 | FcεRIβ |
| CD19 | CD27 | CD8 | FcεRIγ |
| CD19 | CD27 | CD8 | DAP10 |
| CD19 | CD27 | CD8 | DAP12 |
| CD19 | CD27 | CD8 | CD32 |
| CD19 | CD27 | CD8 | CD79a |
| CD19 | CD27 | CD8 | CD79b |
| CD19 | CD27 | CD4 | CD8 |
| CD19 | CD27 | CD4 | CD3ζ |
| CD19 | CD27 | CD4 | CD3δ |
| CD19 | CD27 | CD4 | CD3γ |
| CD19 | CD27 | CD4 | CD3ε |
| CD19 | CD27 | CD4 | FcγRI-γ |
| CD19 | CD27 | CD4 | FcγRIII-γ |
| CD19 | CD27 | CD4 | FcεRIβ |
| CD19 | CD27 | CD4 | FcεRIγ |
| CD19 | CD27 | CD4 | DAP10 |
| CD19 | CD27 | CD4 | DAP12 |
| CD19 | CD27 | CD4 | CD32 |
| CD19 | CD27 | CD4 | CD79a |
| CD19 | CD27 | CD4 | CD79b |
| CD19 | CD27 | b2c | CD8 |
| CD19 | CD27 | b2c | CD3ζ |
| CD19 | CD27 | b2c | CD3δ |
| CD19 | CD27 | b2c | CD3γ |
| CD19 | CD27 | b2c | CD3ε |
| CD19 | CD27 | b2c | FcγRI-γ |
| CD19 | CD27 | b2c | FcγRIII-γ |
| CD19 | CD27 | b2c | FcεRIβ |
| CD19 | CD27 | b2c | FcεRIγ |
| CD19 | CD27 | b2c | DAP10 |
| CD19 | CD27 | b2c | DAP12 |
| CD19 | CD27 | b2c | CD32 |
| CD19 | CD27 | b2c | CD79a |
| CD19 | CD27 | b2c | CD79b |
| CD19 | CD27 | CD137/41BB | CD8 |
| CD19 | CD27 | CD137/41BB | CD3ζ |
| CD19 | CD27 | CD137/41BB | CD3δ |
| CD19 | CD27 | CD137/41BB | CD3γ |
| CD19 | CD27 | CD137/41BB | CD3ε |
| CD19 | CD27 | CD137/41BB | FcγRI-γ |
| CD19 | CD27 | CD137/41BB | FcγRIII-γ |
| CD19 | CD27 | CD137/41BB | FcεRIβ |
| CD19 | CD27 | CD137/41BB | FcεRIγ |
| CD19 | CD27 | CD137/41BB | DAP10 |
| CD19 | CD27 | CD137/41BB | DAP12 |
| CD19 | CD27 | CD137/41BB | CD32 |
| CD19 | CD27 | CD137/41BB | CD79a |
| CD19 | CD27 | CD137/41BB | CD79b |
| CD19 | CD27 | ICOS | CD8 |
| CD19 | CD27 | ICOS | CD3ζ |
| CD19 | CD27 | ICOS | CD3δ |
| CD19 | CD27 | ICOS | CD3γ |
| CD19 | CD27 | ICOS | CD3ε |
| CD19 | CD27 | ICOS | FcγRI-γ |
| CD19 | CD27 | ICOS | FcγRIII-γ |
| CD19 | CD27 | ICOS | FcεRIβ |
| CD19 | CD27 | ICOS | FcεRIγ |
| CD19 | CD27 | ICOS | DAP10 |
| CD19 | CD27 | ICOS | DAP12 |
| CD19 | CD27 | ICOS | CD32 |
| CD19 | CD27 | ICOS | CD79a |
| CD19 | CD27 | ICOS | CD79b |
| CD19 | CD27 | CD27 | CD8 |
| CD19 | CD27 | CD27 | CD3ζ |
| CD19 | CD27 | CD27 | CD3δ |
| CD19 | CD27 | CD27 | CD3γ |
| CD19 | CD27 | CD27 | CD3ε |
| CD19 | CD27 | CD27 | FcγRI-γ |
| CD19 | CD27 | CD27 | FcγRIII-γ |
| CD19 | CD27 | CD27 | FcεRIβ |
| CD19 | CD27 | CD27 | FcεRIγ |
| CD19 | CD27 | CD27 | DAP10 |
| CD19 | CD27 | CD27 | DAP12 |
| CD19 | CD27 | CD27 | CD32 |
| CD19 | CD27 | CD27 | CD79a |
| CD19 | CD27 | CD27 | CD79b |
| CD19 | CD27 | CD28δ | CD8 |
| CD19 | CD27 | CD28δ | CD3ζ |
| CD19 | CD27 | CD28δ | CD3δ |
| CD19 | CD27 | CD28δ | CD3γ |
| CD19 | CD27 | CD28δ | CD3ε |
| CD19 | CD27 | CD28δ | FcγRI-γ |
| CD19 | CD27 | CD28δ | FcγRIII-γ |
| CD19 | CD27 | CD28δ | FcεRIβ |
| CD19 | CD27 | CD28δ | FcεRIγ |
| CD19 | CD27 | CD28δ | DAP10 |
| CD19 | CD27 | CD28δ | DAP12 |
| CD19 | CD27 | CD28δ | CD32 |
| CD19 | CD27 | CD28δ | CD79a |
| CD19 | CD27 | CD28δ | CD79b |
| CD19 | CD27 | CD80 | CD8 |
| CD19 | CD27 | CD80 | CD3ζ |
| CD19 | CD27 | CD80 | CD3δ |
| CD19 | CD27 | CD80 | CD3γ |
| CD19 | CD27 | CD80 | CD3ε |
| CD19 | CD27 | CD80 | FcγRI-γ |
| CD19 | CD27 | CD80 | FcγRIII-γ |
| CD19 | CD27 | CD80 | FcεRIβ |
| CD19 | CD27 | CD80 | FcεRIγ |
| CD19 | CD27 | CD80 | DAP10 |
| CD19 | CD27 | CD80 | DAP12 |

TABLE 3-continued

Third Generation CARs

| ScFv | Co-stimulatory Signal | Co-stimulatory Signal | Signal Domain |
|---|---|---|---|
| CD19 | CD27 | CD80 | CD32 |
| CD19 | CD27 | CD80 | CD79a |
| CD19 | CD27 | CD80 | CD79b |
| CD19 | CD27 | CD86 | CD8 |
| CD19 | CD27 | CD86 | CD3ζ |
| CD19 | CD27 | CD86 | CD3δ |
| CD19 | CD27 | CD86 | CD3γ |
| CD19 | CD27 | CD86 | CD3ε |
| CD19 | CD27 | CD86 | FcγRI-γ |
| CD19 | CD27 | CD86 | FcγRIII-γ |
| CD19 | CD27 | CD86 | FcεRIβ |
| CD19 | CD27 | CD86 | FcεRIγ |
| CD19 | CD27 | CD86 | DAP10 |
| CD19 | CD27 | CD86 | DAP12 |
| CD19 | CD27 | CD86 | CD32 |
| CD19 | CD27 | CD86 | CD79a |
| CD19 | CD27 | CD86 | CD79b |
| CD19 | CD27 | OX40 | CD8 |
| CD19 | CD27 | OX40 | CD3ζ |
| CD19 | CD27 | OX40 | CD3δ |
| CD19 | CD27 | OX40 | CD3γ |
| CD19 | CD27 | OX40 | CD3ε |
| CD19 | CD27 | OX40 | FcγRI-γ |
| CD19 | CD27 | OX40 | FcγRIII-γ |
| CD19 | CD27 | OX40 | FcεRIβ |
| CD19 | CD27 | OX40 | FcεRIγ |
| CD19 | CD27 | OX40 | DAP10 |
| CD19 | CD27 | OX40 | DAP12 |
| CD19 | CD27 | OX40 | CD32 |
| CD19 | CD27 | OX40 | CD79a |
| CD19 | CD27 | OX40 | CD79b |
| CD19 | CD27 | DAP10 | CD8 |
| CD19 | CD27 | DAP10 | CD3ζ |
| CD19 | CD27 | DAP10 | CD3δ |
| CD19 | CD27 | DAP10 | CD3γ |
| CD19 | CD27 | DAP10 | CD3ε |
| CD19 | CD27 | DAP10 | FcγRI-γ |
| CD19 | CD27 | DAP10 | FcγRIII-γ |
| CD19 | CD27 | DAP10 | FcεRIβ |
| CD19 | CD27 | DAP10 | FcεRIγ |
| CD19 | CD27 | DAP10 | DAP10 |
| CD19 | CD27 | DAP10 | DAP12 |
| CD19 | CD27 | DAP10 | CD32 |
| CD19 | CD27 | DAP10 | CD79a |
| CD19 | CD27 | DAP10 | CD79b |
| CD19 | CD27 | DAP12 | CD8 |
| CD19 | CD27 | DAP12 | CD3ζ |
| CD19 | CD27 | DAP12 | CD3δ |
| CD19 | CD27 | DAP12 | CD3γ |
| CD19 | CD27 | DAP12 | CD3ε |
| CD19 | CD27 | DAP12 | FcγRI-γ |
| CD19 | CD27 | DAP12 | FcγRIII-γ |
| CD19 | CD27 | DAP12 | FcεRIβ |
| CD19 | CD27 | DAP12 | FcεRIγ |
| CD19 | CD27 | DAP12 | DAP10 |
| CD19 | CD27 | DAP12 | DAP12 |
| CD19 | CD27 | DAP12 | CD32 |
| CD19 | CD27 | DAP12 | CD79a |
| CD19 | CD27 | DAP12 | CD79b |
| CD19 | CD27 | MyD88 | CD8 |
| CD19 | CD27 | MyD88 | CD3ζ |
| CD19 | CD27 | MyD88 | CD3δ |
| CD19 | CD27 | MyD88 | CD3γ |
| CD19 | CD27 | MyD88 | CD3ε |
| CD19 | CD27 | MyD88 | FcγRI-γ |
| CD19 | CD27 | MyD88 | FcγRIII-γ |
| CD19 | CD27 | MyD88 | FcεRIβ |
| CD19 | CD27 | MyD88 | FcεRIγ |
| CD19 | CD27 | MyD88 | DAP10 |
| CD19 | CD27 | MyD88 | DAP12 |
| CD19 | CD27 | MyD88 | CD32 |
| CD19 | CD27 | MyD88 | CD79a |
| CD19 | CD27 | MyD88 | CD79b |
| CD19 | CD27 | CD7 | CD8 |
| CD19 | CD27 | CD7 | CD3ζ |
| CD19 | CD27 | CD7 | CD3δ |
| CD19 | CD27 | CD7 | CD3γ |
| CD19 | CD27 | CD7 | CD3ε |
| CD19 | CD27 | CD7 | FcγRI-γ |
| CD19 | CD27 | CD7 | FcγRIII-γ |
| CD19 | CD27 | CD7 | FcεRIβ |
| CD19 | CD27 | CD7 | FcεRIγ |
| CD19 | CD27 | CD7 | DAP10 |
| CD19 | CD27 | CD7 | DAP12 |
| CD19 | CD27 | CD7 | CD32 |
| CD19 | CD27 | CD7 | CD79a |
| CD19 | CD27 | CD7 | CD79b |
| CD19 | CD27 | BTNL3 | CD8 |
| CD19 | CD27 | BTNL3 | CD3ζ |
| CD19 | CD27 | BTNL3 | CD3δ |
| CD19 | CD27 | BTNL3 | CD3γ |
| CD19 | CD27 | BTNL3 | CD3ε |
| CD19 | CD27 | BTNL3 | FcγRI-γ |
| CD19 | CD27 | BTNL3 | FcγRIII-γ |
| CD19 | CD27 | BTNL3 | FcεRIβ |
| CD19 | CD27 | BTNL3 | FcεRIγ |
| CD19 | CD27 | BTNL3 | DAP10 |
| CD19 | CD27 | BTNL3 | DAP12 |
| CD19 | CD27 | BTNL3 | CD32 |
| CD19 | CD27 | BTNL3 | CD79a |
| CD19 | CD27 | BTNL3 | CD79b |
| CD19 | CD27 | NKG2D | CD8 |
| CD19 | CD27 | NKG2D | CD3ζ |
| CD19 | CD27 | NKG2D | CD3δ |
| CD19 | CD27 | NKG2D | CD3γ |
| CD19 | CD27 | NKG2D | CD3ε |
| CD19 | CD27 | NKG2D | FcγRI-γ |
| CD19 | CD27 | NKG2D | FcγRIII-γ |
| CD19 | CD27 | NKG2D | FcεRIβ |
| CD19 | CD27 | NKG2D | FcεRIγ |
| CD19 | CD27 | NKG2D | DAP10 |
| CD19 | CD27 | NKG2D | DAP12 |
| CD19 | CD27 | NKG2D | CD32 |
| CD19 | CD27 | NKG2D | CD79a |
| CD19 | CD27 | NKG2D | CD79b |
| CD19 | CD28δ | CD28 | CD8 |
| CD19 | CD28δ | CD28 | CD3ζ |
| CD19 | CD28δ | CD28 | CD3δ |
| CD19 | CD28δ | CD28 | CD3γ |
| CD19 | CD28δ | CD28 | CD3ε |
| CD19 | CD28δ | CD28 | FcγRI-γ |
| CD19 | CD28δ | CD28 | FcγRIII-γ |
| CD19 | CD28δ | CD28 | FcεRIβ |
| CD19 | CD28δ | CD28 | FcεRIγ |
| CD19 | CD28δ | CD28 | DAP10 |
| CD19 | CD28δ | CD28 | DAP12 |
| CD19 | CD28δ | CD28 | CD32 |
| CD19 | CD28δ | CD28 | CD79a |
| CD19 | CD28δ | CD28 | CD79b |
| CD19 | CD28δ | CD8 | CD8 |
| CD19 | CD28δ | CD8 | CD3ζ |
| CD19 | CD28δ | CD8 | CD3δ |
| CD19 | CD28δ | CD8 | CD3γ |
| CD19 | CD28δ | CD8 | CD3ε |
| CD19 | CD28δ | CD8 | FcγRI-γ |
| CD19 | CD28δ | CD8 | FcγRIII-γ |
| CD19 | CD28δ | CD8 | FcεRIβ |
| CD19 | CD28δ | CD8 | FcεRIγ |
| CD19 | CD28δ | CD8 | DAP10 |
| CD19 | CD28δ | CD8 | DAP12 |
| CD19 | CD28δ | CD8 | CD32 |
| CD19 | CD28δ | CD8 | CD79a |
| CD19 | CD28δ | CD8 | CD79b |
| CD19 | CD28δ | CD4 | CD8 |
| CD19 | CD28δ | CD4 | CD3ζ |
| CD19 | CD28δ | CD4 | CD3δ |
| CD19 | CD28δ | CD4 | CD3γ |
| CD19 | CD28δ | CD4 | CD3ε |
| CD19 | CD28δ | CD4 | FcγRI-γ |
| CD19 | CD28δ | CD4 | FcγRIII-γ |

43 44

TABLE 3-continued

| Third Generation CARs | | | | | Third Generation CARs | | | |
|---|---|---|---|---|---|---|---|---|
| ScFv | Co-stimulatory Signal | Co-stimulatory Signal | Signal Domain | 5 | ScFv | Co-stimulatory Signal | Co-stimulatory Signal | Signal Domain |
| CD19 | CD28δ | CD4 | FcεRIβ | | CD19 | CD28δ | CD28δ | CD79a |
| CD19 | CD28δ | CD4 | FcεRIγ | | CD19 | CD28δ | CD28δ | CD79b |
| CD19 | CD28δ | CD4 | DAP10 | | CD19 | CD28δ | CD80 | CD8 |
| CD19 | CD28δ | CD4 | DAP12 | | CD19 | CD28δ | CD80 | CD3ζ |
| CD19 | CD28δ | CD4 | CD32 | 10 | CD19 | CD28δ | CD80 | CD3δ |
| CD19 | CD28δ | CD4 | CD79a | | CD19 | CD28δ | CD80 | CD3γ |
| CD19 | CD28δ | CD4 | CD79b | | CD19 | CD28δ | CD80 | CD3ε |
| CD19 | CD28δ | b2c | CD8 | | CD19 | CD28δ | CD80 | FcγRI-γ |
| CD19 | CD28δ | b2c | CD3ζ | | CD19 | CD28δ | CD80 | FcγRIII-γ |
| CD19 | CD28δ | b2c | CD3δ | | CD19 | CD28δ | CD80 | FcεRIβ |
| CD19 | CD28δ | b2c | CD3γ | 15 | CD19 | CD28δ | CD80 | FcεRIγ |
| CD19 | CD28δ | b2c | CD3ε | | CD19 | CD28δ | CD80 | DAP10 |
| CD19 | CD28δ | b2c | FcγRI-γ | | CD19 | CD28δ | CD80 | DAP12 |
| CD19 | CD28δ | b2c | FcγRIII-γ | | CD19 | CD28δ | CD80 | CD32 |
| CD19 | CD28δ | b2c | FcεRIβ | | CD19 | CD28δ | CD80 | CD79a |
| CD19 | CD28δ | b2c | FcεRIγ | | CD19 | CD28δ | CD80 | CD79b |
| CD19 | CD28δ | b2c | DAP10 | | CD19 | CD28δ | CD86 | CD8 |
| CD19 | CD28δ | b2c | DAP12 | 20 | CD19 | CD28δ | CD86 | CD3ζ |
| CD19 | CD28δ | b2c | CD32 | | CD19 | CD28δ | CD86 | CD3δ |
| CD19 | CD28δ | b2c | CD79a | | CD19 | CD28δ | CD86 | CD3γ |
| CD19 | CD28δ | b2c | CD79b | | CD19 | CD28δ | CD86 | CD3ε |
| CD19 | CD28δ | CD137/41BB | CD8 | | CD19 | CD28δ | CD86 | FcγRI-γ |
| CD19 | CD28δ | CD137/41BB | CD3ζ | | CD19 | CD28δ | CD86 | FcγRIII-γ |
| CD19 | CD28δ | CD137/41BB | CD3δ | 25 | CD19 | CD28δ | CD86 | FcεRIβ |
| CD19 | CD28δ | CD137/41BB | CD3γ | | CD19 | CD28δ | CD86 | FcεRIγ |
| CD19 | CD28δ | CD137/41BB | CD3ε | | CD19 | CD28δ | CD86 | DAP10 |
| CD19 | CD28δ | CD137/41BB | FcγRI-γ | | CD19 | CD28δ | CD86 | DAP12 |
| CD19 | CD28δ | CD137/41BB | FcγRIII-γ | | CD19 | CD28δ | CD86 | CD32 |
| CD19 | CD28δ | CD137/41BB | FcεRIβ | | CD19 | CD28δ | CD86 | CD79a |
| CD19 | CD28δ | CD137/41BB | FcεRIγ | 30 | CD19 | CD28δ | CD86 | CD79b |
| CD19 | CD28δ | CD137/41BB | DAP10 | | CD19 | CD28δ | OX40 | CD8 |
| CD19 | CD28δ | CD137/41BB | DAP12 | | CD19 | CD28δ | OX40 | CD3ζ |
| CD19 | CD28δ | CD137/41BB | CD32 | | CD19 | CD28δ | OX40 | CD3δ |
| CD19 | CD28δ | CD137/41BB | CD79a | | CD19 | CD28δ | OX40 | CD3γ |
| CD19 | CD28δ | CD137/41BB | CD79b | | CD19 | CD28δ | OX40 | CD3ε |
| CD19 | CD28δ | ICOS | CD8 | 35 | CD19 | CD28δ | OX40 | FcγRI-γ |
| CD19 | CD28δ | ICOS | CD3ζ | | CD19 | CD28δ | OX40 | FcγRIII-γ |
| CD19 | CD28δ | ICOS | CD3δ | | CD19 | CD28δ | OX40 | FcεRIβ |
| CD19 | CD28δ | ICOS | CD3γ | | CD19 | CD28δ | OX40 | FcεRIγ |
| CD19 | CD28δ | ICOS | CD3ε | | CD19 | CD28δ | OX40 | DAP10 |
| CD19 | CD28δ | ICOS | FcγRI-γ | | CD19 | CD28δ | OX40 | DAP12 |
| CD19 | CD28δ | ICOS | FcγRIII-γ | | CD19 | CD28δ | OX40 | CD32 |
| CD19 | CD28δ | ICOS | FcεRIβ | 40 | CD19 | CD28δ | OX40 | CD79a |
| CD19 | CD28δ | ICOS | FcεRIγ | | CD19 | CD28δ | OX40 | CD79b |
| CD19 | CD28δ | ICOS | DAP10 | | CD19 | CD28δ | DAP10 | CD8 |
| CD19 | CD28δ | ICOS | DAP12 | | CD19 | CD28δ | DAP10 | CD3ζ |
| CD19 | CD28δ | ICOS | CD32 | | CD19 | CD28δ | DAP10 | CD3δ |
| CD19 | CD28δ | ICOS | CD79a | | CD19 | CD28δ | DAP10 | CD3γ |
| CD19 | CD28δ | ICOS | CD79b | 45 | CD19 | CD28δ | DAP10 | CD3ε |
| CD19 | CD28δ | CD27 | CD8 | | CD19 | CD28δ | DAP10 | FcγRI-γ |
| CD19 | CD28δ | CD27 | CD3ζ | | CD19 | CD28δ | DAP10 | FcγRIII-γ |
| CD19 | CD28δ | CD27 | CD3δ | | CD19 | CD28δ | DAP10 | FcεRIβ |
| CD19 | CD28δ | CD27 | CD3γ | | CD19 | CD28δ | DAP10 | FcεRIγ |
| CD19 | CD28δ | CD27 | CD3ε | | CD19 | CD28δ | DAP10 | DAP10 |
| CD19 | CD28δ | CD27 | FcγRI-γ | 50 | CD19 | CD28δ | DAP10 | DAP12 |
| CD19 | CD28δ | CD27 | FcγRIII-γ | | CD19 | CD28δ | DAP10 | CD32 |
| CD19 | CD28δ | CD27 | FcεRIβ | | CD19 | CD28δ | DAP10 | CD79a |
| CD19 | CD28δ | CD27 | FcεRIγ | | CD19 | CD28δ | DAP10 | CD79b |
| CD19 | CD28δ | CD27 | DAP10 | | CD19 | CD28δ | DAP12 | CD8 |
| CD19 | CD28δ | CD27 | DAP12 | | CD19 | CD28δ | DAP12 | CD3ζ |
| CD19 | CD28δ | CD27 | CD32 | 55 | CD19 | CD28δ | DAP12 | CD3δ |
| CD19 | CD28δ | CD27 | CD79a | | CD19 | CD28δ | DAP12 | CD3γ |
| CD19 | CD28δ | CD27 | CD79b | | CD19 | CD28δ | DAP12 | CD3ε |
| CD19 | CD28δ | CD28δ | CD8 | | CD19 | CD28δ | DAP12 | FcγRI-γ |
| CD19 | CD28δ | CD28δ | CD3ζ | | CD19 | CD28δ | DAP12 | FcγRIII-γ |
| CD19 | CD28δ | CD28δ | CD3δ | | CD19 | CD28δ | DAP12 | FcεRIβ |
| CD19 | CD28δ | CD28δ | CD3γ | | CD19 | CD28δ | DAP12 | FcεRIγ |
| CD19 | CD28δ | CD28δ | CD3ε | 60 | CD19 | CD28δ | DAP12 | DAP10 |
| CD19 | CD28δ | CD28δ | FcγRI-γ | | CD19 | CD28δ | DAP12 | DAP12 |
| CD19 | CD28δ | CD28δ | FcγRIII-γ | | CD19 | CD28δ | DAP12 | CD32 |
| CD19 | CD28δ | CD28δ | FcεRIβ | | CD19 | CD28δ | DAP12 | CD79a |
| CD19 | CD28δ | CD28δ | FcεRIγ | | CD19 | CD28δ | DAP12 | CD79b |
| CD19 | CD28δ | CD28δ | DAP10 | | CD19 | CD28δ | MyD88 | CD8 |
| CD19 | CD28δ | CD28δ | DAP12 | 65 | CD19 | CD28δ | MyD88 | CD3ζ |
| CD19 | CD28δ | CD28δ | CD32 | | CD19 | CD28δ | MyD88 | CD3δ |

TABLE 3-continued

Third Generation CARs

| ScFv | Co-stimulatory Signal | Co-stimulatory Signal | Signal Domain |
| --- | --- | --- | --- |
| CD19 | CD28δ | MyD88 | CD3γ |
| CD19 | CD28δ | MyD88 | CD3ε |
| CD19 | CD28δ | MyD88 | FcγRI-γ |
| CD19 | CD28δ | MyD88 | FcγRIII-γ |
| CD19 | CD28δ | MyD88 | FcεRIβ |
| CD19 | CD28δ | MyD88 | FcεRIγ |
| CD19 | CD28δ | MyD88 | DAP10 |
| CD19 | CD28δ | MyD88 | DAP12 |
| CD19 | CD28δ | MyD88 | CD32 |
| CD19 | CD28δ | MyD88 | CD79a |
| CD19 | CD28δ | MyD88 | CD79b |
| CD19 | CD28δ | CD7 | CD8 |
| CD19 | CD28δ | CD7 | CD3ζ |
| CD19 | CD28δ | CD7 | CD3δ |
| CD19 | CD28δ | CD7 | CD3γ |
| CD19 | CD28δ | CD7 | CD3ε |
| CD19 | CD28δ | CD7 | FcγRI-γ |
| CD19 | CD28δ | CD7 | FcγRIII-γ |
| CD19 | CD28δ | CD7 | FcεRIβ |
| CD19 | CD28δ | CD7 | FcεRIγ |
| CD19 | CD28δ | CD7 | DAP10 |
| CD19 | CD28δ | CD7 | DAP12 |
| CD19 | CD28δ | CD7 | CD32 |
| CD19 | CD28δ | CD7 | CD79a |
| CD19 | CD28δ | CD7 | CD79b |
| CD19 | CD28δ | BTNL3 | CD8 |
| CD19 | CD28δ | BTNL3 | CD3ζ |
| CD19 | CD28δ | BTNL3 | CD3δ |
| CD19 | CD28δ | BTNL3 | CD3γ |
| CD19 | CD28δ | BTNL3 | CD3ε |
| CD19 | CD28δ | BTNL3 | FcγRI-γ |
| CD19 | CD28δ | BTNL3 | FcγRIII-γ |
| CD19 | CD28δ | BTNL3 | FcεRIβ |
| CD19 | CD28δ | BTNL3 | FcεRIγ |
| CD19 | CD28δ | BTNL3 | DAP10 |
| CD19 | CD28δ | BTNL3 | DAP12 |
| CD19 | CD28δ | BTNL3 | CD32 |
| CD19 | CD28δ | BTNL3 | CD79a |
| CD19 | CD28δ | BTNL3 | CD79b |
| CD19 | CD28δ | NKG2D | CD8 |
| CD19 | CD28δ | NKG2D | CD3ζ |
| CD19 | CD28δ | NKG2D | CD3δ |
| CD19 | CD28δ | NKG2D | CD3γ |
| CD19 | CD28δ | NKG2D | CD3ε |
| CD19 | CD28δ | NKG2D | FcγRI-γ |
| CD19 | CD28δ | NKG2D | FcγRIII-γ |
| CD19 | CD28δ | NKG2D | FcεRIβ |
| CD19 | CD28δ | NKG2D | FcεRIγ |
| CD19 | CD28δ | NKG2D | DAP10 |
| CD19 | CD28δ | NKG2D | DAP12 |
| CD19 | CD28δ | NKG2D | CD32 |
| CD19 | CD28δ | NKG2D | CD79a |
| CD19 | CD28δ | NKG2D | CD79b |
| CD19 | CD80 | CD28 | CD8 |
| CD19 | CD80 | CD28 | CD3ζ |
| CD19 | CD80 | CD28 | CD3δ |
| CD19 | CD80 | CD28 | CD3γ |
| CD19 | CD80 | CD28 | CD3ε |
| CD19 | CD80 | CD28 | FcγRI-γ |
| CD19 | CD80 | CD28 | FcγRIII-γ |
| CD19 | CD80 | CD28 | FcεRIβ |
| CD19 | CD80 | CD28 | FcεRIγ |
| CD19 | CD80 | CD28 | DAP10 |
| CD19 | CD80 | CD28 | DAP12 |
| CD19 | CD80 | CD28 | CD32 |
| CD19 | CD80 | CD28 | CD79a |
| CD19 | CD80 | CD28 | CD79b |
| CD19 | CD80 | CD8 | CD8 |
| CD19 | CD80 | CD8 | CD3ζ |
| CD19 | CD80 | CD8 | CD3δ |
| CD19 | CD80 | CD8 | CD3γ |
| CD19 | CD80 | CD8 | CD3ε |
| CD19 | CD80 | CD8 | FcγRI-γ |
| CD19 | CD80 | CD8 | FcγRIII-γ |
| CD19 | CD80 | CD8 | FcεRIβ |

TABLE 3-continued

Third Generation CARs

| ScFv | Co-stimulatory Signal | Co-stimulatory Signal | Signal Domain |
| --- | --- | --- | --- |
| CD19 | CD80 | CD8 | FcεRIγ |
| CD19 | CD80 | CD8 | DAP10 |
| CD19 | CD80 | CD8 | DAP12 |
| CD19 | CD80 | CD8 | CD32 |
| CD19 | CD80 | CD8 | CD79a |
| CD19 | CD80 | CD8 | CD79b |
| CD19 | CD80 | CD4 | CD8 |
| CD19 | CD80 | CD4 | CD3ζ |
| CD19 | CD80 | CD4 | CD3δ |
| CD19 | CD80 | CD4 | CD3γ |
| CD19 | CD80 | CD4 | CD3ε |
| CD19 | CD80 | CD4 | FcγRI-γ |
| CD19 | CD80 | CD4 | FcγRIII-γ |
| CD19 | CD80 | CD4 | FcεRIβ |
| CD19 | CD80 | CD4 | FcεRIγ |
| CD19 | CD80 | CD4 | DAP10 |
| CD19 | CD80 | CD4 | DAP12 |
| CD19 | CD80 | CD4 | CD32 |
| CD19 | CD80 | CD4 | CD79a |
| CD19 | CD80 | CD4 | CD79b |
| CD19 | CD80 | b2c | CD8 |
| CD19 | CD80 | b2c | CD3ζ |
| CD19 | CD80 | b2c | CD3δ |
| CD19 | CD80 | b2c | CD3γ |
| CD19 | CD80 | b2c | CD3ε |
| CD19 | CD80 | b2c | FcγRI-γ |
| CD19 | CD80 | b2c | FcγRIII-γ |
| CD19 | CD80 | b2c | FcεRIβ |
| CD19 | CD80 | b2c | FcεRIγ |
| CD19 | CD80 | b2c | DAP10 |
| CD19 | CD80 | b2c | DAP12 |
| CD19 | CD80 | b2c | CD32 |
| CD19 | CD80 | b2c | CD79a |
| CD19 | CD80 | b2c | CD79b |
| CD19 | CD80 | CD137/41BB | CD8 |
| CD19 | CD80 | CD137/41BB | CD3ζ |
| CD19 | CD80 | CD137/41BB | CD3δ |
| CD19 | CD80 | CD137/41BB | CD3γ |
| CD19 | CD80 | CD137/41BB | CD3ε |
| CD19 | CD80 | CD137/41BB | FcγRI-γ |
| CD19 | CD80 | CD137/41BB | FcγRIII-γ |
| CD19 | CD80 | CD137/41BB | FcεRIβ |
| CD19 | CD80 | CD137/41BB | FcεRIγ |
| CD19 | CD80 | CD137/41BB | DAP10 |
| CD19 | CD80 | CD137/41BB | DAP12 |
| CD19 | CD80 | CD137/41BB | CD32 |
| CD19 | CD80 | CD137/41BB | CD79a |
| CD19 | CD80 | CD137/41BB | CD79b |
| CD19 | CD80 | ICOS | CD8 |
| CD19 | CD80 | ICOS | CD3ζ |
| CD19 | CD80 | ICOS | CD3δ |
| CD19 | CD80 | ICOS | CD3γ |
| CD19 | CD80 | ICOS | CD3ε |
| CD19 | CD80 | ICOS | FcγRI-γ |
| CD19 | CD80 | ICOS | FcγRIII-γ |
| CD19 | CD80 | ICOS | FcεRIβ |
| CD19 | CD80 | ICOS | FcεRIγ |
| CD19 | CD80 | ICOS | DAP10 |
| CD19 | CD80 | ICOS | DAP12 |
| CD19 | CD80 | ICOS | CD32 |
| CD19 | CD80 | ICOS | CD79a |
| CD19 | CD80 | ICOS | CD79b |
| CD19 | CD80 | CD27 | CD8 |
| CD19 | CD80 | CD27 | CD3ζ |
| CD19 | CD80 | CD27 | CD3δ |
| CD19 | CD80 | CD27 | CD3γ |
| CD19 | CD80 | CD27 | CD3ε |
| CD19 | CD80 | CD27 | FcγRI-γ |
| CD19 | CD80 | CD27 | FcγRIII-γ |
| CD19 | CD80 | CD27 | FcεRIβ |
| CD19 | CD80 | CD27 | FcεRIγ |
| CD19 | CD80 | CD27 | DAP10 |
| CD19 | CD80 | CD27 | DAP12 |
| CD19 | CD80 | CD27 | CD32 |
| CD19 | CD80 | CD27 | CD79a |

TABLE 3-continued

Third Generation CARs

| ScFv | Co-stimulatory Signal | Co-stimulatory Signal | Signal Domain |
|---|---|---|---|
| CD19 | CD80 | CD27 | CD79b |
| CD19 | CD80 | CD28δ | CD8 |
| CD19 | CD80 | CD28δ | CD3ζ |
| CD19 | CD80 | CD28δ | CD3δ |
| CD19 | CD80 | CD28δ | CD3γ |
| CD19 | CD80 | CD28δ | CD3ε |
| CD19 | CD80 | CD28δ | FcγRI-γ |
| CD19 | CD80 | CD28δ | FcγRIII-γ |
| CD19 | CD80 | CD28δ | FcεRIβ |
| CD19 | CD80 | CD28δ | FcεRIγ |
| CD19 | CD80 | CD28δ | DAP10 |
| CD19 | CD80 | CD28δ | DAP12 |
| CD19 | CD80 | CD28δ | CD32 |
| CD19 | CD80 | CD28δ | CD79a |
| CD19 | CD80 | CD28δ | CD79b |
| CD19 | CD80 | CD80 | CD8 |
| CD19 | CD80 | CD80 | CD3ζ |
| CD19 | CD80 | CD80 | CD3δ |
| CD19 | CD80 | CD80 | CD3γ |
| CD19 | CD80 | CD80 | CD3ε |
| CD19 | CD80 | CD80 | FcγRI-γ |
| CD19 | CD80 | CD80 | FcγRIII-γ |
| CD19 | CD80 | CD80 | FcεRIβ |
| CD19 | CD80 | CD80 | FcεRIγ |
| CD19 | CD80 | CD80 | DAP10 |
| CD19 | CD80 | CD80 | DAP12 |
| CD19 | CD80 | CD80 | CD32 |
| CD19 | CD80 | CD80 | CD79a |
| CD19 | CD80 | CD80 | CD79b |
| CD19 | CD80 | CD86 | CD8 |
| CD19 | CD80 | CD86 | CD3ζ |
| CD19 | CD80 | CD86 | CD3δ |
| CD19 | CD80 | CD86 | CD3γ |
| CD19 | CD80 | CD86 | CD3ε |
| CD19 | CD80 | CD86 | FcγRI-γ |
| CD19 | CD80 | CD86 | FcγRIII-γ |
| CD19 | CD80 | CD86 | FcεRIβ |
| CD19 | CD80 | CD86 | FcεRIγ |
| CD19 | CD80 | CD86 | DAP10 |
| CD19 | CD80 | CD86 | DAP12 |
| CD19 | CD80 | CD86 | CD32 |
| CD19 | CD80 | CD86 | CD79a |
| CD19 | CD80 | CD86 | CD79b |
| CD19 | CD80 | OX40 | CD8 |
| CD19 | CD80 | OX40 | CD3ζ |
| CD19 | CD80 | OX40 | CD3δ |
| CD19 | CD80 | OX40 | CD3γ |
| CD19 | CD80 | OX40 | CD3ε |
| CD19 | CD80 | OX40 | FcγRI-γ |
| CD19 | CD80 | OX40 | FcγRIII-γ |
| CD19 | CD80 | OX40 | FcεRIβ |
| CD19 | CD80 | OX40 | FcεRIγ |
| CD19 | CD80 | OX40 | DAP10 |
| CD19 | CD80 | OX40 | DAP12 |
| CD19 | CD80 | OX40 | CD32 |
| CD19 | CD80 | OX40 | CD79a |
| CD19 | CD80 | OX40 | CD79b |
| CD19 | CD80 | DAP10 | CD8 |
| CD19 | CD80 | DAP10 | CD3ζ |
| CD19 | CD80 | DAP10 | CD3δ |
| CD19 | CD80 | DAP10 | CD3γ |
| CD19 | CD80 | DAP10 | CD3ε |
| CD19 | CD80 | DAP10 | FcγRI-γ |
| CD19 | CD80 | DAP10 | FcγRIII-γ |
| CD19 | CD80 | DAP10 | FcεRIβ |
| CD19 | CD80 | DAP10 | FcεRIγ |
| CD19 | CD80 | DAP10 | DAP10 |
| CD19 | CD80 | DAP10 | DAP12 |
| CD19 | CD80 | DAP10 | CD32 |
| CD19 | CD80 | DAP10 | CD79a |
| CD19 | CD80 | DAP10 | CD79b |
| CD19 | CD80 | DAP12 | CD8 |
| CD19 | CD80 | DAP12 | CD3ζ |
| CD19 | CD80 | DAP12 | CD3δ |
| CD19 | CD80 | DAP12 | CD3γ |

TABLE 3-continued

Third Generation CARs

| ScFv | Co-stimulatory Signal | Co-stimulatory Signal | Signal Domain |
|---|---|---|---|
| CD19 | CD80 | DAP12 | CD3ε |
| CD19 | CD80 | DAP12 | FcγRI-γ |
| CD19 | CD80 | DAP12 | FcγRIII-γ |
| CD19 | CD80 | DAP12 | FcεRIβ |
| CD19 | CD80 | DAP12 | FcεRIγ |
| CD19 | CD80 | DAP12 | DAP10 |
| CD19 | CD80 | DAP12 | DAP12 |
| CD19 | CD80 | DAP12 | CD32 |
| CD19 | CD80 | DAP12 | CD79a |
| CD19 | CD80 | DAP12 | CD79b |
| CD19 | CD80 | MyD88 | CD8 |
| CD19 | CD80 | MyD88 | CD3ζ |
| CD19 | CD80 | MyD88 | CD3δ |
| CD19 | CD80 | MyD88 | CD3γ |
| CD19 | CD80 | MyD88 | CD3ε |
| CD19 | CD80 | MyD88 | FcγRI-γ |
| CD19 | CD80 | MyD88 | FcγRIII-γ |
| CD19 | CD80 | MyD88 | FcεRIβ |
| CD19 | CD80 | MyD88 | FcεRIγ |
| CD19 | CD80 | MyD88 | DAP10 |
| CD19 | CD80 | MyD88 | DAP12 |
| CD19 | CD80 | MyD88 | CD32 |
| CD19 | CD80 | MyD88 | CD79a |
| CD19 | CD80 | MyD88 | CD79b |
| CD19 | CD80 | CD7 | CD8 |
| CD19 | CD80 | CD7 | CD3ζ |
| CD19 | CD80 | CD7 | CD3δ |
| CD19 | CD80 | CD7 | CD3γ |
| CD19 | CD80 | CD7 | CD3ε |
| CD19 | CD80 | CD7 | FcγRI-γ |
| CD19 | CD80 | CD7 | FcγRIII-γ |
| CD19 | CD80 | CD7 | FcεRIβ |
| CD19 | CD80 | CD7 | FcεRIγ |
| CD19 | CD80 | CD7 | DAP10 |
| CD19 | CD80 | CD7 | DAP12 |
| CD19 | CD80 | CD7 | CD32 |
| CD19 | CD80 | CD7 | CD79a |
| CD19 | CD80 | CD7 | CD79b |
| CD19 | CD80 | BTNL3 | CD8 |
| CD19 | CD80 | BTNL3 | CD3ζ |
| CD19 | CD80 | BTNL3 | CD3δ |
| CD19 | CD80 | BTNL3 | CD3γ |
| CD19 | CD80 | BTNL3 | CD3ε |
| CD19 | CD80 | BTNL3 | FcγRI-γ |
| CD19 | CD80 | BTNL3 | FcγRIII-γ |
| CD19 | CD80 | BTNL3 | FcεRIβ |
| CD19 | CD80 | BTNL3 | FcεRIγ |
| CD19 | CD80 | BTNL3 | DAP10 |
| CD19 | CD80 | BTNL3 | DAP12 |
| CD19 | CD80 | BTNL3 | CD32 |
| CD19 | CD80 | BTNL3 | CD79a |
| CD19 | CD80 | BTNL3 | CD79b |
| CD19 | CD80 | NKG2D | CD8 |
| CD19 | CD80 | NKG2D | CD3ζ |
| CD19 | CD80 | NKG2D | CD3δ |
| CD19 | CD80 | NKG2D | CD3γ |
| CD19 | CD80 | NKG2D | CD3ε |
| CD19 | CD80 | NKG2D | FcγRI-γ |
| CD19 | CD80 | NKG2D | FcγRIII-γ |
| CD19 | CD80 | NKG2D | FcεRIβ |
| CD19 | CD80 | NKG2D | FcεRIγ |
| CD19 | CD80 | NKG2D | DAP10 |
| CD19 | CD80 | NKG2D | DAP12 |
| CD19 | CD80 | NKG2D | CD32 |
| CD19 | CD80 | NKG2D | CD79a |
| CD19 | CD80 | NKG2D | CD79b |
| CD19 | CD86 | CD28 | CD8 |
| CD19 | CD86 | CD28 | CD3ζ |
| CD19 | CD86 | CD28 | CD3δ |
| CD19 | CD86 | CD28 | CD3γ |
| CD19 | CD86 | CD28 | CD3ε |
| CD19 | CD86 | CD28 | FcγRI-γ |
| CD19 | CD86 | CD28 | FcγRIII-γ |
| CD19 | CD86 | CD28 | FcεRIβ |
| CD19 | CD86 | CD28 | FcεRIγ |

TABLE 3-continued

| | Third Generation CARs | | |
|---|---|---|---|
| ScFv | Co-stimulatory Signal | Co-stimulatory Signal | Signal Domain |
| CD19 | CD86 | CD28 | DAP10 |
| CD19 | CD86 | CD28 | DAP12 |
| CD19 | CD86 | CD28 | CD32 |
| CD19 | CD86 | CD28 | CD79a |
| CD19 | CD86 | CD28 | CD79b |
| CD19 | CD86 | CD8 | CD8 |
| CD19 | CD86 | CD8 | CD3ζ |
| CD19 | CD86 | CD8 | CD3δ |
| CD19 | CD86 | CD8 | CD3γ |
| CD19 | CD86 | CD8 | CD3ε |
| CD19 | CD86 | CD8 | FcγRI-γ |
| CD19 | CD86 | CD8 | FcγRIII-γ |
| CD19 | CD86 | CD8 | FcεRIβ |
| CD19 | CD86 | CD8 | FcεRIγ |
| CD19 | CD86 | CD8 | DAP10 |
| CD19 | CD86 | CD8 | DAP12 |
| CD19 | CD86 | CD8 | CD32 |
| CD19 | CD86 | CD8 | CD79a |
| CD19 | CD86 | CD8 | CD79b |
| CD19 | CD86 | CD4 | CD8 |
| CD19 | CD86 | CD4 | CD3ζ |
| CD19 | CD86 | CD4 | CD3δ |
| CD19 | CD86 | CD4 | CD3γ |
| CD19 | CD86 | CD4 | CD3ε |
| CD19 | CD86 | CD4 | FcγRI-γ |
| CD19 | CD86 | CD4 | FcγRIII-γ |
| CD19 | CD86 | CD4 | FcεRIβ |
| CD19 | CD86 | CD4 | FcεRIγ |
| CD19 | CD86 | CD4 | DAP10 |
| CD19 | CD86 | CD4 | DAP12 |
| CD19 | CD86 | CD4 | CD32 |
| CD19 | CD86 | CD4 | CD79a |
| CD19 | CD86 | CD4 | CD79b |
| CD19 | CD86 | b2c | CD8 |
| CD19 | CD86 | b2c | CD3ζ |
| CD19 | CD86 | b2c | CD3δ |
| CD19 | CD86 | b2c | CD3γ |
| CD19 | CD86 | b2c | CD3ε |
| CD19 | CD86 | b2c | FcγRI-γ |
| CD19 | CD86 | b2c | FcγRIII-γ |
| CD19 | CD86 | b2c | FcεRIβ |
| CD19 | CD86 | b2c | FcεRIγ |
| CD19 | CD86 | b2c | DAP10 |
| CD19 | CD86 | b2c | DAP12 |
| CD19 | CD86 | b2c | CD32 |
| CD19 | CD86 | b2c | CD79a |
| CD19 | CD86 | b2c | CD79b |
| CD19 | CD86 | CD137/41BB | CD8 |
| CD19 | CD86 | CD137/41BB | CD3ζ |
| CD19 | CD86 | CD137/41BB | CD3δ |
| CD19 | CD86 | CD137/41BB | CD3γ |
| CD19 | CD86 | CD137/41BB | CD3ε |
| CD19 | CD86 | CD137/41BB | FcγRI-γ |
| CD19 | CD86 | CD137/41BB | FcγRIII-γ |
| CD19 | CD86 | CD137/41BB | FcεRIβ |
| CD19 | CD86 | CD137/41BB | FcεRIγ |
| CD19 | CD86 | CD137/41BB | DAP10 |
| CD19 | CD86 | CD137/41BB | DAP12 |
| CD19 | CD86 | CD137/41BB | CD32 |
| CD19 | CD86 | CD137/41BB | CD79a |
| CD19 | CD86 | CD137/41BB | CD79b |
| CD19 | CD86 | ICOS | CD8 |
| CD19 | CD86 | ICOS | CD3ζ |
| CD19 | CD86 | ICOS | CD3δ |
| CD19 | CD86 | ICOS | CD3γ |
| CD19 | CD86 | ICOS | CD3ε |
| CD19 | CD86 | ICOS | FcγRI-γ |
| CD19 | CD86 | ICOS | FcγRIII-γ |
| CD19 | CD86 | ICOS | FcεRIβ |
| CD19 | CD86 | ICOS | FcεRIγ |
| CD19 | CD86 | ICOS | DAP10 |
| CD19 | CD86 | ICOS | DAP12 |
| CD19 | CD86 | ICOS | CD32 |
| CD19 | CD86 | ICOS | CD79a |
| CD19 | CD86 | ICOS | CD79b |

TABLE 3-continued

| | Third Generation CARs | | |
|---|---|---|---|
| ScFv | Co-stimulatory Signal | Co-stimulatory Signal | Signal Domain |
| CD19 | CD86 | CD27 | CD8 |
| CD19 | CD86 | CD27 | CD3ζ |
| CD19 | CD86 | CD27 | CD3δ |
| CD19 | CD86 | CD27 | CD3γ |
| CD19 | CD86 | CD27 | CD3ε |
| CD19 | CD86 | CD27 | FcγRI-γ |
| CD19 | CD86 | CD27 | FcγRIII-γ |
| CD19 | CD86 | CD27 | FcεRIβ |
| CD19 | CD86 | CD27 | FcεRIγ |
| CD19 | CD86 | CD27 | DAP10 |
| CD19 | CD86 | CD27 | DAP12 |
| CD19 | CD86 | CD27 | CD32 |
| CD19 | CD86 | CD27 | CD79a |
| CD19 | CD86 | CD27 | CD79b |
| CD19 | CD86 | CD28δ | CD8 |
| CD19 | CD86 | CD28δ | CD3ζ |
| CD19 | CD86 | CD28δ | CD3δ |
| CD19 | CD86 | CD28δ | CD3γ |
| CD19 | CD86 | CD28δ | CD3ε |
| CD19 | CD86 | CD28δ | FcγRI-γ |
| CD19 | CD86 | CD28δ | FcγRIII-γ |
| CD19 | CD86 | CD28δ | FcεRIβ |
| CD19 | CD86 | CD28δ | FcεRIγ |
| CD19 | CD86 | CD28δ | DAP10 |
| CD19 | CD86 | CD28δ | DAP12 |
| CD19 | CD86 | CD28δ | CD32 |
| CD19 | CD86 | CD28δ | CD79a |
| CD19 | CD86 | CD28δ | CD79b |
| CD19 | CD86 | CD80 | CD8 |
| CD19 | CD86 | CD80 | CD3ζ |
| CD19 | CD86 | CD80 | CD3δ |
| CD19 | CD86 | CD80 | CD3γ |
| CD19 | CD86 | CD80 | CD3ε |
| CD19 | CD86 | CD80 | FcγRI-γ |
| CD19 | CD86 | CD80 | FcγRIII-γ |
| CD19 | CD86 | CD80 | FcεRIβ |
| CD19 | CD86 | CD80 | FcεRIγ |
| CD19 | CD86 | CD80 | DAP10 |
| CD19 | CD86 | CD80 | DAP12 |
| CD19 | CD86 | CD80 | CD32 |
| CD19 | CD86 | CD80 | CD79a |
| CD19 | CD86 | CD80 | CD79b |
| CD19 | CD86 | CD86 | CD8 |
| CD19 | CD86 | CD86 | CD3ζ |
| CD19 | CD86 | CD86 | CD3δ |
| CD19 | CD86 | CD86 | CD3γ |
| CD19 | CD86 | CD86 | CD3ε |
| CD19 | CD86 | CD86 | FcγRI-γ |
| CD19 | CD86 | CD86 | FcγRIII-γ |
| CD19 | CD86 | CD86 | FcεRIβ |
| CD19 | CD86 | CD86 | FcεRIγ |
| CD19 | CD86 | CD86 | DAP10 |
| CD19 | CD86 | CD86 | DAP12 |
| CD19 | CD86 | CD86 | CD32 |
| CD19 | CD86 | CD86 | CD79a |
| CD19 | CD86 | CD86 | CD79b |
| CD19 | CD86 | OX40 | CD8 |
| CD19 | CD86 | OX40 | CD3ζ |
| CD19 | CD86 | OX40 | CD3δ |
| CD19 | CD86 | OX40 | CD3γ |
| CD19 | CD86 | OX40 | CD3ε |
| CD19 | CD86 | OX40 | FcγRI-γ |
| CD19 | CD86 | OX40 | FcγRIII-γ |
| CD19 | CD86 | OX40 | FcεRIβ |
| CD19 | CD86 | OX40 | FcεRIγ |
| CD19 | CD86 | OX40 | DAP10 |
| CD19 | CD86 | OX40 | DAP12 |
| CD19 | CD86 | OX40 | CD32 |
| CD19 | CD86 | OX40 | CD79a |
| CD19 | CD86 | OX40 | CD79b |
| CD19 | CD86 | DAP10 | CD8 |
| CD19 | CD86 | DAP10 | CD3ζ |
| CD19 | CD86 | DAP10 | CD3δ |
| CD19 | CD86 | DAP10 | CD3γ |
| CD19 | CD86 | DAP10 | CD3ε |

TABLE 3-continued

Third Generation CARs

| ScFv | Co-stimulatory Signal | Co-stimulatory Signal | Signal Domain |
|---|---|---|---|
| CD19 | CD86 | DAP10 | FcγRI-γ |
| CD19 | CD86 | DAP10 | FcγRIII-γ |
| CD19 | CD86 | DAP10 | FcεRIβ |
| CD19 | CD86 | DAP10 | FcεRIγ |
| CD19 | CD86 | DAP10 | DAP10 |
| CD19 | CD86 | DAP10 | DAP12 |
| CD19 | CD86 | DAP10 | CD32 |
| CD19 | CD86 | DAP10 | CD79a |
| CD19 | CD86 | DAP10 | CD79b |
| CD19 | CD86 | DAP12 | CD8 |
| CD19 | CD86 | DAP12 | CD3ζ |
| CD19 | CD86 | DAP12 | CD3δ |
| CD19 | CD86 | DAP12 | CD3γ |
| CD19 | CD86 | DAP12 | CD3ε |
| CD19 | CD86 | DAP12 | FcγRI-γ |
| CD19 | CD86 | DAP12 | FcγRIII-γ |
| CD19 | CD86 | DAP12 | FcεRIβ |
| CD19 | CD86 | DAP12 | FcεRIγ |
| CD19 | CD86 | DAP12 | DAP10 |
| CD19 | CD86 | DAP12 | DAP12 |
| CD19 | CD86 | DAP12 | CD32 |
| CD19 | CD86 | DAP12 | CD79a |
| CD19 | CD86 | DAP12 | CD79b |
| CD19 | CD86 | MyD88 | CD8 |
| CD19 | CD86 | MyD88 | CD3ζ |
| CD19 | CD86 | MyD88 | CD3δ |
| CD19 | CD86 | MyD88 | CD3γ |
| CD19 | CD86 | MyD88 | CD3ε |
| CD19 | CD86 | MyD88 | FcγRI-γ |
| CD19 | CD86 | MyD88 | FcγRIII-γ |
| CD19 | CD86 | MyD88 | FcεRIβ |
| CD19 | CD86 | MyD88 | FcεRIγ |
| CD19 | CD86 | MyD88 | DAP10 |
| CD19 | CD86 | MyD88 | DAP12 |
| CD19 | CD86 | MyD88 | CD32 |
| CD19 | CD86 | MyD88 | CD79a |
| CD19 | CD86 | MyD88 | CD79b |
| CD19 | CD86 | CD7 | CD8 |
| CD19 | CD86 | CD7 | CD3ζ |
| CD19 | CD86 | CD7 | CD3δ |
| CD19 | CD86 | CD7 | CD3γ |
| CD19 | CD86 | CD7 | CD3ε |
| CD19 | CD86 | CD7 | FcγRI-γ |
| CD19 | CD86 | CD7 | FcγRIII-γ |
| CD19 | CD86 | CD7 | FcεRIβ |
| CD19 | CD86 | CD7 | FcεRIγ |
| CD19 | CD86 | CD7 | DAP10 |
| CD19 | CD86 | CD7 | DAP12 |
| CD19 | CD86 | CD7 | CD32 |
| CD19 | CD86 | CD7 | CD79a |
| CD19 | CD86 | CD7 | CD79b |
| CD19 | CD86 | BTNL3 | CD8 |
| CD19 | CD86 | BTNL3 | CD3ζ |
| CD19 | CD86 | BTNL3 | CD3δ |
| CD19 | CD86 | BTNL3 | CD3γ |
| CD19 | CD86 | BTNL3 | CD3ε |
| CD19 | CD86 | BTNL3 | FcγRI-γ |
| CD19 | CD86 | BTNL3 | FcγRIII-γ |
| CD19 | CD86 | BTNL3 | FcεRIβ |
| CD19 | CD86 | BTNL3 | FcεRIγ |
| CD19 | CD86 | BTNL3 | DAP10 |
| CD19 | CD86 | BTNL3 | DAP12 |
| CD19 | CD86 | BTNL3 | CD32 |
| CD19 | CD86 | BTNL3 | CD79a |
| CD19 | CD86 | BTNL3 | CD79b |
| CD19 | CD86 | NKG2D | CD8 |
| CD19 | CD86 | NKG2D | CD3ζ |
| CD19 | CD86 | NKG2D | CD3δ |
| CD19 | CD86 | NKG2D | CD3γ |
| CD19 | CD86 | NKG2D | CD3ε |
| CD19 | CD86 | NKG2D | FcγRI-γ |
| CD19 | CD86 | NKG2D | FcγRIII-γ |
| CD19 | CD86 | NKG2D | FcεRIβ |
| CD19 | CD86 | NKG2D | FcεRIγ |
| CD19 | CD86 | NKG2D | DAP10 |
| CD19 | CD86 | NKG2D | DAP12 |
| CD19 | CD86 | NKG2D | CD32 |
| CD19 | CD86 | NKG2D | CD79a |
| CD19 | CD86 | NKG2D | CD79b |
| CD19 | OX40 | CD28 | CD8 |
| CD19 | OX40 | CD28 | CD3ζ |
| CD19 | OX40 | CD28 | CD3δ |
| CD19 | OX40 | CD28 | CD3γ |
| CD19 | OX40 | CD28 | CD3ε |
| CD19 | OX40 | CD28 | FcγRI-γ |
| CD19 | OX40 | CD28 | FcγRIII-γ |
| CD19 | OX40 | CD28 | FcεRIβ |
| CD19 | OX40 | CD28 | FcεRIγ |
| CD19 | OX40 | CD28 | DAP10 |
| CD19 | OX40 | CD28 | DAP12 |
| CD19 | OX40 | CD28 | CD32 |
| CD19 | OX40 | CD28 | CD79a |
| CD19 | OX40 | CD28 | CD79b |
| CD19 | OX40 | CD8 | CD8 |
| CD19 | OX40 | CD8 | CD3ζ |
| CD19 | OX40 | CD8 | CD3δ |
| CD19 | OX40 | CD8 | CD3γ |
| CD19 | OX40 | CD8 | CD3ε |
| CD19 | OX40 | CD8 | FcγRI-γ |
| CD19 | OX40 | CD8 | FcγRIII-γ |
| CD19 | OX40 | CD8 | FcεRIβ |
| CD19 | OX40 | CD8 | FcεRIγ |
| CD19 | OX40 | CD8 | DAP10 |
| CD19 | OX40 | CD8 | DAP12 |
| CD19 | OX40 | CD8 | CD32 |
| CD19 | OX40 | CD8 | CD79a |
| CD19 | OX40 | CD8 | CD79b |
| CD19 | OX40 | CD4 | CD8 |
| CD19 | OX40 | CD4 | CD3ζ |
| CD19 | OX40 | CD4 | CD3δ |
| CD19 | OX40 | CD4 | CD3γ |
| CD19 | OX40 | CD4 | CD3ε |
| CD19 | OX40 | CD4 | FcγRI-γ |
| CD19 | OX40 | CD4 | FcγRIII-γ |
| CD19 | OX40 | CD4 | FcεRIβ |
| CD19 | OX40 | CD4 | FcεRIγ |
| CD19 | OX40 | CD4 | DAP10 |
| CD19 | OX40 | CD4 | DAP12 |
| CD19 | OX40 | CD4 | CD32 |
| CD19 | OX40 | CD4 | CD79a |
| CD19 | OX40 | CD4 | CD79b |
| CD19 | OX40 | b2c | CD8 |
| CD19 | OX40 | b2c | CD3ζ |
| CD19 | OX40 | b2c | CD3δ |
| CD19 | OX40 | b2c | CD3γ |
| CD19 | OX40 | b2c | CD3ε |
| CD19 | OX40 | b2c | FcγRI-γ |
| CD19 | OX40 | b2c | FcγRIII-γ |
| CD19 | OX40 | b2c | FcεRIβ |
| CD19 | OX40 | b2c | FcεRIγ |
| CD19 | OX40 | b2c | DAP10 |
| CD19 | OX40 | b2c | DAP12 |
| CD19 | OX40 | b2c | CD32 |
| CD19 | OX40 | b2c | CD79a |
| CD19 | OX40 | b2c | CD79b |
| CD19 | OX40 | CD137/41BB | CD8 |
| CD19 | OX40 | CD137/41BB | CD3ζ |
| CD19 | OX40 | CD137/41BB | CD3δ |
| CD19 | OX40 | CD137/41BB | CD3γ |
| CD19 | OX40 | CD137/41BB | CD3ε |
| CD19 | OX40 | CD137/41BB | FcγRI-γ |
| CD19 | OX40 | CD137/41BB | FcγRIII-γ |
| CD19 | OX40 | CD137/41BB | FcεRIβ |
| CD19 | OX40 | CD137/41BB | FcεRIγ |
| CD19 | OX40 | CD137/41BB | DAP10 |
| CD19 | OX40 | CD137/41BB | DAP12 |
| CD19 | OX40 | CD137/41BB | CD32 |
| CD19 | OX40 | CD137/41BB | CD79a |
| CD19 | OX40 | CD137/41BB | CD79b |
| CD19 | OX40 | ICOS | CD8 |

TABLE 3-continued

| | Third Generation CARs | | |
|---|---|---|---|
| ScFv | Co-stimulatory Signal | Co-stimulatory Signal | Signal Domain |
| CD19 | OX40 | ICOS | CD3ζ |
| CD19 | OX40 | ICOS | CD3δ |
| CD19 | OX40 | ICOS | CD3γ |
| CD19 | OX40 | ICOS | CD3ε |
| CD19 | OX40 | ICOS | FcγRI-γ |
| CD19 | OX40 | ICOS | FcγRIII-γ |
| CD19 | OX40 | ICOS | FcεRIβ |
| CD19 | OX40 | ICOS | FcεRIγ |
| CD19 | OX40 | ICOS | DAP10 |
| CD19 | OX40 | ICOS | DAP12 |
| CD19 | OX40 | ICOS | CD32 |
| CD19 | OX40 | ICOS | CD79a |
| CD19 | OX40 | ICOS | CD79b |
| CD19 | OX40 | CD27 | CD8 |
| CD19 | OX40 | CD27 | CD3ζ |
| CD19 | OX40 | CD27 | CD3δ |
| CD19 | OX40 | CD27 | CD3γ |
| CD19 | OX40 | CD27 | CD3ε |
| CD19 | OX40 | CD27 | FcγRI-γ |
| CD19 | OX40 | CD27 | FcγRIII-γ |
| CD19 | OX40 | CD27 | FcεRIβ |
| CD19 | OX40 | CD27 | FcεRIγ |
| CD19 | OX40 | CD27 | DAP10 |
| CD19 | OX40 | CD27 | DAP12 |
| CD19 | OX40 | CD27 | CD32 |
| CD19 | OX40 | CD27 | CD79a |
| CD19 | OX40 | CD27 | CD79b |
| CD19 | OX40 | CD28δ | CD8 |
| CD19 | OX40 | CD28δ | CD3ζ |
| CD19 | OX40 | CD28δ | CD3δ |
| CD19 | OX40 | CD28δ | CD3γ |
| CD19 | OX40 | CD28δ | CD3ε |
| CD19 | OX40 | CD28δ | FcγRI-γ |
| CD19 | OX40 | CD28δ | FcγRIII-γ |
| CD19 | OX40 | CD28δ | FcεRIβ |
| CD19 | OX40 | CD28δ | FcεRIγ |
| CD19 | OX40 | CD28δ | DAP10 |
| CD19 | OX40 | CD28δ | DAP12 |
| CD19 | OX40 | CD28δ | CD32 |
| CD19 | OX40 | CD28δ | CD79a |
| CD19 | OX40 | CD28δ | CD79b |
| CD19 | OX40 | CD80 | CD8 |
| CD19 | OX40 | CD80 | CD3ζ |
| CD19 | OX40 | CD80 | CD3δ |
| CD19 | OX40 | CD80 | CD3γ |
| CD19 | OX40 | CD80 | CD3ε |
| CD19 | OX40 | CD80 | FcγRI-γ |
| CD19 | OX40 | CD80 | FcγRIII-γ |
| CD19 | OX40 | CD80 | FcεRIβ |
| CD19 | OX40 | CD80 | FcεRIγ |
| CD19 | OX40 | CD80 | DAP10 |
| CD19 | OX40 | CD80 | DAP12 |
| CD19 | OX40 | CD80 | CD32 |
| CD19 | OX40 | CD80 | CD79a |
| CD19 | OX40 | CD80 | CD79b |
| CD19 | OX40 | CD86 | CD8 |
| CD19 | OX40 | CD86 | CD3ζ |
| CD19 | OX40 | CD86 | CD3δ |
| CD19 | OX40 | CD86 | CD3γ |
| CD19 | OX40 | CD86 | CD3ε |
| CD19 | OX40 | CD86 | FcγRI-γ |
| CD19 | OX40 | CD86 | FcγRIII-γ |
| CD19 | OX40 | CD86 | FcεRIβ |
| CD19 | OX40 | CD86 | FcεRIγ |
| CD19 | OX40 | CD86 | DAP10 |
| CD19 | OX40 | CD86 | DAP12 |
| CD19 | OX40 | CD86 | CD32 |
| CD19 | OX40 | CD86 | CD79a |
| CD19 | OX40 | CD86 | CD79b |
| CD19 | OX40 | OX40 | CD8 |
| CD19 | OX40 | OX40 | CD3ζ |
| CD19 | OX40 | OX40 | CD3δ |
| CD19 | OX40 | OX40 | CD3γ |
| CD19 | OX40 | OX40 | CD3ε |
| CD19 | OX40 | OX40 | FcγRI-γ |

TABLE 3-continued

| | Third Generation CARs | | |
|---|---|---|---|
| ScFv | Co-stimulatory Signal | Co-stimulatory Signal | Signal Domain |
| CD19 | OX40 | OX40 | FcγRIII-γ |
| CD19 | OX40 | OX40 | FcεRIβ |
| CD19 | OX40 | OX40 | FcεRIγ |
| CD19 | OX40 | OX40 | DAP10 |
| CD19 | OX40 | OX40 | DAP12 |
| CD19 | OX40 | OX40 | CD32 |
| CD19 | OX40 | OX40 | CD79a |
| CD19 | OX40 | OX40 | CD79b |
| CD19 | OX40 | DAP10 | CD8 |
| CD19 | OX40 | DAP10 | CD3ζ |
| CD19 | OX40 | DAP10 | CD3δ |
| CD19 | OX40 | DAP10 | CD3γ |
| CD19 | OX40 | DAP10 | CD3ε |
| CD19 | OX40 | DAP10 | FcγRI-γ |
| CD19 | OX40 | DAP10 | FcγRIII-γ |
| CD19 | OX40 | DAP10 | FcεRIβ |
| CD19 | OX40 | DAP10 | FcεRIγ |
| CD19 | OX40 | DAP10 | DAP10 |
| CD19 | OX40 | DAP10 | DAP12 |
| CD19 | OX40 | DAP10 | CD32 |
| CD19 | OX40 | DAP10 | CD79a |
| CD19 | OX40 | DAP10 | CD79b |
| CD19 | OX40 | DAP12 | CD8 |
| CD19 | OX40 | DAP12 | CD3ζ |
| CD19 | OX40 | DAP12 | CD3δ |
| CD19 | OX40 | DAP12 | CD3γ |
| CD19 | OX40 | DAP12 | CD3ε |
| CD19 | OX40 | DAP12 | FcγRI-γ |
| CD19 | OX40 | DAP12 | FcγRIII-γ |
| CD19 | OX40 | DAP12 | FcεRIβ |
| CD19 | OX40 | DAP12 | FcεRIγ |
| CD19 | OX40 | DAP12 | DAP10 |
| CD19 | OX40 | DAP12 | DAP12 |
| CD19 | OX40 | DAP12 | CD32 |
| CD19 | OX40 | DAP12 | CD79a |
| CD19 | OX40 | DAP12 | CD79b |
| CD19 | OX40 | MyD88 | CD8 |
| CD19 | OX40 | MyD88 | CD3ζ |
| CD19 | OX40 | MyD88 | CD3δ |
| CD19 | OX40 | MyD88 | CD3γ |
| CD19 | OX40 | MyD88 | CD3ε |
| CD19 | OX40 | MyD88 | FcγRI-γ |
| CD19 | OX40 | MyD88 | FcγRIII-γ |
| CD19 | OX40 | MyD88 | FcεRIβ |
| CD19 | OX40 | MyD88 | FcεRIγ |
| CD19 | OX40 | MyD88 | DAP10 |
| CD19 | OX40 | MyD88 | DAP12 |
| CD19 | OX40 | MyD88 | CD32 |
| CD19 | OX40 | MyD88 | CD79a |
| CD19 | OX40 | MyD88 | CD79b |
| CD19 | OX40 | CD7 | CD8 |
| CD19 | OX40 | CD7 | CD3ζ |
| CD19 | OX40 | CD7 | CD3δ |
| CD19 | OX40 | CD7 | CD3γ |
| CD19 | OX40 | CD7 | CD3ε |
| CD19 | OX40 | CD7 | FcγRI-γ |
| CD19 | OX40 | CD7 | FcγRIII-γ |
| CD19 | OX40 | CD7 | FcεRIβ |
| CD19 | OX40 | CD7 | FcεRIγ |
| CD19 | OX40 | CD7 | DAP10 |
| CD19 | OX40 | CD7 | DAP12 |
| CD19 | OX40 | CD7 | CD32 |
| CD19 | OX40 | CD7 | CD79a |
| CD19 | OX40 | CD7 | CD79b |
| CD19 | OX40 | BTNL3 | CD8 |
| CD19 | OX40 | BTNL3 | CD3ζ |
| CD19 | OX40 | BTNL3 | CD3δ |
| CD19 | OX40 | BTNL3 | CD3γ |
| CD19 | OX40 | BTNL3 | CD3ε |
| CD19 | OX40 | BTNL3 | FcγRI-γ |
| CD19 | OX40 | BTNL3 | FcγRIII-γ |
| CD19 | OX40 | BTNL3 | FcεRIβ |
| CD19 | OX40 | BTNL3 | FcεRIγ |
| CD19 | OX40 | BTNL3 | DAP10 |
| CD19 | OX40 | BTNL3 | DAP12 |

TABLE 3-continued

| | Third Generation CARs | | |
|---|---|---|---|
| ScFv | Co-stimulatory Signal | Co-stimulatory Signal | Signal Domain |
| CD19 | OX40 | BTNL3 | CD32 |
| CD19 | OX40 | BTNL3 | CD79a |
| CD19 | OX40 | BTNL3 | CD79b |
| CD19 | OX40 | NKG2D | CD8 |
| CD19 | OX40 | NKG2D | CD3ζ |
| CD19 | OX40 | NKG2D | CD3δ |
| CD19 | OX40 | NKG2D | CD3γ |
| CD19 | OX40 | NKG2D | CD3ε |
| CD19 | OX40 | NKG2D | FcγRI-γ |
| CD19 | OX40 | NKG2D | FcγRIII-γ |
| CD19 | OX40 | NKG2D | FcεRIβ |
| CD19 | OX40 | NKG2D | FcεRIγ |
| CD19 | OX40 | NKG2D | DAP10 |
| CD19 | OX40 | NKG2D | DAP12 |
| CD19 | OX40 | NKG2D | CD32 |
| CD19 | OX40 | NKG2D | CD79a |
| CD19 | OX40 | NKG2D | CD79b |
| CD19 | DAP10 | CD28 | CD8 |
| CD19 | DAP10 | CD28 | CD3ζ |
| CD19 | DAP10 | CD28 | CD3δ |
| CD19 | DAP10 | CD28 | CD3γ |
| CD19 | DAP10 | CD28 | CD3ε |
| CD19 | DAP10 | CD28 | FcγRI-γ |
| CD19 | DAP10 | CD28 | FcγRIII-γ |
| CD19 | DAP10 | CD28 | FcεRIβ |
| CD19 | DAP10 | CD28 | FcεRIγ |
| CD19 | DAP10 | CD28 | DAP10 |
| CD19 | DAP10 | CD28 | DAP12 |
| CD19 | DAP10 | CD28 | CD32 |
| CD19 | DAP10 | CD28 | CD79a |
| CD19 | DAP10 | CD28 | CD79b |
| CD19 | DAP10 | CD8 | CD8 |
| CD19 | DAP10 | CD8 | CD3ζ |
| CD19 | DAP10 | CD8 | CD3δ |
| CD19 | DAP10 | CD8 | CD3γ |
| CD19 | DAP10 | CD8 | CD3ε |
| CD19 | DAP10 | CD8 | FcγRI-γ |
| CD19 | DAP10 | CD8 | FcγRIII-γ |
| CD19 | DAP10 | CD8 | FcεRIβ |
| CD19 | DAP10 | CD8 | FcεRIγ |
| CD19 | DAP10 | CD8 | DAP10 |
| CD19 | DAP10 | CD8 | DAP12 |
| CD19 | DAP10 | CD8 | CD32 |
| CD19 | DAP10 | CD8 | CD79a |
| CD19 | DAP10 | CD8 | CD79b |
| CD19 | DAP10 | CD4 | CD8 |
| CD19 | DAP10 | CD4 | CD3ζ |
| CD19 | DAP10 | CD4 | CD3δ |
| CD19 | DAP10 | CD4 | CD3γ |
| CD19 | DAP10 | CD4 | CD3ε |
| CD19 | DAP10 | CD4 | FcγRI-γ |
| CD19 | DAP10 | CD4 | FcγRIII-γ |
| CD19 | DAP10 | CD4 | FcεRIβ |
| CD19 | DAP10 | CD4 | FcεRIγ |
| CD19 | DAP10 | CD4 | DAP10 |
| CD19 | DAP10 | CD4 | DAP12 |
| CD19 | DAP10 | CD4 | CD32 |
| CD19 | DAP10 | CD4 | CD79a |
| CD19 | DAP10 | CD4 | CD79b |
| CD19 | DAP10 | b2c | CD8 |
| CD19 | DAP10 | b2c | CD3ζ |
| CD19 | DAP10 | b2c | CD3δ |
| CD19 | DAP10 | b2c | CD3γ |
| CD19 | DAP10 | b2c | CD3ε |
| CD19 | DAP10 | b2c | FcγRI-γ |
| CD19 | DAP10 | b2c | FcγRIII-γ |
| CD19 | DAP10 | b2c | FcεRIβ |
| CD19 | DAP10 | b2c | FcεRIγ |
| CD19 | DAP10 | b2c | DAP10 |
| CD19 | DAP10 | b2c | DAP12 |
| CD19 | DAP10 | b2c | CD32 |
| CD19 | DAP10 | b2c | CD79a |
| CD19 | DAP10 | b2c | CD79b |
| CD19 | DAP10 | CD137/41BB | CD8 |
| CD19 | DAP10 | CD137/41BB | CD3ζ |

TABLE 3-continued

| | Third Generation CARs | | |
|---|---|---|---|
| ScFv | Co-stimulatory Signal | Co-stimulatory Signal | Signal Domain |
| CD19 | DAP10 | CD137/41BB | CD3δ |
| CD19 | DAP10 | CD137/41BB | CD3γ |
| CD19 | DAP10 | CD137/41BB | CD3ε |
| CD19 | DAP10 | CD137/41BB | FcγRI-γ |
| CD19 | DAP10 | CD137/41BB | FcγRIII-γ |
| CD19 | DAP10 | CD137/41BB | FcεRIβ |
| CD19 | DAP10 | CD137/41BB | FcεRIγ |
| CD19 | DAP10 | CD137/41BB | DAP10 |
| CD19 | DAP10 | CD137/41BB | DAP12 |
| CD19 | DAP10 | CD137/41BB | CD32 |
| CD19 | DAP10 | CD137/41BB | CD79a |
| CD19 | DAP10 | CD137/41BB | CD79b |
| CD19 | DAP10 | ICOS | CD8 |
| CD19 | DAP10 | ICOS | CD3ζ |
| CD19 | DAP10 | ICOS | CD3δ |
| CD19 | DAP10 | ICOS | CD3γ |
| CD19 | DAP10 | ICOS | CD3ε |
| CD19 | DAP10 | ICOS | FcγRI-γ |
| CD19 | DAP10 | ICOS | FcγRIII-γ |
| CD19 | DAP10 | ICOS | FcεRIβ |
| CD19 | DAP10 | ICOS | FcεRIγ |
| CD19 | DAP10 | ICOS | DAP10 |
| CD19 | DAP10 | ICOS | DAP12 |
| CD19 | DAP10 | ICOS | CD32 |
| CD19 | DAP10 | ICOS | CD79a |
| CD19 | DAP10 | ICOS | CD79b |
| CD19 | DAP10 | CD27 | CD8 |
| CD19 | DAP10 | CD27 | CD3ζ |
| CD19 | DAP10 | CD27 | CD3δ |
| CD19 | DAP10 | CD27 | CD3γ |
| CD19 | DAP10 | CD27 | CD3ε |
| CD19 | DAP10 | CD27 | FcγRI-γ |
| CD19 | DAP10 | CD27 | FcγRIII-γ |
| CD19 | DAP10 | CD27 | FcεRIβ |
| CD19 | DAP10 | CD27 | FcεRIγ |
| CD19 | DAP10 | CD27 | DAP10 |
| CD19 | DAP10 | CD27 | DAP12 |
| CD19 | DAP10 | CD27 | CD32 |
| CD19 | DAP10 | CD27 | CD79a |
| CD19 | DAP10 | CD27 | CD79b |
| CD19 | DAP10 | CD28δ | CD8 |
| CD19 | DAP10 | CD28δ | CD3ζ |
| CD19 | DAP10 | CD28δ | CD3δ |
| CD19 | DAP10 | CD28δ | CD3γ |
| CD19 | DAP10 | CD28δ | CD3ε |
| CD19 | DAP10 | CD28δ | FcγRI-γ |
| CD19 | DAP10 | CD28δ | FcγRIII-γ |
| CD19 | DAP10 | CD28δ | FcεRIβ |
| CD19 | DAP10 | CD28δ | FcεRIγ |
| CD19 | DAP10 | CD28δ | DAP10 |
| CD19 | DAP10 | CD28δ | DAP12 |
| CD19 | DAP10 | CD28δ | CD32 |
| CD19 | DAP10 | CD28δ | CD79a |
| CD19 | DAP10 | CD28δ | CD79b |
| CD19 | DAP10 | CD80 | CD8 |
| CD19 | DAP10 | CD80 | CD3ζ |
| CD19 | DAP10 | CD80 | CD3δ |
| CD19 | DAP10 | CD80 | CD3γ |
| CD19 | DAP10 | CD80 | CD3ε |
| CD19 | DAP10 | CD80 | FcγRI-γ |
| CD19 | DAP10 | CD80 | FcγRIII-γ |
| CD19 | DAP10 | CD80 | FcεRIβ |
| CD19 | DAP10 | CD80 | FcεRIγ |
| CD19 | DAP10 | CD80 | DAP10 |
| CD19 | DAP10 | CD80 | DAP12 |
| CD19 | DAP10 | CD80 | CD32 |
| CD19 | DAP10 | CD80 | CD79a |
| CD19 | DAP10 | CD80 | CD79b |
| CD19 | DAP10 | CD86 | CD8 |
| CD19 | DAP10 | CD86 | CD3ζ |
| CD19 | DAP10 | CD86 | CD3δ |
| CD19 | DAP10 | CD86 | CD3γ |
| CD19 | DAP10 | CD86 | CD3ε |
| CD19 | DAP10 | CD86 | FcγRI-γ |
| CD19 | DAP10 | CD86 | FcγRIII-γ |

57

TABLE 3-continued

| | Third Generation CARs | | |
| --- | --- | --- | --- |
| ScFv | Co-stimulatory Signal | Co-stimulatory Signal | Signal Domain |
| CD19 | DAP10 | CD86 | FcεRIβ |
| CD19 | DAP10 | CD86 | FcεRIγ |
| CD19 | DAP10 | CD86 | DAP10 |
| CD19 | DAP10 | CD86 | DAP12 |
| CD19 | DAP10 | CD86 | CD32 |
| CD19 | DAP10 | CD86 | CD79a |
| CD19 | DAP10 | CD86 | CD79b |
| CD19 | DAP10 | OX40 | CD8 |
| CD19 | DAP10 | OX40 | CD3ζ |
| CD19 | DAP10 | OX40 | CD3δ |
| CD19 | DAP10 | OX40 | CD3γ |
| CD19 | DAP10 | OX40 | CD3ε |
| CD19 | DAP10 | OX40 | FcγRI-γ |
| CD19 | DAP10 | OX40 | FcγRIII-γ |
| CD19 | DAP10 | OX40 | FcεRIβ |
| CD19 | DAP10 | OX40 | FcεRIγ |
| CD19 | DAP10 | OX40 | DAP10 |
| CD19 | DAP10 | OX40 | DAP12 |
| CD19 | DAP10 | OX40 | CD32 |
| CD19 | DAP10 | OX40 | CD79a |
| CD19 | DAP10 | OX40 | CD79b |
| CD19 | DAP10 | DAP10 | CD8 |
| CD19 | DAP10 | DAP10 | CD3ζ |
| CD19 | DAP10 | DAP10 | CD3δ |
| CD19 | DAP10 | DAP10 | CD3γ |
| CD19 | DAP10 | DAP10 | CD3ε |
| CD19 | DAP10 | DAP10 | FcγRI-γ |
| CD19 | DAP10 | DAP10 | FcγRIII-γ |
| CD19 | DAP10 | DAP10 | FcεRIβ |
| CD19 | DAP10 | DAP10 | FcεRIγ |
| CD19 | DAP10 | DAP10 | DAP10 |
| CD19 | DAP10 | DAP10 | DAP12 |
| CD19 | DAP10 | DAP10 | CD32 |
| CD19 | DAP10 | DAP10 | CD79a |
| CD19 | DAP10 | DAP10 | CD79b |
| CD19 | DAP10 | DAP12 | CD8 |
| CD19 | DAP10 | DAP12 | CD3ζ |
| CD19 | DAP10 | DAP12 | CD3δ |
| CD19 | DAP10 | DAP12 | CD3γ |
| CD19 | DAP10 | DAP12 | CD3ε |
| CD19 | DAP10 | DAP12 | FcγRI-γ |
| CD19 | DAP10 | DAP12 | FcγRIII-γ |
| CD19 | DAP10 | DAP12 | FcεRIβ |
| CD19 | DAP10 | DAP12 | FcεRIγ |
| CD19 | DAP10 | DAP12 | DAP10 |
| CD19 | DAP10 | DAP12 | DAP12 |
| CD19 | DAP10 | DAP12 | CD32 |
| CD19 | DAP10 | DAP12 | CD79a |
| CD19 | DAP10 | DAP12 | CD79b |
| CD19 | DAP10 | MyD88 | CD8 |
| CD19 | DAP10 | MyD88 | CD3ζ |
| CD19 | DAP10 | MyD88 | CD3δ |
| CD19 | DAP10 | MyD88 | CD3γ |
| CD19 | DAP10 | MyD88 | CD3ε |
| CD19 | DAP10 | MyD88 | FcγRI-γ |
| CD19 | DAP10 | MyD88 | FcγRIII-γ |
| CD19 | DAP10 | MyD88 | FcεRIβ |
| CD19 | DAP10 | MyD88 | FcεRIγ |
| CD19 | DAP10 | MyD88 | DAP10 |
| CD19 | DAP10 | MyD88 | DAP12 |
| CD19 | DAP10 | MyD88 | CD32 |
| CD19 | DAP10 | MyD88 | CD79a |
| CD19 | DAP10 | MyD88 | CD79b |
| CD19 | DAP10 | CD7 | CD8 |
| CD19 | DAP10 | CD7 | CD3ζ |
| CD19 | DAP10 | CD7 | CD3δ |
| CD19 | DAP10 | CD7 | CD3γ |
| CD19 | DAP10 | CD7 | CD3ε |
| CD19 | DAP10 | CD7 | FcγRI-γ |
| CD19 | DAP10 | CD7 | FcγRIII-γ |
| CD19 | DAP10 | CD7 | FcεRIβ |
| CD19 | DAP10 | CD7 | FcεRIγ |
| CD19 | DAP10 | CD7 | DAP10 |
| CD19 | DAP10 | CD7 | DAP12 |
| CD19 | DAP10 | CD7 | CD32 |

58

TABLE 3-continued

| | Third Generation CARs | | |
| --- | --- | --- | --- |
| ScFv | Co-stimulatory Signal | Co-stimulatory Signal | Signal Domain |
| CD19 | DAP10 | CD7 | CD79a |
| CD19 | DAP10 | CD7 | CD79b |
| CD19 | DAP10 | BTNL3 | CD8 |
| CD19 | DAP10 | BTNL3 | CD3ζ |
| CD19 | DAP10 | BTNL3 | CD3δ |
| CD19 | DAP10 | BTNL3 | CD3γ |
| CD19 | DAP10 | BTNL3 | CD3ε |
| CD19 | DAP10 | BTNL3 | FcγRI-γ |
| CD19 | DAP10 | BTNL3 | FcγRIII-γ |
| CD19 | DAP10 | BTNL3 | FcεRIβ |
| CD19 | DAP10 | BTNL3 | FcεRIγ |
| CD19 | DAP10 | BTNL3 | DAP10 |
| CD19 | DAP10 | BTNL3 | DAP12 |
| CD19 | DAP10 | BTNL3 | CD32 |
| CD19 | DAP10 | BTNL3 | CD79a |
| CD19 | DAP10 | BTNL3 | CD79b |
| CD19 | DAP10 | NKG2D | CD8 |
| CD19 | DAP10 | NKG2D | CD3ζ |
| CD19 | DAP10 | NKG2D | CD3δ |
| CD19 | DAP10 | NKG2D | CD3γ |
| CD19 | DAP10 | NKG2D | CD3ε |
| CD19 | DAP10 | NKG2D | FcγRI-γ |
| CD19 | DAP10 | NKG2D | FcγRIII-γ |
| CD19 | DAP10 | NKG2D | FcεRIβ |
| CD19 | DAP10 | NKG2D | FcεRIγ |
| CD19 | DAP10 | NKG2D | DAP10 |
| CD19 | DAP10 | NKG2D | DAP12 |
| CD19 | DAP10 | NKG2D | CD32 |
| CD19 | DAP10 | NKG2D | CD79a |
| CD19 | DAP10 | NKG2D | CD79b |
| CD19 | DAP12 | CD28 | CD8 |
| CD19 | DAP12 | CD28 | CD3ζ |
| CD19 | DAP12 | CD28 | CD3δ |
| CD19 | DAP12 | CD28 | CD3γ |
| CD19 | DAP12 | CD28 | CD3ε |
| CD19 | DAP12 | CD28 | FcγRI-γ |
| CD19 | DAP12 | CD28 | FcγRIII-γ |
| CD19 | DAP12 | CD28 | FcεRIβ |
| CD19 | DAP12 | CD28 | FcεRIγ |
| CD19 | DAP12 | CD28 | DAP10 |
| CD19 | DAP12 | CD28 | DAP12 |
| CD19 | DAP12 | CD28 | CD32 |
| CD19 | DAP12 | CD28 | CD79a |
| CD19 | DAP12 | CD28 | CD79b |
| CD19 | DAP12 | CD8 | CD8 |
| CD19 | DAP12 | CD8 | CD3ζ |
| CD19 | DAP12 | CD8 | CD3δ |
| CD19 | DAP12 | CD8 | CD3γ |
| CD19 | DAP12 | CD8 | CD3ε |
| CD19 | DAP12 | CD8 | FcγRI-γ |
| CD19 | DAP12 | CD8 | FcγRIII-γ |
| CD19 | DAP12 | CD8 | FcεRIβ |
| CD19 | DAP12 | CD8 | FcεRIγ |
| CD19 | DAP12 | CD8 | DAP10 |
| CD19 | DAP12 | CD8 | DAP12 |
| CD19 | DAP12 | CD8 | CD32 |
| CD19 | DAP12 | CD8 | CD79a |
| CD19 | DAP12 | CD8 | CD79b |
| CD19 | DAP12 | CD4 | CD8 |
| CD19 | DAP12 | CD4 | CD3ζ |
| CD19 | DAP12 | CD4 | CD3δ |
| CD19 | DAP12 | CD4 | CD3γ |
| CD19 | DAP12 | CD4 | CD3ε |
| CD19 | DAP12 | CD4 | FcγRI-γ |
| CD19 | DAP12 | CD4 | FcγRIII-γ |
| CD19 | DAP12 | CD4 | FcεRIβ |
| CD19 | DAP12 | CD4 | FcεRIγ |
| CD19 | DAP12 | CD4 | DAP10 |
| CD19 | DAP12 | CD4 | DAP12 |
| CD19 | DAP12 | CD4 | CD32 |
| CD19 | DAP12 | CD4 | CD79a |
| CD19 | DAP12 | CD4 | CD79b |
| CD19 | DAP12 | b2c | CD8 |
| CD19 | DAP12 | b2c | CD3ζ |
| CD19 | DAP12 | b2c | CD3δ |

TABLE 3-continued                                      TABLE 3-continued

Third Generation CARs                                  Third Generation CARs

| ScFv | Co-stimulatory Signal | Co-stimulatory Signal | Signal Domain | | ScFv | Co-stimulatory Signal | Co-stimulatory Signal | Signal Domain |
|---|---|---|---|---|---|---|---|---|
| CD19 | DAP12 | b2c | CD3γ | | CD19 | DAP12 | CD80 | FcεRIγ |
| CD19 | DAP12 | b2c | CD3ε | | CD19 | DAP12 | CD80 | DAP10 |
| CD19 | DAP12 | b2c | FcγRI-γ | | CD19 | DAP12 | CD80 | DAP12 |
| CD19 | DAP12 | b2c | FcγRIII-γ | | CD19 | DAP12 | CD80 | CD32 |
| CD19 | DAP12 | b2c | FcεRIβ | | CD19 | DAP12 | CD80 | CD79a |
| CD19 | DAP12 | b2c | FcεRIγ | | CD19 | DAP12 | CD80 | CD79b |
| CD19 | DAP12 | b2c | DAP10 | | CD19 | DAP12 | CD86 | CD8 |
| CD19 | DAP12 | b2c | DAP12 | | CD19 | DAP12 | CD86 | CD3ζ |
| CD19 | DAP12 | b2c | CD32 | | CD19 | DAP12 | CD86 | CD3δ |
| CD19 | DAP12 | b2c | CD79a | | CD19 | DAP12 | CD86 | CD3γ |
| CD19 | DAP12 | b2c | CD79b | | CD19 | DAP12 | CD86 | CD3ε |
| CD19 | DAP12 | CD137/41BB | CD8 | | CD19 | DAP12 | CD86 | FcγRI-γ |
| CD19 | DAP12 | CD137/41BB | CD3ζ | | CD19 | DAP12 | CD86 | FcγRIII-γ |
| CD19 | DAP12 | CD137/41BB | CD3δ | | CD19 | DAP12 | CD86 | FcεRIβ |
| CD19 | DAP12 | CD137/41BB | CD3γ | | CD19 | DAP12 | CD86 | FcεRIγ |
| CD19 | DAP12 | CD137/41BB | CD3ε | | CD19 | DAP12 | CD86 | DAP10 |
| CD19 | DAP12 | CD137/41BB | FcγRI-γ | | CD19 | DAP12 | CD86 | DAP12 |
| CD19 | DAP12 | CD137/41BB | FcγRIII-γ | | CD19 | DAP12 | CD86 | CD32 |
| CD19 | DAP12 | CD137/41BB | FcεRIβ | | CD19 | DAP12 | CD86 | CD79a |
| CD19 | DAP12 | CD137/41BB | FcεRIγ | | CD19 | DAP12 | CD86 | CD79b |
| CD19 | DAP12 | CD137/41BB | DAP10 | | CD19 | DAP12 | OX40 | CD8 |
| CD19 | DAP12 | CD137/41BB | DAP12 | | CD19 | DAP12 | OX40 | CD3ζ |
| CD19 | DAP12 | CD137/41BB | CD32 | | CD19 | DAP12 | OX40 | CD3δ |
| CD19 | DAP12 | CD137/41BB | CD79a | | CD19 | DAP12 | OX40 | CD3γ |
| CD19 | DAP12 | CD137/41BB | CD79b | | CD19 | DAP12 | OX40 | CD3ε |
| CD19 | DAP12 | ICOS | CD8 | | CD19 | DAP12 | OX40 | FcγRI-γ |
| CD19 | DAP12 | ICOS | CD3ζ | | CD19 | DAP12 | OX40 | FcγRIII-γ |
| CD19 | DAP12 | ICOS | CD3δ | | CD19 | DAP12 | OX40 | FcεRIβ |
| CD19 | DAP12 | ICOS | CD3γ | | CD19 | DAP12 | OX40 | FcεRIγ |
| CD19 | DAP12 | ICOS | CD3ε | | CD19 | DAP12 | OX40 | DAP10 |
| CD19 | DAP12 | ICOS | FcγRI-γ | | CD19 | DAP12 | OX40 | DAP12 |
| CD19 | DAP12 | ICOS | FcγRIII-γ | | CD19 | DAP12 | OX40 | CD32 |
| CD19 | DAP12 | ICOS | FcεRIβ | | CD19 | DAP12 | OX40 | CD79a |
| CD19 | DAP12 | ICOS | FcεRIγ | | CD19 | DAP12 | OX40 | CD79b |
| CD19 | DAP12 | ICOS | DAP10 | | CD19 | DAP12 | DAP10 | CD8 |
| CD19 | DAP12 | ICOS | DAP12 | | CD19 | DAP12 | DAP10 | CD3ζ |
| CD19 | DAP12 | ICOS | CD32 | | CD19 | DAP12 | DAP10 | CD3δ |
| CD19 | DAP12 | ICOS | CD79a | | CD19 | DAP12 | DAP10 | CD3γ |
| CD19 | DAP12 | ICOS | CD79b | | CD19 | DAP12 | DAP10 | CD3ε |
| CD19 | DAP12 | CD27 | CD8 | | CD19 | DAP12 | DAP10 | FcγRI-γ |
| CD19 | DAP12 | CD27 | CD3ζ | | CD19 | DAP12 | DAP10 | FcγRIII-γ |
| CD19 | DAP12 | CD27 | CD3δ | | CD19 | DAP12 | DAP10 | FcεRIβ |
| CD19 | DAP12 | CD27 | CD3γ | | CD19 | DAP12 | DAP10 | FcεRIγ |
| CD19 | DAP12 | CD27 | CD3ε | | CD19 | DAP12 | DAP10 | DAP10 |
| CD19 | DAP12 | CD27 | FcγRI-γ | | CD19 | DAP12 | DAP10 | DAP12 |
| CD19 | DAP12 | CD27 | FcγRIII-γ | | CD19 | DAP12 | DAP10 | CD32 |
| CD19 | DAP12 | CD27 | FcεRIβ | | CD19 | DAP12 | DAP10 | CD79a |
| CD19 | DAP12 | CD27 | FcεRIγ | | CD19 | DAP12 | DAP10 | CD79b |
| CD19 | DAP12 | CD27 | DAP10 | | CD19 | DAP12 | DAP12 | CD8 |
| CD19 | DAP12 | CD27 | DAP12 | | CD19 | DAP12 | DAP12 | CD3ζ |
| CD19 | DAP12 | CD27 | CD32 | | CD19 | DAP12 | DAP12 | CD3δ |
| CD19 | DAP12 | CD27 | CD79a | | CD19 | DAP12 | DAP12 | CD3γ |
| CD19 | DAP12 | CD27 | CD79b | | CD19 | DAP12 | DAP12 | CD3ε |
| CD19 | DAP12 | CD28δ | CD8 | | CD19 | DAP12 | DAP12 | FcγRI-γ |
| CD19 | DAP12 | CD28δ | CD3ζ | | CD19 | DAP12 | DAP12 | FcγRIII-γ |
| CD19 | DAP12 | CD28δ | CD3δ | | CD19 | DAP12 | DAP12 | FcεRIβ |
| CD19 | DAP12 | CD28δ | CD3γ | | CD19 | DAP12 | DAP12 | FcεRIγ |
| CD19 | DAP12 | CD28δ | CD3ε | | CD19 | DAP12 | DAP12 | DAP10 |
| CD19 | DAP12 | CD28δ | FcγRI-γ | | CD19 | DAP12 | DAP12 | DAP12 |
| CD19 | DAP12 | CD28δ | FcγRIII-γ | | CD19 | DAP12 | DAP12 | CD32 |
| CD19 | DAP12 | CD28δ | FcεRIβ | | CD19 | DAP12 | DAP12 | CD79a |
| CD19 | DAP12 | CD28δ | FcεRIγ | | CD19 | DAP12 | DAP12 | CD79b |
| CD19 | DAP12 | CD28δ | DAP10 | | CD19 | DAP12 | MyD88 | CD8 |
| CD19 | DAP12 | CD28δ | DAP12 | | CD19 | DAP12 | MyD88 | CD3ζ |
| CD19 | DAP12 | CD28δ | CD32 | | CD19 | DAP12 | MyD88 | CD3δ |
| CD19 | DAP12 | CD28δ | CD79a | | CD19 | DAP12 | MyD88 | CD3γ |
| CD19 | DAP12 | CD28δ | CD79b | | CD19 | DAP12 | MyD88 | CD3ε |
| CD19 | DAP12 | CD80 | CD8 | | CD19 | DAP12 | MyD88 | FcγRI-γ |
| CD19 | DAP12 | CD80 | CD3ζ | | CD19 | DAP12 | MyD88 | FcγRIII-γ |
| CD19 | DAP12 | CD80 | CD3δ | | CD19 | DAP12 | MyD88 | FcεRIβ |
| CD19 | DAP12 | CD80 | CD3γ | | CD19 | DAP12 | MyD88 | FcεRIγ |
| CD19 | DAP12 | CD80 | CD3ε | | CD19 | DAP12 | MyD88 | DAP10 |
| CD19 | DAP12 | CD80 | FcγRI-γ | | CD19 | DAP12 | MyD88 | DAP12 |
| CD19 | DAP12 | CD80 | FcγRIII-γ | | CD19 | DAP12 | MyD88 | CD32 |
| CD19 | DAP12 | CD80 | FcεRIβ | | CD19 | DAP12 | MyD88 | CD79a |

61

TABLE 3-continued

| | Third Generation CARs | | |
| --- | --- | --- | --- |
| ScFv | Co-stimulatory Signal | Co-stimulatory Signal | Signal Domain |
| CD19 | DAP12 | MyD88 | CD79b |
| CD19 | DAP12 | CD7 | CD8 |
| CD19 | DAP12 | CD7 | CD3ζ |
| CD19 | DAP12 | CD7 | CD3δ |
| CD19 | DAP12 | CD7 | CD3γ |
| CD19 | DAP12 | CD7 | CD3ε |
| CD19 | DAP12 | CD7 | FcγRI-γ |
| CD19 | DAP12 | CD7 | FcγRIII-γ |
| CD19 | DAP12 | CD7 | FcεRIβ |
| CD19 | DAP12 | CD7 | FcεRIγ |
| CD19 | DAP12 | CD7 | DAP10 |
| CD19 | DAP12 | CD7 | DAP12 |
| CD19 | DAP12 | CD7 | CD32 |
| CD19 | DAP12 | CD7 | CD79a |
| CD19 | DAP12 | CD7 | CD79b |
| CD19 | DAP12 | BTNL3 | CD8 |
| CD19 | DAP12 | BTNL3 | CD3ζ |
| CD19 | DAP12 | BTNL3 | CD3δ |
| CD19 | DAP12 | BTNL3 | CD3γ |
| CD19 | DAP12 | BTNL3 | CD3ε |
| CD19 | DAP12 | BTNL3 | FcγRI-γ |
| CD19 | DAP12 | BTNL3 | FcγRIII-γ |
| CD19 | DAP12 | BTNL3 | FcεRIβ |
| CD19 | DAP12 | BTNL3 | FcεRIγ |
| CD19 | DAP12 | BTNL3 | DAP10 |
| CD19 | DAP12 | BTNL3 | DAP12 |
| CD19 | DAP12 | BTNL3 | CD32 |
| CD19 | DAP12 | BTNL3 | CD79a |
| CD19 | DAP12 | BTNL3 | CD79b |
| CD19 | DAP12 | NKG2D | CD8 |
| CD19 | DAP12 | NKG2D | CD3ζ |
| CD19 | DAP12 | NKG2D | CD3δ |
| CD19 | DAP12 | NKG2D | CD3γ |
| CD19 | DAP12 | NKG2D | CD3ε |
| CD19 | DAP12 | NKG2D | FcγRI-γ |
| CD19 | DAP12 | NKG2D | FcγRIII-γ |
| CD19 | DAP12 | NKG2D | FcεRIβ |
| CD19 | DAP12 | NKG2D | FcεRIγ |
| CD19 | DAP12 | NKG2D | DAP10 |
| CD19 | DAP12 | NKG2D | DAP12 |
| CD19 | DAP12 | NKG2D | CD32 |
| CD19 | DAP12 | NKG2D | CD79a |
| CD19 | DAP12 | NKG2D | CD79b |
| CD19 | MyD88 | CD28 | CD8 |
| CD19 | MyD88 | CD28 | CD3ζ |
| CD19 | MyD88 | CD28 | CD3δ |
| CD19 | MyD88 | CD28 | CD3γ |
| CD19 | MyD88 | CD28 | CD3ε |
| CD19 | MyD88 | CD28 | FcγRI-γ |
| CD19 | MyD88 | CD28 | FcγRIII-γ |
| CD19 | MyD88 | CD28 | FcεRIβ |
| CD19 | MyD88 | CD28 | FcεRIγ |
| CD19 | MyD88 | CD28 | DAP10 |
| CD19 | MyD88 | CD28 | DAP12 |
| CD19 | MyD88 | CD28 | CD32 |
| CD19 | MyD88 | CD28 | CD79a |
| CD19 | MyD88 | CD28 | CD79b |
| CD19 | MyD88 | CD8 | CD8 |
| CD19 | MyD88 | CD8 | CD3ζ |
| CD19 | MyD88 | CD8 | CD3δ |
| CD19 | MyD88 | CD8 | CD3γ |
| CD19 | MyD88 | CD8 | CD3ε |
| CD19 | MyD88 | CD8 | FcγRI-γ |
| CD19 | MyD88 | CD8 | FcγRIII-γ |
| CD19 | MyD88 | CD8 | FcεRIβ |
| CD19 | MyD88 | CD8 | FcεRIγ |
| CD19 | MyD88 | CD8 | DAP10 |
| CD19 | MyD88 | CD8 | DAP12 |
| CD19 | MyD88 | CD8 | CD32 |
| CD19 | MyD88 | CD8 | CD79a |
| CD19 | MyD88 | CD8 | CD79b |
| CD19 | MyD88 | CD4 | CD8 |
| CD19 | MyD88 | CD4 | CD3ζ |
| CD19 | MyD88 | CD4 | CD3δ |
| CD19 | MyD88 | CD4 | CD3γ |

62

TABLE 3-continued

| | Third Generation CARs | | |
| --- | --- | --- | --- |
| ScFv | Co-stimulatory Signal | Co-stimulatory Signal | Signal Domain |
| CD19 | MyD88 | CD4 | CD3ε |
| CD19 | MyD88 | CD4 | FcγRI-γ |
| CD19 | MyD88 | CD4 | FcγRIII-γ |
| CD19 | MyD88 | CD4 | FcεRIβ |
| CD19 | MyD88 | CD4 | FcεRIγ |
| CD19 | MyD88 | CD4 | DAP10 |
| CD19 | MyD88 | CD4 | DAP12 |
| CD19 | MyD88 | CD4 | CD32 |
| CD19 | MyD88 | CD4 | CD79a |
| CD19 | MyD88 | CD4 | CD79b |
| CD19 | MyD88 | b2c | CD8 |
| CD19 | MyD88 | b2c | CD3ζ |
| CD19 | MyD88 | b2c | CD3δ |
| CD19 | MyD88 | b2c | CD3γ |
| CD19 | MyD88 | b2c | CD3ε |
| CD19 | MyD88 | b2c | FcγRI-γ |
| CD19 | MyD88 | b2c | FcγRIII-γ |
| CD19 | MyD88 | b2c | FcεRIβ |
| CD19 | MyD88 | b2c | FcεRIγ |
| CD19 | MyD88 | b2c | DAP10 |
| CD19 | MyD88 | b2c | DAP12 |
| CD19 | MyD88 | b2c | CD32 |
| CD19 | MyD88 | b2c | CD79a |
| CD19 | MyD88 | b2c | CD79b |
| CD19 | MyD88 | CD137/41BB | CD8 |
| CD19 | MyD88 | CD137/41BB | CD3ζ |
| CD19 | MyD88 | CD137/41BB | CD3δ |
| CD19 | MyD88 | CD137/41BB | CD3γ |
| CD19 | MyD88 | CD137/41BB | CD3ε |
| CD19 | MyD88 | CD137/41BB | FcγRI-γ |
| CD19 | MyD88 | CD137/41BB | FcγRIII-γ |
| CD19 | MyD88 | CD137/41BB | FcεRIβ |
| CD19 | MyD88 | CD137/41BB | FcεRIγ |
| CD19 | MyD88 | CD137/41BB | DAP10 |
| CD19 | MyD88 | CD137/41BB | DAP12 |
| CD19 | MyD88 | CD137/41BB | CD32 |
| CD19 | MyD88 | CD137/41BB | CD79a |
| CD19 | MyD88 | CD137/41BB | CD79b |
| CD19 | MyD88 | ICOS | CD8 |
| CD19 | MyD88 | ICOS | CD3ζ |
| CD19 | MyD88 | ICOS | CD3δ |
| CD19 | MyD88 | ICOS | CD3γ |
| CD19 | MyD88 | ICOS | CD3ε |
| CD19 | MyD88 | ICOS | FcγRI-γ |
| CD19 | MyD88 | ICOS | FcγRIII-γ |
| CD19 | MyD88 | ICOS | FcεRIβ |
| CD19 | MyD88 | ICOS | FcεRIγ |
| CD19 | MyD88 | ICOS | DAP10 |
| CD19 | MyD88 | ICOS | DAP12 |
| CD19 | MyD88 | ICOS | CD32 |
| CD19 | MyD88 | ICOS | CD79a |
| CD19 | MyD88 | ICOS | CD79b |
| CD19 | MyD88 | CD27 | CD8 |
| CD19 | MyD88 | CD27 | CD3ζ |
| CD19 | MyD88 | CD27 | CD3δ |
| CD19 | MyD88 | CD27 | CD3γ |
| CD19 | MyD88 | CD27 | CD3ε |
| CD19 | MyD88 | CD27 | FcγRI-γ |
| CD19 | MyD88 | CD27 | FcγRIII-γ |
| CD19 | MyD88 | CD27 | FcεRIβ |
| CD19 | MyD88 | CD27 | FcεRIγ |
| CD19 | MyD88 | CD27 | DAP10 |
| CD19 | MyD88 | CD27 | DAP12 |
| CD19 | MyD88 | CD27 | CD32 |
| CD19 | MyD88 | CD27 | CD79a |
| CD19 | MyD88 | CD27 | CD79b |
| CD19 | MyD88 | CD28δ | CD8 |
| CD19 | MyD88 | CD28δ | CD3ζ |
| CD19 | MyD88 | CD28δ | CD3δ |
| CD19 | MyD88 | CD28δ | CD3γ |
| CD19 | MyD88 | CD28δ | CD3ε |
| CD19 | MyD88 | CD28δ | FcγRI-γ |
| CD19 | MyD88 | CD28δ | FcγRIII-γ |
| CD19 | MyD88 | CD28δ | FcεRIβ |
| CD19 | MyD88 | CD28δ | FcεRIγ |

TABLE 3-continued

Third Generation CARs

| ScFv | Co-stimulatory Signal | Co-stimulatory Signal | Signal Domain |
|---|---|---|---|
| CD19 | MyD88 | CD28δ | DAP10 |
| CD19 | MyD88 | CD28δ | DAP12 |
| CD19 | MyD88 | CD28δ | CD32 |
| CD19 | MyD88 | CD28δ | CD79a |
| CD19 | MyD88 | CD28δ | CD79b |
| CD19 | MyD88 | CD80 | CD8 |
| CD19 | MyD88 | CD80 | CD3ζ |
| CD19 | MyD88 | CD80 | CD3δ |
| CD19 | MyD88 | CD80 | CD3γ |
| CD19 | MyD88 | CD80 | CD3ε |
| CD19 | MyD88 | CD80 | FcγRI-γ |
| CD19 | MyD88 | CD80 | FcγRIII-γ |
| CD19 | MyD88 | CD80 | FcεRIβ |
| CD19 | MyD88 | CD80 | FcεRIγ |
| CD19 | MyD88 | CD80 | DAP10 |
| CD19 | MyD88 | CD80 | DAP12 |
| CD19 | MyD88 | CD80 | CD32 |
| CD19 | MyD88 | CD80 | CD79a |
| CD19 | MyD88 | CD80 | CD79b |
| CD19 | MyD88 | CD86 | CD8 |
| CD19 | MyD88 | CD86 | CD3ζ |
| CD19 | MyD88 | CD86 | CD3δ |
| CD19 | MyD88 | CD86 | CD3γ |
| CD19 | MyD88 | CD86 | CD3ε |
| CD19 | MyD88 | CD86 | FcγRI-γ |
| CD19 | MyD88 | CD86 | FcγRIII-γ |
| CD19 | MyD88 | CD86 | FcεRIβ |
| CD19 | MyD88 | CD86 | FcεRIγ |
| CD19 | MyD88 | CD86 | DAP10 |
| CD19 | MyD88 | CD86 | DAP12 |
| CD19 | MyD88 | CD86 | CD32 |
| CD19 | MyD88 | CD86 | CD79a |
| CD19 | MyD88 | CD86 | CD79b |
| CD19 | MyD88 | OX40 | CD8 |
| CD19 | MyD88 | OX40 | CD3ζ |
| CD19 | MyD88 | OX40 | CD3δ |
| CD19 | MyD88 | OX40 | CD3γ |
| CD19 | MyD88 | OX40 | CD3ε |
| CD19 | MyD88 | OX40 | FcγRI-γ |
| CD19 | MyD88 | OX40 | FcγRIII-γ |
| CD19 | MyD88 | OX40 | FcεRIβ |
| CD19 | MyD88 | OX40 | FcεRIγ |
| CD19 | MyD88 | OX40 | DAP10 |
| CD19 | MyD88 | OX40 | DAP12 |
| CD19 | MyD88 | OX40 | CD32 |
| CD19 | MyD88 | OX40 | CD79a |
| CD19 | MyD88 | OX40 | CD79b |
| CD19 | MyD88 | DAP10 | CD8 |
| CD19 | MyD88 | DAP10 | CD3ζ |
| CD19 | MyD88 | DAP10 | CD3δ |
| CD19 | MyD88 | DAP10 | CD3γ |
| CD19 | MyD88 | DAP10 | CD3ε |
| CD19 | MyD88 | DAP10 | FcγRI-γ |
| CD19 | MyD88 | DAP10 | FcγRIII-γ |
| CD19 | MyD88 | DAP10 | FcεRIβ |
| CD19 | MyD88 | DAP10 | FcεRIγ |
| CD19 | MyD88 | DAP10 | DAP10 |
| CD19 | MyD88 | DAP10 | DAP12 |
| CD19 | MyD88 | DAP10 | CD32 |
| CD19 | MyD88 | DAP10 | CD79a |
| CD19 | MyD88 | DAP10 | CD79b |
| CD19 | MyD88 | DAP12 | CD8 |
| CD19 | MyD88 | DAP12 | CD3ζ |
| CD19 | MyD88 | DAP12 | CD3δ |
| CD19 | MyD88 | DAP12 | CD3γ |
| CD19 | MyD88 | DAP12 | CD3ε |
| CD19 | MyD88 | DAP12 | FcγRI-γ |
| CD19 | MyD88 | DAP12 | FcγRIII-γ |
| CD19 | MyD88 | DAP12 | FcεRIβ |
| CD19 | MyD88 | DAP12 | FcεRIγ |
| CD19 | MyD88 | DAP12 | DAP10 |
| CD19 | MyD88 | DAP12 | DAP12 |
| CD19 | MyD88 | DAP12 | CD32 |
| CD19 | MyD88 | DAP12 | CD79a |
| CD19 | MyD88 | DAP12 | CD79b |

TABLE 3-continued

Third Generation CARs

| ScFv | Co-stimulatory Signal | Co-stimulatory Signal | Signal Domain |
|---|---|---|---|
| CD19 | MyD88 | MyD88 | CD8 |
| CD19 | MyD88 | MyD88 | CD3ζ |
| CD19 | MyD88 | MyD88 | CD3δ |
| CD19 | MyD88 | MyD88 | CD3γ |
| CD19 | MyD88 | MyD88 | CD3ε |
| CD19 | MyD88 | MyD88 | FcγRI-γ |
| CD19 | MyD88 | MyD88 | FcγRIII-γ |
| CD19 | MyD88 | MyD88 | FcεRIβ |
| CD19 | MyD88 | MyD88 | FcεRIγ |
| CD19 | MyD88 | MyD88 | DAP10 |
| CD19 | MyD88 | MyD88 | DAP12 |
| CD19 | MyD88 | MyD88 | CD32 |
| CD19 | MyD88 | MyD88 | CD79a |
| CD19 | MyD88 | MyD88 | CD79b |
| CD19 | MyD88 | CD7 | CD8 |
| CD19 | MyD88 | CD7 | CD3ζ |
| CD19 | MyD88 | CD7 | CD3δ |
| CD19 | MyD88 | CD7 | CD3γ |
| CD19 | MyD88 | CD7 | CD3ε |
| CD19 | MyD88 | CD7 | FcγRI-γ |
| CD19 | MyD88 | CD7 | FcγRIII-γ |
| CD19 | MyD88 | CD7 | FcεRIβ |
| CD19 | MyD88 | CD7 | FcεRIγ |
| CD19 | MyD88 | CD7 | DAP10 |
| CD19 | MyD88 | CD7 | DAP12 |
| CD19 | MyD88 | CD7 | CD32 |
| CD19 | MyD88 | CD7 | CD79a |
| CD19 | MyD88 | CD7 | CD79b |
| CD19 | MyD88 | BTNL3 | CD8 |
| CD19 | MyD88 | BTNL3 | CD3ζ |
| CD19 | MyD88 | BTNL3 | CD3δ |
| CD19 | MyD88 | BTNL3 | CD3γ |
| CD19 | MyD88 | BTNL3 | CD3ε |
| CD19 | MyD88 | BTNL3 | FcγRI-γ |
| CD19 | MyD88 | BTNL3 | FcγRIII-γ |
| CD19 | MyD88 | BTNL3 | FcεRIβ |
| CD19 | MyD88 | BTNL3 | FcεRIγ |
| CD19 | MyD88 | BTNL3 | DAP10 |
| CD19 | MyD88 | BTNL3 | DAP12 |
| CD19 | MyD88 | BTNL3 | CD32 |
| CD19 | MyD88 | BTNL3 | CD79a |
| CD19 | MyD88 | BTNL3 | CD79b |
| CD19 | MyD88 | NKG2D | CD8 |
| CD19 | MyD88 | NKG2D | CD3ζ |
| CD19 | MyD88 | NKG2D | CD3δ |
| CD19 | MyD88 | NKG2D | CD3γ |
| CD19 | MyD88 | NKG2D | CD3ε |
| CD19 | MyD88 | NKG2D | FcγRI-γ |
| CD19 | MyD88 | NKG2D | FcγRIII-γ |
| CD19 | MyD88 | NKG2D | FcεRIβ |
| CD19 | MyD88 | NKG2D | FcεRIγ |
| CD19 | MyD88 | NKG2D | DAP10 |
| CD19 | MyD88 | NKG2D | DAP12 |
| CD19 | MyD88 | NKG2D | CD32 |
| CD19 | MyD88 | NKG2D | CD79a |
| CD19 | MyD88 | NKG2D | CD79b |
| CD19 | CD7 | CD28 | CD8 |
| CD19 | CD7 | CD28 | CD3ζ |
| CD19 | CD7 | CD28 | CD3δ |
| CD19 | CD7 | CD28 | CD3γ |
| CD19 | CD7 | CD28 | CD3ε |
| CD19 | CD7 | CD28 | FcγRI-γ |
| CD19 | CD7 | CD28 | FcγRIII-γ |
| CD19 | CD7 | CD28 | FcεRIβ |
| CD19 | CD7 | CD28 | FcεRIγ |
| CD19 | CD7 | CD28 | DAP10 |
| CD19 | CD7 | CD28 | DAP12 |
| CD19 | CD7 | CD28 | CD32 |
| CD19 | CD7 | CD28 | CD79a |
| CD19 | CD7 | CD28 | CD79b |
| CD19 | CD7 | CD8 | CD8 |
| CD19 | CD7 | CD8 | CD3ζ |
| CD19 | CD7 | CD8 | CD3δ |
| CD19 | CD7 | CD8 | CD3γ |
| CD19 | CD7 | CD8 | CD3ε |

TABLE 3-continued

| | Third Generation CARs | | |
|---|---|---|---|
| ScFv | Co-stimulatory Signal | Co-stimulatory Signal | Signal Domain |
| CD19 | CD7 | CD8 | FcγRI-γ |
| CD19 | CD7 | CD8 | FcγRIII-γ |
| CD19 | CD7 | CD8 | FcεRIβ |
| CD19 | CD7 | CD8 | FcεRIγ |
| CD19 | CD7 | CD8 | DAP10 |
| CD19 | CD7 | CD8 | DAP12 |
| CD19 | CD7 | CD8 | CD32 |
| CD19 | CD7 | CD8 | CD79a |
| CD19 | CD7 | CD8 | CD79b |
| CD19 | CD7 | CD4 | CD8 |
| CD19 | CD7 | CD4 | CD3ζ |
| CD19 | CD7 | CD4 | CD3δ |
| CD19 | CD7 | CD4 | CD3γ |
| CD19 | CD7 | CD4 | CD3ε |
| CD19 | CD7 | CD4 | FcγRI-γ |
| CD19 | CD7 | CD4 | FcγRIII-γ |
| CD19 | CD7 | CD4 | FcεRIβ |
| CD19 | CD7 | CD4 | FcεRIγ |
| CD19 | CD7 | CD4 | DAP10 |
| CD19 | CD7 | CD4 | DAP12 |
| CD19 | CD7 | CD4 | CD32 |
| CD19 | CD7 | CD4 | CD79a |
| CD19 | CD7 | CD4 | CD79b |
| CD19 | CD7 | b2c | CD8 |
| CD19 | CD7 | b2c | CD3ζ |
| CD19 | CD7 | b2c | CD3δ |
| CD19 | CD7 | b2c | CD3γ |
| CD19 | CD7 | b2c | CD3ε |
| CD19 | CD7 | b2c | FcγRI-γ |
| CD19 | CD7 | b2c | FcγRIII-γ |
| CD19 | CD7 | b2c | FcεRIβ |
| CD19 | CD7 | b2c | FcεRIγ |
| CD19 | CD7 | b2c | DAP10 |
| CD19 | CD7 | b2c | DAP12 |
| CD19 | CD7 | b2c | CD32 |
| CD19 | CD7 | b2c | CD79a |
| CD19 | CD7 | b2c | CD79b |
| CD19 | CD7 | CD137/41BB | CD8 |
| CD19 | CD7 | CD137/41BB | CD3ζ |
| CD19 | CD7 | CD137/41BB | CD3δ |
| CD19 | CD7 | CD137/41BB | CD3γ |
| CD19 | CD7 | CD137/41BB | CD3ε |
| CD19 | CD7 | CD137/41BB | FcγRI-γ |
| CD19 | CD7 | CD137/41BB | FcγRIII-γ |
| CD19 | CD7 | CD137/41BB | FcεRIβ |
| CD19 | CD7 | CD137/41BB | FcεRIγ |
| CD19 | CD7 | CD137/41BB | DAP10 |
| CD19 | CD7 | CD137/41BB | DAP12 |
| CD19 | CD7 | CD137/41BB | CD32 |
| CD19 | CD7 | CD137/41BB | CD79a |
| CD19 | CD7 | CD137/41BB | CD79b |
| CD19 | CD7 | ICOS | CD8 |
| CD19 | CD7 | ICOS | CD3ζ |
| CD19 | CD7 | ICOS | CD3δ |
| CD19 | CD7 | ICOS | CD3γ |
| CD19 | CD7 | ICOS | CD3ε |
| CD19 | CD7 | ICOS | FcγRI-γ |
| CD19 | CD7 | ICOS | FcγRIII-γ |
| CD19 | CD7 | ICOS | FcεRIβ |
| CD19 | CD7 | ICOS | FcεRIγ |
| CD19 | CD7 | ICOS | DAP10 |
| CD19 | CD7 | ICOS | DAP12 |
| CD19 | CD7 | ICOS | CD32 |
| CD19 | CD7 | ICOS | CD79a |
| CD19 | CD7 | ICOS | CD79b |
| CD19 | CD7 | CD27 | CD8 |
| CD19 | CD7 | CD27 | CD3ζ |
| CD19 | CD7 | CD27 | CD3δ |
| CD19 | CD7 | CD27 | CD3γ |
| CD19 | CD7 | CD27 | CD3ε |
| CD19 | CD7 | CD27 | FcγRI-γ |
| CD19 | CD7 | CD27 | FcγRIII-γ |
| CD19 | CD7 | CD27 | FcεRIβ |
| CD19 | CD7 | CD27 | FcεRIγ |
| CD19 | CD7 | CD27 | DAP10 |

TABLE 3-continued

| | Third Generation CARs | | |
|---|---|---|---|
| ScFv | Co-stimulatory Signal | Co-stimulatory Signal | Signal Domain |
| CD19 | CD7 | CD27 | DAP12 |
| CD19 | CD7 | CD27 | CD32 |
| CD19 | CD7 | CD27 | CD79a |
| CD19 | CD7 | CD27 | CD79b |
| CD19 | CD7 | CD28δ | CD8 |
| CD19 | CD7 | CD28δ | CD3ζ |
| CD19 | CD7 | CD28δ | CD3δ |
| CD19 | CD7 | CD28δ | CD3γ |
| CD19 | CD7 | CD28δ | CD3ε |
| CD19 | CD7 | CD28δ | FcγRI-γ |
| CD19 | CD7 | CD28δ | FcγRIII-γ |
| CD19 | CD7 | CD28δ | FcεRIβ |
| CD19 | CD7 | CD28δ | FcεRIγ |
| CD19 | CD7 | CD28δ | DAP10 |
| CD19 | CD7 | CD28δ | DAP12 |
| CD19 | CD7 | CD28δ | CD32 |
| CD19 | CD7 | CD28δ | CD79a |
| CD19 | CD7 | CD28δ | CD79b |
| CD19 | CD7 | CD80 | CD8 |
| CD19 | CD7 | CD80 | CD3ζ |
| CD19 | CD7 | CD80 | CD3δ |
| CD19 | CD7 | CD80 | CD3γ |
| CD19 | CD7 | CD80 | CD3ε |
| CD19 | CD7 | CD80 | FcγRI-γ |
| CD19 | CD7 | CD80 | FcγRIII-γ |
| CD19 | CD7 | CD80 | FcεRIβ |
| CD19 | CD7 | CD80 | FcεRIγ |
| CD19 | CD7 | CD80 | DAP10 |
| CD19 | CD7 | CD80 | DAP12 |
| CD19 | CD7 | CD80 | CD32 |
| CD19 | CD7 | CD80 | CD79a |
| CD19 | CD7 | CD80 | CD79b |
| CD19 | CD7 | CD86 | CD8 |
| CD19 | CD7 | CD86 | CD3ζ |
| CD19 | CD7 | CD86 | CD3δ |
| CD19 | CD7 | CD86 | CD3γ |
| CD19 | CD7 | CD86 | CD3ε |
| CD19 | CD7 | CD86 | FcγRI-γ |
| CD19 | CD7 | CD86 | FcγRIII-γ |
| CD19 | CD7 | CD86 | FcεRIβ |
| CD19 | CD7 | CD86 | FcεRIγ |
| CD19 | CD7 | CD86 | DAP10 |
| CD19 | CD7 | CD86 | DAP12 |
| CD19 | CD7 | CD86 | CD32 |
| CD19 | CD7 | CD86 | CD79a |
| CD19 | CD7 | CD86 | CD79b |
| CD19 | CD7 | OX40 | CD8 |
| CD19 | CD7 | OX40 | CD3ζ |
| CD19 | CD7 | OX40 | CD3δ |
| CD19 | CD7 | OX40 | CD3γ |
| CD19 | CD7 | OX40 | CD3ε |
| CD19 | CD7 | OX40 | FcγRI-γ |
| CD19 | CD7 | OX40 | FcγRIII-γ |
| CD19 | CD7 | OX40 | FcεRIβ |
| CD19 | CD7 | OX40 | FcεRIγ |
| CD19 | CD7 | OX40 | DAP10 |
| CD19 | CD7 | OX40 | DAP12 |
| CD19 | CD7 | OX40 | CD32 |
| CD19 | CD7 | OX40 | CD79a |
| CD19 | CD7 | OX40 | CD79b |
| CD19 | CD7 | DAP10 | CD8 |
| CD19 | CD7 | DAP10 | CD3ζ |
| CD19 | CD7 | DAP10 | CD3δ |
| CD19 | CD7 | DAP10 | CD3γ |
| CD19 | CD7 | DAP10 | CD3ε |
| CD19 | CD7 | DAP10 | FcγRI-γ |
| CD19 | CD7 | DAP10 | FcγRIII-γ |
| CD19 | CD7 | DAP10 | FcεRIβ |
| CD19 | CD7 | DAP10 | FcεRIγ |
| CD19 | CD7 | DAP10 | DAP10 |
| CD19 | CD7 | DAP10 | DAP12 |
| CD19 | CD7 | DAP10 | CD32 |
| CD19 | CD7 | DAP10 | CD79a |
| CD19 | CD7 | DAP10 | CD79b |
| CD19 | CD7 | DAP12 | CD8 |

TABLE 3-continued

Third Generation CARs

| ScFv | Co-stimulatory Signal | Co-stimulatory Signal | Signal Domain |
|---|---|---|---|
| CD19 | CD7 | DAP12 | CD3ζ |
| CD19 | CD7 | DAP12 | CD3δ |
| CD19 | CD7 | DAP12 | CD3γ |
| CD19 | CD7 | DAP12 | CD3ε |
| CD19 | CD7 | DAP12 | FcγRI-γ |
| CD19 | CD7 | DAP12 | FcγRIII-γ |
| CD19 | CD7 | DAP12 | FcεRIβ |
| CD19 | CD7 | DAP12 | FcεRIγ |
| CD19 | CD7 | DAP12 | DAP10 |
| CD19 | CD7 | DAP12 | DAP12 |
| CD19 | CD7 | DAP12 | CD32 |
| CD19 | CD7 | DAP12 | CD79a |
| CD19 | CD7 | DAP12 | CD79b |
| CD19 | CD7 | MyD88 | CD8 |
| CD19 | CD7 | MyD88 | CD3ζ |
| CD19 | CD7 | MyD88 | CD3δ |
| CD19 | CD7 | MyD88 | CD3γ |
| CD19 | CD7 | MyD88 | CD3ε |
| CD19 | CD7 | MyD88 | FcγRI-γ |
| CD19 | CD7 | MyD88 | FcγRIII-γ |
| CD19 | CD7 | MyD88 | FcεRIβ |
| CD19 | CD7 | MyD88 | FcεRIγ |
| CD19 | CD7 | MyD88 | DAP10 |
| CD19 | CD7 | MyD88 | DAP12 |
| CD19 | CD7 | MyD88 | CD32 |
| CD19 | CD7 | MyD88 | CD79a |
| CD19 | CD7 | MyD88 | CD79b |
| CD19 | CD7 | CD7 | CD8 |
| CD19 | CD7 | CD7 | CD3ζ |
| CD19 | CD7 | CD7 | CD3δ |
| CD19 | CD7 | CD7 | CD3γ |
| CD19 | CD7 | CD7 | CD3ε |
| CD19 | CD7 | CD7 | FcγRI-γ |
| CD19 | CD7 | CD7 | FcγRIII-γ |
| CD19 | CD7 | CD7 | FcεRIβ |
| CD19 | CD7 | CD7 | FcεRIγ |
| CD19 | CD7 | CD7 | DAP10 |
| CD19 | CD7 | CD7 | DAP12 |
| CD19 | CD7 | CD7 | CD32 |
| CD19 | CD7 | CD7 | CD79a |
| CD19 | CD7 | CD7 | CD79b |
| CD19 | CD7 | BTNL3 | CD8 |
| CD19 | CD7 | BTNL3 | CD3ζ |
| CD19 | CD7 | BTNL3 | CD3δ |
| CD19 | CD7 | BTNL3 | CD3γ |
| CD19 | CD7 | BTNL3 | CD3ε |
| CD19 | CD7 | BTNL3 | FcγRI-γ |
| CD19 | CD7 | BTNL3 | FcγRIII-γ |
| CD19 | CD7 | BTNL3 | FcεRIβ |
| CD19 | CD7 | BTNL3 | FcεRIγ |
| CD19 | CD7 | BTNL3 | DAP10 |
| CD19 | CD7 | BTNL3 | DAP12 |
| CD19 | CD7 | BTNL3 | CD32 |
| CD19 | CD7 | BTNL3 | CD79a |
| CD19 | CD7 | BTNL3 | CD79b |
| CD19 | CD7 | NKG2D | CD8 |
| CD19 | CD7 | NKG2D | CD3ζ |
| CD19 | CD7 | NKG2D | CD3δ |
| CD19 | CD7 | NKG2D | CD3γ |
| CD19 | CD7 | NKG2D | CD3ε |
| CD19 | CD7 | NKG2D | FcγRI-γ |
| CD19 | CD7 | NKG2D | FcγRIII-γ |
| CD19 | CD7 | NKG2D | FcεRIβ |
| CD19 | CD7 | NKG2D | FcεRIγ |
| CD19 | CD7 | NKG2D | DAP10 |
| CD19 | CD7 | NKG2D | DAP12 |
| CD19 | CD7 | NKG2D | CD32 |
| CD19 | CD7 | NKG2D | CD79a |
| CD19 | CD7 | NKG2D | CD79b |
| CD19 | BTNL3 | CD28 | CD8 |
| CD19 | BTNL3 | CD28 | CD3ζ |
| CD19 | BTNL3 | CD28 | CD3δ |
| CD19 | BTNL3 | CD28 | CD3γ |
| CD19 | BTNL3 | CD28 | CD3ε |
| CD19 | BTNL3 | CD28 | FcγRI-γ |

TABLE 3-continued

Third Generation CARs

| ScFv | Co-stimulatory Signal | Co-stimulatory Signal | Signal Domain |
|---|---|---|---|
| CD19 | BTNL3 | CD28 | FcγRIII-γ |
| CD19 | BTNL3 | CD28 | FcεRIβ |
| CD19 | BTNL3 | CD28 | FcεRIγ |
| CD19 | BTNL3 | CD28 | DAP10 |
| CD19 | BTNL3 | CD28 | DAP12 |
| CD19 | BTNL3 | CD28 | CD32 |
| CD19 | BTNL3 | CD28 | CD79a |
| CD19 | BTNL3 | CD28 | CD79b |
| CD19 | BTNL3 | CD8 | CD8 |
| CD19 | BTNL3 | CD8 | CD3ζ |
| CD19 | BTNL3 | CD8 | CD3δ |
| CD19 | BTNL3 | CD8 | CD3γ |
| CD19 | BTNL3 | CD8 | CD3ε |
| CD19 | BTNL3 | CD8 | FcγRI-γ |
| CD19 | BTNL3 | CD8 | FcγRIII-γ |
| CD19 | BTNL3 | CD8 | FcεRIβ |
| CD19 | BTNL3 | CD8 | FcεRIγ |
| CD19 | BTNL3 | CD8 | DAP10 |
| CD19 | BTNL3 | CD8 | DAP12 |
| CD19 | BTNL3 | CD8 | CD32 |
| CD19 | BTNL3 | CD8 | CD79a |
| CD19 | BTNL3 | CD8 | CD79b |
| CD19 | BTNL3 | CD4 | CD8 |
| CD19 | BTNL3 | CD4 | CD3ζ |
| CD19 | BTNL3 | CD4 | CD3δ |
| CD19 | BTNL3 | CD4 | CD3γ |
| CD19 | BTNL3 | CD4 | CD3ε |
| CD19 | BTNL3 | CD4 | FcγRI-γ |
| CD19 | BTNL3 | CD4 | FcγRIII-γ |
| CD19 | BTNL3 | CD4 | FcεRIβ |
| CD19 | BTNL3 | CD4 | FcεRIγ |
| CD19 | BTNL3 | CD4 | DAP10 |
| CD19 | BTNL3 | CD4 | DAP12 |
| CD19 | BTNL3 | CD4 | CD32 |
| CD19 | BTNL3 | CD4 | CD79a |
| CD19 | BTNL3 | CD4 | CD79b |
| CD19 | BTNL3 | b2c | CD8 |
| CD19 | BTNL3 | b2c | CD3ζ |
| CD19 | BTNL3 | b2c | CD3δ |
| CD19 | BTNL3 | b2c | CD3γ |
| CD19 | BTNL3 | b2c | CD3ε |
| CD19 | BTNL3 | b2c | FcγRI-γ |
| CD19 | BTNL3 | b2c | FcγRIII-γ |
| CD19 | BTNL3 | b2c | FcεRIβ |
| CD19 | BTNL3 | b2c | FcεRIγ |
| CD19 | BTNL3 | b2c | DAP10 |
| CD19 | BTNL3 | b2c | DAP12 |
| CD19 | BTNL3 | b2c | CD32 |
| CD19 | BTNL3 | b2c | CD79a |
| CD19 | BTNL3 | b2c | CD79b |
| CD19 | BTNL3 | CD137/41BB | CD8 |
| CD19 | BTNL3 | CD137/41BB | CD3ζ |
| CD19 | BTNL3 | CD137/41BB | CD3δ |
| CD19 | BTNL3 | CD137/41BB | CD3γ |
| CD19 | BTNL3 | CD137/41BB | CD3ε |
| CD19 | BTNL3 | CD137/41BB | FcγRI-γ |
| CD19 | BTNL3 | CD137/41BB | FcγRIII-γ |
| CD19 | BTNL3 | CD137/41BB | FcεRIβ |
| CD19 | BTNL3 | CD137/41BB | FcεRIγ |
| CD19 | BTNL3 | CD137/41BB | DAP10 |
| CD19 | BTNL3 | CD137/41BB | DAP12 |
| CD19 | BTNL3 | CD137/41BB | CD32 |
| CD19 | BTNL3 | CD137/41BB | CD79a |
| CD19 | BTNL3 | CD137/41BB | CD79b |
| CD19 | BTNL3 | ICOS | CD8 |
| CD19 | BTNL3 | ICOS | CD3ζ |
| CD19 | BTNL3 | ICOS | CD3δ |
| CD19 | BTNL3 | ICOS | CD3γ |
| CD19 | BTNL3 | ICOS | CD3ε |
| CD19 | BTNL3 | ICOS | FcγRI-γ |
| CD19 | BTNL3 | ICOS | FcγRIII-γ |
| CD19 | BTNL3 | ICOS | FcεRIβ |
| CD19 | BTNL3 | ICOS | FcεRIγ |
| CD19 | BTNL3 | ICOS | DAP10 |
| CD19 | BTNL3 | ICOS | DAP12 |

TABLE 3-continued

| | Third Generation CARs | | |
|---|---|---|---|
| ScFv | Co-stimulatory Signal | Co-stimulatory Signal | Signal Domain |
| CD19 | BTNL3 | ICOS | CD32 |
| CD19 | BTNL3 | ICOS | CD79a |
| CD19 | BTNL3 | ICOS | CD79b |
| CD19 | BTNL3 | CD27 | CD8 |
| CD19 | BTNL3 | CD27 | CD3ζ |
| CD19 | BTNL3 | CD27 | CD3δ |
| CD19 | BTNL3 | CD27 | CD3γ |
| CD19 | BTNL3 | CD27 | CD3ε |
| CD19 | BTNL3 | CD27 | FcγRI-γ |
| CD19 | BTNL3 | CD27 | FcγRIII-γ |
| CD19 | BTNL3 | CD27 | FcεRIβ |
| CD19 | BTNL3 | CD27 | FcεRIγ |
| CD19 | BTNL3 | CD27 | DAP10 |
| CD19 | BTNL3 | CD27 | DAP12 |
| CD19 | BTNL3 | CD27 | CD32 |
| CD19 | BTNL3 | CD27 | CD79a |
| CD19 | BTNL3 | CD27 | CD79b |
| CD19 | BTNL3 | CD28δ | CD8 |
| CD19 | BTNL3 | CD28δ | CD3ζ |
| CD19 | BTNL3 | CD28δ | CD3δ |
| CD19 | BTNL3 | CD28δ | CD3γ |
| CD19 | BTNL3 | CD28δ | CD3ε |
| CD19 | BTNL3 | CD28δ | FcγRI-γ |
| CD19 | BTNL3 | CD28δ | FcγRIII-γ |
| CD19 | BTNL3 | CD28δ | FcεRIβ |
| CD19 | BTNL3 | CD28δ | FcεRIγ |
| CD19 | BTNL3 | CD28δ | DAP10 |
| CD19 | BTNL3 | CD28δ | DAP12 |
| CD19 | BTNL3 | CD28δ | CD32 |
| CD19 | BTNL3 | CD28δ | CD79a |
| CD19 | BTNL3 | CD28δ | CD79b |
| CD19 | BTNL3 | CD80 | CD8 |
| CD19 | BTNL3 | CD80 | CD3ζ |
| CD19 | BTNL3 | CD80 | CD3δ |
| CD19 | BTNL3 | CD80 | CD3γ |
| CD19 | BTNL3 | CD80 | CD3ε |
| CD19 | BTNL3 | CD80 | FcγRI-γ |
| CD19 | BTNL3 | CD80 | FcγRIII-γ |
| CD19 | BTNL3 | CD80 | FcεRIβ |
| CD19 | BTNL3 | CD80 | FcεRIγ |
| CD19 | BTNL3 | CD80 | DAP10 |
| CD19 | BTNL3 | CD80 | DAP12 |
| CD19 | BTNL3 | CD80 | CD32 |
| CD19 | BTNL3 | CD80 | CD79a |
| CD19 | BTNL3 | CD80 | CD79b |
| CD19 | BTNL3 | CD86 | CD8 |
| CD19 | BTNL3 | CD86 | CD3ζ |
| CD19 | BTNL3 | CD86 | CD3δ |
| CD19 | BTNL3 | CD86 | CD3γ |
| CD19 | BTNL3 | CD86 | CD3ε |
| CD19 | BTNL3 | CD86 | FcγRI-γ |
| CD19 | BTNL3 | CD86 | FcγRIII-γ |
| CD19 | BTNL3 | CD86 | FcεRIβ |
| CD19 | BTNL3 | CD86 | FcεRIγ |
| CD19 | BTNL3 | CD86 | DAP10 |
| CD19 | BTNL3 | CD86 | DAP12 |
| CD19 | BTNL3 | CD86 | CD32 |
| CD19 | BTNL3 | CD86 | CD79a |
| CD19 | BTNL3 | CD86 | CD79b |
| CD19 | BTNL3 | OX40 | CD8 |
| CD19 | BTNL3 | OX40 | CD3ζ |
| CD19 | BTNL3 | OX40 | CD3δ |
| CD19 | BTNL3 | OX40 | CD3γ |
| CD19 | BTNL3 | OX40 | CD3ε |
| CD19 | BTNL3 | OX40 | FcγRI-γ |
| CD19 | BTNL3 | OX40 | FcγRIII-γ |
| CD19 | BTNL3 | OX40 | FcεRIβ |
| CD19 | BTNL3 | OX40 | FcεRIγ |
| CD19 | BTNL3 | OX40 | DAP10 |
| CD19 | BTNL3 | OX40 | DAP12 |
| CD19 | BTNL3 | OX40 | CD32 |
| CD19 | BTNL3 | OX40 | CD79a |
| CD19 | BTNL3 | OX40 | CD79b |
| CD19 | BTNL3 | DAP10 | CD8 |
| CD19 | BTNL3 | DAP10 | CD3ζ |

TABLE 3-continued

| | Third Generation CARs | | |
|---|---|---|---|
| ScFv | Co-stimulatory Signal | Co-stimulatory Signal | Signal Domain |
| CD19 | BTNL3 | DAP10 | CD3δ |
| CD19 | BTNL3 | DAP10 | CD3γ |
| CD19 | BTNL3 | DAP10 | CD3ε |
| CD19 | BTNL3 | DAP10 | FcγRI-γ |
| CD19 | BTNL3 | DAP10 | FcγRIII-γ |
| CD19 | BTNL3 | DAP10 | FcεRIβ |
| CD19 | BTNL3 | DAP10 | FcεRIγ |
| CD19 | BTNL3 | DAP10 | DAP10 |
| CD19 | BTNL3 | DAP10 | DAP12 |
| CD19 | BTNL3 | DAP10 | CD32 |
| CD19 | BTNL3 | DAP10 | CD79a |
| CD19 | BTNL3 | DAP10 | CD79b |
| CD19 | BTNL3 | DAP12 | CD8 |
| CD19 | BTNL3 | DAP12 | CD3ζ |
| CD19 | BTNL3 | DAP12 | CD3δ |
| CD19 | BTNL3 | DAP12 | CD3γ |
| CD19 | BTNL3 | DAP12 | CD3ε |
| CD19 | BTNL3 | DAP12 | FcγRI-γ |
| CD19 | BTNL3 | DAP12 | FcγRIII-γ |
| CD19 | BTNL3 | DAP12 | FcεRIβ |
| CD19 | BTNL3 | DAP12 | FcεRIγ |
| CD19 | BTNL3 | DAP12 | DAP10 |
| CD19 | BTNL3 | DAP12 | DAP12 |
| CD19 | BTNL3 | DAP12 | CD32 |
| CD19 | BTNL3 | DAP12 | CD79a |
| CD19 | BTNL3 | DAP12 | CD79b |
| CD19 | BTNL3 | MyD88 | CD8 |
| CD19 | BTNL3 | MyD88 | CD3ζ |
| CD19 | BTNL3 | MyD88 | CD3δ |
| CD19 | BTNL3 | MyD88 | CD3γ |
| CD19 | BTNL3 | MyD88 | CD3ε |
| CD19 | BTNL3 | MyD88 | FcγRI-γ |
| CD19 | BTNL3 | MyD88 | FcγRIII-γ |
| CD19 | BTNL3 | MyD88 | FcεRIβ |
| CD19 | BTNL3 | MyD88 | FcεRIγ |
| CD19 | BTNL3 | MyD88 | DAP10 |
| CD19 | BTNL3 | MyD88 | DAP12 |
| CD19 | BTNL3 | MyD88 | CD32 |
| CD19 | BTNL3 | MyD88 | CD79a |
| CD19 | BTNL3 | MyD88 | CD79b |
| CD19 | BTNL3 | CD7 | CD8 |
| CD19 | BTNL3 | CD7 | CD3ζ |
| CD19 | BTNL3 | CD7 | CD3δ |
| CD19 | BTNL3 | CD7 | CD3γ |
| CD19 | BTNL3 | CD7 | CD3ε |
| CD19 | BTNL3 | CD7 | FcγRI-γ |
| CD19 | BTNL3 | CD7 | FcγRIII-γ |
| CD19 | BTNL3 | CD7 | FcεRIβ |
| CD19 | BTNL3 | CD7 | FcεRIγ |
| CD19 | BTNL3 | CD7 | DAP10 |
| CD19 | BTNL3 | CD7 | DAP12 |
| CD19 | BTNL3 | CD7 | CD32 |
| CD19 | BTNL3 | CD7 | CD79a |
| CD19 | BTNL3 | CD7 | CD79b |
| CD19 | BTNL3 | BTNL3 | CD8 |
| CD19 | BTNL3 | BTNL3 | CD3ζ |
| CD19 | BTNL3 | BTNL3 | CD3δ |
| CD19 | BTNL3 | BTNL3 | CD3γ |
| CD19 | BTNL3 | BTNL3 | CD3ε |
| CD19 | BTNL3 | BTNL3 | FcγRI-γ |
| CD19 | BTNL3 | BTNL3 | FcγRIII-γ |
| CD19 | BTNL3 | BTNL3 | FcεRIβ |
| CD19 | BTNL3 | BTNL3 | FcεRIγ |
| CD19 | BTNL3 | BTNL3 | DAP10 |
| CD19 | BTNL3 | BTNL3 | DAP12 |
| CD19 | BTNL3 | BTNL3 | CD32 |
| CD19 | BTNL3 | BTNL3 | CD79a |
| CD19 | BTNL3 | BTNL3 | CD79b |
| CD19 | BTNL3 | NKG2D | CD8 |
| CD19 | BTNL3 | NKG2D | CD3ζ |
| CD19 | BTNL3 | NKG2D | CD3δ |
| CD19 | BTNL3 | NKG2D | CD3γ |
| CD19 | BTNL3 | NKG2D | CD3ε |
| CD19 | BTNL3 | NKG2D | FcγRI-γ |
| CD19 | BTNL3 | NKG2D | FcγRIII-γ |

TABLE 3-continued

Third Generation CARs

| ScFv | Co-stimulatory Signal | Co-stimulatory Signal | Signal Domain |
|---|---|---|---|
| CD19 | BTNL3 | NKG2D | FcεRIβ |
| CD19 | BTNL3 | NKG2D | FcεRIγ |
| CD19 | BTNL3 | NKG2D | DAP10 |
| CD19 | BTNL3 | NKG2D | DAP12 |
| CD19 | BTNL3 | NKG2D | CD32 |
| CD19 | BTNL3 | NKG2D | CD79a |
| CD19 | BTNL3 | NKG2D | CD79b |
| CD19 | NKG2D | CD28 | CD8 |
| CD19 | NKG2D | CD28 | CD3ζ |
| CD19 | NKG2D | CD28 | CD3δ |
| CD19 | NKG2D | CD28 | CD3γ |
| CD19 | NKG2D | CD28 | CD3ε |
| CD19 | NKG2D | CD28 | FcγRI-γ |
| CD19 | NKG2D | CD28 | FcγRIII-γ |
| CD19 | NKG2D | CD28 | FcεRIβ |
| CD19 | NKG2D | CD28 | FcεRIγ |
| CD19 | NKG2D | CD28 | DAP10 |
| CD19 | NKG2D | CD28 | DAP12 |
| CD19 | NKG2D | CD28 | CD32 |
| CD19 | NKG2D | CD28 | CD79a |
| CD19 | NKG2D | CD28 | CD79b |
| CD19 | NKG2D | CD8 | CD8 |
| CD19 | NKG2D | CD8 | CD3ζ |
| CD19 | NKG2D | CD8 | CD3δ |
| CD19 | NKG2D | CD8 | CD3γ |
| CD19 | NKG2D | CD8 | CD3ε |
| CD19 | NKG2D | CD8 | FcγRI-γ |
| CD19 | NKG2D | CD8 | FcγRIII-γ |
| CD19 | NKG2D | CD8 | FcεRIβ |
| CD19 | NKG2D | CD8 | FcεRIγ |
| CD19 | NKG2D | CD8 | DAP10 |
| CD19 | NKG2D | CD8 | DAP12 |
| CD19 | NKG2D | CD8 | CD32 |
| CD19 | NKG2D | CD8 | CD79a |
| CD19 | NKG2D | CD8 | CD79b |
| CD19 | NKG2D | CD4 | CD8 |
| CD19 | NKG2D | CD4 | CD3ζ |
| CD19 | NKG2D | CD4 | CD3δ |
| CD19 | NKG2D | CD4 | CD3γ |
| CD19 | NKG2D | CD4 | CD3ε |
| CD19 | NKG2D | CD4 | FcγRI-γ |
| CD19 | NKG2D | CD4 | FcγRIII-γ |
| CD19 | NKG2D | CD4 | FcεRIβ |
| CD19 | NKG2D | CD4 | FcεRIγ |
| CD19 | NKG2D | CD4 | DAP10 |
| CD19 | NKG2D | CD4 | DAP12 |
| CD19 | NKG2D | CD4 | CD32 |
| CD19 | NKG2D | CD4 | CD79a |
| CD19 | NKG2D | CD4 | CD79b |
| CD19 | NKG2D | b2c | CD8 |
| CD19 | NKG2D | b2c | CD3ζ |
| CD19 | NKG2D | b2c | CD3δ |
| CD19 | NKG2D | b2c | CD3γ |
| CD19 | NKG2D | b2c | CD3ε |
| CD19 | NKG2D | b2c | FcγRI-γ |
| CD19 | NKG2D | b2c | FcγRIII-γ |
| CD19 | NKG2D | b2c | FcεRIβ |
| CD19 | NKG2D | b2c | FcεRIγ |
| CD19 | NKG2D | b2c | DAP10 |
| CD19 | NKG2D | b2c | DAP12 |
| CD19 | NKG2D | b2c | CD32 |
| CD19 | NKG2D | b2c | CD79a |
| CD19 | NKG2D | b2c | CD79b |
| CD19 | NKG2D | CD137/41BB | CD8 |
| CD19 | NKG2D | CD137/41BB | CD3ζ |
| CD19 | NKG2D | CD137/41BB | CD3δ |
| CD19 | NKG2D | CD137/41BB | CD3γ |
| CD19 | NKG2D | CD137/41BB | CD3ε |
| CD19 | NKG2D | CD137/41BB | FcγRI-γ |
| CD19 | NKG2D | CD137/41BB | FcγRIII-γ |
| CD19 | NKG2D | CD137/41BB | FcεRIβ |
| CD19 | NKG2D | CD137/41BB | FcεRIγ |
| CD19 | NKG2D | CD137/41BB | DAP10 |
| CD19 | NKG2D | CD137/41BB | DAP12 |
| CD19 | NKG2D | CD137/41BB | CD32 |
| CD19 | NKG2D | CD137/41BB | CD79a |
| CD19 | NKG2D | CD137/41BB | CD79b |
| CD19 | NKG2D | ICOS | CD8 |
| CD19 | NKG2D | ICOS | CD3ζ |
| CD19 | NKG2D | ICOS | CD3δ |
| CD19 | NKG2D | ICOS | CD3γ |
| CD19 | NKG2D | ICOS | CD3ε |
| CD19 | NKG2D | ICOS | FcγRI-γ |
| CD19 | NKG2D | ICOS | FcγRIII-γ |
| CD19 | NKG2D | ICOS | FcεRIβ |
| CD19 | NKG2D | ICOS | FcεRIγ |
| CD19 | NKG2D | ICOS | DAP10 |
| CD19 | NKG2D | ICOS | DAP12 |
| CD19 | NKG2D | ICOS | CD32 |
| CD19 | NKG2D | ICOS | CD79a |
| CD19 | NKG2D | ICOS | CD79b |
| CD19 | NKG2D | CD27 | CD8 |
| CD19 | NKG2D | CD27 | CD3ζ |
| CD19 | NKG2D | CD27 | CD3δ |
| CD19 | NKG2D | CD27 | CD3γ |
| CD19 | NKG2D | CD27 | CD3ε |
| CD19 | NKG2D | CD27 | FcγRI-γ |
| CD19 | NKG2D | CD27 | FcγRIII-γ |
| CD19 | NKG2D | CD27 | FcεRIβ |
| CD19 | NKG2D | CD27 | FcεRIγ |
| CD19 | NKG2D | CD27 | DAP10 |
| CD19 | NKG2D | CD27 | DAP12 |
| CD19 | NKG2D | CD27 | CD32 |
| CD19 | NKG2D | CD27 | CD79a |
| CD19 | NKG2D | CD27 | CD79b |
| CD19 | NKG2D | CD28δ | CD8 |
| CD19 | NKG2D | CD28δ | CD3ζ |
| CD19 | NKG2D | CD28δ | CD3δ |
| CD19 | NKG2D | CD28δ | CD3γ |
| CD19 | NKG2D | CD28δ | CD3ε |
| CD19 | NKG2D | CD28δ | FcγRI-γ |
| CD19 | NKG2D | CD28δ | FcγRIII-γ |
| CD19 | NKG2D | CD28δ | FcεRIβ |
| CD19 | NKG2D | CD28δ | FcεRIγ |
| CD19 | NKG2D | CD28δ | DAP10 |
| CD19 | NKG2D | CD28δ | DAP12 |
| CD19 | NKG2D | CD28δ | CD32 |
| CD19 | NKG2D | CD28δ | CD79a |
| CD19 | NKG2D | CD28δ | CD79b |
| CD19 | NKG2D | CD80 | CD8 |
| CD19 | NKG2D | CD80 | CD3ζ |
| CD19 | NKG2D | CD80 | CD3δ |
| CD19 | NKG2D | CD80 | CD3γ |
| CD19 | NKG2D | CD80 | CD3ε |
| CD19 | NKG2D | CD80 | FcγRI-γ |
| CD19 | NKG2D | CD80 | FcγRIII-γ |
| CD19 | NKG2D | CD80 | FcεRIβ |
| CD19 | NKG2D | CD80 | FcεRIγ |
| CD19 | NKG2D | CD80 | DAP10 |
| CD19 | NKG2D | CD80 | DAP12 |
| CD19 | NKG2D | CD80 | CD32 |
| CD19 | NKG2D | CD80 | CD79a |
| CD19 | NKG2D | CD80 | CD79b |
| CD19 | NKG2D | CD86 | CD8 |
| CD19 | NKG2D | CD86 | CD3ζ |
| CD19 | NKG2D | CD86 | CD3δ |
| CD19 | NKG2D | CD86 | CD3γ |
| CD19 | NKG2D | CD86 | CD3ε |
| CD19 | NKG2D | CD86 | FcγRI-γ |
| CD19 | NKG2D | CD86 | FcγRIII-γ |
| CD19 | NKG2D | CD86 | FcεRIβ |
| CD19 | NKG2D | CD86 | FcεRIγ |
| CD19 | NKG2D | CD86 | DAP10 |
| CD19 | NKG2D | CD86 | DAP12 |
| CD19 | NKG2D | CD86 | CD32 |
| CD19 | NKG2D | CD86 | CD79a |
| CD19 | NKG2D | CD86 | CD79b |
| CD19 | NKG2D | OX40 | CD8 |
| CD19 | NKG2D | OX40 | CD3ζ |
| CD19 | NKG2D | OX40 | CD3δ |

TABLE 3-continued

Third Generation CARs

| ScFv | Co-stimulatory Signal | Co-stimulatory Signal | Signal Domain |
|---|---|---|---|
| CD19 | NKG2D | OX40 | CD3γ |
| CD19 | NKG2D | OX40 | CD3ε |
| CD19 | NKG2D | OX40 | FcγRI-γ |
| CD19 | NKG2D | OX40 | FcγRIII-γ |
| CD19 | NKG2D | OX40 | FcεRIβ |
| CD19 | NKG2D | OX40 | FcεRIγ |
| CD19 | NKG2D | OX40 | DAP10 |
| CD19 | NKG2D | OX40 | DAP12 |
| CD19 | NKG2D | OX40 | CD32 |
| CD19 | NKG2D | OX40 | CD79a |
| CD19 | NKG2D | OX40 | CD79b |
| CD19 | NKG2D | DAP10 | CD8 |
| CD19 | NKG2D | DAP10 | CD3ζ |
| CD19 | NKG2D | DAP10 | CD3δ |
| CD19 | NKG2D | DAP10 | CD3γ |
| CD19 | NKG2D | DAP10 | CD3ε |
| CD19 | NKG2D | DAP10 | FcγRI-γ |
| CD19 | NKG2D | DAP10 | FcγRIII-γ |
| CD19 | NKG2D | DAP10 | FcεRIβ |
| CD19 | NKG2D | DAP10 | FcεRIγ |
| CD19 | NKG2D | DAP10 | DAP10 |
| CD19 | NKG2D | DAP10 | DAP12 |
| CD19 | NKG2D | DAP10 | CD32 |
| CD19 | NKG2D | DAP10 | CD79a |
| CD19 | NKG2D | DAP10 | CD79b |
| CD19 | NKG2D | DAP12 | CD8 |
| CD19 | NKG2D | DAP12 | CD3ζ |
| CD19 | NKG2D | DAP12 | CD3δ |
| CD19 | NKG2D | DAP12 | CD3γ |
| CD19 | NKG2D | DAP12 | CD3ε |
| CD19 | NKG2D | DAP12 | FcγRI-γ |
| CD19 | NKG2D | DAP12 | FcγRIII-γ |
| CD19 | NKG2D | DAP12 | FcεRIβ |
| CD19 | NKG2D | DAP12 | FcεRIγ |
| CD19 | NKG2D | DAP12 | DAP10 |
| CD19 | NKG2D | DAP12 | DAP12 |
| CD19 | NKG2D | DAP12 | CD32 |
| CD19 | NKG2D | DAP12 | CD79a |
| CD19 | NKG2D | DAP12 | CD79b |
| CD19 | NKG2D | MyD88 | CD8 |
| CD19 | NKG2D | MyD88 | CD3ζ |
| CD19 | NKG2D | MyD88 | CD3δ |
| CD19 | NKG2D | MyD88 | CD3γ |
| CD19 | NKG2D | MyD88 | CD3ε |
| CD19 | NKG2D | MyD88 | FcγRI-γ |
| CD19 | NKG2D | MyD88 | FcγRIII-γ |
| CD19 | NKG2D | MyD88 | FcεRIβ |
| CD19 | NKG2D | MyD88 | FcεRIγ |
| CD19 | NKG2D | MyD88 | DAP10 |
| CD19 | NKG2D | MyD88 | DAP12 |
| CD19 | NKG2D | MyD88 | CD32 |
| CD19 | NKG2D | MyD88 | CD79a |
| CD19 | NKG2D | MyD88 | CD79b |
| CD19 | NKG2D | CD7 | CD8 |
| CD19 | NKG2D | CD7 | CD3ζ |
| CD19 | NKG2D | CD7 | CD3δ |
| CD19 | NKG2D | CD7 | CD3γ |
| CD19 | NKG2D | CD7 | CD3ε |
| CD19 | NKG2D | CD7 | FcγRI-γ |
| CD19 | NKG2D | CD7 | FcγRIII-γ |
| CD19 | NKG2D | CD7 | FcεRIβ |
| CD19 | NKG2D | CD7 | FcεRIγ |
| CD19 | NKG2D | CD7 | DAP10 |
| CD19 | NKG2D | CD7 | DAP12 |
| CD19 | NKG2D | CD7 | CD32 |
| CD19 | NKG2D | CD7 | CD79a |
| CD19 | NKG2D | CD7 | CD79b |
| CD19 | NKG2D | BTNL3 | CD8 |
| CD19 | NKG2D | BTNL3 | CD3ζ |
| CD19 | NKG2D | BTNL3 | CD3δ |
| CD19 | NKG2D | BTNL3 | CD3γ |
| CD19 | NKG2D | BTNL3 | CD3ε |
| CD19 | NKG2D | BTNL3 | FcγRI-γ |
| CD19 | NKG2D | BTNL3 | FcγRIII-γ |
| CD19 | NKG2D | BTNL3 | FcεRIβ |

TABLE 3-continued

Third Generation CARs

| ScFv | Co-stimulatory Signal | Co-stimulatory Signal | Signal Domain |
|---|---|---|---|
| CD19 | NKG2D | BTNL3 | FcεRIγ |
| CD19 | NKG2D | BTNL3 | DAP10 |
| CD19 | NKG2D | BTNL3 | DAP12 |
| CD19 | NKG2D | BTNL3 | CD32 |
| CD19 | NKG2D | BTNL3 | CD79a |
| CD19 | NKG2D | BTNL3 | CD79b |
| CD19 | NKG2D | NKG2D | CD8 |
| CD19 | NKG2D | NKG2D | CD3ζ |
| CD19 | NKG2D | NKG2D | CD3δ |
| CD19 | NKG2D | NKG2D | CD3γ |
| CD19 | NKG2D | NKG2D | CD3ε |
| CD19 | NKG2D | NKG2D | FcγRI-γ |
| CD19 | NKG2D | NKG2D | FcγRIII-γ |
| CD19 | NKG2D | NKG2D | FcεRIβ |
| CD19 | NKG2D | NKG2D | FcεRIγ |
| CD19 | NKG2D | NKG2D | DAP10 |
| CD19 | NKG2D | NKG2D | DAP12 |
| CD19 | NKG2D | NKG2D | CD32 |
| CD19 | NKG2D | NKG2D | CD79a |
| CD19 | NKG2D | NKG2D | CD79b |

TABLE 4

CARs lacking Co-Stimulatory Signal (for dual CAR approach)

| ScFv | Co-stimulatory Signal | Signal Domain |
|---|---|---|
| CD19 | none | CD8 |
| CD19 | none | CD3ζ |
| CD19 | none | CD3δ |
| CD19 | none | CD3γ |
| CD19 | none | CD3ε |
| CD19 | none | FcγRI-γ |
| CD19 | none | FcγRIII-γ |
| CD19 | none | FcεRIβ |
| CD19 | none | FcεRIγ |
| CD19 | none | DAP10 |
| CD19 | none | DAP12 |
| CD19 | none | CD32 |
| CD19 | none | CD79a |
| CD19 | none | CD8 |
| CD19 | none | CD3ζ |
| CD19 | none | CD3δ |
| CD19 | none | CD3γ |
| CD19 | none | CD3ε |
| CD19 | none | FcγRI-γ |

TABLE 5

CARs lacking Signal Domain (for dual CAR approach)

| ScFv | Co-stimulatory Signal | Signal Domain |
|---|---|---|
| CD19 | CD28 | none |
| CD19 | CD8 | none |
| CD19 | CD4 | none |
| CD19 | b2c | none |
| CD19 | CD137/41BB | none |
| CD19 | ICOS | none |
| CD19 | CD27 | none |
| CD19 | CD28δ | none |
| CD19 | CD80 | none |
| CD19 | CD86 | none |
| CD19 | OX40 | none |
| CD19 | DAP10 | none |
| CD19 | MyD88 | none |
| CD19 | CD7 | none |
| CD19 | DAP12 | none |

TABLE 5-continued

| | CARs lacking Signal Domain (for dual CAR approach) | |
| --- | --- | --- |
| ScFv | Co-stimulatory Signal | Signal Domain |
| CD19 | MyD88 | none |
| CD19 | CD7 | none |
| CD19 | BTNL3 | none |
| CD19 | NKG2D | none |

TABLE 6

| | Third Generation CARs lacking Signal Domain (for dual CAR approach) | | |
| --- | --- | --- | --- |
| ScFv | Co-stimulatory Signal | Co-stimulatory Signal | Signal Domain |
| CD19 | CD28 | CD28 | none |
| CD19 | CD28 | CD8 | none |
| CD19 | CD28 | CD4 | none |
| CD19 | CD28 | b2c | none |
| CD19 | CD28 | CD137/41BB | none |
| CD19 | CD28 | ICOS | none |
| CD19 | CD28 | CD27 | none |
| CD19 | CD28 | CD28δ | none |
| CD19 | CD28 | CD80 | none |
| CD19 | CD28 | CD86 | none |
| CD19 | CD28 | OX40 | none |
| CD19 | CD28 | DAP10 | none |
| CD19 | CD28 | MyD88 | none |
| CD19 | CD28 | CD7 | none |
| CD19 | CD28 | DAP12 | none |
| CD19 | CD28 | MyD88 | none |
| CD19 | CD28 | CD7 | none |
| CD19 | CD8 | CD28 | none |
| CD19 | CD8 | CD8 | none |
| CD19 | CD8 | CD4 | none |
| CD19 | CD8 | b2c | none |
| CD19 | CD8 | CD137/41BB | none |
| CD19 | CD8 | ICOS | none |
| CD19 | CD8 | CD27 | none |
| CD19 | CD8 | CD28δ | none |
| CD19 | CD8 | CD80 | none |
| CD19 | CD8 | CD86 | none |
| CD19 | CD8 | OX40 | none |
| CD19 | CD8 | DAP10 | none |
| CD19 | CD8 | MyD88 | none |
| CD19 | CD8 | CD7 | none |
| CD19 | CD8 | DAP12 | none |
| CD19 | CD8 | MyD88 | none |
| CD19 | CD8 | CD7 | none |
| CD19 | CD4 | CD28 | none |
| CD19 | CD4 | CD8 | none |
| CD19 | CD4 | CD4 | none |
| CD19 | CD4 | b2c | none |
| CD19 | CD4 | CD137/41BB | none |
| CD19 | CD4 | ICOS | none |
| CD19 | CD4 | CD27 | none |
| CD19 | CD4 | CD28δ | none |
| CD19 | CD4 | CD80 | none |
| CD19 | CD4 | CD86 | none |
| CD19 | CD4 | OX40 | none |
| CD19 | CD4 | DAP10 | none |
| CD19 | CD4 | MyD88 | none |
| CD19 | CD4 | CD7 | none |
| CD19 | CD4 | DAP12 | none |
| CD19 | CD4 | MyD88 | none |
| CD19 | CD4 | CD7 | none |
| CD19 | b2c | CD28 | none |
| CD19 | b2c | CD8 | none |
| CD19 | b2c | CD4 | none |
| CD19 | b2c | b2c | none |
| CD19 | b2c | CD137/41BB | none |
| CD19 | b2c | ICOS | none |
| CD19 | b2c | CD27 | none |
| CD19 | b2c | CD28δ | none |

TABLE 6-continued

| | Third Generation CARs lacking Signal Domain (for dual CAR approach) | | |
| --- | --- | --- | --- |
| ScFv | Co-stimulatory Signal | Co-stimulatory Signal | Signal Domain |
| CD19 | b2c | CD80 | none |
| CD19 | b2c | CD86 | none |
| CD19 | b2c | OX40 | none |
| CD19 | b2c | DAP10 | none |
| CD19 | b2c | MyD88 | none |
| CD19 | b2c | CD7 | none |
| CD19 | b2c | DAP12 | none |
| CD19 | b2c | MyD88 | none |
| CD19 | b2c | CD7 | none |
| CD19 | CD137/41BB | CD28 | none |
| CD19 | CD137/41BB | CD8 | none |
| CD19 | CD137/41BB | CD4 | none |
| CD19 | CD137/41BB | b2c | none |
| CD19 | CD137/41BB | CD137/41BB | none |
| CD19 | CD137/41BB | ICOS | none |
| CD19 | CD137/41BB | CD27 | none |
| CD19 | CD137/41BB | CD28δ | none |
| CD19 | CD137/41BB | CD80 | none |
| CD19 | CD137/41BB | CD86 | none |
| CD19 | CD137/41BB | OX40 | none |
| CD19 | CD137/41BB | DAP10 | none |
| CD19 | CD137/41BB | MyD88 | none |
| CD19 | CD137/41BB | CD7 | none |
| CD19 | CD137/41BB | DAP12 | none |
| CD19 | CD137/41BB | MyD88 | none |
| CD19 | CD137/41BB | CD7 | none |
| CD19 | ICOS | CD28 | none |
| CD19 | ICOS | CD8 | none |
| CD19 | ICOS | CD4 | none |
| CD19 | ICOS | b2c | none |
| CD19 | ICOS | CD137/41BB | none |
| CD19 | ICOS | ICOS | none |
| CD19 | ICOS | CD27 | none |
| CD19 | ICOS | CD28δ | none |
| CD19 | ICOS | CD80 | none |
| CD19 | ICOS | CD86 | none |
| CD19 | ICOS | OX40 | none |
| CD19 | ICOS | DAP10 | none |
| CD19 | ICOS | MyD88 | none |
| CD19 | ICOS | CD7 | none |
| CD19 | ICOS | DAP12 | none |
| CD19 | ICOS | MyD88 | none |
| CD19 | ICOS | CD7 | none |
| CD19 | ICOS | CD28 | none |
| CD19 | ICOS | CD8 | none |
| CD19 | ICOS | CD4 | none |
| CD19 | ICOS | b2c | none |
| CD19 | ICOS | CD137/41BB | none |
| CD19 | ICOS | ICOS | none |
| CD19 | ICOS | CD27 | none |
| CD19 | ICOS | CD28δ | none |
| CD19 | ICOS | CD80 | none |
| CD19 | ICOS | CD86 | none |
| CD19 | ICOS | OX40 | none |
| CD19 | ICOS | DAP10 | none |
| CD19 | ICOS | MyD88 | none |
| CD19 | ICOS | CD7 | none |
| CD19 | ICOS | DAP12 | none |
| CD19 | ICOS | MyD88 | none |
| CD19 | ICOS | CD7 | none |
| CD19 | CD27 | CD28 | none |
| CD19 | CD27 | CD8 | none |
| CD19 | CD27 | CD4 | none |
| CD19 | CD27 | b2c | none |
| CD19 | CD27 | CD137/41BB | none |
| CD19 | CD27 | ICOS | none |
| CD19 | CD27 | CD27 | none |
| CD19 | CD27 | CD28δ | none |
| CD19 | CD27 | CD80 | none |
| CD19 | CD27 | CD86 | none |
| CD19 | CD27 | OX40 | none |
| CD19 | CD27 | DAP10 | none |
| CD19 | CD27 | MyD88 | none |
| CD19 | CD27 | CD7 | none |

TABLE 6-continued

Third Generation CARs lacking Signal Domain (for dual CAR approach)

| ScFv | Co-stimulatory Signal | Co-stimulatory Signal | Signal Domain |
|------|------|------|------|
| CD19 | CD27 | DAP12 | none |
| CD19 | CD27 | MyD88 | none |
| CD19 | CD27 | CD7 | none |
| CD19 | CD28δ | CD28 | none |
| CD19 | CD28δ | CD8 | none |
| CD19 | CD28δ | CD4 | none |
| CD19 | CD28δ | b2c | none |
| CD19 | CD28δ | CD137/41BB | none |
| CD19 | CD28δ | ICOS | none |
| CD19 | CD28δ | CD27 | none |
| CD19 | CD28δ | CD28δ | none |
| CD19 | CD28δ | CD80 | none |
| CD19 | CD28δ | CD86 | none |
| CD19 | CD28δ | OX40 | none |
| CD19 | CD28δ | DAP10 | none |
| CD19 | CD28δ | MyD88 | none |
| CD19 | CD28δ | CD7 | none |
| CD19 | CD28δ | DAP12 | none |
| CD19 | CD28δ | MyD88 | none |
| CD19 | CD28δ | CD7 | none |
| CD19 | CD80 | CD28 | none |
| CD19 | CD80 | CD8 | none |
| CD19 | CD80 | CD4 | none |
| CD19 | CD80 | b2c | none |
| CD19 | CD80 | CD137/41BB | none |
| CD19 | CD80 | ICOS | none |
| CD19 | CD80 | CD27 | none |
| CD19 | CD80 | CD28δ | none |
| CD19 | CD80 | CD80 | none |
| CD19 | CD80 | CD86 | none |
| CD19 | CD80 | OX40 | none |
| CD19 | CD80 | DAP10 | none |
| CD19 | CD80 | MyD88 | none |
| CD19 | CD80 | CD7 | none |
| CD19 | CD80 | DAP12 | none |
| CD19 | CD80 | MyD88 | none |
| CD19 | CD80 | CD7 | none |
| CD19 | CD86 | CD28 | none |
| CD19 | CD86 | CD8 | none |
| CD19 | CD86 | CD4 | none |
| CD19 | CD86 | b2c | none |
| CD19 | CD86 | CD137/41BB | none |
| CD19 | CD86 | ICOS | none |
| CD19 | CD86 | CD27 | none |
| CD19 | CD86 | CD28δ | none |
| CD19 | CD86 | CD80 | none |
| CD19 | CD86 | CD86 | none |
| CD19 | CD86 | OX40 | none |
| CD19 | CD86 | DAP10 | none |
| CD19 | CD86 | MyD88 | none |
| CD19 | CD86 | CD7 | none |
| CD19 | CD86 | DAP12 | none |
| CD19 | CD86 | MyD88 | none |
| CD19 | CD86 | CD7 | none |
| CD19 | OX40 | CD28 | none |
| CD19 | OX40 | CD8 | none |
| CD19 | OX40 | CD4 | none |
| CD19 | OX40 | b2c | none |
| CD19 | OX40 | CD137/41BB | none |
| CD19 | OX40 | ICOS | none |
| CD19 | OX40 | CD27 | none |
| CD19 | OX40 | CD28δ | none |
| CD19 | OX40 | CD80 | none |
| CD19 | OX40 | CD86 | none |
| CD19 | OX40 | OX40 | none |
| CD19 | OX40 | DAP10 | none |
| CD19 | OX40 | MyD88 | none |
| CD19 | OX40 | CD7 | none |
| CD19 | OX40 | DAP12 | none |
| CD19 | OX40 | MyD88 | none |
| CD19 | OX40 | CD7 | none |
| CD19 | DAP10 | CD28 | none |
| CD19 | DAP10 | CD8 | none |
| CD19 | DAP10 | CD4 | none |
| CD19 | DAP10 | b2c | none |
| CD19 | DAP10 | CD137/41BB | none |
| CD19 | DAP10 | ICOS | none |
| CD19 | DAP10 | CD27 | none |
| CD19 | DAP10 | CD28δ | none |
| CD19 | DAP10 | CD80 | none |
| CD19 | DAP10 | CD86 | none |
| CD19 | DAP10 | OX40 | none |
| CD19 | DAP10 | DAP10 | none |
| CD19 | DAP10 | MyD88 | none |
| CD19 | DAP10 | CD7 | none |
| CD19 | DAP10 | DAP12 | none |
| CD19 | DAP10 | MyD88 | none |
| CD19 | DAP10 | CD7 | none |
| CD19 | DAP12 | CD28 | none |
| CD19 | DAP12 | CD8 | none |
| CD19 | DAP12 | CD4 | none |
| CD19 | DAP12 | b2c | none |
| CD19 | DAP12 | CD137/41BB | none |
| CD19 | DAP12 | ICOS | none |
| CD19 | DAP12 | CD27 | none |
| CD19 | DAP12 | CD28δ | none |
| CD19 | DAP12 | CD80 | none |
| CD19 | DAP12 | CD86 | none |
| CD19 | DAP12 | OX40 | none |
| CD19 | DAP12 | DAP10 | none |
| CD19 | DAP12 | MyD88 | none |
| CD19 | DAP12 | CD7 | none |
| CD19 | DAP12 | DAP12 | none |
| CD19 | DAP12 | MyD88 | none |
| CD19 | DAP12 | CD7 | none |
| CD19 | MyD88 | CD28 | none |
| CD19 | MyD88 | CD8 | none |
| CD19 | MyD88 | CD4 | none |
| CD19 | MyD88 | b2c | none |
| CD19 | MyD88 | CD137/41BB | none |
| CD19 | MyD88 | ICOS | none |
| CD19 | MyD88 | CD27 | none |
| CD19 | MyD88 | CD28δ | none |
| CD19 | MyD88 | CD80 | none |
| CD19 | MyD88 | CD86 | none |
| CD19 | MyD88 | OX40 | none |
| CD19 | MyD88 | DAP10 | none |
| CD19 | MyD88 | MyD88 | none |
| CD19 | MyD88 | CD7 | none |
| CD19 | MyD88 | DAP12 | none |
| CD19 | MyD88 | MyD88 | none |
| CD19 | MyD88 | CD7 | none |
| CD19 | CD7 | CD28 | none |
| CD19 | CD7 | CD8 | none |
| CD19 | CD7 | CD4 | none |
| CD19 | CD7 | b2c | none |
| CD19 | CD7 | CD137/41BB | none |
| CD19 | CD7 | ICOS | none |
| CD19 | CD7 | CD27 | none |
| CD19 | CD7 | CD28δ | none |
| CD19 | CD7 | CD80 | none |
| CD19 | CD7 | CD86 | none |
| CD19 | CD7 | OX40 | none |
| CD19 | CD7 | DAP10 | none |
| CD19 | CD7 | MyD88 | none |
| CD19 | CD7 | CD7 | none |
| CD19 | CD7 | DAP12 | none |
| CD19 | CD7 | MyD88 | none |
| CD19 | CD7 | CD7 | none |
| CD19 | BTNL3 | CD28 | none |
| CD19 | BTNL3 | CD8 | none |
| CD19 | BTNL3 | CD4 | none |
| CD19 | BTNL3 | b2c | none |
| CD19 | BTNL3 | CD137/41BB | none |
| CD19 | BTNL3 | ICOS | none |
| CD19 | BTNL3 | CD27 | none |
| CD19 | BTNL3 | CD28δ | none |
| CD19 | BTNL3 | CD80 | none |

TABLE 6-continued

| | Third Generation CARs lacking Signal Domain (for dual CAR approach) | | |
| ScFv | Co-stimulatory Signal | Co-stimulatory Signal | Signal Domain |
|---|---|---|---|
| CD19 | BTNL3 | CD86 | none |
| CD19 | BTNL3 | OX40 | none |
| CD19 | BTNL3 | DAP10 | none |
| CD19 | BTNL3 | MyD88 | none |
| CD19 | BTNL3 | CD7 | none |
| CD19 | BTNL3 | DAP12 | none |
| CD19 | BTNL3 | MyD88 | none |
| CD19 | BTNL3 | CD7 | none |
| CD19 | NKG2D | CD28 | none |
| CD19 | NKG2D | CD8 | none |
| CD19 | NKG2D | CD4 | none |
| CD19 | NKG2D | b2c | none |
| CD19 | NKG2D | CD137/41BB | none |
| CD19 | NKG2D | ICOS | none |
| CD19 | NKG2D | CD27 | none |
| CD19 | NKG2D | CD28δ | none |
| CD19 | NKG2D | CD80 | none |
| CD19 | NKG2D | CD86 | none |
| CD19 | NKG2D | OX40 | none |
| CD19 | NKG2D | DAP10 | none |
| CD19 | NKG2D | MyD88 | none |
| CD19 | NKG2D | CD7 | none |
| CD19 | NKG2D | DAP12 | none |
| CD19 | NKG2D | MyD88 | none |
| CD19 | NKG2D | CD7 | none |

In some embodiments, the anti-B-lymphocyte antigen binding agent is a single chain variable fragment (scFv) antibody. Preferably, such an anti-B-lymphocyte antigen binding agent is a single chain variable fragment (scFv) anti-CD19 antibody. The affinity/specificity of an anti-CD19 scFv is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3).

In some embodiments, the anti-CD19 binding agent is derived from natural antibodies, such as monoclonal antibodies. In some cases, the antibody is human. In some cases, the antibody has undergone an alteration to render it less immunogenic when administered to humans. For example, the alteration comprises one or more techniques selected from chimerization, humanization, CDR-grafting, deimmunization, and mutation of framework amino acids to correspond to the closest human germline sequence. Preferably, the antibody is FMC63.

In preferred embodiments, the anti-CD19 binding agent is a single chain variable fragment (scFv) antibody derived from antibody FMC63.

Also disclosed are bi-specific CARs that target anti-B-lymphocyte antigen such as CD19 and at least one additional cancer-associated antigen (e.g., a tumor antigen). Also disclosed are CARs designed to work only in conjunction with another CAR that binds a different antigen, such as another cancer-associated antigen. For example, in these embodiments, the endodomain of the disclosed CAR can contain only an signaling domain (SD) or a co-stimulatory signaling region (CSR), but not both. The second CAR (or endogenous T-cell) provides the missing signal if it is activated. For example, if the disclosed CAR contains an SD but not a CSR, then the immune effector cell containing this CAR is only activated if another CAR (or T-cell) containing a CSR binds its respective antigen. Likewise, if the disclosed CAR contains a CSR but not a SD, then the immune effector cell containing this CAR is only activated if another CAR (or T-cell) containing an SD binds its respective antigen.

Said tumor antigens include proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-11Ra, IL-13Ra, EGFR, FAP, B7H3, Kit, CA LX, CS-1, MUC1, BCMA, bcr-abl, HER2, β-human chorionic gonadotropin, α-fetoprotein (AFP), ALK, alternate and/or specific CD19 epitopes, TIM3, cyclin Bl, lectin-reactive AFP, Fos-related antigen 1, ADRB3, thyroglobulin, EphA2, RAGE-1, RU1, RU2, SSX2, AKAP-4, LCK, OY-TESl, PAX5, SART3, CLL-1, fucosyl GM1, GloboH, MN-CA IX, EPCAM, EVT6-AML, TGS5, human telomerase reverse transcriptase, plysialic acid, PLAC1, RU1, RU2 (AS), intestinal carboxyl esterase, lewisY, sLe, LY6K, HSP70, HSP27, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-β, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAGE-A2, MAGE-C1, MAGE-C2, Annexin-A2, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRC5D, GPR20, CXORF61, folate receptor (FRa), folate receptor β, ROR1, Flt3, TAG72, TN Ag, Tie 2, TEM1, TEM7R, CLDN6, TSHR, UPK2, and mesothelin. In certain preferred embodiments, the tumor antigen is selected from folate receptor (FRa), mesothelin, EGFRvIII, IL-13Ra, CD123, CD19, TIM3, BCMA, GD2, CLL-1, CA-IX, MUCl, HER2, and any combination thereof.

Further non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include SCCA, GP73, FC-GP73, TSP-180, MAGE-4, MAGE-5, MAGE-6, RAGE, NY-ESO, pl85erbB2, pl80erbB-3, c-met, nm-23H1, PSA, CA 19-9, CA 72-4, CAM 17.1, NuMa, K-ras, β-Catenin, CDK4, Mum-1, p 15, p 16, 43-9F, 5T4, 791Tgp72, α-fetoprotein, j-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASl, SDCCAG1 6, TA-90\Mac-2 binding protein\cyclophilm C-associated protein, TAAL6, TAG72, TLP, TPS, GPC3, MUC16, TAG-72, LMP1, EBMA-1, BARF-1, CS1, CD319, HER1, B7H6, L1CAM, IL6, and MET.

CAR Ligand-Binding Domains

The extracellular domain of the CARs disclosed herein generally comprise an antigen recognition domain that binds a target antigen. Such antigen-specific binding domains are typically derived from an antibody. In some embodiments, the antigen-binding domain is a functional antibody fragment or derivative thereof (e.g., an scFv or a Fab, or any suitable antigen binding fragment of an antibody). In preferred embodiments, the antigen-binding domain is a single-chain variable fragment (scFv). In some such embodiments, the scFv is from a monoclonal antibody (mAb). In certain preferred embodiments, the antigen-specific binding domain (e.g., the scFv) is fused to the transmembrane and/or signaling motifs involved in lymphocyte activation as disclosed in Sadelain, et al. Nat Rev Cancer 2003 3:35-45, incorporated herein by reference in its entirety.

Anti-B-Lymphocyte Antigen scFv

In some embodiments, the anti-B-lymphocyte antigen scFv can comprise a variable heavy ($V_H$) domain having CDR1, CDR2 and CDR3 sequences and a variable light ($V_L$) domain having CDR1, CDR2 and CDR3 sequences. In preferred embodiments, the anti-B-lymphocyte antigen scFv is an anti-CD19, anti-CD20, or anti-CD22 scFv. Most preferably, the scFv is an anti-CD19 scFv.

Some such antibodies are described, for example, in Zola et al., "Preparation and characterization of a chimeric CD19 monoclonal antibody." *Immunology and Cell Biology* 1991, 69, 411-422; and Nicholson et al., "Construction and Characterization of a Functional CD19 Specific Single Chain Fv Fragment For Immunotherapy of B Lineage Leukemia AND Lymphoma." *Molecular Immunology* 1997, (34) 16-17, 1147-1165. These publications are hereby incorporated by reference in their entirety, and in particular for the antibodies described therein.

Nucleic Acids and Vectors

Also disclosed are polynucleotides and polynucleotide vectors encoding the disclosed B-lymphocyte antigen-specific CARs that allow expression of the B-lymphocyte antigen-specific CARs in the disclosed immune effector cells.

Nucleic acid sequences encoding the disclosed CARs, and regions thereof, can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned. An exemplary nucleic acid sequence may encode a CAR comprising each of a CD8 leader sequence, an FMC63 scFv targeting domain, a CD28 Domain, a mutant CD3ζ domain (e.g., a CD3ζ domain lacking functionality in the two C-terminal ITAM domains, i.e., ITAM2 and ITAM3), or any combination thereof. Preferably, such a CAR may be encoded by a nucleic acid sequence comprising the sequence set forth in SEQ ID NO. 1.

```
CAR nucleic acid sequence:
                                      (SEQ ID NO. 1)
ATGGCTCTCCCAGTGACTGCCCTACTGCTTCCCCTAGCGCTTCTCCTGCA

TGCAGACATCCAGATGACCCAGACCACAAGCAGCCTGTCTGCCAGCCTGG

GCGATAGAGTGACCATCAGCTGTAGAGCCAGCCAGGACATCAGCAAGTAC

CTGAACTGGTATCAGCAGAAACCCGACGGCACCGTGAAGCTGCTGATCTA
```

-continued

```
CCACACCAGCAGACTGCACAGCGGCGTGCCAAGCAGATTTTCTGGCAGCG

GCTCTGGCACCGACTACAGCCTGACAATCAGCAACCTGGAACAAGAGGAT

ATCGCTACCTACTTCTGCCAGCAAGGCAACACCCTGCCTTACACCTTTGG

CGGAGGCACCAAGCTGGAAATCACCGGCTCTACAAGCGGCAGCGGCAAAC

CTGGATCTGGCGAGGGATCTACCAAGGGCGAAGTGAAACTGCAAGAGTCT

GGCCCTGGACTGGTGGCCCCATCTCAGTCTCTGAGCGTGACCTGTACAGT

CAGCGGAGTGTCCCTGCCTGATTACGGCGTGTCCTGGATCAGACAGCCTC

CTCGGAAAGGCCTGGAATGGCTGGGAGTGATCTGGGGCAGCGAGACAACC

TACTACAACAGCGCCCTGAAGTCCCGGCTGACCATCATCAAGGACAACTC

CAAGAGCCAGGTGTTCCTGAAGATGAACAGCCTGCAGACCGACGACACCG

CCATCTACTATTGCGCCAAGCACTACTACTACGGCGGCAGCTACGCCATG

GATTATTGGGGCCAGGGCACCAGCGTGACCGTTTCTTCTGCGGCCGCAAT

TGAAGTTATGTATCCTCCTCCTTACCTAGACAATGAGAAGAGCAATGGAA

CCATTATCCATGTGAAAGGGAAACACCTTTGTCCAAGTCCCCTATTTCCC

GGACCTTCTAAGCCCTTTTGGGTGCTGGTGGTGGTTGGTGGAGTCCTGGC

TTGCTATAGCTTGCTAGTAACAGTGGCCTTTATTATTTTCTGGGTGAGGA

GTAAGAGGAGCAGGCTCCTGCACAGTGACTACATGAACATGACTCCCCGC

CGCCCCGGGCCCACCCGCAAGCATTACCAGCCCTATGCCCCACCACGCGA

CTTCGCAGCCTATCGCTCCAGAGTGAAGTTCAGCAGGAGCGCAGACGCCC

CCGCGTACCAGCAGGGCCAGAACCAGCTCTATAACGAGCTCAATCTAGGA

CGAAGAGAGGAGTACGATGTTTTGGACAAGAGACGTGGCCGGGACCCTGA

GATGGGGGGAAAGCCGAGAAGGAAGAACCCTCAGGAAGGCCTGTTCAATG

AACTGCAGAAAGATAAGATGGCGGAGGCCTTCAGTGAGATTGGGATGAAA

GGCGAGCGCCGGAGGGGCAAGGGGCACGATGGCCTTTTCCAGGGGCTCAG

TACAGCCACCAAGGACACCTTCGACGCCCTTCACATGCAGGCCCTGCCCC

CTCGC
```

```
CD8 Leader Sequence
(nucleotides 1-54)
                                      (SEQ ID NO. 2)
ATGGCTCTCCCAGTGACTGCCCTACTGCTTCCCCTAGCGCTTCTCCTGCA

TGCA
```

```
FMC63 scFv
(nucleotides 55-789)
                                      (SEQ ID NO. 3)
GACATCCAGATGACCCAGACCACAAGCAGCCTGTCTGCCAGCCTGGGCGA

TAGAGTGACCATCAGCTGTAGAGCCAGCCAGGACATCAGCAAGTACCTGA

ACTGGTATCAGCAGAAACCCGACGGCACCGTGAAGCTGCTGATCTACCAC

ACCAGCAGACTGCACAGCGGCGTGCCAAGCAGATTTTCTGGCAGCGGCTC

TGGCACCGACTACAGCCTGACAATCAGCAACCTGGAACAAGAGGATATCG

CTACCTACTTCTGCCAGCAAGGCAACACCCTGCCTTACACCTTTGGCGGA

GGCACCAAGCTGGAAATCACCGGCTCTACAAGCGGCAGCGGCAAACCTGG

ATCTGGCGAGGGATCTACCAAGGGCGAAGTGAAACTGCAAGAGTCTGGCC

CTGGACTGGTGGCCCCATCTCAGTCTCTGAGCGTGACCTGTACAGTCAGC

GGAGTGTCCCTGCCTGATTACGGCGTGTCCTGGATCAGACAGCCTCCTCG
```

-continued

```
GAAAGGCCTGGAATGGCTGGGAGTGATCTGGGGCAGCGAGACAACCTACT

ACAACAGCGCCCTGAAGTCCCGGCTGACCATCATCAAGGACAACTCCAAG

AGCCAGGTGTTCCTGAAGATGAACAGCCTGCAGACCGACGACACCGCCAT

CTACTATTGCGCCAAGCACTACTACTACGGCGGCAGCTACGCCATGGATT

ATTGGGGCCAGGGCACCAGCGTGACCGTTTCTTCT
```

CD28 Domain
(nucleotides 799-1119)
                                        (SEQ ID NO. 4)
```
ATTGAAGTTATGTATCCTCCTCCTTACCTAGACAATGAGAAGAGCAATGG

AACCATTATCCATGTGAAAGGGAAACACCTTTGTCCAAGTCCCCTATTTC

CCGGACCTTCTAAGCCCTTTTGGGTGCTGGTGGTGGTTGGTGGAGTCCTG

GCTTGCTATAGCTTGCTAGTAACAGTGGCCTTTATTATTTTCTGGGTGAG

GAGTAAGAGGAGCAGGCTCCTGCACAGTGACTACATGAACATGACTCCCC

GCCGCCCCGGGCCCACCCGCAAGCATTACCAGCCCTATGCCCCACCACGC

GACTTCGCAGCCTATCGCTCC
```

1XX CD3ζ Domain
(nucleotides 1120-1455)
                                        (SEQ ID NO. 5)
```
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTTCAATGAACTGCAGAAAGATAAGAT

GGCGGAGGCCTTCAGTGAGATTGGGATGAAAGGCGAGCGCCGGAGGGGCA

AGGGGCACGATGGCCTTTTCCAGGGGCTCAGTACAGCCACCAAGGACACC

TTCGACGCCCTTCACATGCAGGCCCTGCCCCCTCGC
```

Expression of nucleic acids encoding CARs are typically achieved by operably linking a nucleic acid encoding the CAR polypeptide to a promoter, and incorporating the construct into an expression vector. Typical cloning vectors contain transcription and translation terminators, initiation sequences, and promoters useful for regulation of the expression of the desired nucleic acid sequence.

The disclosed nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. In some embodiments, the polynucleotide vectors are lentiviral or retroviral vectors.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, MND (myeloproliferative sarcoma virus) promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. The promoter can alternatively be an inducible promoter. Examples of inducible promoters include, but are not limited to a metallothionine promoter, a glucocorticoid promoter, a progesterone promoter, and a tetracycline promoter.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, fluorescence, specific binding to a detectable ligand. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene. For example, in some embodiments, the CARs disclosed herein, and/or the nucleic acid sequence encoding said CARs, may further comprise at least one molecular tag as are known in the art. Without wishing to be bound by any one particular theory or strategy, the tag may comprise Low-affinity nerve growth factor receptor (LNGFR) as a transduction tag which binds labeled ligand [124]I-NGF. The [124]I-NGF/LNGFR interaction can be monitored noninvasively (e.g., by positron emission tomography). In some such embodiments, the nucleic acid sequences of the vector encoding the CARs described herein may comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons. Thus, two polypeptides can be synthesized from a single, contiguous open reading frame within an mRNA when the polypeptides are separated by a 2A oligopeptide sequence that is in frame (e.g., when a CAR and a reporter gene, such as molecular tag, are separated by a 2A oligopeptide sequence). Such ribosomal "skip" or "self-cleaving" mechanisms or are well known in the art and are known to be used by several vectors for the expression of several proteins encoded by a single messenger RNA.

To direct polypeptides (e.g., secreted, transmembrane, and/or cell-surface polypeptides) into the secretory pathway of a host cell, a secretory signal sequence (also known simply as a signal sequence, leader sequence, pre-pro sequence or pre sequence) is provided in the polynucleotide sequence or vector sequence. The secretory signal sequence is operably linked to the nucleic acid sequence encoding the polypeptide of interest (e.g., a CAR). The two sequences are joined in the correct reading frame and positioned to direct the newly synthesized polypeptide into the secretory pathway of the host cell. Such secretory signal sequences are typically positioned 5' to the nucleic acid sequence encoding the polypeptide of interest, although certain secretory signal sequences may be positioned elsewhere in the nucleic acid sequence of interest. Accordingly, in preferred embodiments, the CARs disclosed herein, and/or the nucleic acid sequence encoding said CARs, may further comprise a signal sequence. Most preferably, the signal sequence comprises a CD8α leader sequence or fragment thereof. It will be appreciated by those of skill in the art that posttranslational modifications may remove such leader sequences from the CAR polypeptide presented at the cell surface (i.e., the mature CAR polypeptide).

Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription. Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

Biological methods for introducing a polynucleotide of interest into a host cell include the use of DNA and RNA vectors. Viral vectors, and especially retroviral vectors, have become the most widely used method for inserting genes into mammalian, e.g., human cells.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y); cholesterol ("Chol") can be obtained from Calbiochem-Behring; dimyristyl phosphatidylglycerol ("DMPG") and other lipids may be obtained from Avanti Polar Lipids, Inc, (Birmingham, Ala.).

Immune Effector Cells

Also disclosed are immune effector cells that are engineered to express the disclosed CARs (also referred to herein as "CAR-T cells"). These cells are preferably obtained from the subject to be treated (i.e., are autologous). However, in some embodiments, immune effector cell lines or donor effector cells (allogeneic) are used. Immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors. Immune effector cells can be obtained from blood collected from a subject using any number of techniques known to the skilled artisan, such as Ficoll™ separation. For example, cells from the circulating blood of an individual may be obtained by apheresis. In some embodiments, immune effector cells are isolated from peripheral blood lymphocytes by lysing the red blood cells and depleting the monocytes, for example, by centrifugation through a PERCOLL™ gradient or by counterflow centrifugal elutriation. A specific subpopulation of immune effector cells can be further isolated by positive or negative selection techniques. For example, immune effector cells can be isolated using a combination of antibodies directed to surface markers unique to the positively selected cells, e.g., by incubation with antibody-conjugated beads for a time period sufficient for positive selection of the desired immune effector cells. Alternatively, enrichment of immune effector cells population can be accomplished by negative selection using a combination of antibodies directed to surface markers unique to the negatively selected cells.

In some embodiments, the immune effector cells comprise any leukocyte involved in defending the body against infectious disease and foreign materials. For example, the immune effector cells can comprise lymphocytes, monocytes, macrophages, dendritic cells, mast cells, neutrophils, basophils, eosinophils, or any combinations thereof. For example, the immune effector cells can comprise T lymphocytes, preferably cytotoxic T lymphocytes (CTLs).

T cells or T lymphocytes can be distinguished from other lymphocytes, such as B cells and natural killer cells (NK cells), by the presence of a T-cell receptor (TCR) on the cell surface. They are called T cells because they mature in the thymus (although some also mature in the tonsils). There are several subsets of T cells, each with a distinct function.

T helper cells (T$_H$ cells) assist other white blood cells in immunologic processes, including maturation of B cells into plasma cells and memory B cells, and activation of cytotoxic T cells and macrophages. These cells are also known as CD4$^+$ T cells because they express the CD4 glycoprotein on their surface. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including T$_H$1, T$_H$2, T$_H$3, T$_H$17, T$_H$9, or T$_{FH}$, which secrete different cytokines to facilitate a different type of immune response.

Cytotoxic T cells (Tc cells, or CTLs) destroy virally infected cells and tumor cells, and are also implicated in transplant rejection. These cells are also known as CD8$^+$ T cells since they express the CD8 glycoprotein at their surface. These cells recognize their targets by binding to antigen associated with MHC class I molecules, which are present on the surface of all nucleated cells. Through IL-10, adenosine and other molecules secreted by regulatory T cells, the CD8$^+$ cells can be inactivated to an anergic state, which prevents autoimmune diseases.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory cells may be either CD4$^+$ or CD8$^+$. Memory T cells typically express the cell surface protein CD45RO.

Regulatory T cells (T$_{reg}$ cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus. Two major classes of CD4$^+$ T$_{reg}$ cells have been described—naturally occurring T$_{reg}$ cells and adaptive T$_{reg}$ cells.

Natural killer T (NKT) cells (not to be confused with natural killer (NK) cells) bridge the adaptive immune system with the innate immune system. Unlike conventional T cells that recognize peptide antigens presented by major histocompatibility complex (MHC) molecules, NKT cells recognize glycolipid antigen presented by a molecule called CD1d.

In some embodiments, the T cells comprise a mixture of CD4$^+$ cells. In other embodiments, the T cells are enriched for one or more subsets based on cell surface expression. For example, in some cases, the T comprise are cytotoxic CD8$^+$ T lymphocytes. In some embodiments, the T cells comprise γδ T cells, which possess a distinct T-cell receptor (TCR) having one γ chain and one δ chain instead of α and β chains.

Natural-killer (NK) cells are CD56$^+$CD3$^-$ large granular lymphocytes that can kill virally infected and transformed cells, and constitute a critical cellular subset of the innate immune system (Godfrey J, et al. Leuk Lymphoma 2012 53:1666-1676). Unlike cytotoxic CD8$^+$ T lymphocytes, NK cells launch cytotoxicity against tumor cells without the requirement for prior sensitization, and can also eradicate MHC-I-negative cells (Narni-Mancinelli E, et al. Int Immunol 2011 23:427-431). NK cells are safer effector cells, as they may avoid the potentially lethal complications of cytokine storms (Morgan R A, et al. Mol Ther 2010 18:843-851), tumor lysis syndrome (Porter D L, et al. N Engl J Med 2011 365:725-733), and on-target, off-tumor effects. Although NK cells have a well-known role as killers of cancer cells, and NK cell impairment has been extensively documented as crucial for progression of Multiple myeloma (MM) (Godfrey J, et al. Leuk Lymphoma 2012 53:1666-1676; Fauriat C, et al. Leukemia 2006 20:732-733), the means by which one might enhance NK cell-mediated anti-MM activity has been largely unexplored prior to the disclosed CARs.

Epstein-Barr virus (EBV)-induced lymphoproliferative diseases (EBV-LPDs) and other EBV-associated cancers are a significant cause of morbidity and mortality for recipients of allogeneic hematopoietic cell transplantation (HCT) or solid organ transplants (SOT), particularly in those who have received certain T-cell reactive Abs to prevent or treat Graft versus host disease (GVHD). Prophylaxis and treatment by the adoptive transfer of autologous or allogeneic EBV-specific cytotoxic T cells and the subsequent long-term restoration of immunity against EBV-associated lymphoproliferation have provided positive outcomes in the management of these uniformly fatal complications of allogeneic tissue transfer. Therefore, in some embodiments, the disclosed immune effector cells that comprise one or more of the CAR polypeptides of the present invention are allogeneic or autologous EBV-specific cytotoxic T lymphocytes (CTLs). For example, generation of EBV-specific cytotoxic T cells may involve isolating PBMCs from of an EBV-seropositive autologous or allogenic donor and enriching them for T cells by depletion of monocytes and NK cells. EBV-specific cytotoxic T cells may also be produced by contacting donor PBMCs or purified donor T cells with a "stimulator" cell that expresses one or more EBV antigen(s) and presents the EBV antigen(s) to unstimulated T cells, thereby causing stimulation and expansion of EBV-specific CTLs. EBV antigens include, for example, latent membrane protein (LMP) and EBV nuclear antigen (EBNA) proteins, such as LMP-1, LMP-2A, and LMP-2B and EBNA-1, EBNA-2, EBNA-3A, EBNA-3B, EBNA-3C and EBNA-LP. Cytotoxic T cells that comprise T cell receptor(s) which recognize one or more EBV-specific antigens are deemed to have been "sensitized" to those EBV antigen(s) and are therefore termed "EBV-sensitized cytotoxic T cells" herein. Known methods for generating allogeneic or autologous EBV-specific cytotoxic T cell populations that may comprise one or more of the CAR polypeptides of the present invention are described, for example, in Barker et al., Blood 2010 116(23):5045-49; Doubrovina, et al., Blood 2012 119(11): 2644-56; Koehne, et al. Blood 2002 99(5):1730-40; and Smith et al. Cancer Res 2012 72(5):1116-25, which are incorporated by reference for these teachings. Similarly, cytotoxic T cells may be "sensitized" to other viral antigens, including cytomegalovirus (CMV), papillomavirus (e.g., HPV), adenovirus, polyomavirus (e.g., BKV, JCV, and Merkel cell virus), retrovirus (e.g., HTLV-I, also including lentivirus such as HIV), picornavirus (e.g., Hepatitis A virus), hepadnavirus (e.g., Hepatitis B virus), hepacivirus (e.g., Hepatitis C virus), deltavirus (e.g., Hepatitis D virus), hepevirus (e.g., Hepatitis E virus), and the like. In some preferred embodiments, the target antigen is from an onco-virus. In some such embodiments, the T cells used for generating the CAR-T cells of the invention are polyfunc-tional T-cells, i.e., those T cells that are capable of inducing multiple immune effector functions, that provide a more effective immune response to a pathogen than do cells that produce, for example, only a single immune effector (e.g. a single biomarker such as a cytokine or CD107a). Less-polyfunctional, monofunctional, or even "exhausted" T cells may dominate immune responses during chronic infections, thus negatively impacting protection against virus-associ-ated complications. In further preferred embodiments, the CAR-T cells of the invention are polyfunctional. In certain embodiments, at least 50% of the T cells used for generating the CAR-T cells of the invention are CD4$^+$ T cells. In some such embodiments, said T cells are less than 50% CD4$^+$ T cells. In still further embodiments, said T cells are predomi-nantly CD4$^+$ T cells. In some embodiments, at least 50% of the T cells used for generating the CAR-T cells of the invention are CD8$^+$ T cells. In some such embodiments, said T cells are less than 50% CD8$^+$ T cells. In still further embodiments, said T cells are predominantly CD8$^+$ T cells. In some embodiments, the T cells (e.g., the sensitized T cells and/or CAR-T cells described herein) are stored in a cell library or bank before they are administered to the subject. The methods disclosed herein, (e.g., the selection and/or preparation of immune effector cells disclosed herein, including the CAR-T cells of the invention) include the selection and/or modification of allogeneic immune effector cells (e.g., PBMCs, CD4$^+$ T cells, CD8$^+$ T cells, and/or CAR-T cells) from a cell bank such as a pre-generated third-party-donor-derived bank of cells. Such a cell bank may comprise donor PBMC samples. Preferably the cell bank comprises donor samples wherein the immune effector cells have been enriched. Most preferably, the bank com-prises donor CD4$^+$ and/or CD8$^+$ T cells. In some such embodiments, the donor-derived cell bank comprises anti-gen-specific immune effector cells (e.g., the sensitized T cells and/or CAR-T cells described herein). In preferred embodiments, the HLA type of the donor-derived cells described herein is known. Accordingly, the methods dis-closed herein further include selecting allogeneic immune effector cells (e.g., the T cells and/or CAR-T cells described herein) because they express a TCR restricted to a class I MHC that is encoded by an HLA allele that is present in the subject. For example, allogeneic T cells (e.g., CD4$^+$ T cells, CD8$^+$ T cells, and/or CAR-T cells described herein) are selected if said T cells and the recipient (e.g., subject in need of treatment) share at least 2 (e.g., at least 3, at least 4, at least 5, at least 6) HLA alleles and the cells are restricted through a shared HLA allele. Preferably, such methods comprise testing the TCR repertoire of the pre-generated third-party-donor-derived epitope-specific T cells (i.e., allo-geneic T cells and/or CAR-T cells) by means known in the art, such as flow cytometry, tetramer assay, ELISA assay, western blot assay, fluorescent microscopy, Edman degra-dation assay, and/or a mass spectrometry assay (e.g., protein sequencing). In some embodiments, the TCR repertoire is analyzed using a nucleic acid probe, a nucleic acid ampli-fication assay and/or a sequencing assay.

In some embodiments, the engineered CAR-T cells expressing the disclosed CARs further express a dominant-negative mutation that effects immune checkpoint blockade (e.g., express a dominant-negative form of an immune checkpoint molecule such as PD-1). Without intending to be an exhaustive list, the immune checkpoint molecule is selected from programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immu-noreceptor with Ig and ITIM domains (TIGIT), leukocyte-associated immunoglobulin-like receptor 1 (LAIR1), natural killer cell receptor 2B4 (2B4), and CD160. The immune checkpoint molecule may also be transforming growth fac-tor β (TGF-β) receptor. Preferably, the immune checkpoint molecule is CTLA-4. Most preferably, the immune check-point molecule is PD-1.

PCT application WO2017/040945 describes methods of engineering CAR-T cells, which express a dominant nega-tive form of an inhibitor of a cell-mediated immune response. The WO2017/040945 application is hereby incor-porated by reference.

Therapeutic Methods

Immune effector cells expressing the disclosed CARs can elicit a therapeutically beneficial immune response against B-lymphocyte antigen-expressing cancer cells (e.g., CD19-associated cancers). For example, an anti-tumor immune response elicited by the disclosed CAR-modified immune effector cells may be an active or a passive immune response. In addition, the CAR-mediated immune response may be part of an adoptive immunotherapy approach in which CAR-modified immune effector cells induce an immune response specific to a B-lymphocyte antigen such as CD19.

Adoptive transfer of immune effector cells expressing chimeric antigen receptors is a promising anti-cancer thera-peutic. Following the collection of a patient's immune effector cells, the cells may be genetically engineered to express the disclosed B-lymphocyte antigen-specific CARs, and then infused back into the patient. Moreover, immune effector cells obtained from a donor other than the patient (i.e., allogeneic to the patient) may be genetically engineered to express the disclosed B-lymphocyte antigen-specific CARs, then the CAR-containing cells infused into the patient. In certain specific embodiments, the immune effec-tor cells which comprise an anti-B-lymphocyte antigen CAR polypeptide are allogeneic EBV-specific cytotoxic T cells.

The disclosed CAR-modified immune effector cells may be administered either alone, or as a pharmaceutical com-position in combination with diluents and/or with other components such as IL-2, IL-15, or other cytokines or cell populations. Briefly, pharmaceutical compositions may comprise a target cell population as described herein, in combination with one or more pharmaceutically or physi-ologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions for use in the disclosed methods are in some embodiments formulated for intravenous administration. Pharmaceutical compositions may be administered in any manner appropriate treat MM. The quantity and frequency of administration will be determined by such factors as the condition of the patient, and the severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, such as $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently re-draw blood (or have an apheresis performed), activate T cells therefrom according to the disclosed methods, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Using this multiple blood draw/multiple reinfusion protocol may serve to select out certain populations of T cells.

The administration of the disclosed compositions may be carried out in any convenient manner, including by injection, transfusion, or implantation. The compositions described herein may be administered to a patient subcutaneously, intradermally, intratumorally, intranodally, intramedullary, intramuscularly, by intravenous (i.v.) injection, or intraperitoneally. In some embodiments, the disclosed compositions are administered to a patient by intradermal or subcutaneous injection. In some embodiments, the disclosed compositions are administered by i.v. injection. The compositions may also be injected directly into a tumor, lymph node, or site of infection.

In certain embodiments, the disclosed CAR-modified immune effector cells are administered to a patient in conjunction with (e.g., before, simultaneously or following) any number of relevant treatment modalities, including but not limited to thalidomide, dexamethasone, bortezomib, and lenalidomide. In further embodiments, the CAR-modified immune effector cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. In some embodiments, the CAR-modified immune effector cells are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In other embodiments, the cell compositions of the present invention are administered following B-cell ablative therapy such as agents that react with CD20, e.g., Rituxan. For example, in some embodiments, subjects may undergo standard treatment with high dose chemotherapy followed by peripheral blood stem cell transplantation. In certain embodiments, following the transplant, subjects receive an infusion of the expanded immune cells of the present invention. In additional embodiments, expanded cells are administered before or following surgery.

The cancer of the disclosed methods can be any B-lymphocyte antigen-expressing cell, (e.g., any CD19-expressing cell) in a subject undergoing unregulated growth, invasion, or metastasis. Cancers that express a B-lymphocyte antigen (such as CD19), include leukemias and lymphomas such as acute leukemias, chronic leukemias, lymphocytic leukemias, myelogenous leukemias, pre-leukemic conditions, Hodgkin lymphoma, Non-Hodgkin lymphoma, EBV-associated lymphoproliferative diseases, mature B cell neoplasms, mature T cell and natural killer (NK) cell neoplasms, precursor lymphoid neoplasms, and immunodeficiency-associated lymphoproliferative disorders.

In some embodiments, the cancer can be any neoplasm or tumor of the hematopoietic and/or lymphatic tissues. Thus, the cancer can be any malignancy affecting the blood, bone marrow, lymph, and/or lymphatic system; and any such disease resulting in unregulated myeloproliferation and/or lymphoproliferation. A representative but non-limiting list of cancers that the disclosed compositions can be used to treat include acute lymphoblastic leukemia (ALL), precursor B acute lymphoblastic leukemia, precursor T acute lymphoblastic leukemia, Burkitt's leukemia, acute biphenotypic leukemia, chronic lymphocytic leukemia (CLL), B-cell prolymphocytic leukemia, acute myelogenous leukemia (AML), acute promyelocytic leukemia (PML), acute myeloblastic leukemia, acute megakaryoblastic leukemia, chronic myelogenous leukemia (CML), chronic myelomonocytic leukemia, hairy cell leukemia (HCL), T-cell prolymphocytic leukemia (T-PLL), large granular lymphocytic leukemia, adult T-cell leukemia, clonal eosinophilias, B-cell chronic lymphocytic leukemia/small cell lymphoma, lymphoplasmacytic lymphoma (such as Waldenström macroglobulinemia), splenic marginal zone lymphoma, plasma cell neoplasms such as plasma cell myeloma (multiple myeloma), plasmacytoma, monoclonal immunoglobulin deposition diseases, Heavy chain diseases, extranodal marginal zone B cell lymphoma (MALT lymphoma), nodal marginal zone B cell lymphoma, follicular lymphoma, primary cutaneous follicle center lymphoma, mantle cell lymphoma, diffuse large B cell lymphoma (with or without chronic inflammation), Epstein-Barr virus-positive DLBCL of the elderly, lymphomatoid granulomatosis, primary mediastinal (thymic) large B-cell lymphoma, intravascular large B-cell lymphoma, ALK$^+$ large B-cell lymphoma, plasmablastic lymphoma, primary effusion lymphoma, large B-cell lymphoma arising in HHV8-associated multicentric Castleman's disease, Burkitt lymphoma/leukemia, T-cell prolymphocytic leukemia, T-cell large granular lymphocyte leukemia, aggressive NK cell leukemia, adult T-cell leukemia/lymphoma, extranodal NK/T-cell lymphoma, enteropathy-associated T-cell lymphoma, hepatosplenic T-cell lymphoma, blastic NK cell lymphoma, mycosis fungoides/Sezary syndrome, primary cutaneous CD30-positive T cell lymphoproliferative disorders, peripheral T-cell lymphomas, angioimmunoblastic T cell lymphoma, anaplastic large cell lymphoma, B-lymphoblastic leukemia/lymphoma not otherwise specified, B-lymphoblastic leukemia/lymphoma with recurrent genetic abnormalities, T-lymphoblastic leukemia/lymphoma; classical Hodgkin lymphomas such as nodular sclerosis form, mixed cellularity Hodgkin lymphoma, lymphocyte-rich Hodgkin lymphoma, lymphocyte depleted or not depleted Hodgkin lymphoma, nodular lymphocyte-predominant Hodgkin lymphoma; and immunodeficiency-associated lymphoproliferative disorders associated with a primary immune disorder, associated with the human immunodeficiency virus (HIV), associated with methotrexate therapy, post-transplant, and primary central nervous system lymphoma.

The disclosed CARs can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed CARs can be used in combination with an immune checkpoint inhibitor. Two known immune checkpoint pathways involve signaling through the cytotoxic T-lymphocyte antigen-4 (CTLA-4) and programmed-death 1 (PD-1) receptors. These proteins are members of the CD28-B7 family of co-signaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to aptamers and antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016). Techniques for combining CARs with checkpoint inhibitors in immune effector cells and use thereof for the treatment of various disorders are described, for example, in WO 2017/040945, which is incorporated by reference herein.

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD-1 inhibitor comprises an antibody that specifically binds PD-1, such as lambrolizumab (Merck), nivolumab (Bristol-Myers Squibb), or MEDI4736 (Astra-Zeneca). Human monoclonal antibodies to PD-1 and methods for treating cancer using anti-PD-1 antibodies alone or in combination with other immunotherapeutics are described in U.S. Pat. No. 8,008,449. Anti-PD-L1 antibodies and uses therefor are described in U.S. Pat. No. 8,552,154, which is incorporated by reference for these antibodies. Anticancer agent comprising anti-PD-1 antibody or anti-PD- L1 antibody are described in U.S. Pat. No. 8,617,546, which is incorporated by reference for these antibodies.

The disclosed CARs can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM 1 or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec STI571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a CARs for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C-C chemokine families. Suitable cytokines include cytokine derivatives, cytokine variants, cytokine fragments, and cytokine fusion proteins.

In some embodiments, a therapeutic agent for use in combination with a CARs for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a CARs for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with CARs for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed CARs are administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed CARs are administered in combination with surgery.

CAR-T cells may be designed in several ways that enhance tumor cytotoxicity and specificity, evade tumor immunosuppression, avoid host rejection, and prolong their therapeutic half-life. TRUCK (T-cells Redirected for Universal Cytokine Killing) T cells for example, possess a CAR but are also engineered to release cytokines such as IL-12 that promote tumor killing. Because these cells are designed to release a molecular payload upon activation of the CAR once localized to the tumor environment, these CAR-T cells are sometimes also referred to as 'armored CARs'. Several cytokines are being investigated, both pre-clinically and clinically, as cancer therapies, and may also prove useful when similarly incorporated into a TRUCK form of CAR-T therapy. Among these include IL-2, IL-3. IL-4, IL-5, IL-6, IL-7, IL-10, IL-12, IL-13, IL-15, IL-18, M-CSF, GM-CSF, IFN-α, IFN-γ, TNF-α, TRAIL, FLT3 ligand, Lymphotactin, and TGF-β (Dranoff, (2004). "Cytokines in Cancer Pathogenesis and Cancer Therapy." *Nat Rev Cancer* January 4(1):11-22). "Self-driving" or "homing" CAR-T cells are engineered to express a chemokine receptor in addition to their CAR. As certain chemokines can be upregulated in tumors, incorporation of a chemokine receptor aids in tumor trafficking to and infiltration by the adoptive T-cell, thereby enhancing both specificity and functionality of the CAR-T (Moon (2011). "Expression of a functional CCR2 receptor enhances tumor localization and tumor eradication by retargeted human T cells expressing a mesothelin-specific chimeric antibody receptor." *Clin Cancer Res.* 2011 Jul. 15; 17(14):4719-30). Universal CAR-T cells also possess a CAR, but are engineered such that they do not express endogenous TCR (T-cell receptor) or MHC (major histocompatibility complex) proteins. Removal of these two proteins from the signaling repertoire of the adoptive T-cell therapy prevents graft-versus-host-disease and rejection, respectively. Armored CAR-T cells are additionally so named for their ability to evade tumor immunosuppression and tumor-induced CAR-T hypofunction. These particular CAR-Ts possess a CAR, and may be engineered to not express checkpoint inhibitors. Alternatively, these CAR-Ts can be co-administered with a monoclonal antibody (mAb) that blocks checkpoint signaling. Administration of an anti-PDL1 antibody significantly restored the killing ability of CAR TILs (tumor infiltrating lymphocytes). While PD-1-PD-L1 and CTLA-4-CD80/CD86 signaling pathways have been investigated, it is possible to target other immune checkpoint signaling molecules in the design of an armored CAR-T including LAG-3, Tim-3, IDO-1, 2B4, and KIR. Other intracellular inhibitors of TILs include phosphatases (SHP1), ubiquitin-ligases (i.e., cbl-b), and kinases (i.e., diacylglycerol kinase). Armored CAR-Ts may also be engineered to express proteins or receptors that protect them against or make them resistant to the effects of tumor-secreted cytokines. For example, CTLs (cytotoxic T lymphocytes) transduced with the double negative form of the TGF-β receptor are resistant to the immunosuppression by lymphoma secreted TGF-β. These transduced cells showed notably increased antitumor activity in vivo when compared to their control counterparts.

Tandem and dual CAR-T cells are unique in that they possess two distinct antigen binding domains. A tandem CAR contains two sequential antigen binding domains facing the extracellular environment connected to the intracellular costimulatory and stimulatory domains. A dual CAR is engineered such that one extracellular antigen binding domain is connected to the intracellular costimulatory domain and a second, distinct extracellular antigen binding domain is connected to the intracellular stimulatory domain. Because the stimulatory and costimulatory domains are split between two separate antigen binding domains, dual CARs are also referred to as "split CARs". In both tandem and dual CAR designs, binding of both antigen binding domains is necessary to allow signaling of the CAR circuit in the T-cell. Because these two CAR designs have binding affinities for different, distinct antigens, they are also referred to as "bi-specific" CARs.

One primary concern with CAR-T cells as a form of "living therapeutic" is their manipulability in vivo and their potential immune-stimulating side effects. To better control CAR-T therapy and prevent against unwanted side effects, a variety of features have been engineered including off-switches, safety mechanisms, and conditional control mechanisms. Both self-destruct and marked/tagged CAR-T cells for example, are engineered to have an "off-switch" that promotes clearance of the CAR-expressing T-cell. A self-destruct CAR-T contains a CAR, but is also engineered to express a pro-apoptotic suicide gene or "elimination gene" inducible upon administration of an exogenous molecule. A variety of suicide genes may be employed for this purpose, including HSV-TK (herpes simplex virus thymidine kinase), Fas, iCasp9 (inducible caspase 9), CD20, MYC TAG, and truncated EGFR (endothelial growth factor receptor). HSK for example, will convert the prodrug ganciclovir (GCV) into GCV-triphosphate that incorporates itself into replicating DNA, ultimately leading to cell death. iCasp9 is a chimeric protein containing components of FK506-binding protein that binds the small molecule AP1903, leading to caspase 9 dimerization and apoptosis. A marked/tagged CAR-T cell however, is one that possesses a CAR but also is engineered to express a selection marker. Administration of a mAb against this selection marker will promote clearance of the CAR-T cell. Truncated EGFR is one such targetable antigen by the anti-EGFR mAb, and administration of cetuximab works to promotes elimination of the CAR-T cell. CARs created to have these features are also referred to as sCARs for 'switchable CARs', and RCARs for 'regulatable CARs'. A "safety CAR", also known as an "inhibitory CAR" (iCAR), is engineered to express two antigen binding domains. One of these ectodomains is directed against a tumor related antigen and bound to an intracellular costimulatory and stimulatory domain. The second extracellular antigen binding domain however is specific for normal tissue and bound to an intracellular checkpoint domain such as CTLA4, PD-1, or CD45. Incorporation of multiple intracellular inhibitory domains to the iCAR is also possible. Some inhibitory molecules that may provide these inhibitory domains include B7-H1, B7-1, CD160, PIH, 2B4, CEACAM (CEACAM-1. CEACAM-3, and/or CEACAM-5), LAG-3, TIGIT, BTLA, LAIR1, and TGFβ-R. In the presence of normal tissue, stimulation of this second antigen binding domain will work to inhibit the CAR. It should be noted that due to this dual antigen specificity, iCARs are also a form of bi-specific CAR-T cells. The safety CAR-T engineering enhances specificity of the CAR-T cell for tumor tissue, and is advantageous in situations where certain normal tissues may express very low levels of a tumor associated antigen that would lead to off target effects with a standard CAR (Morgan (2010). "Case report of a serious adverse event following the administration of T cells transduced with a chimeric antigen receptor recognizing ERBB2." *Molecular Therapy* 2010; 18(4):843-851). A conditional CAR-T cell expresses an extracellular antigen binding domain connected to an intracellular costimulatory domain and a separate, intracellular costimulator. The costimulatory and stimulatory domain sequences are engineered in such a way that upon administration of an exogenous molecule the resultant proteins will come together intracellularly to complete the CAR circuit. In this way, CAR-T activation can be modulated, and possibly even 'fine-tuned' or personalized to a specific patient. Similar to a dual CAR design, the stimulatory and costimulatory domains are physically separated when inactive in the conditional CAR; for this reason, these too are also referred to as a "split CAR".

In some embodiments, two or more of these engineered features may be combined to create an enhanced, multifunctional CAR-T. For example, it is possible to create a CAR-T cell with either dual- or conditional-CAR design that also releases cytokines like a TRUCK. In some embodiments, a dual-conditional CAR-T cell could be made such that it expresses two CARs with two separate antigen binding domains against two distinct cancer antigens, each bound to their respective costimulatory domains. The costimulatory domain would only become functional with the stimulatory domain after the activating molecule is administered. For this CAR-T cell to be effective the cancer must express both cancer antigens and the activating molecule must be administered to the patient; this design thereby incorporating features of both dual and conditional CAR-T cells.

Typically, CAR-T cells are created using α-β T cells, however γ-δ T cells may also be used. In some embodiments, the described CAR constructs, domains, and engineered features used to generate CAR-T cells could similarly be employed in the generation of other types of CAR-expressing immune cells including NK (natural killer) cells, B cells, mast cells, myeloid-derived phagocytes, and NKT cells. Alternatively, a CAR-expressing cell may be created to have properties of both T-cell and NK cells. In additional embodiments, the cells transduced with CARs may be autologous or allogeneic to a patient to which they are administered.

Several different methods for CAR expression may be used including retroviral transduction (including γ-retroviral), lentiviral transduction, transposon/transposases (Sleeping Beauty and PiggyBac systems), and messenger RNA transfer-mediated gene expression. Gene editing (gene insertion or gene deletion/disruption) has become of increasing importance with respect to the possibility for engineering CAR-T cells as well. CRISPR-Cas9, ZFN (zinc finger nuclease), and TALEN (transcription activator like effector nuclease) systems are three potential methods through which CAR-T cells may be generated.

EXEMPLIFICATION

Example 1: CD19-CAR Design

Cytotoxic T-cells (CTLS), sensitized to EBV antigen, were used to engineer CAR T cells that selectively target at least one cancer-associated CD19 epitope. The CAR polypeptide was specifically designed to reduce CAR T cell exhaustion and enhance CAR T cell persistence in the subject. Briefly, the expressed CAR polypeptide comprised a leader sequence (i.e., the amino acid sequence set forth in SEQ ID NO. 8), which is N-terminal to the CD19-targeting domain (i.e., the FMC63 scFv amino acid sequence set forth in SEQ ID NO. 9). The skilled individual will appreciate that when the CAR is expressed inside a cell, such as EBV-sensitized CTLs, the nascent protein (i.e., a protein comprising the amino acid sequence set forth in SEQ ID NO. 6) is processed, which includes removal of the leader sequence. The resultant mature polypeptide (i.e., a polypeptide comprising the amino acid sequence set forth in SEQ TD NO. 7) is translocated to the cell surface. Moreover, the CAR domains were optimized through a combination of a hinge region, a transmembrane domain, and an intracellular domain comprising co-stimulatory domains (i.e., the amino acid sequence set forth in SEQ ID NO. 10, comprising the CD28 hinge region, transmembrane domain and intracellular domain set forth in SEQ ID NOs. 12, 13, and 14) and signaling domain mutants (i.e., a 1XX CD3ζ mutant wherein the CD3ζ domain lacks functionality in the two C-terminal ITAM domains, as in the amino acid sequence set forth in SEQ ID NO. 11).

Nascent CAR polypeptide:
(SEQ ID NO. 6)
MALPVTALLLPLALLLHADIQMTQTTSSLSASLGDRVTISCRASQDISKY

LNWYQQKPDGTVKLLIYHTSRLHSGVPSRFSGSGSGTDYSLTISNLEQED

IATYFCQQGNTLPYTFGGGTKLEITGSTSGSGKPGSGEGSTKGEVKLQES

GPGLVAPSQSLSVTCTVSGVSLPDYGVSWIRQPPRKGLEWLGVIWGSETT

YYNSALKSRLTIIKDNSKSQVFLKMNSLQTDDTAIYYCAKHYYYGGSYAM

DYWGQGTSVTVSSAAAIEVMYPPPYLDNEKSNGTIIHVKGKHLCPSPLFP

GPSKPFWVLVVVGGVLACYSLLVTVAFIIFWVRSKRSRLLHSDYMNMTPR

RPGPTRKHYQPYAPPRDFAAYRSRVKFSRSADAPAYQQGQNQLYNELNLG

RREEYDVLDKRRGRDPEMGGKPRRKNPQEGLFNELQKDKMAEAFSEIGMK

GERRRGKGHDGLFQGLSTATKDTFDALHMQALPPR

Anti-CD19 CAR polypeptide:
(SEQ ID NO. 7)
DIQMTQTTSSLSASLGDRVTISCRASQDISKYLNWYQQKPDGTVKLLIYH

TSRLHSGVPSRFSGSGSGTDYSLTISNLEQEDIATYFCQQGNTLPYTFGG

GTKLEITGSTSGSGKPGSGEGSTKGEVKLQESGPGLVAPSQSLSVTCTVS

GVSLPDYGVSWIRQPPRKGLEWLGVIWGSETTYYNSALKSRLTIIKDNSK

SQVFLKMNSLQTDDTAIYYCAKHYYYGGSYAMDYWGQGTSVTVSSAAAIE

VMYPPPYLDNEKSNGTIIHVKGKHLCPSPLFPGPSKPFWVLVVVGGVLAC

YSLLVTVAFIIFWVRSKRSRLLHSDYMNMTPRRPGPTRKHYQPYAPPRDF

AAYRSRVKFSRSADAPAYQQGQNQLYNELNLGRREEYDVLDKRRGRDPEM

GGKPRRKNPQEGLFNELQKDKMAEAFSEIGMKGERRRGKGHDGLFQGLST

ATKDTFDALHMQALPPR

CD8 Leader Sequence
(SEQ ID NO. 8)
MALPVTALLLPLALLLHA

FMC63 scFv
(SEQ ID NO. 9)
DIQMTQTTSSLSASLGDRVTISCRASQDISKYLNWYQQKPDGTVKLLI

YHTSRLHSGVPSRFSGSGSGTDYSLTISNLEQEDIATYFCQQGNTLPY

-continued

TFGGGTKLEITGSTSGSGKPGSGEGSTKGEVKLQESGPGLVAPSQSLS

VTCTVSGVSLPDYGVSWIRQPPRKGLEWLGVIWGSETTYYNSALKSRL

TIIKDNSKSQVFLKMNSLQTDDTAIYYCAKHYYYGGSYAMDYWGQGTS

VTVSS

CD28 Domain
(SEQ ID NO. 10)
IEVMYPPPYLDNEKSNGTIIHVKGKHLCPSPLFPGPSKPFWVLVVVGG

VLACYSLLVTVAFIIFWVRSKRSRLLHSDYMNMTPRRPGPTRKHYQPY

APPRDFAAYRS

CD28 Domain components
Hinge region
(SEQ ID NO. 12)
IEVMYPPPYLDNEKSNGTIIHVKGKHLCPSPLFP

GPSKP

Transmembrane
(SEQ ID NO. 13)
FWVLVVVGGVLACYSLLVTVAFIIFWV

Intracellular
(SEQ ID NO. 14)
RSKRSRLLHSDYMNMTPRRPGPTRKHYQPYAPPR

DFAAYRS

1XX CD3ζ Domain
(SEQ ID NO. 11)
RVKFSRSADAPAYQQGQNQLYNELNLGRREEYDVLDKRRGRDPEMGGK

PRRKNPQEGLFNELQKDKMAEAFSEIGMKGERRRGKGHDGLFQGLSTA

TKDTFDALHMQALPPR

Alternatively, the CAR may further comprise an LNGFR domain capable of binding a detectable ligand, e.g., $^{124}$I-NGF, and thus acting as a molecular tag.

Optionally, the CAR T cells are capable of expressing an inhibitor of an immune checkpoint molecule (i.e., a dominant-negative PD-1 polypeptide), thus overcoming the immunosuppressive microenvironment found among many tumors.

Figure 2:
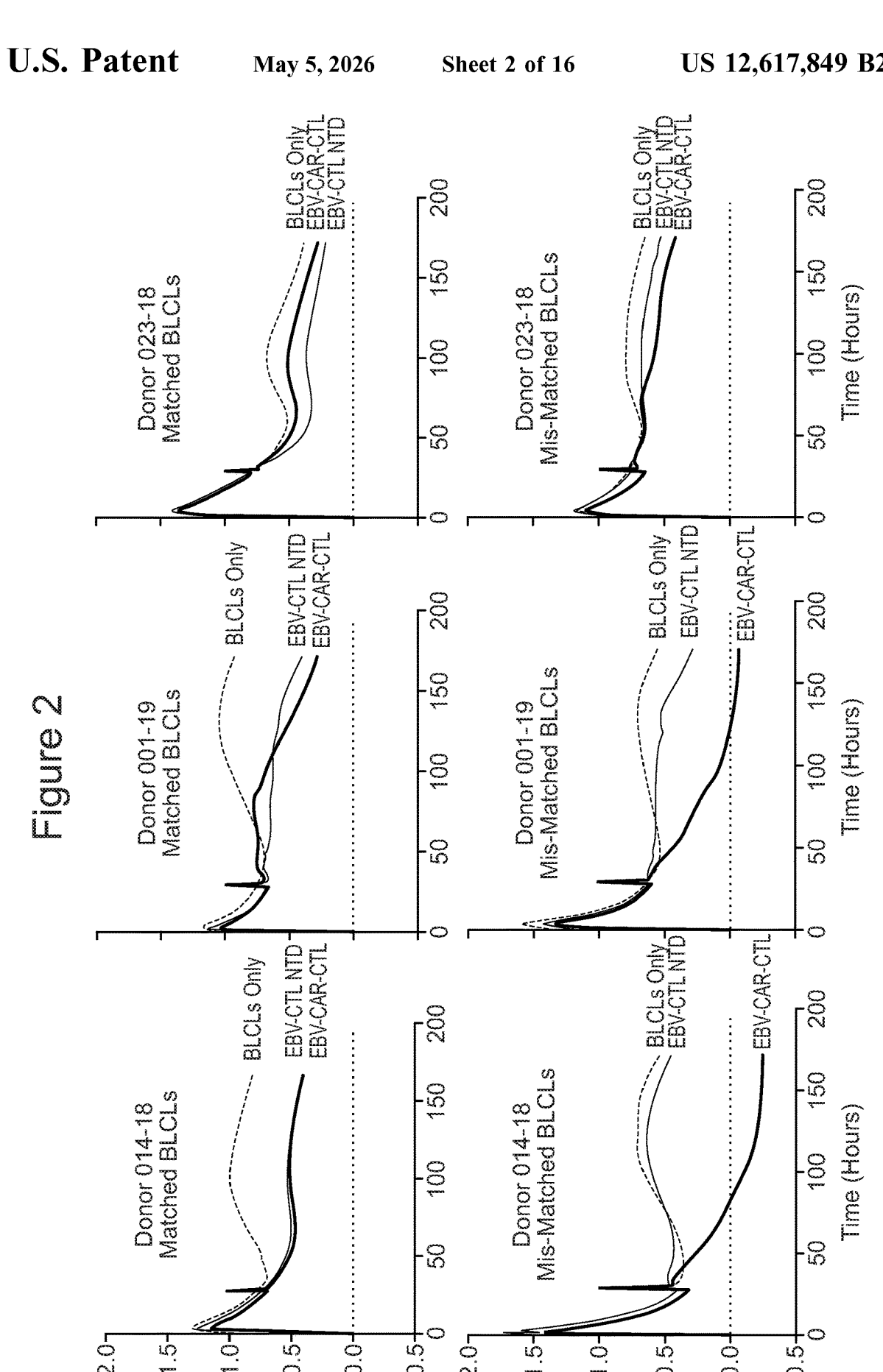
FIG. 2 shows data from electrical impedance assays to assess targeted cytotoxicity and allo-reactivity induced by donor-derived EBV-sensitized anti-CD19 CAR-T cells when co-cultured with matched (autologous) or mis-matched target BLCLs. Cytolytic activity is induced by both non-transduced (NTD) EBV-CTLs and CAR-expressing EBV-CTLs (top row). However, CAR EBV-CTLs are capable of inducing CD19-targeted, TCR-independent cytolytic activity in response to contacting mis-matched target BLCLs while NTD EBV-CTLs exhibit limited EBV-specific, TCR-directed cytolytic activity.

Example 2: Electrical Impedance Assays for Targeted Cytotoxicity and Allo-Reactivity Electrical impedance by targeted cells was used to assess the specific cytoxicity induced by EBV-sensitized anti-CD19CAR-T cells (EBV-CAR-T). Briefly, donor-derived B-lymphocyte (BLCL) target cells for which CD-19 expression has been characterized (see FIG. 1) were plated in anti-CD40-coated, 96-well impedance plates, thus effectively forming a monolayer of cells for analysis. Changes in electrical impedance relative to a voltage applied to the antibody-bound cell monolayer were measured in response to addition of effector cells (e.g., EBV-CAR-T), thus allowing measurement of cytotoxicity and/or allo-reactivity.
Results Donor-matched (autologous) BLCLs exhibit lysis in the presence of both EBV-CAR-T cells and in non-transduced EBV-sensitized T cells (NTD-EBV-T). (See FIG. 2, upper row) In contrast, EBV-CAR-T cells are capable of CD19-antigen-targeted cytolytic activity in mis-matched donor target cells relative to NTD-EBV-T cells which are capable of only limited EBV-TCR-directed cytolytic activity against mis-matched target cells. (See FIG. 2, lower row)

Example 3: Luciferase Assays for Targeted Cytolytic Activity

Figure 3:
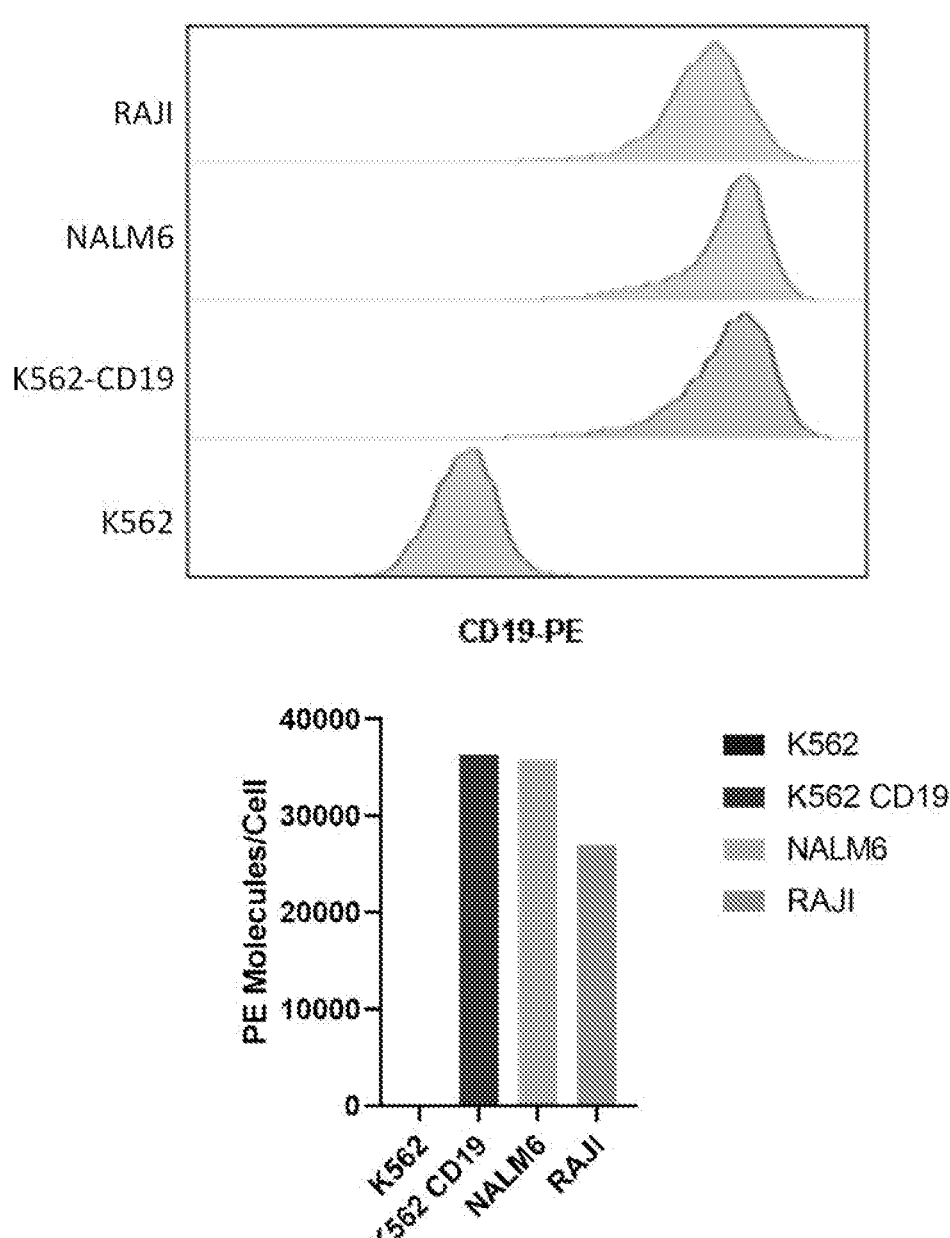
FIG. 3 shows the characterization of CD19 expression in each target cell line used in luciferase assays. It should be appreciated that the K562 cell line does not express CD19 or EBV antigen, and acts as a double, negative control.

The cytotlytic activity of antigen-specific T cells transduced with anti-CD19 CAR (i.e., EBV-CAR-T cells) was also determined by standard luciferase-based assays. Cell lines endogenously expressing CD19, as well as K562 control cells (non-transduced and transduced with a CD19 expression construct) were engineered to express luciferase and served as target cells as summarized in Table 7 and FIG. 3.

The effector and tumor target cells were co-cultured at the different effector:target ratios (1:4, 1:2; 1:1; 2:1 and 4:1) using black-walled 96-well plates with $5 \times 10^4$ target cells in a total volume of 100 µl per well. Target cells alone were plated at the same cell density to determine the maximal luciferase expression (relative light units (RLU)). 24 hr and 48 hr later, 100 µl luciferase substrate was directly added to each well. Emitted light was detected in a luminescence plate reader. Lysis is generally determined as (1−(RLUsample/RLUmax))×100.

TABLE 7

| Target Cell Lines | |
|---|---|
| Cell Line | Derivation |
| K562-Luc | Pleural effusion of a 53-year-old female with chronic myelogenous leukemia. CD19 and EBNA negative |
| K562-CD19-Luc | Transduced with CD19 under EF1a promoter, puromycin selection |
| NALM 6-Luc | Acute lymphoblastic leukemia (ALL) 19-year-old male. CD19 positive; EBNA negative in virus testing (ATCC) |
| RAJI-Luc | Burkitt's Lymphoma, 11-year-old male. CD19 positive; EBNA positive |

Briefly, luciferase-expressing target cells and effector mock-transduced or EBV-CAR-T cells were plated at the desired effector-to-target (E:T) ratios as described above. Non-transduced cells of the same donor were used to normalize total cell number in all the wells such that all wells containing T cells have the same total cell number. The co-culture plate was placed in an incubator overnight at 37° C. and 5% $CO_2$. At 24 hours, 50 µl of supernatant was removed from the co-culture for use in multiplex cytokine detection assays. To measure cytotoxic activity of the effector cells, 50 µl of culture medium was added into each well to compensate for the volume taken out for cytokine/chemokine analysis. D-Luciferin (luciferase substrate) was added to each well and the plate incubated for 10 min at room temperature. The plate was then read and RLUs were recorded and specific lysis was calculated. Following the 24-hour luciferase read, cells were placed back in the incubator overnight and re-read for a second time at 48 hours. The percentage of tumor lysis was calculated by the following formula:

$$\% \text{ tumor lysis} = (1 - (RLU_{tumor\ cells + T\ cells}/RLU_{tumor\ cells})) \times 100$$

Results

Figure 4:
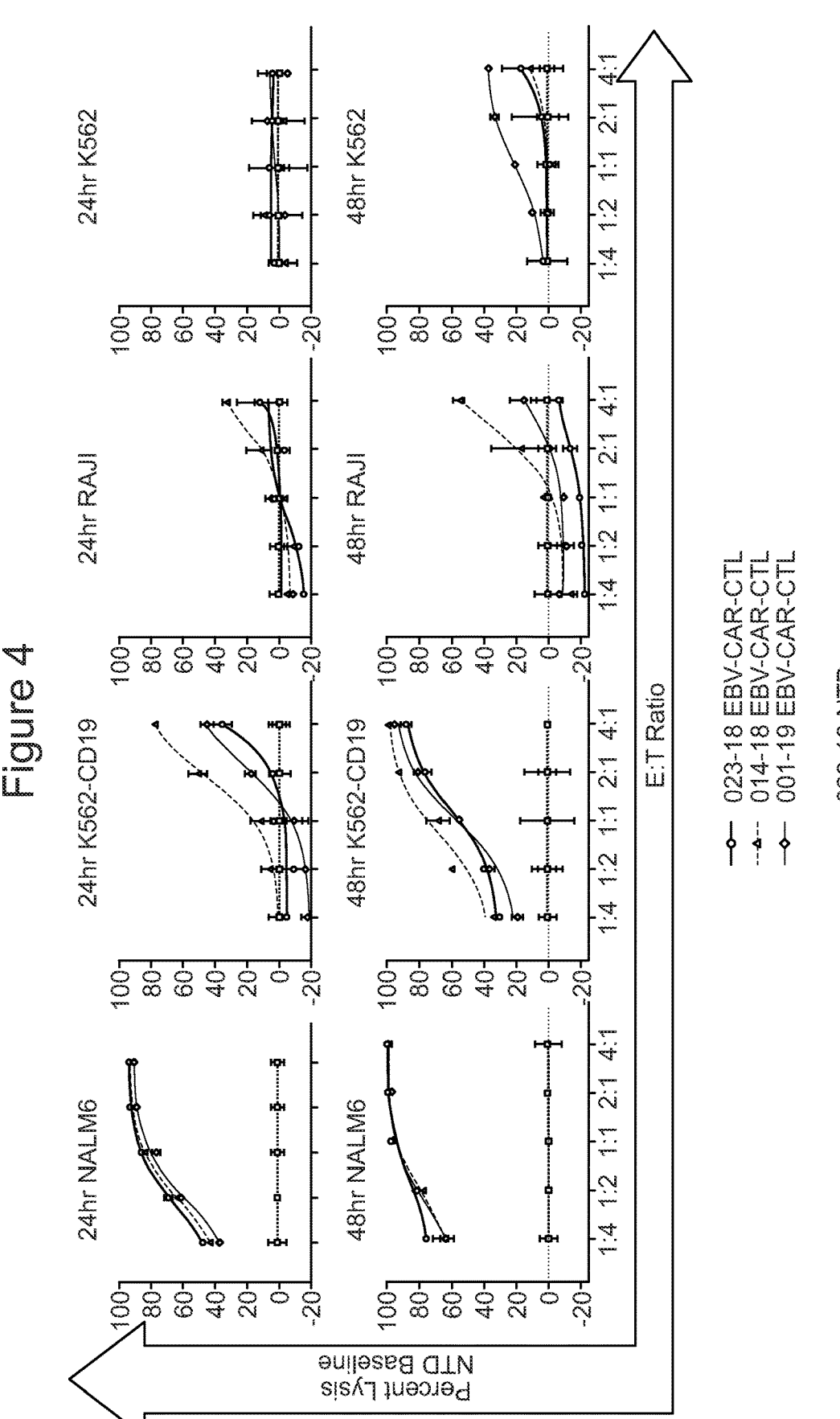
FIG. 4 shows luciferase assay data demonstrating targeted cytolytic activity induced by EBV-CAR-T cells. EBV-CAR-T cells exhibited CAR-directed cytolysis of the CD19-expressing cells lines NALM6 and RAJI, and K562 cells engineered to express CD19. Minimal cytolytic activity was observed in control K562 cells.

EBV-CAR-T cells exhibit CAR-directed cytolysis of CD19-expressing cells lines (i.e., NALM6, K562-CD19, and RAJI). (See FIG. 4) Notably, cytolysis was most efficient in the NALM6 cell line (CD19 positive; EBNA negative) followed by K562-CD19. RAJI cells (CD19 positive; EBNA positive) exhibited more resistance to directed cytolysis.

Figure 5:
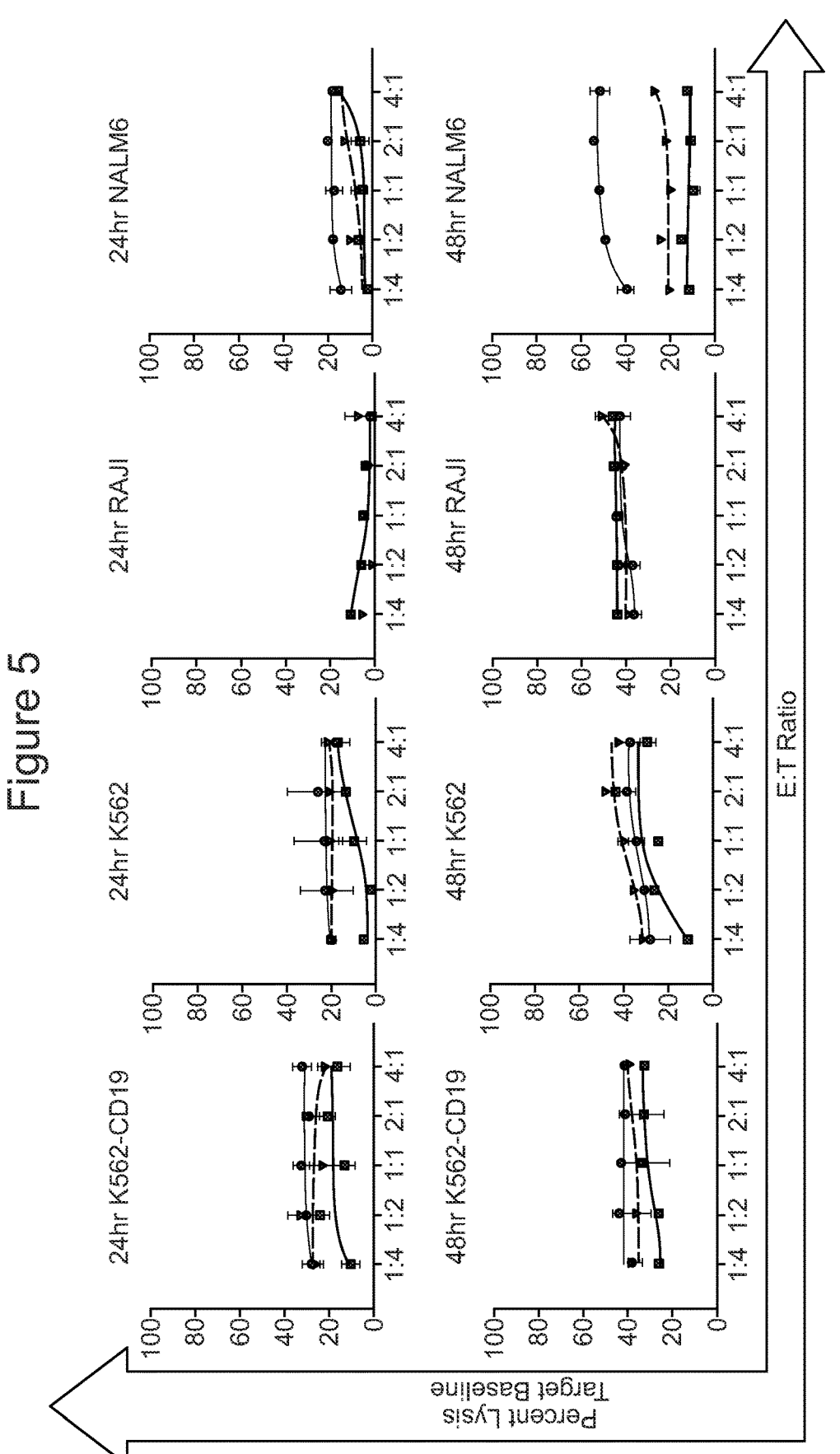
FIG. 5 shows donor-to-donor variability in nonspecific cytolysis induced by non-transduced effector cells.
Figure 6:
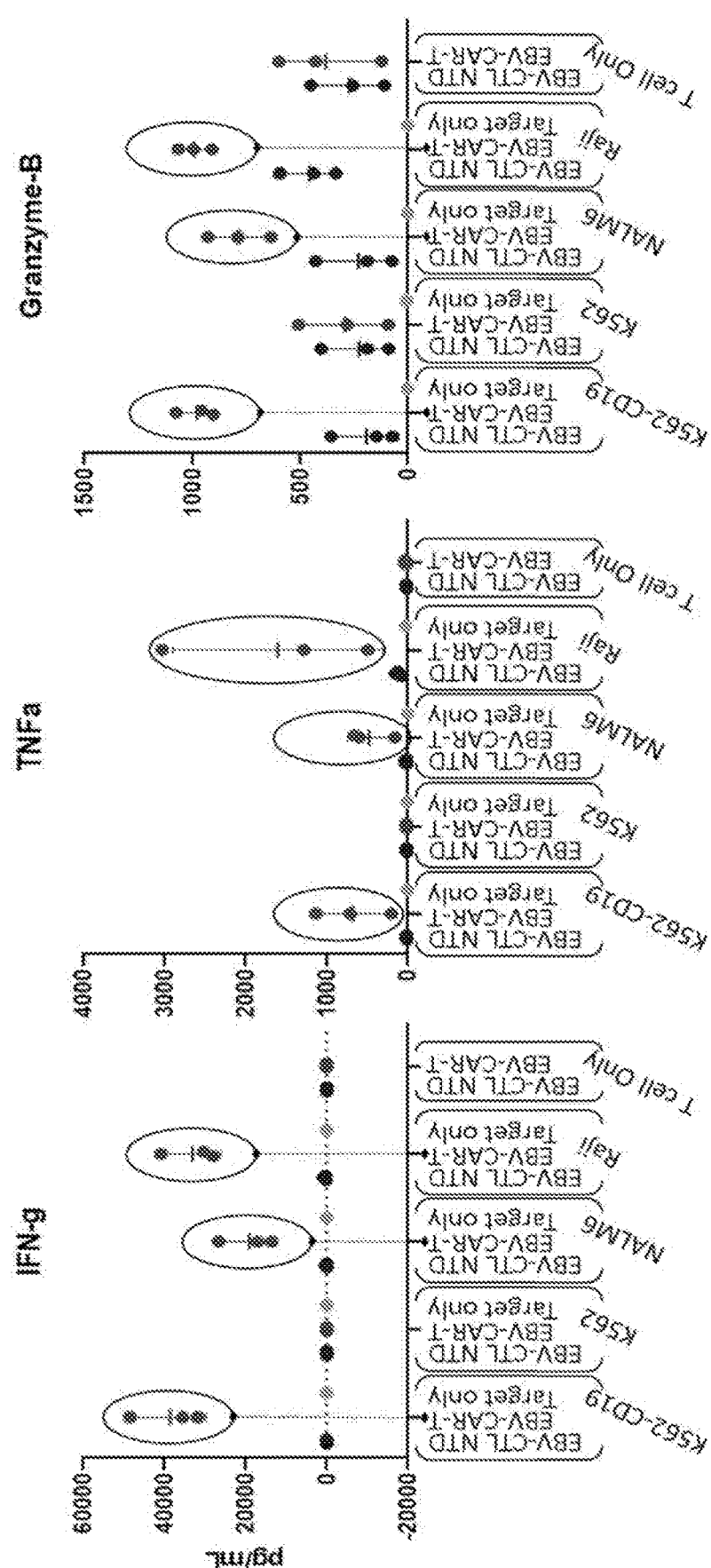
FIG. 6 shows exemplary cytokine release data across multiple target cells lines.
Figure 7:
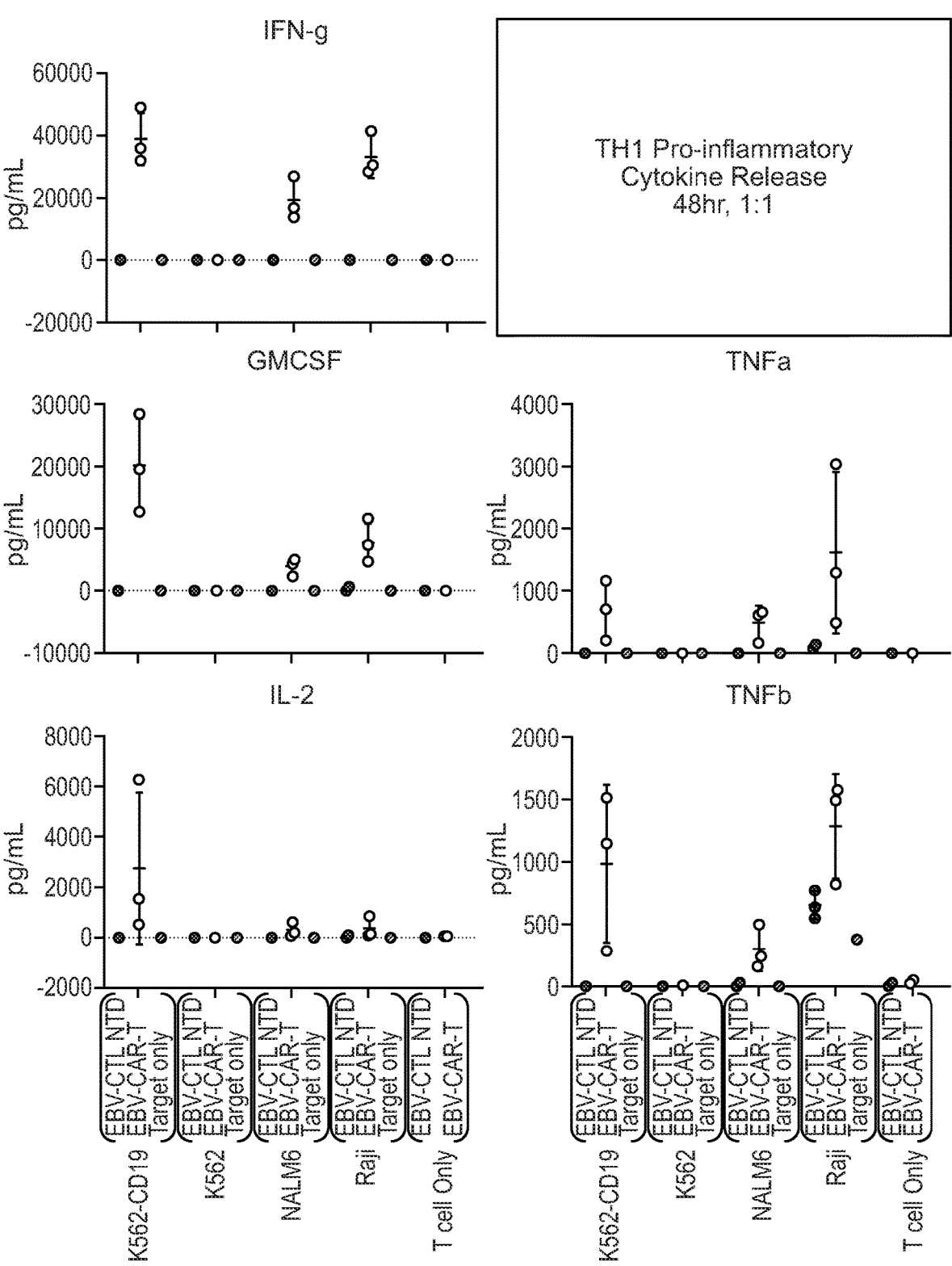
FIG. 7 shows TH1 pro-inflammatory cytokine release data across multiple target cells lines.
Figure 8:
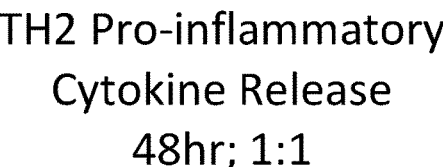
FIG. 8 shows TH2 pro-inflammatory cytokine release data across multiple target cells lines.
Figure 10:
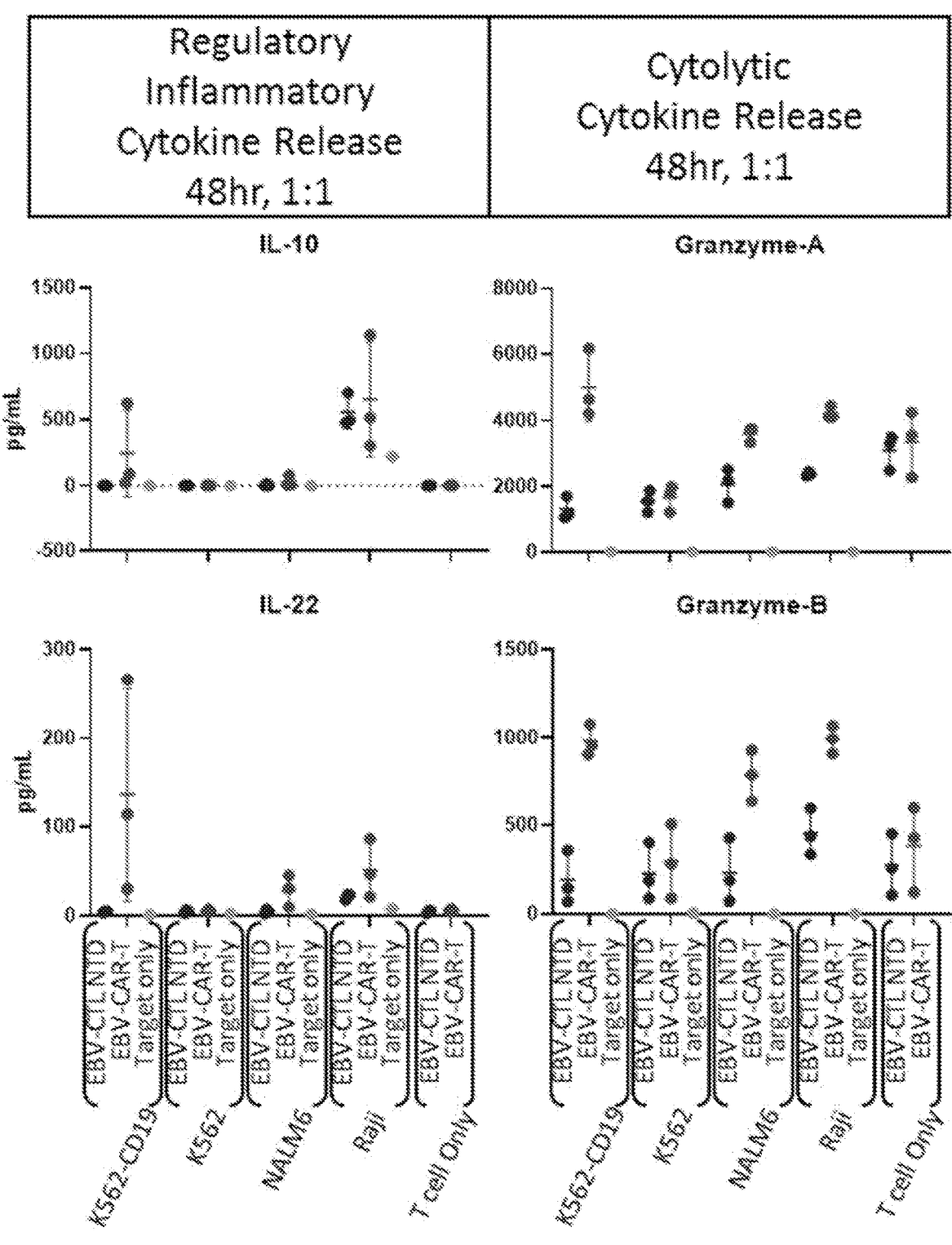
FIG. 10 shows regulatory inflammatory cytokine release data and cytolytic cytokine release data across multiple target cells lines.
Figure 13:
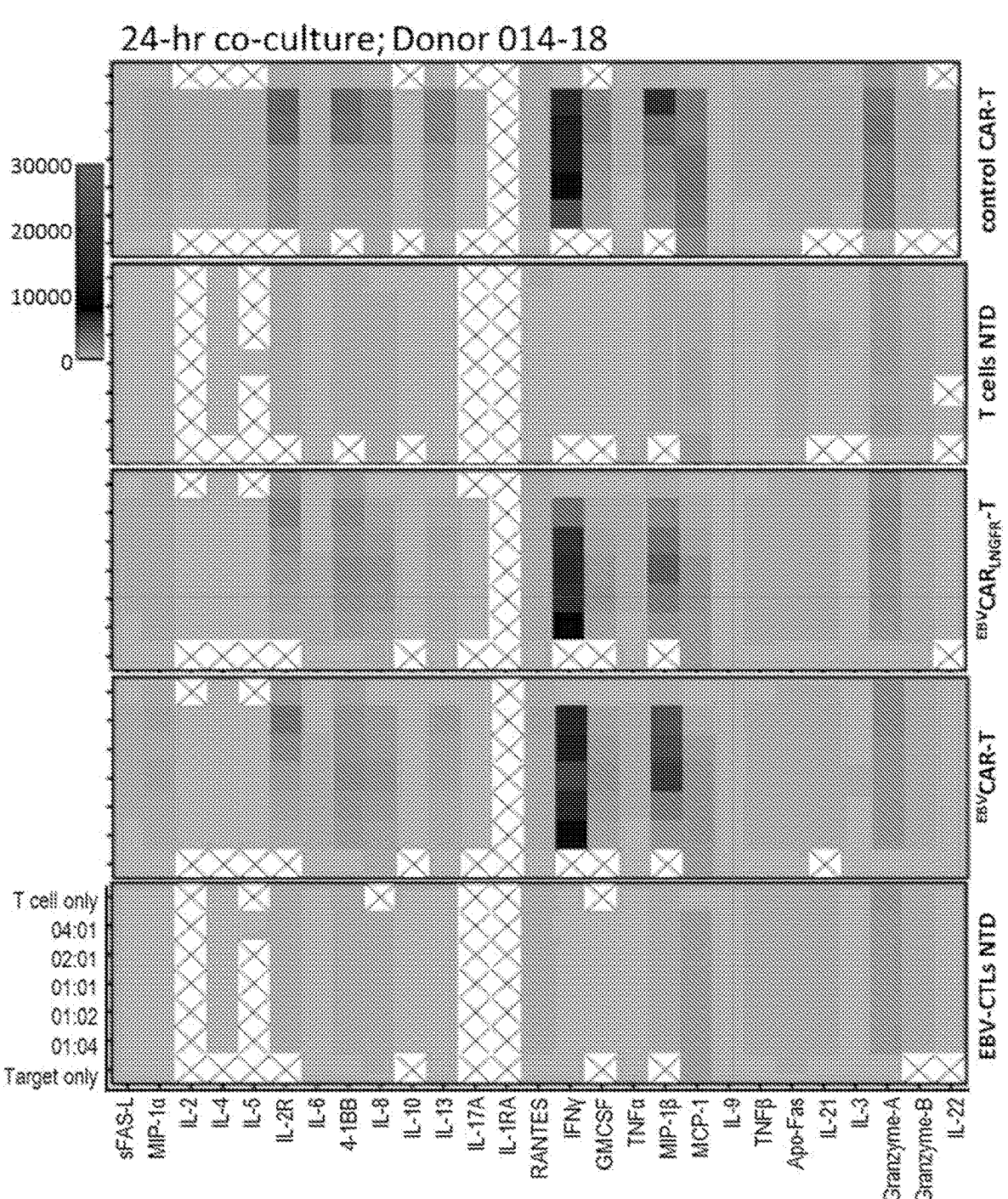
FIG. 13 depicts a cytokine release heat map for effector T cells generated from donor 014-18 and target K562-CD19 cells at different E:T ratios.
Figure 14:
FIG. 14 depicts a cytokine release heat map for effector T cells generated from donor 023-18 and target K562-CD19 cells at different E:T ratios.
Figure 14:
Figure 15:
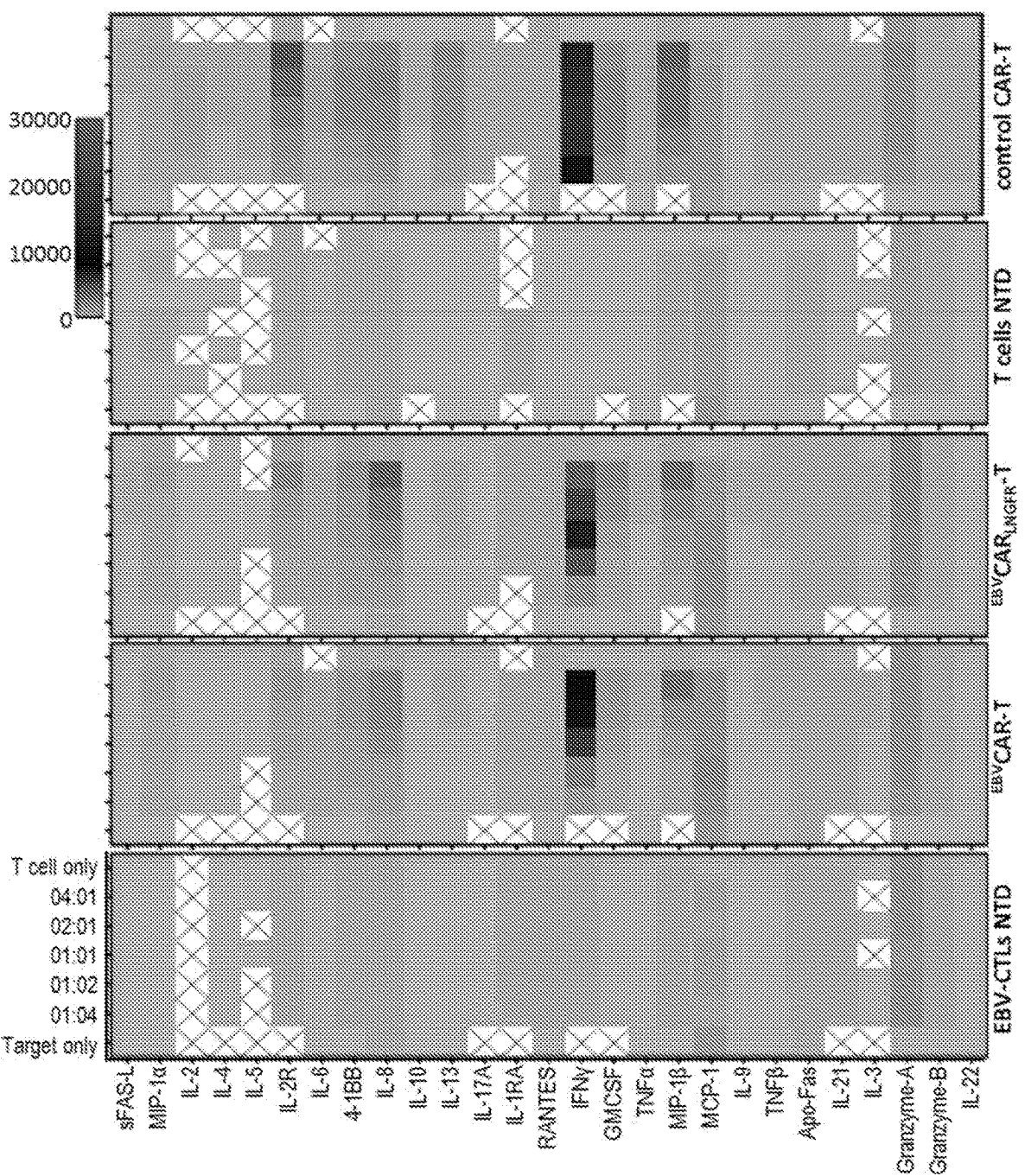
FIG. 15 depicts a cytokine release heat map for effector T cells generated from donor 009-19 and target K562-CD19 cells at different E:T ratios.
Figure 16:
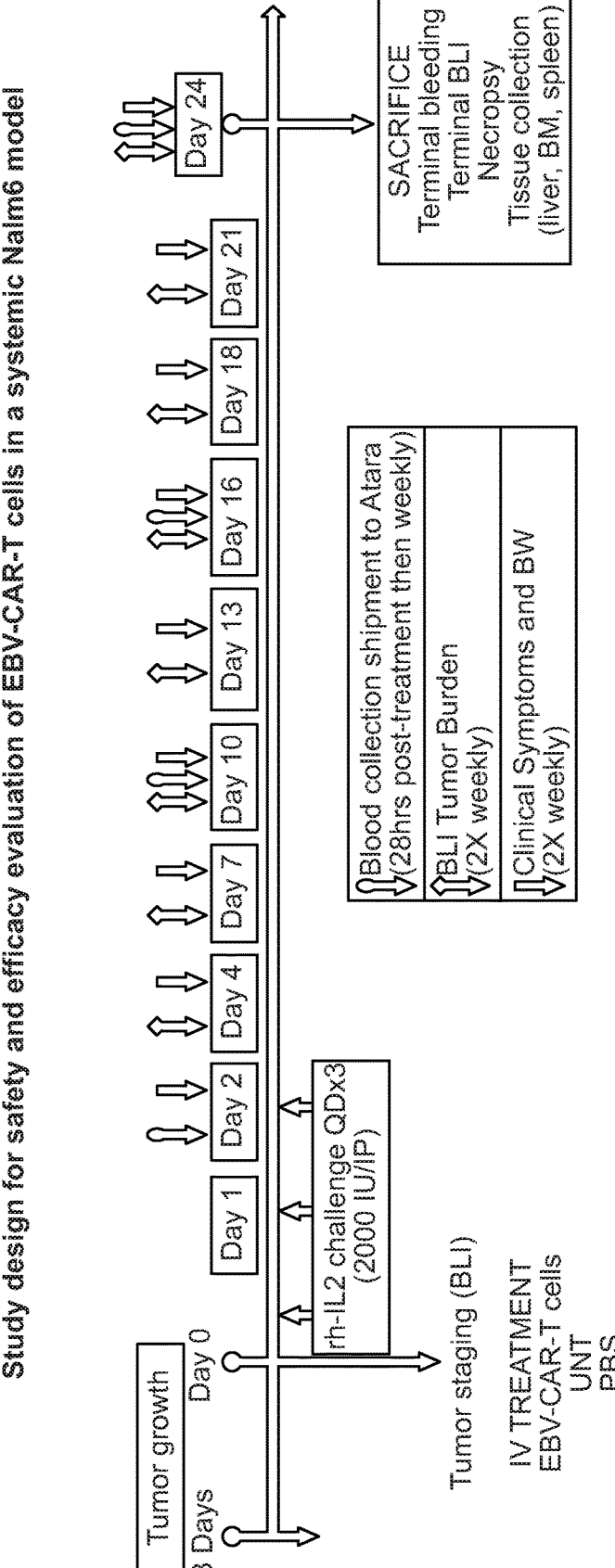
FIG. 16 illustrates the study design for the safety and efficacy evaluation of EBV-sensitized, anti-CD19 CAR-expressing T cells in a systemic Nalm6-induced mouse model.

Minimal non-specific cytolysis was observed in the antigen-negative cell line (K562), with some cytolysis observed with increasing E:T ratio of Donor 001-19 EBV-CAR-T cells (001-19 X). However, it was noted that effector cells displayed donor-to-donor variability in nonspecific cytolysis but with no evidence of dose-dependent killing. Donor 001-19 exhibited the highest level of non-specific cytolysis compared to the other two donors. (See FIG. 5) In subsequent assays donor 001-19 exhibited the highest basal cytokine release and has much less lysis compared to positive target control.

Example 4: Cytokine Release Profile of EBV-CD19CAR-T Cells

The cytokine secretion of antigen-specific T cells transduced with anti-CD19 CAR (i.e., EBV-CAR-T cells) was determined using bead-based multiplex cytokine detection assays (e.g., Luminex® Technology Multiplex Assays; ThermoFisher Scientific, U.S.A.). Cytokine profiling was conducted using the supernatant from co-cultures previously described (i.e., the co-cultures of Example 3).

Briefly, as indicated above, cytokine profiling was conducted using the supernatant from the aforementioned co-cultures of the luciferase assays. The supernatant (50 µL) from each well (either 24-hour or 48-hour co-culture) was transferred to a 96-well storage plate sealed with a peelable foil seal and stored at −80° C. until use. A 27-plex cytokine panel in a preconfigured mixture of target-specific beads was used for quantitative analysis of the select cytokines. (See Table 8) Thawed samples were added to the multiplex panel plate, as well as T cells alone, co-cultures, and target cell lines alone, across all test articles and non-transduced controls. Samples were read measured on a microplate reader.

TABLE 8

| Multiplex Cytokine Panel | |
|---|---|
| Category | Cytokines |
| Th1 ProInflammatory | IL-2, IFNγ, GMCSF, TNFα, TNFβ, |
| Th2 ProInflammatory | IL-4, IL-5, IL-9, IL-13 |
| Th17 Proinflammatory | IL-6, IL-17A, IL-21 |
| Regulatory | IL-10, IL-22, IL-1RA |
| Chemoactractive | IL-8, MCP-1, MIP-1α, MIP-1β, RANTES |
| Cytolytic | Granzyme A, Granzyme B |
| Activation | 4-1BB, IL-2R, SFAS-L, IL-3, APO-FAS |

Results

Analysis of supernatant from 48-hour co-cultures, at 1:1 E:T ratio, indicated that EBV-CAR-T cells induced elevated cytokine levels compared to NTD control T cells and target cell lines alone. (See Table 9 and FIGS. 6-18)

TABLE 9

| Summary of Polyfunctionality in Antigen-Specific Cytokine Release | | |
|---|---|---|
| Category | Cytokines | Response in at least one CD19+ cell lines |
| Th1 ProInflammatory | IL-2, IFNγ, GMCSF, TNFα, TNFβ, | 3/3 donors |
| Th2 ProInflammatory | IL-4, IL-5, IL-9, IL-13 | 3/3 donors |
| Th17 Proinflammatory | IL-6, IL-17A, IL-21 | 3/3 donors |
| Regulatory | IL-10, IL-22, IL-1RA | 3/3 donors |
| Chemoactractive | IL-8, MCP-1, MIP-1α, MIP-1β, RANTES | 3/3 donors |

TABLE 9-continued

Summary of Polyfunctionality in
Antigen-Specific Cytokine Release

| Category | Cytokines | Response in at least one CD19+ cell lines |
|---|---|---|
| Cytolytic | Granzyme A, Granzyme B | 3/3 donors |
| Activation | 4-1BB, IL-2R, SFAS-L, IL-3, APO-FAS | 3/3 donors |

Though EBV-CAR-T cells exhibit high degree of poly-functionality in presence of CD19-expressing cell lines, the cytokine release profile may have been, in part, determined by the intrinsic properties of the cell lines used, as observed in cytolysis assays above. Notably, K562-CD19 cells provide the greatest amount of antigen-induced cytokine release compared to RAJI or NALM6. (See FIGS. 6-12)

Analysis in K562-CD19 cells, comprising T cells alone, (E:F) 2:1, 1:1, 1:2, 1:4 and targets alone, for each T cell donor (001-19, 014-18, 023-18) was also performed. Exemplary data for T cells (e.g., EBV-T cells and EBV-CAR-T cells) derived from Donor 014-18 are provided in Tables 10 to 13.

TABLE 10

| | | | | Cytokine secretion profile of NTD T cells using Donor 014-18 | | | |
|---|---|---|---|---|---|---|---|
| cytokine | T cell Only | 4:1 | 2:1 | 1:1 | 1:2 | 1:4 | Targets only |
| sFAS-L | 25.87 | 29.36 | 32.02 | 27.61 | 24.14 | 33.35 | 0.84 |
| MIP-1α | 45.38 | 57.48 | 59.58 | 55.36 | 51.04 | 60.80 | 1.06 |
| IL-2 | ND | ND | ND | ND | ND | ND | ND |
| IL-4 | 2.03 | 1.17 | 3.65 | 1.17 | 1.17 | 0.23 | ND |
| IL-5 | ND | ND | ND | 1.49 | ND | ND | ND |
| IL-2R | 673.51 | 687.11 | 767.70 | 698.41 | 595.35 | 769.91 | ND |
| IL-6 | 2.61 | 22.04 | 17.78 | 22.04 | 24.17 | 25.23 | 13.50 |
| 4-1BB | 89.45 | 178.01 | 200.95 | 151.22 | 136.20 | 184.22 | ND |
| IL-8 | 30.02 | 190.41 | 222.00 | 231.19 | 188.99 | 220.84 | 119.04 |
| IL-10 | 0.48 | 0.38 | 0.64 | 0.75 | 0.48 | 0.92 | ND |
| IL-13 | 12.64 | 22.47 | 26.18 | 20.75 | 14.03 | 25.25 | 1.18 |
| IL-17A | ND | ND | ND | ND | ND | ND | ND |
| IL-1RA | ND | ND | ND | ND | ND | ND | ND |
| RANTES | 79.70 | 50.13 | 56.80 | 51.06 | 52.64 | 51.47 | 0.74 |
| IFNγ | 10.99 | 19.79 | 22.68 | 13.96 | 16.88 | 22.68 | ND |
| GMCSF | 7.81 | 44.45 | 42.19 | 43.32 | 26.82 | 47.80 | ND |
| TNFα | 9.54 | 13.32 | 11.42 | 13.32 | 9.54 | 13.32 | 2.28 |
| MIP-1β | 86.43 | 103.81 | 114.46 | 106.19 | 94.86 | 110.66 | ND |
| MCP-1 | 3.66 | 645.81 | 699.82 | 897.10 | 939.60 | 811.71 | 1961.57 |
| IL-9 | 2.49 | 7.78 | 7.18 | 6.58 | 5.39 | 7.18 | 3.64 |
| TNFβ | 19.78 | 28.27 | 21.46 | 31.70 | 18.10 | 24.85 | 11.48 |
| Apo-Fas | 87.34 | 127.11 | 127.11 | 127.11 | 127.11 | 127.11 | 12.18 |
| IL-21 | 60.06 | 60.06 | 74.44 | 69.13 | 54.03 | 67.62 | ND |
| IL-3 | 4.48 | 1.94 | 3.87 | 6.81 | 4.48 | 4.48 | ND |
| Granzyme-A | 2238.06 | 1784.84 | 1945.78 | 1779.49 | 1509.25 | 2022.89 | 2.20 |
| Granzyme-B | 141.02 | 186.46 | 202.35 | 182.21 | 156.26 | 248.08 | 0.43 |
| IL-22 | 0.50 | 0.50 | 1.81 | 1.81 | ND | 1.81 | ND |

ND: Not Determined

TABLE 11

| | | | | Cytokine secretion profile of $^{EBV}CAR_{LNGFR}$-T cells using Donor 014-18 | | | |
|---|---|---|---|---|---|---|---|
| cytokine | T cell Only | 4:1 | 2:1 | 1:1 | 1:2 | 1:4 | Targets only |
| sFAS-L | 70.78 | 190.94 | 163.48 | 137.06 | 104.07 | 56.86 | 0.84 |
| MIP-1α | 219.18 | 721.77 | 749.91 | 852.82 | 785.54 | 729.75 | 1.35 |
| IL-2 | ND | 2.92 | 10.22 | 16.02 | 21.20 | 16.02 | ND |
| IL-4 | 2.85 | 9.60 | 14.50 | 15.19 | 17.23 | 6.69 | ND |
| IL-5 | ND | 10.91 | 25.37 | 27.80 | 15.70 | 1.49 | ND |
| IL-2R | 2647.65 | 4551.73 | 3230.88 | 2339.75 | 1404.34 | 776.55 | ND |
| IL-6 | 4.83 | 15.64 | 49.41 | 160.72 | 172.98 | 140.26 | 17.78 |
| 4-1BB | 1947.54 | 3453.80 | 2952.91 | 3353.54 | 2782.36 | 1792.51 | 0.80 |
| IL-8 | 12.53 | 896.94 | 1723.50 | 2529.47 | 2452.08 | 1493.81 | 111.03 |
| IL-10 | 0.28 | 1.37 | 1.83 | 1.95 | 0.81 | 0.81 | ND |
| IL-13 | 11.98 | 693.09 | 915.30 | 808.02 | 458.12 | 174.77 | 0.82 |
| IL-17A | ND | 1.98 | 2.33 | 1.98 | 1.98 | 1.26 | ND |
| IL-1RA | ND | ND | ND | ND | ND | ND | ND |
| RANTES | 620.17 | 711.60 | 625.04 | 580.93 | 520.03 | 422.51 | 0.74 |
| IFNγ | 37.15 | 6214.57 | 11483.55 | 19720.46 | 20865.20 | 15330.95 | ND |
| GMCSF | 0.56 | 562.91 | 1139.74 | 2451.03 | 2645.68 | 1515.19 | ND |
| TNFα | 15.24 | 132.54 | 205.90 | 255.87 | 154.54 | 65.96 | 4.04 |
| MIP-1β | 624.69 | 4160.79 | 6006.35 | 7816.09 | 5282.29 | 2986.56 | ND |

TABLE 11-continued

Cytokine secretion profile of $^{EBV}$CAR$_{LNGFR}$-T cells using Donor 014-18

| cytokine | T cell Only | 4:1 | 2:1 | 1:1 | 1:2 | 1:4 | Targets only |
|---|---|---|---|---|---|---|---|
| MCP-1 | 4.73 | 104.16 | 1068.43 | 2509.35 | 2745.00 | 2355.75 | 1970.19 |
| IL-9 | 1.92 | 17.66 | 27.23 | 29.82 | 35.04 | 22.74 | 5.39 |
| TNFβ | 45.66 | 77.95 | 122.43 | 156.63 | 145.16 | 103.73 | 14.77 |
| Apo-Fas | 292.95 | 292.95 | 250.72 | 250.72 | 250.72 | 167.70 | 12.18 |
| IL-21 | 156.82 | 299.98 | 278.96 | 253.25 | 210.25 | 174.02 | 0.79 |
| IL-3 | 3.25 | 7.94 | 15.47 | 44.98 | 50.04 | 30.83 | 0.44 |
| Granzyme-A | 3290.13 | 3636.20 | 3324.04 | 2945.88 | 2613.31 | 2460.13 | 1.82 |
| Granzyme-B | 457.96 | 685.23 | 657.62 | 624.66 | 589.20 | 498.95 | 1.33 |
| IL-22 | 1.81 | 5.77 | 8.41 | 7.09 | 5.77 | 5.77 | ND |

ND: Not Determined

TABLE 12

Cytokine secretion profile of $^{EBV}$CAR-T cells using Donor 014-18

| cytokine | T cell Only | 4:1 | 2:1 | 1:1 | 1:2 | 1:4 | Targets only |
|---|---|---|---|---|---|---|---|
| sFAS-L | 55.91 | 205.66 | 165.08 | 138.11 | 92.98 | 67.39 | 1.45 |
| MIP-1α | 231.20 | 926.65 | 842.33 | 978.12 | 826.20 | 714.37 | 1.62 |
| IL-2 | ND | 8.06 | 17.80 | 26.00 | 22.83 | 15.10 | ND |
| IL-4 | 2.85 | 30.05 | 35.47 | 24.53 | 18.57 | 8.88 | ND |
| IL-5 | ND | 30.23 | 35.11 | 20.52 | 8.53 | 3.81 | ND |
| IL-2R | 2466.34 | 5510.00 | 3536.79 | 2165.41 | 1159.25 | 700.66 | ND |
| IL-6 | 4.83 | 36.84 | 99.18 | 213.75 | 199.50 | 134.11 | 16.71 |
| 4-1BB | 1266.74 | 3002.77 | 2955.75 | 3595.90 | 2536.31 | 1805.36 | 3.77 |
| IL-8 | 10.66 | 1689.72 | 2395.90 | 3045.11 | 2076.46 | 1414.78 | 101.68 |
| IL-10 | 0.18 | 9.30 | 6.74 | 4.50 | 1.83 | 1.14 | ND |
| IL-13 | 21.32 | 1735.21 | 1521.99 | 997.28 | 400.61 | 152.61 | 0.82 |
| IL-17A | 0.10 | 2.85 | 2.68 | 4.37 | 1.98 | 0.89 | ND |
| IL-1RA | ND | ND | ND | ND | ND | ND | ND |
| RANTES | 576.54 | 890.34 | 727.46 | 676.24 | 581.75 | 551.31 | 0.42 |
| IFNγ | 34.25 | 12374.28 | 18530.80 | 23736.09 | 19543.54 | 14348.76 | ND |
| GMCSF | 6.21 | 1191.17 | 2079.25 | 3129.03 | 2304.77 | 1449.53 | ND |
| TNFα | 15.24 | 235.34 | 343.83 | 294.98 | 124.89 | 68.06 | 2.28 |
| MIP-1β | 509.46 | 8841.19 | 9646.39 | 10617.64 | 5315.47 | 2716.35 | ND |
| MCP-1 | 5.25 | 385.36 | 2120.71 | 3172.52 | 2674.09 | 2603.34 | 1773.97 |
| IL-9 | 1.92 | 27.88 | 30.47 | 36.35 | 31.77 | 26.59 | 3.64 |
| TNFβ | 50.96 | 103.73 | 152.80 | 183.64 | 129.97 | 107.45 | 14.77 |
| Apo-Fas | 271.78 | 400.20 | 335.59 | 292.95 | 250.72 | 250.72 | 48.74 |
| IL-21 | 124.99 | 348.09 | 295.12 | 256.46 | 205.51 | 168.53 | ND |
| IL-3 | 3.25 | 18.59 | 37.91 | 73.58 | 63.28 | 37.91 | 1.94 |
| Granzyme-A | 3393.86 | 3831.52 | 3192.70 | 2867.08 | 2557.77 | 2540.22 | 1.82 |
| Granzyme-B | 378.52 | 759.14 | 722.76 | 692.80 | 547.28 | 490.95 | 0.43 |
| IL-22 | 1.81 | 12.37 | 10.39 | 11.05 | 11.05 | 7.09 | 0.50 |

ND: Not Determined

TABLE 13

Cytokine secretion profile of NTD EBV-CTLs using Donor 014-18

| cytokine | T cell Only | 4:1 | 2:1 | 1:1 | 1:2 | 1:4 | Targets only |
|---|---|---|---|---|---|---|---|
| sFAS-L | 70.78 | 190.94 | 163.48 | 137.06 | 104.07 | 56.86 | 0.84 |
| MIP-1α | 219.18 | 721.77 | 749.91 | 852.82 | 785.54 | 729.75 | 1.35 |
| IL-2 | ND | 2.92 | 10.22 | 16.02 | 21.20 | 16.02 | ND |
| IL-4 | 2.85 | 9.60 | 14.50 | 15.19 | 17.23 | 6.69 | ND |
| IL-5 | ND | 10.91 | 25.37 | 27.80 | 15.70 | 1.49 | ND |
| IL-2R | 2647.65 | 4551.73 | 3230.88 | 2339.75 | 1404.34 | 776.55 | ND |
| IL-6 | 4.83 | 15.64 | 49.41 | 160.72 | 172.98 | 140.26 | 17.78 |
| 4-1BB | 1947.54 | 3453.80 | 2952.91 | 3353.54 | 2782.36 | 1792.51 | 0.80 |
| IL-8 | 12.53 | 896.94 | 1723.50 | 2529.47 | 2452.08 | 1493.81 | 111.03 |
| IL-10 | 0.28 | 1.37 | 1.83 | 1.95 | 0.81 | 0.81 | ND |
| IL-13 | 11.98 | 693.09 | 915.30 | 808.02 | 458.12 | 174.77 | 0.82 |
| IL-17A | ND | 1.98 | 2.33 | 1.98 | 1.98 | 1.26 | ND |

TABLE 13-continued

| | | | | | | | |
|---|---|---|---|---|---|---|---|
| | Cytokine secretion profile of NTD EBV-CTLs using Donor 014-18 | | | | | | |
| cytokine | T cell Only | 4:1 | 2:1 | 1:1 | 1:2 | 1:4 | Targets only |
| IL-1RA | ND | ND | ND | ND | ND | ND | ND |
| RANTES | 620.17 | 711.60 | 625.04 | 580.93 | 520.03 | 422.51 | 0.74 |
| IFNγ | 37.15 | 6214.57 | 11483.55 | 19720.46 | 20865.20 | 15330.95 | ND |
| GMCSF | 0.56 | 562.91 | 1139.74 | 2451.03 | 2645.68 | 1515.19 | ND |
| TNFα | 15.24 | 132.54 | 205.90 | 255.87 | 154.54 | 65.96 | 4.04 |
| MIP-1β | 624.69 | 4160.79 | 6006.35 | 7816.09 | 5282.29 | 2986.56 | ND |
| MCP-1 | 4.73 | 104.16 | 1068.43 | 2509.35 | 2745.00 | 2355.75 | 1970.19 |
| IL-9 | 1.92 | 17.66 | 27.23 | 29.82 | 35.04 | 22.74 | 5.39 |
| TNFβ | 45.66 | 77.95 | 122.43 | 156.63 | 145.16 | 103.73 | 14.77 |
| Apo-Fas | 292.95 | 292.95 | 250.72 | 250.72 | 250.72 | 167.70 | 12.18 |
| IL-21 | 156.82 | 299.98 | 278.96 | 253.25 | 210.25 | 174.02 | 0.79 |
| IL-3 | 3.25 | 7.94 | 15.47 | 44.98 | 50.04 | 30.83 | 0.44 |
| Granzyme-A | 3290.13 | 3636.20 | 3324.04 | 2945.88 | 2613.31 | 2460.13 | 1.82 |
| Granzyme-B | 457.96 | 685.23 | 657.62 | 624.66 | 589.20 | 498.95 | 1.33 |
| IL-22 | 1.81 | 5.77 | 8.41 | 7.09 | 5.77 | 5.77 | ND |

ND: Not Determined

EBV-CAR-T cells (i.e., $^{EBV}$CAR-T cells and $^{EBV}$CAR$_{LNGFR}$-T cells), derived from all donors produced elevated cytokine levels (such as IFNγ, Granzyme-B, IL6, TNFα, MCP-1) compared to NTD control and T cells alone, and across all E:F ratios. (See Tables 10-13 and FIGS. 13-15)

Example 5: In Vivo Safety and Efficacy Evaluation of EBV-CAR-T Cells

The efficacy of engineered EBV-specific, anti-CD19-CAR-expressing T cells is evaluated in a NALM6-induced systemic B cell acute lymphoblastic leukemia (B-ALL) mouse model. The study includes the staging of tumor burden following treatment with two to three doses of human donor-derived EBV-CAR-T cells ($0.6 \times 10^6$ cells or more per dose in mouse=human equivalent of at least $2 \times 10^6$ cells/kg).

Briefly, luciferase-expressing NALM6 cells are injected into immune-deficient mice ($0.5 \times 10^6$/mouse on Day −3) and tumor growth is allowed to progress for 3 days. Tumor staging is performed by bioluminescence imaging on Day 0 and treatment is administered intravenously or intraperitoneally. Animals are divided into treatment groups (eight animals per group) as described in Table 14. Recombinant human IL-2 (rhIL-2) is administered (2000 IU) just after treatment dose, with additional doses of rhIL-2 on Days 1 and 2 (2000 IU each day). Blood samples are collected 48 hours post-treatment and then weekly (e.g., Days 2, 10, 16, and 24). Tumor burden is measured by bioluminescent imaging twice-weekly (e.g., Days 4, 7, 10, 13, 16, 18, 21, and 24). Clinical symptoms and body weight are assessed twice-weekly (e.g., Days 2, 4, 7, 10, 13, 16, 18, 21, and 24). On Day 24 animals are sacrificed and tissue samples are collected (e.g., liver, bone marrow, and spleen) following necropsy. (See FIG. 16)

TABLE 14

| | safety and efficacy evaluation study groups | |
|---|---|---|
| Group ID | Treatment | Dose (cells) |
| 1 | Donor 1: EBV-CAR-T | $1 \times 10^6$ |
| 2 | Donor 1: EBV-CAR-T | $5 \times 10^6$ |
| 3 | Donor 1: EBV-CTLs UNT | $5 \times 10^6$ |

TABLE 14-continued

| | safety and efficacy evaluation study groups | |
|---|---|---|
| Group ID | Treatment | Dose (cells) |
| 4 | Donor 1: anti-CD19 CAR-T | $5 \times 10^6$ |
| 5 | Donor 2: EBV-CAR-T | $1 \times 10^6$ |
| 6 | Donor 2: EBV-CAR-T | $5 \times 10^6$ |
| 7 | Donor 2: EBV-CTLs UNT | $5 \times 10^6$ |
| 8 | Donor 2: anti-CD19 CAR-T | $5 \times 10^6$ |
| 9 | PBS | n/a |

Results

Animals receiving EBV-CAR-T cells exhibit a statistically significant reduction in clinical symptoms, including reduced tumor burden, and increased survival. Additional analysis demonstrates that EBV-CAR-T cells persist in mice over the course of the study and exhibit a polyfunctional cytokine profile with minimal adverse effects while avoiding acute toxicity.

Example 6: Safety of EBV-CAR-T Cell Therapy for Relapsed/Refractory Aggressive B-Cell Non-Hodgkin Lymphoma This study represents a single arm, open-label, multi-center study consisting of (a) dose escalation followed by (b) dose-expansion at maximum-tolerated biologically active dose to further define safety, tolerability and preliminary clinical outcome in human subjects treated with allogeneic (off-the-shelf) EBV-CAR-T cells.

Briefly, the study group includes adult subjects (≥18 years) with histologically confirmed aggressive B-cell non-Hodgkin lymphoma (NHL), defined as diffuse large B-cell lymphoma (DLBCL) not otherwise specified, including transformed indolent NHL, follicular lymphoma Grade 3B, T cell/histiocyte-rich large B-cell lymphoma, EBV-positive DLBCL not otherwise specified, primary mediastinal (thymic) large B-cell lymphoma, or high grade B-cell lymphoma with MYC and BCL2 and/or BCL6 rearrangements with DLBCL histology (double/triple-hit lymphoma)

who must have relapsed or be refractory to at least 2 prior lines of systemic therapy for the disease under study.

Previous therapy must have included a CD20-targeted agent and an anthracycline. Subjects treated with an autologous anti-CD19-CAR-T therapy are allowed but they must be CD 19+.

Dose levels to be explored include:

Low dose: $1 \times 10^6$ cells/kg

Intermediate dose: $3 \times 10^6$ cells/kg

High dose: $6 \times 10^6$ cells/kg

Each dose escalation uses a sample size of at least 3 dose-limiting toxicity (DLT) evaluable subjects per dose level. The dose expansion cohort is opened at the dose level that has been shown to be safe with at least 6 DLT evaluable subjects who completed the DLT period. All subjects from the dose escalation and dose expansion are followed for 24 months following EBV-CAR-T cell infusion for disease status and treatment related adverse events.

Further objectives include:

overall response rate at 1, 3, 6, 12 and 24 months and how its relationship to HLA mis-match; and safety with respect to HLA mis-match and its relationship to cytokine release syndrome (CRS), neurotoxicity, and graft versus host disease (GVHD).

Results

The disclosed doses of EBV-CAR-T cells are capable of inducing and/or increasing progression-free survival with minimal adverse effects. EBV-CAR-T cells are capable of both expansion and persistence in human subjects, exhibiting a polyfunctional cytokine profile and avoiding CAR-T exhaustion.

A number of embodiments of the invention have been described. Nevertheless, it will be understood that various modifications may be made without departing from the spirit and scope of the invention. Accordingly, other embodiments are within the scope of the following claims.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

What is claimed is:

1. An immune cell expressing a chimeric antigen receptor (CAR) polypeptide comprising a CD19-binding domain comprising the amino acid sequence set forth in SEQ ID NO:9, a hinge region comprising the amino acid sequence set forth in SEQ ID NO:12, a transmembrane domain comprising the amino acid sequence set forth in SEQ ID NO:13, an intracellular domain comprising the amino acid sequence set forth in SEQ ID NO: 14, and an intracellular signaling domain comprising the amino acid sequence set forth in SEQ ID NO: 11;

wherein the immune cell is an EBV-antigen sensitized cytotoxic T lymphocyte (CTL); and wherein the CAR-expressing immune cell is not derived from the subject to whom the cell is to be administered.

2. A method of treating a B-lymphocyte antigen-associated cancer in a subject, the method comprising administering to the subject an effective amount of an adoptive immunotherapy composition comprising the CAR-expressing immune cell of claim 1.

3. The method of claim 2, wherein the B-lymphocyte antigen-associated cancer is an EBV-associated lymphoproliferative disease.

4. The immune cell of claim 1, wherein the CAR polypeptide comprises at least one co-stimulatory signaling region, wherein the co-stimulatory signaling region comprises a signaling domain of any one of the polypeptides CD8, CD3ζ, CD3δ, CD3γ, CD3ε, FcγRI-γ, FcγRIII-γ, FcεRIβ, FcεRIγ, DAP10, DAP12, CD32, CD79a, CD79b, CD28, CD3C, CD4, b2c, CD137 (41BB), ICOS, CD27, CD288, CD80, NKp30, OX40, mutants thereof, or any combination thereof.

5. The immune cell of claim 1, wherein the CAR polypeptide comprises a signal peptide comprising the amino acid sequence set forth in SEQ ID NO:8.

6. The immune cell of claim 1, wherein the CAR polypeptide comprises the amino acid sequence set forth in SEQ ID NO:6 or SEQ ID NO:7.

7. The immune cell of claim 1, wherein the immune cell is derived from a donor sample, or from a bank or library of donor samples.

8. The method of claim 2, wherein the B-lymphocyte antigen-associated cancer is a hematologic cancer selected from: acute leukemia, chronic leukemia, lymphocytic leukemia, myelogenous leukemia, a pre-leukemic condition, Hodgkin lymphoma, Non-Hodgkin lymphoma, an EBV-associated lymphoproliferative disease, mature B cell neoplasm, mature T cell or natural killer (NK) cell neoplasm, precursor lymphoid neoplasm, and immunodeficiency-associated lymphoproliferative disorder.

9. The method of claim 2, wherein the subject is human.

* * * * *